US011072628B2

(12) United States Patent
Hulpia et al.

(10) Patent No.: US 11,072,628 B2
(45) Date of Patent: Jul. 27, 2021

(54) NUCLEOSIDE ANALOGUES FOR THE TREATMENT OF PARASITIC INFECTIONS

(71) Applicants: UNIVERSITEIT GENT, Ghent (BE); UNIVERSITEIT ANTWERPEN, Antwerp (BE)

(72) Inventors: Fabian Hulpia, Sint-Niklaas (BE); Serge Van Calenbergh, De Pinte (BE); Guy Caljon, Hever (BE); Louis Maes, Wechelderzande (BE)

(73) Assignees: Universiteit Gent, Ghent (BE); Universiteit Antwerpen, Antwerp (BE)

( * ) Notice: Subject to any disclaimer, the term of this patent is extended or adjusted under 35 U.S.C. 154(b) by 0 days.

(21) Appl. No.: 16/756,902

(22) PCT Filed: Oct. 3, 2018

(86) PCT No.: PCT/EP2018/076894
§ 371 (c)(1),
(2) Date: Apr. 17, 2020

(87) PCT Pub. No.: WO2019/076633
PCT Pub. Date: Apr. 25, 2019

(65) Prior Publication Data
US 2021/0024566 A1 Jan. 28, 2021

(30) Foreign Application Priority Data
Oct. 19, 2017 (EP) .................................. 17197416

(51) Int. Cl.
C07H 19/23 (2006.01)
(52) U.S. Cl.
CPC .................................. C07H 19/23 (2013.01)
(58) Field of Classification Search
None
See application file for complete search history.

(56) References Cited

FOREIGN PATENT DOCUMENTS

| WO | 9616664 A1 | 6/1996 |
| WO | 9618398 A1 | 6/1996 |
| WO | 2005020885 A2 | 3/2005 |
| WO | 2008157438 A1 | 12/2008 |
| WO | 2010121576 A2 | 10/2010 |

OTHER PUBLICATIONS

De Clercq, Antimicrobial Agents and Chemotherapy, Nov. 1986, p. 719-724, vol. 30, No. 5. (Year: 1986).*
Schram, Journal of carbohydrates, Nucleosides, Nucleotides, vol. 1, Issue 1, 1974, SciFinder record only. (Year: 1974).*
Kondo, Agric. Biol. Chem. 41 (8), 1501-1507, 1977. (Year: 1977).*
Naus, J. Med. Chem. 2014, 57, 1097-1110. (Year: 2014).*

International Search Report dated Nov. 19, 2018, in reference to co-pending European Patent Application No. PCT/EP2018/076894 filed Oct. 3, 2018.
Aureli Bourderioux, et al., "Synthesis and Significant Cytostatic Activity of 7-Hetaryl-7-deazaadenosines", Journal of Medicinal Chemistry, vol. 54, No. 15, Aug. 11, 2011 (Aug. 11, 2011), pp. 5498-5507, XP055485165.
Jan Snasel, et al., "Structural Basis for Inhibition of Mycobacterial and Human Adenosine Kinase by ?-Substituted 7-(Het)aryl-7-deazaadenine Ribonucleotides", Journal of Medicinal Chemistry, vol. 57, No. 20, Oct. 23, 2014 (Oct. 23, 2014), pp. 8268-8279, XP055485305.
European Patent Office Search Report in reference to co-pending European Patent Application No. 17197416.5-1110 filed Jun. 27, 2018.
Wallace, et al., "Different Substrate Recognition Motfits of Human and Trypanosome Nucleobase Transporters", The Journal of Biological Chemistry, vol. 277, No. 29, pp. 26149-26156, Jul. 19, 2002.
Berg, et al., "Inhibitors of the Purine Salvage Pathway: A Valuable Approach for Antriprtozoal Chemotherapy", Current Medicinal Chemistry, vol. 17, No. 23, pp. 2456-2481, 2010.
Shelton, et al., "Metabolism, Biochemical Actions, and Chemical Synthesis of Anticancer Nucleosides, Nucleotides, and Base Analogs", Chemical Reviews, pp. 14379-14455, Nov. 23, 2016.
Seela, et al., "7-Functionalized 7-Deazapurine Ribonucleosides related to 2-Aminoadenosine, Guanosine, and Xanthosine: Glycosylation of Pyrrolo (2,3-d)pyrimidines with 1-O-Acetyl-2,3,5-tri-O-benzoyl-D-ribofuranose", JOC Article, Aug. 8, 2005.
Robbins, et al., "A Mild Conversion of Vicinal Diols to Alkenes. Efficient Transformation of Ribonucleosides into 2'-Ene and 2',3'-Dideoxynucleosides", Tetrahedron Letters, vol. 25, No. 4, pp. 367-370, 1984.
Robins, et al., "Nucleic Aced Related Compounds. 5. The Transformation of Formycin and Tubercidin into 2'-and 3'-Deoxynucleosides", Canadian Journal of Chemistry, vol. 51, No. 9, pp. 1313-1321, May 1, 1973.
Omar, et al., "Chemical characterisation of Nigerian red propolis and its biological activity against Trypanosoma Brucei", Phytochemical Analysis, pp. 107-115, Dec. 11, 2015.
Miline, et al., "An Extremely Active Catalyst for the Negishi Cross-Coupling Reaction", JACS Article, vol. 126, No. 40, pp. 13028-13032, Aug. 30, 2004.
Miles, et al., "Nucleid Acid Related Compounds. 86. Nucleophillic Functionalization of Adenine, Adenosine, Tubercidin, and Formycin Dervatives via Elaboration of Heterocyclic Amino Group into a Readily Displaced 1,2,4-Triazol-4-yl Substituent", J. Am. Chem. Soc. vol. 117, No. 22, pp. 5951-5957, Feb. 1, 1995.
Kudo, et al., "A Versatile Method for Suzuki Cross-Coupling Reactions of Nitrogen Heterocycles", Angewandte Chem., Int. Edition 2006, 45, 1282-1284.

(Continued)

Primary Examiner — Layla D Berry
(74) Attorney, Agent, or Firm — Dinsmore & Shohl LLP

(57) ABSTRACT

The present invention relates to novel nucleoside analogues and compositions containing said nucleoside analogues. Moreover, the present invention provides processes for the preparation of the disclosed compounds, as well as methods of using them, for instance as a medicine, in particular for the diagnosis, prevention and/or treatment of parasitic infections, more specifically for use in the diagnosis, prevention and/or treatment of a *Trypanosoma* infection.

21 Claims, 5 Drawing Sheets

(56) References Cited

OTHER PUBLICATIONS

Kawana, et al., "Facile Transformation of B-D-Ribofuranosyl Purines and Pyrimidines into Their Respective 3'-Deoxy-threo-pentofuranosyl Nucleosides", J. Chem. Soc. Perkin Trans. pp. 1593-1596, Nov. 1, 1989.

Jordheim, et al., "Advances in the development of nucleoside and nucleotide analogues for cancer and viral diseases", Nature Reviews-Drug Discovery, vol. 12, pp. 447-464, Jun. 2013.

Jain, et al., "Reactions of 2-Acyloxyisobutyryl Halides with Nucleosides. III Reactions of Tubercidin or Formycin", J. Org. Chem., vol. 38, No. 18, pp. 3179-3186, Mar. 22, 1973.

Honeker, et al., "Transition-Metal-Free Trifluoromethylthiolation of N-Heteroarenes", Chemistry a European Journal Communication, pp. 8047-8051, 2015.

Hansske, et al., "Regiospecific and Stereoselective Conversion of Ribonucleosides to 3'-Deoxynucleosides. A High Yield Three-Stage Synthesis of Cordycepin from Adensine", Tetrahedron Letter, vol. 26, No. 36, pp. 4295-4298, 1985.

Gonda, et al., "Efficient Copper-Catalyzed Trifluoromethylation of Aromatic and Heteroaromatic Iodides: The Beneficial Anchoring Effect of Borates", Organic Letters, pp. 4268-4271, Jul. 28, 2014.

Garcia, et al., "A Simplified Approach to N- and N,N'-Linked 1,2,4-Triazoles by Transamination", Practical Synthetic Procedures, No. 1, pp. 149-154, Jun. 8, 2007.

Buckner, et al., "Efficiant Technique for Screening Drugs for Activity against Trypanosoma cruzi Using Prasites Expressing B-Galactosidase", Antimicrobial Agents and Chemotherapy, vol. 40, No. 11, pp. 2592-2597, Nov. 1996.

Bourderioux, et al., "Synthesis and Significant Cytostatic Activity of 7-Hetaryl-7-deazaadenosines", Journal of Medicinal Chemistry, pp. 5498-5507, Jun. 29, 2011.

Gonzalez, et al., "Conjugates of 2,4-Dihydroxybenzoate and Salicylhydroxamate and Lipocations Display Potent Antiparasite Effects by Efficiently Targeting the Trypanosoma brucei and Trypanosoma congolense Mitochondrion", Journal of Medicinal Chemistry, pp. 1509-1522, Jan. 23, 2017.

* cited by examiner

A

B

A

B

A

B

NUCLEOSIDE ANALOGUES FOR THE TREATMENT OF PARASITIC INFECTIONS

FIELD OF THE INVENTION

The present invention relates to novel nucleoside analogues and compositions containing said nucleoside analogues. Moreover, the present invention provides processes for the preparation of the disclosed compounds, as well as methods of using them, for instance as a medicine, in particular for the diagnosis, prevention and/or treatment of parasitic infections, more specifically for use in the diagnosis, prevention and/or treatment of a *Trypanosoma* infection.

BACKGROUND TO THE INVENTION

Human African Trypanosomiasis (HAT) is a deadly infectious disease, prevalent on the African continent, caused by *Trypanosoma brucei* spp. parasites (*T. b. rhodesiense* (East- and Southern Africa) and *T. b. gambiense* (West- and Central-Africa)). Transmission occurs via bites of the tsetse fly. HAT exhibits two characteristic disease stages that are linked to parasite distribution in the body. Initially, parasites reside in the hemolymphatic system and cause rather non-specific symptoms (e.g. general malaise and fever) often leading to incorrect diagnosis. The second phase consists of parasites invading the brain, causing neurological symptoms (e.g. altered sleep/wake cycles, hence the name 'sleeping sickness'). If untreated, HAT is fatal in most cases.

Treatment of HAT is cumbersome and greatly ineffective at present. Some of the approved drugs are only effective in Stage-I (suramin and pentamidine). For Stage-II disease, currently three drugs/drug combinations are approved: melarsoprol, eflornithine and nifurtimox/eflornithine. Melarsoprol, although effective against Stage-II disease, suffers from a high toxicity burden. Additionally, it requires parenteral administration, which is also the case for eflornithine (either as mono-therapy or in combination with nifurtimox (oral)). Recently, novel entities have reached phase II/III clinical trials and could greatly improve treatment options, e.g. fexinidazole and oxaborole SCYX-7158. However, fexinidazole is expected to show cross-resistance with nifurtimox, as they exhibit a similar mode-of-action.

These findings highlight the ever-pressing need for novel therapies in the treatment of parasitic infections in general, especially using molecules from other structural classes.

In that respect, nucleoside analogues have received considerable interest over the past six decades, with respect to many therapeutic areas, with most of the focus being their evaluation as either antiviral or anti-tumor agents (Jordheim et al., 2013; Shelton et al., 2016; WO2005/020885; WO2010/121576). Parasites in general, and *T. brucei* in particular, can be especially vulnerable to the effects of purine nucleoside analogues, because of their sole dependency on purine salvage, as they lack the enzymes for de novo purine synthesis. In this regard, potential inhibitors for enzymes of the salvage pathway, as well as so-called 'subversive' substrates (analogues that use the parasite's salvage pathway enzyme(s) to exert their toxic effect(s)), bearing a nucleoside structure, have been conceived or discovered by screening efforts (Berg et al., 2010). One such subversive analogue, is the naturally occurring nucleoside antibiotic tubercidin. This analogue was found to exert a plethora of biological effects (as it is a close structural mimic of adenosine), but unfortunately, it is overly cytotoxic to mammalian cells and thus non-selective, which makes it of little practical value.

Recent work by the research group of Hocek showed that certain C-7 substituted 7-deaza-adenosines were only poorly cytotoxic (6-membered rings; versus cytotoxic 5-membered rings) to both tumor as well as fibroblast cells (Snášel et al., 2014; Bourderioux et al., 2011).

WO9618398, WO2008157438 and WO9616664 disclose deazapurine ribose derivatives, 5'-amino derivatives, and adenosine derivatives respectively, however neither of these comply with the requirements of the present invention.

In the present invention, we explored a further subset of nucleoside compounds to evaluate their in vitro and in vivo effects, and identified several subgroups of very interesting and potent compounds useful in the treatment of parasitic infection, more specifically *Trypanosoma* infections.

SUMMARY OF THE INVENTION

In a first aspect, the present invention provides a compound according to formula I or a stereoisomer, tautomer, racemic, metabolite, pro-or-predrug, salt, hydrate, N—oxide form or solvate thereof,

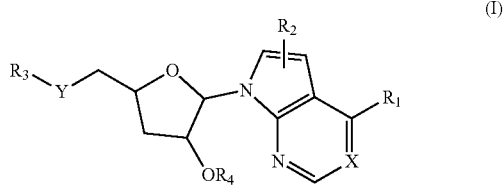

wherein

X is selected from C and N;

Y is selected from O and S;

$R_1$ is selected from —H, —$NR_5R_6$, —OH, —S—$C_{1-6}$alkyl and —O—$C_{1-6}$alkyl;

$R_2$ is selected from —$C_{1-6}$alkyl, —$C_{3-7}$cycloalkyl, —$C_{2-10}$alkenyl, —$C_{2-10}$alkynyl, —$CF_3$, —S—$CF_3$, —$Cy_1$ and —$Ar_1$; wherein said —$C_{1-6}$alkyl, —$C_{2-10}$alkynyl, or —$C_{2-10}$alkenyl is optionally further substituted with one or more —$Cy_2$, or —$Ar_2$;

$R_3$ is selected from —H, —$C_{1-6}$alkyl, —$SO_2$—$NH_2$, and optionally substituted silyl; wherein said —$C_{1-6}$alkyl is optionally further substituted with one or more —OH;

$R_4$ is selected from —H, —$C_{1-6}$alkyl, and tert-butyldimethylsilyl;

$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N and S;

$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, and —$OCF_3$; and $Ar_1$ and $Ar_2$ are each independently selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, and —$OCF_3$.

In a further specific embodiment, the present invention provides a compound in accordance with formula (Ia),

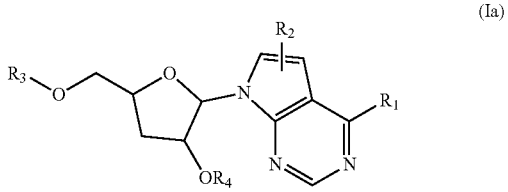

wherein $R_1$ is selected from —H, —NR$_5$R$_6$, —OH, —S—C$_{1-6}$alkyl and —O—C$_{1-6}$alkyl;

$R_2$ is selected from —C$_{1-6}$alkyl, —C$_{3-7}$cycloalkyl, —C$_{2-10}$alkenyl, —C$_{2-10}$alkynyl, —CF$_3$, —S—CF$_3$, —Cy$_1$ and —Ar$_1$; wherein said —C$_{1-6}$alkyl, —C$_{2-10}$alkynyl, or —C$_{2-10}$alkenyl is optionally further substituted with one or more —Cy$_2$, or —Ar$_2$;

$R_3$ is selected from —H, —C$_{1-6}$alkyl, —SO$_2$—NH$_2$, and optionally substituted silyl; wherein said —C$_{1-6}$alkyl is optionally further substituted with one or more —OH;

$R_4$ is selected from —H, —C$_{1-6}$alkyl, -tert-butyldimethylsilyl;

$R_5$, $R_6$ are each independently selected from —H, —C$_{3-7}$cycloalkyl and —C$_{1-6}$alkyl; or $R_5$ and $R_6$ taken together with the N atom to which they are attached form a 5- to 6-membered heterocycle, further optionally comprising one or more heteroatoms selected from O, N and S;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

In another specific embodiment, the present invention provides a compound in accordance with formula (Ib)

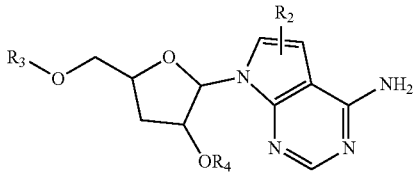

wherein $R_2$ is selected from —C$_{1-6}$alkyl, —C$_{3-7}$cycloalkyl, —C$_{2-10}$alkenyl, —C$_{2-10}$alkynyl, —CF$_3$, —S—CF$_3$, —Cy$_1$ and —Ar$_1$; wherein said —C$_{1-6}$alkyl, —C$_{2-10}$alkynyl, or —C$_{2-10}$alkenyl is optionally further substituted with one or more —Cy$_2$, or —Ar$_2$;

$R_3$ is selected from —H, —C$_{1-6}$alkyl, —SO$_2$—NH$_2$, and optionally substituted silyl; wherein said —C$_{1-6}$alkyl is optionally further substituted with one or more —OH;

$R_4$ is selected from —H, —C$_{1-6}$alkyl, -tert-butyldimethylsilyl;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

In yet a further embodiment, the present invention provides a compound in accordance with formula (Ic)

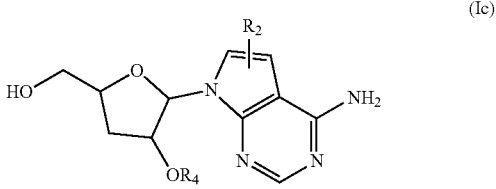

wherein $R_2$ is selected from —C$_{1-6}$alkyl, —C$_{3-7}$cycloalkyl, —C$_{2-10}$alkenyl, —C$_{2-10}$alkynyl, —CF$_3$, —S—CF$_3$, —Cy$_1$ and —Ar$_1$; wherein said —C$_{1-6}$alkyl, —C$_{2-10}$alkynyl, or —C$_{2-10}$alkenyl is optionally further substituted with one or more —Cy$_2$, or —Ar$_2$;

$R_4$ is selected from —H, —C$_{1-6}$alkyl, -tert-butyldimethylsilyl;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

More specifically the present invention provides a compound in accordance with formula (Ic)

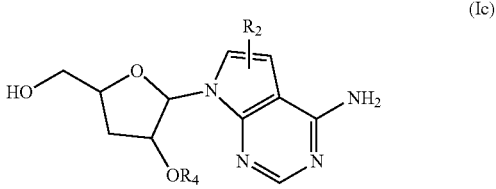

wherein $R_2$ is —C$_{1-6}$alkynyl, optionally further substituted with one or more —Ar$_2$, or —C$_{1-6}$alkyl;

$R_4$ is selected from —H, —C$_{1-6}$alkyl, -tert-butyldimethylsilyl;

Ar$_2$ is selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

The present invention also provides a compound in accordance with formula (Ic)

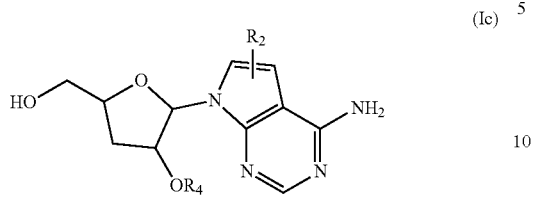

(Ic)

wherein $R_2$ is —$Ar_1$;

$R_4$ is selected from —H, —$C_{1-6}$alkyl, -tert-butyldimethyl-silyl $Ar_1$ is selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, and —$OCF_3$.

In a specific embodiment, in the compounds of the present invention, the ribose moiety has the D-stereochemistry as defined in formula (Id)

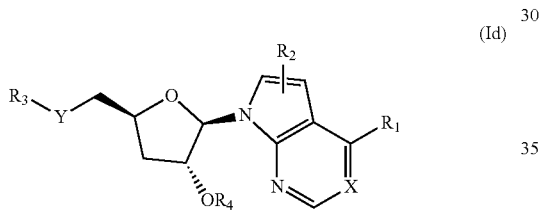

(Id)

In a very specific embodiment, the present invention provides a compound selected from the list comprising:

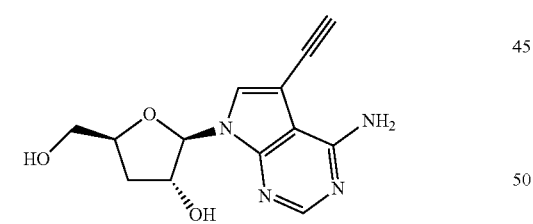

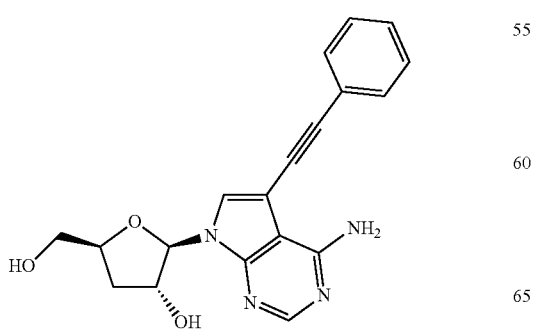

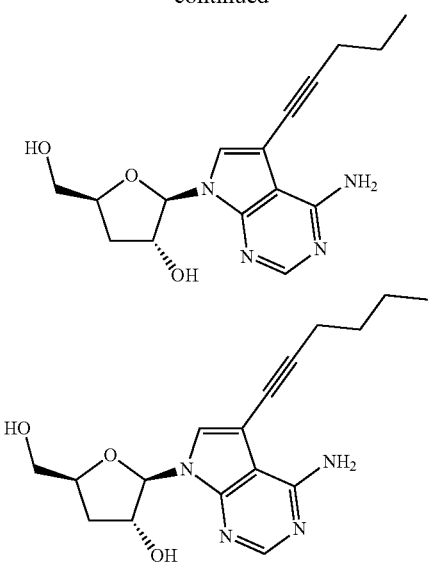

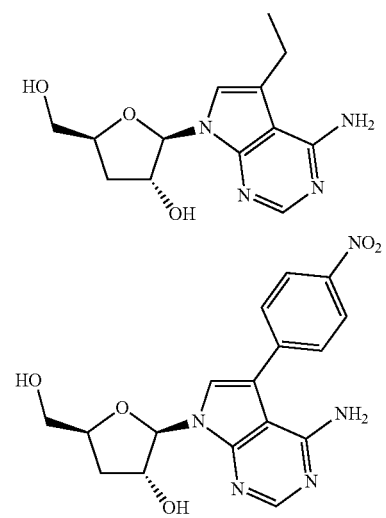

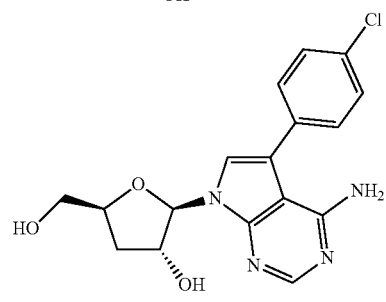

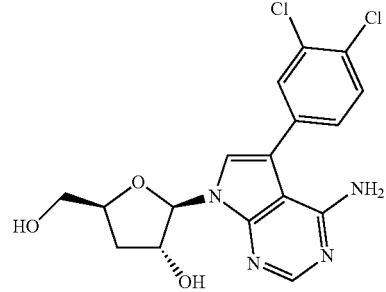

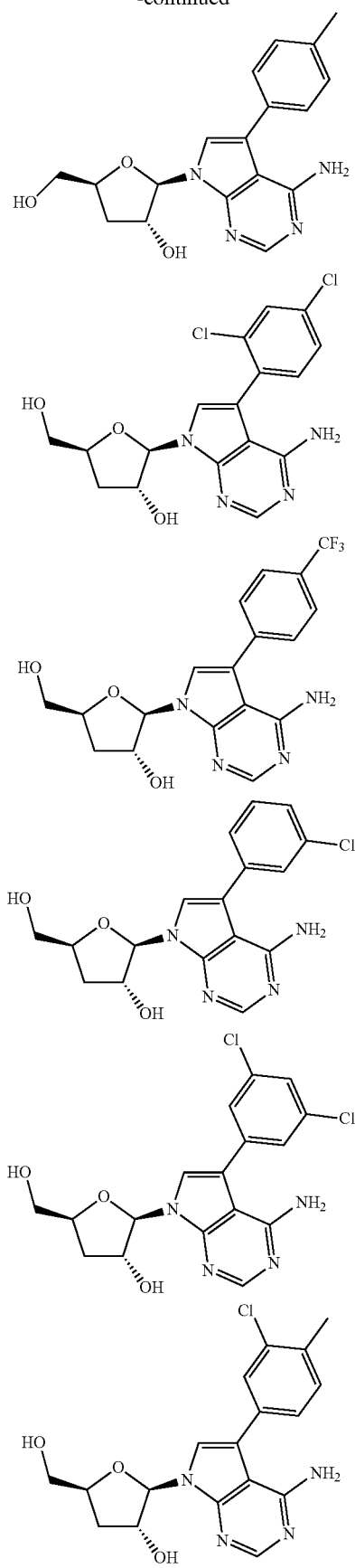
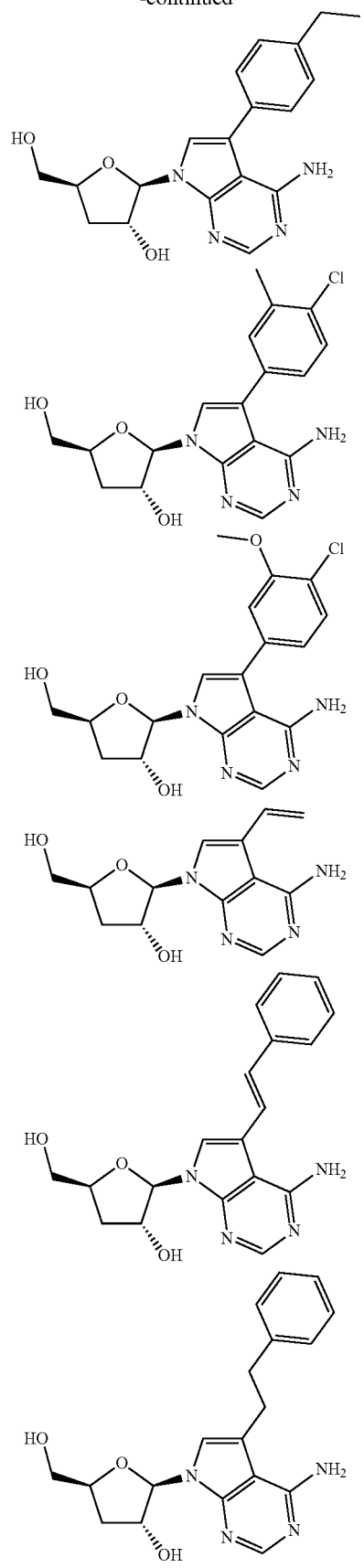

In a further aspect, the present invention also provides a compound according to formula II or a stereoisomer, tautomer, racemic, metabolite, pro-or-predrug, salt, hydrate, N—oxide form or solvate thereof,

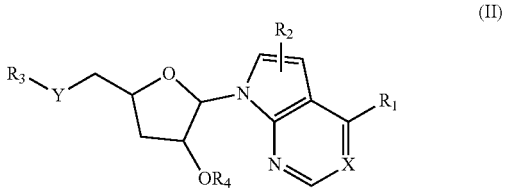

wherein
X is selected from C and N;
Y is selected from O and S;
R₁ is selected from —H, —NR₅R₆, —OH, —S—C₁₋₆alkyl and —O—C₁₋₆alkyl;
R₂ is selected from —H, halo, —C₁₋₆alkyl, —C₃₋₇cycloalkyl, —C₂₋₁₀alkenyl, —C₂₋₁₀alkynyl, —CF₃, —S—CF₃, —Cy and —Ar₁; wherein said —C₁₋₆alkyl, —C₂₋₁₀alkynyl, or —C₂₋₁₀alkenyl is optionally further substituted with one or more —Cy₂, or —Ar₂;
R₃ is selected from —H, —C₁₋₆alkyl, —SO₂—NH₂, and optionally substituted silyl; wherein said —C₁₋₆alkyl is optionally further substituted with one or more —OH;
R₄ is selected from —H, —C₁₋₆alkyl, -tert-butyldimethylsilyl;
R₅, R₆ are each independently selected from —H, —C₃₋₇ cycloalkyl and —C₁₋₆alkyl; or R₅ and R₆ taken together with the N atom to which they are attached form a 5- to 6-membered heterocycle, further optionally comprising one or more heteroatoms selected from O, N and S;
Cy₁ and Cy₂ are each independently selected from a mono- or bicyclic non-aromatic cycle optionally containing one or more heteroatoms, and optionally being further substituted with one or more halo, —C₁₋₆alkyl, —CF₃, —NO₂, —O—C₁₋₆alkyl, and —OCF₃;
Ar₁ and Ar₂ are each independently selected from a mono- or bicyclic aromatic cycle optionally containing one or more heteroatoms, and optionally being further substituted with one or more halo, —C₁₋₆alkyl, —CF₃, —NO₂, —O—C₁₋₆alkyl, and —OCF₃;
for use in the prevention and/or treatment of a parasite infection in a subject; more specifically for use in the prevention and/or treatment of a *Trypanosoma* infection in a subject.

The present invention further provides a compound for use as defined herein and in accordance with formula (IIa),

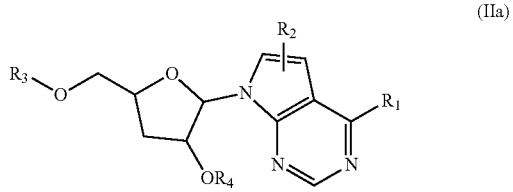

wherein
R₁ is selected from —H, —NR₅R₆, —OH, —S—C₁₋₆alkyl and —O—C₁₋₆alkyl;
R₂ is selected from —H, halo, —C₁₋₆alkyl, —C₃₋₇cycloalkyl, —C₂₋₁₀alkenyl, —C₂₋₁₀alkynyl, —CF₃, —S—CF₃, —Cy and —Ar₁; wherein said —C₁₋₆alkyl, —C₂₋₁₀alkynyl, or —C₂₋₁₀alkenyl is optionally further substituted with one or more —Cy₂, or —Ar₂;
R₃ is selected from —H, —C₁₋₆alkyl, —SO₂—NH₂, and optionally substituted silyl; wherein said —C₁₋₆alkyl is optionally further substituted with one or more —OH;
R₄ is selected from —H, —C₁₋₆alkyl, -tert-butyldimethylsilyl;
R₅, R₆ are each independently selected from —H, —C₃₋₇ cycloalkyl and —C₁₋₆alkyl; or R₅ and R₆ taken together with the N atom to which they are attached form a 5- to 6-membered heterocycle, further optionally comprising one or more heteroatoms selected from O, N and S;
Cy₁ and Cy₂ are each independently selected from a mono- or bicyclic non-aromatic cycle optionally containing one or more heteroatoms, and optionally being further substituted with one or more halo, —C₁₋₆alkyl, —CF₃, —NO₂, —O—C₁₋₆alkyl, and —OCF₃; and
Ar₁ and Ar₂ are each independently selected from a mono- or bicyclic aromatic cycle optionally containing one or more heteroatoms, and optionally being further substituted with one or more halo, —C₁₋₆alkyl, —CF₃, —NO₂, —O—C₁₋₆alkyl, and —OCF₃.

The present invention further provides a compound for use as defined herein and in accordance with formula (IIb)

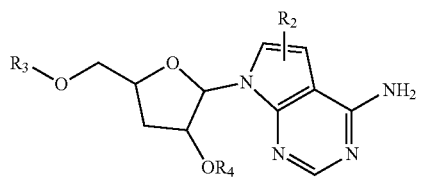

wherein
R₂ is selected from —H, halo, —C₁₋₆alkyl, —C₃₋₇cycloalkyl, —C₂₋₁₀alkenyl, —C₂₋₁₀alkynyl, —CF₃, —S—CF₃, —Cy and —Ar₁; wherein said —C₁₋₆alkyl, —C₂₋₁₀alkynyl, or —C₂₋₁₀alkenyl is optionally further substituted with one or more —Cy₂, or —Ar₂;
R₃ is selected from —H, —C₁₋₆alkyl, —SO₂—NH₂, and optionally substituted silyl; wherein said —C₁₋₆alkyl is optionally further substituted with one or more —OH;
R₄ is selected from —H, —C₁₋₆alkyl, -tert-butyldimethylsilyl; R₅, R₆ are each independently selected from —H, —C₃₋₇ cycloalkyl and —C₁₋₆alkyl; or R₅ and R taken together with the N atom to which they are attached form a 5- to 6-membered heterocycle, further optionally comprising one or more heteroatoms selected from O, N and S;
Cy₁ and Cy₂ are each independently selected from a mono- or bicyclic non-aromatic cycle optionally containing one or more heteroatoms, and optionally being further substituted with one or more halo, —C₁₋₆alkyl, —CF₃, —NO₂, —O—C₁₋₆alkyl, and —OCF₃; and
Ar₁ and Ar₂ are each independently selected from a mono- or bicyclic aromatic cycle optionally containing one or more heteroatoms, and optionally being further substituted with one or more halo, —C₁₋₆alkyl, —CF₃, —NO₂, —O—C₁₋₆alkyl, and —OCF₃.

The present invention further provides a compound for use as defined herein and in accordance with formula (IIc)

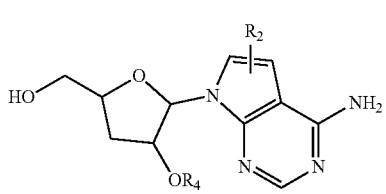

(IIc)

wherein

R$_2$ is selected from —H, halo, —C$_{1-6}$alkyl, —C$_{3-7}$cycloalkyl, —C$_{2-10}$alkenyl, —C$_{2-10}$alkynyl, —CF$_3$, —S—CF$_3$, —Cy$_1$ and —Ar$_1$; wherein said —C$_{1-6}$alkyl, —C$_{2-10}$alkynyl, or —C$_{2-10}$alkenyl is optionally further substituted with one or more —Cy$_2$, or —Ar$_2$;

R$_4$ is selected from —H, —C$_{1-6}$alkyl, -tert-butyldimethylsilyl;

R$_5$, R$_6$ are each independently selected from —H, —C$_{3-7}$cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

The present invention further provides a compound for use as defined herein and in accordance with formula (IIc)

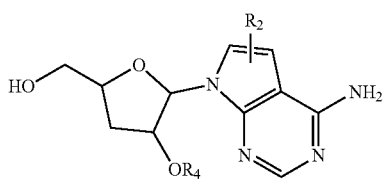

(IIc)

wherein

R$_2$ is —C$_{2-10}$alkynyl, optionally further substituted with one or more —Cy$_2$, or —Ar$_2$;

R$_4$ is selected from —H, —C$_{1-6}$alkyl, -tert-butyldimethylsilyl;

Cy$_2$ is selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar$_2$ is selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

The present invention further provides a compound for use as defined herein and in accordance with formula (IIc)

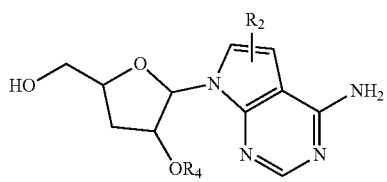

(IIc)

wherein

R$_2$ is —Ar$_1$;

R$_4$ is selected from —H, —C$_{1-6}$alkyl, -tert-butyldimethylsilyl; and

Ar$_1$ is selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

The present invention further provides a compound for use as defined herein wherein the ribose moiety has the D-stereochemistry as defined in formula (IId)

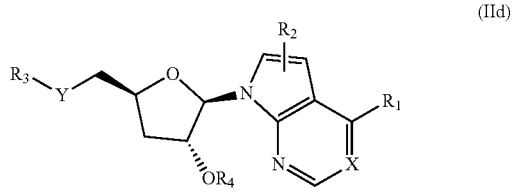

(IId)

In a particular embodiment, with respect to each of the enclosed formula (I), (II), and any subgroups thereof (Ia-Id; IIa-IId), R$_4$ is preferably selected to be —H.

In yet a further aspect, the present invention provides a compound according to formula III or a stereoisomer, tautomer, racemic, metabolite, pro-or-predrug, salt, hydrate, N—oxide form or solvate thereof

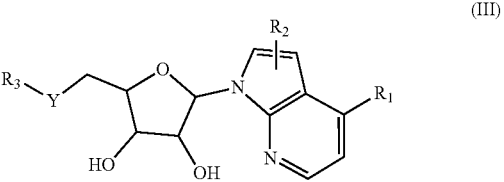

(III)

wherein

Y is selected from O and S;

R$_1$ is selected from —H, —NR$_5$R$_6$, halo, —OH, S—C$_{1-6}$alkyl and —O—C$_{1-6}$alkyl;

R$_2$ is selected from —C$_{1-6}$alkyl, —C$_{3-7}$cycloalkyl, —C$_{2-10}$alkenyl, —C$_{2-10}$alkynyl, halo, —CF$_3$, —S—CF$_3$, —Cy$_1$ and —Ar$_1$; wherein said —C$_{1-6}$alkyl, —C$_{2-10}$alkynyl, or —C$_{2-10}$alkenyl is optionally further substituted with one or more —Cy$_2$, or —Ar$_2$;

R$_3$ is selected from —H, —C$_{1-6}$alkyl, —SO$_2$—NH$_2$, and optionally substituted silyl; wherein said —C$_{1-6}$alkyl is optionally further substituted with one or more —OH;

R$_5$, R$_6$ are each independently selected from —H, —C$_{3-7}$cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S;

Cy₁ and Cy₂ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar₁ and Ar₂ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

The present invention further provides a compound according to formula III or a stereoisomer, tautomer, racemic, metabolite, pro-or-predrug, salt, hydrate, N—oxide form or solvate thereof

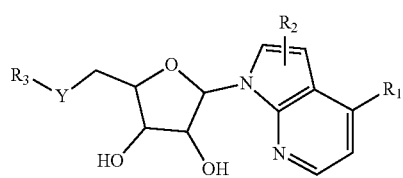
(III)

wherein

Y is selected from O and S;

R₁ is selected from —H, —NR$_5$R$_6$, halo, —OH, S—C$_{1-6}$alkyl and —O—C$_{1-6}$alkyl;

R₂ is selected from —C$_{1-6}$alkyl, —C$_{3-7}$cycloalkyl, —C$_{2-10}$alkenyl, —C$_{2-10}$alkynyl, halo, —CF$_3$, —S—CF$_3$, —Cy₁ and —Ar₁; wherein said —C$_{1-6}$alkyl, —C$_{2-10}$alkynyl, or —C$_{2-10}$alkenyl is optionally further substituted with one or more —Cy₂, or —Ar₂;

R₃ is selected from —H, —C$_{1-6}$alkyl, —SO$_2$—NH$_2$, and optionally substituted silyl; wherein said —C$_{1-6}$alkyl is optionally further substituted with one or more —OH; R$_5$, R$_6$ are each independently selected from —H, —C$_{3-7}$cycloalkyl and —C$_{1-6}$alkyl; or R$_5$ and R taken together with the N atom to which they are attached form a 5- to 6-membered heterocycle, further optionally comprising one or more heteroatoms selected from O, N and S;

Cy₁ and Cy₂ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and Ar₁ and Ar₂ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$;

for use in the prevention and/or treatment of a parasite infection in a subject; more specifically for use in the prevention and/or treatment of a *Trypanosoma* infection in a subject.

The present invention also provides a compound according to formula IV or a stereoisomer, tautomer, racemic, metabolite, pro-or-predrug, salt, hydrate, N—oxide form or solvate thereof

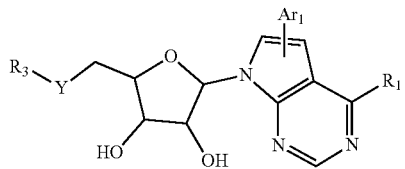
(IV)

wherein

Y is selected from O;

R₁ is selected from —H, —NR$_5$R$_6$, halo, —OH, S—C$_{1-6}$alkyl and —O—C$_{1-6}$alkyl;

R₃ is selected from —H, —C$_{1-6}$alkyl, —SO$_2$—NH$_2$, and optionally substituted silyl; wherein said —C$_{1-6}$alkyl is optionally further substituted with one or more —OH R$_5$, R$_6$ are each independently selected from —H, —C$_{3-7}$cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S Ar₁ is selected from a mono- or bicyclic aromatic cycle optionally containing one or heteroatoms, and optionally being further substituted with one or more halo, —C$_{1-6}$alkyl, —CF$_3$, —NO$_2$, —O—C$_{1-6}$alkyl, and —OCF$_3$;

for use in the prevention and/or treatment of a parasite infection in a subject; more specifically for use in the prevention and/or treatment of a *Trypanosoma* infection in a subject.

In a further embodiment, the present invention provides a compound according to formula V or a stereoisomer, tautomer, racemic, metabolite, pro-or-predrug, salt, hydrate, N—oxide form or solvate thereof

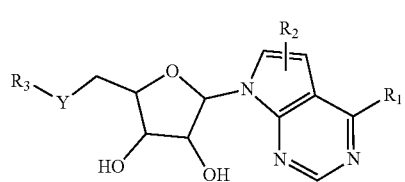
(V)

wherein

Y is selected O;

R₁ is —O—C$_{1-6}$alkyl;

R₂ is selected from —C$_{1-6}$alkyl, —C$_{3-7}$cycloalkyl, —C$_{2-10}$alkenyl, —C$_{2-10}$alkynyl, halo, —CF$_3$, —S—CF$_3$, —Cy₁ and —Ar₁; wherein said —C$_{1-6}$alkyl, —C$_{2-10}$alkynyl, or —C$_{2-10}$alkenyl is optionally further substituted with one or more —Cy₂, or —Ar₂;

R₃ is selected from —H, —C$_{1-6}$alkyl, —SO$_2$—NH$_2$, and optionally substituted silyl; wherein said —C$_{1-6}$alkyl is optionally further substituted with one or more —OH;

R$_5$, R$_6$ are each independently selected from —H, —C$_{3-7}$cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S;

Ar₁ is selected from a mono- or bicyclic aromatic cycle optionally containing one or heteroatoms, and optionally being further substituted with one or more halo, —C$_{1-6}$alkyl, —CF$_3$, —NO$_2$, —O—C$_{1-6}$alkyl, and —OCF$_3$;

for use in the prevention and/or treatment of a parasite infection in a subject; more specifically for use in the prevention and/or treatment of a *Trypanosoma* infection in a subject.

In one embodiment, the present invention provides the compounds as defined in any one of Formulas I, Ia, Ib, Ic, Id, II, IIa, IIb, IIc, IId, III, IV or V, or a stereoisomer, tautomer, racemic, salt, hydrate, N—oxide form or solvate thereof.

The present invention also provides a pharmaceutical composition comprising a compound as defined herein and at least one pharmaceutically acceptable excipient, diluent and/or carrier.

The present invention also provides compounds and compositions as defined herein, for use in human or veterinary medicine; more specifically for use as provided herein, in particular for use in the diagnosis, prevention and/or treatment of a parasite infection; even more specifically for use in the diagnosis, prevention and/or treatment of a protozoa infection.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
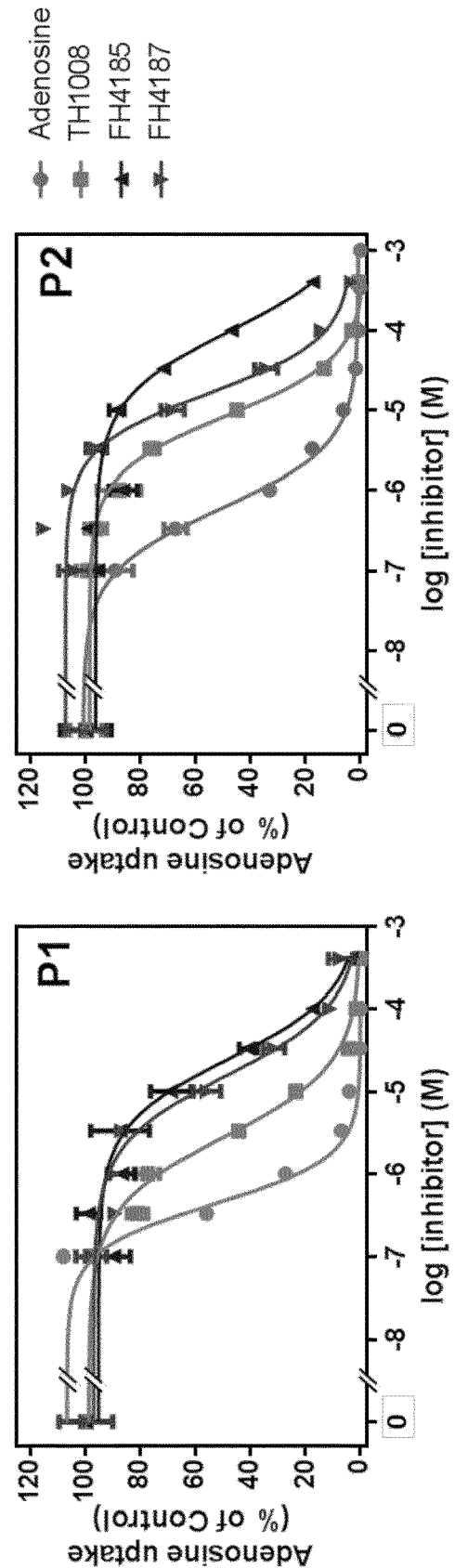
FIG. 1: Transport of [$^3$H]-Adenosine via P1 and P2 transporters in the presence of increasing concentrations of nucleoside analogues TH1008, FH4185 and FH4187. Transport via P1 was measured in B48 cells, while transport via P2 was evaluated in B48 (lacking P2) transfected with a construct overexpressing the TbAT1/P2 transporter, in the presence of 100 μM inosine to block P1. The graphs show one representative of three independent experiments in triplicate. Error bars are SEM, when not shown, fall within the symbol.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Compounds

In a first aspect the present invention provides compounds of Formula I, or a stereoisomer, tautomer, racemic, metabolite, pro-or-predrug, salt, hydrate, N—oxide form or solvate thereof,

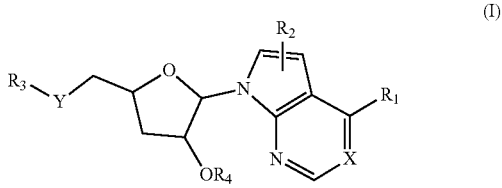

wherein
X is selected from C and N;
Y is selected from O and S;
$R_1$ is selected from —H, —NR$_5$R$_6$, —OH, —S—C$_{1-6}$alkyl and —O—C$_{1-6}$alkyl;
$R_2$ is selected from —C$_{1-6}$alkyl, —C$_{3-7}$cycloalkyl, —C$_{2-10}$alkenyl, —C$_{2-10}$alkynyl, —CF$_3$, —S—CF$_3$, —Cy$_1$ and —Ar$_1$; wherein said —C$_{1-6}$alkyl, —C$_{2-10}$alkynyl, or —C$_{2-10}$alkenyl is optionally further substituted with one or more —Cy$_2$, or —Ar$_2$;
$R_3$ is selected from —H, —C$_{1-6}$alkyl, —SO$_2$—NH$_2$, and optionally substituted silyl; wherein said —C$_{1-6}$alkyl is optionally further substituted with one or more —OH;
$R_4$ is selected from —H, —C$_{1-6}$alkyl, and tert-butyldimethylsilyl;
$R_5$, $R_5$ are each independently selected from —H, —C$_{3-7}$cycloalkyl and —C$_{1-6}$alkyl; or $R_5$ and Re taken together with the N atom to which they are attached form a 5- to 6-membered heterocycle, further optionally comprising one or more heteroatoms selected from O, N and S;
Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$; and
Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, and —OCF$_3$.

When describing the compounds of the invention, the terms used are to be construed in accordance with the following definitions, unless a context dictates otherwise.

The term "alkyl" by itself or as part of another substituent refers to a fully saturated hydrocarbon of Formula C$_x$H$_{2x+1}$ wherein x is a number greater than or equal to 1. Generally, alkyl groups of this invention comprise from 1 to 20 carbon atoms; more specifically from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, C$_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sulfonamido and the like.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, propynyl, butynyl, isobutynyl, and pentynyl, hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structures. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl and cyclodecyl. An "optionally substituted cycloalkyl" refers to a cycloalkyl having optionally one or more substituents (for example 1 to 3 substituents, for example 1, 2, 3 or 4 substituents), selected from those defined above for substituted alkyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

The terms "heterocyclyl" or "heterocyclo" as used herein by itself or as part of another group refer to non-aromatic cyclic groups (for example, 3 to 13 membered monocyclic, 7 to 17 membered bicyclic, or 10 to 20 membered tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinylsulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N—formylpiperazinyl, and morpholinyl.

The term "aryl" as used herein refers to an aromatic hydrocarbyl group having a single ring (i.e. phenyl) or multiple aromatic rings fused together (e.g. naphthalene or anthracene) or linked covalently, typically containing 5 to 12 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cycloheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, arylalkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO$_2$R$^a$, alkylthio, carboxyl, and the like, wherein R$^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, phthalazinyl, 1,2,3-benzotriazinyl, 1,2,4-benzotriazinyl, 7-azaindolyl, 6-azaindolyl, 5-azaindolyl, 4-azaindolyl, 1,5-naphtyridinyl, 1,6-naphtyridinyl, 1,7-naphtyridinyl, 1,8-naphtyridinyl, 2,6-naphtyridinyl, 2,7-naphtyridinyl.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR wherein R$_b$ is alkyl. Preferably, alkoxy is C$_1$-C$_{10}$ alkoxy, C$_1$-C$_6$ alkoxy, or C$_1$-C$_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

Preferred compounds will bear the D configuration. Further, preferred compounds will have either the ribofuranose or arabinofuranose configuration, as illustrated below.

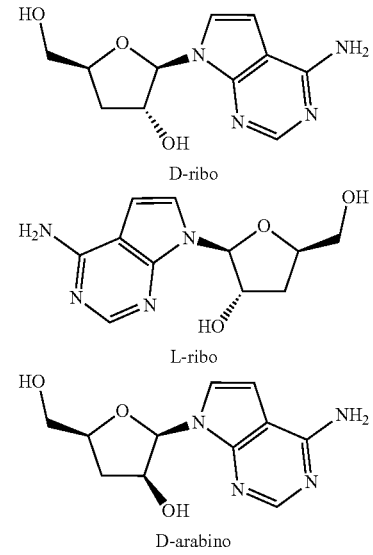

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I, II, III, IV, and V, and any subgroup thereof. This term also refers to the exemplified compounds as depicted in Tables 1 to 8, and in particular Table 8, their derivatives, N—oxides, salts, solvates, hydrates, stereoisomeric forms, racemic mixtures, tautomeric forms, optical isomers, analogues, pro-drugs, esters, and metabolites, as well as their quaternized nitrogen analogues. The N—oxide forms of said compounds are meant to comprise compounds wherein one or several nitrogen atoms are oxidized to the so-called N—oxide.

As used in the specification and the claims, the singular forms "a", "an", and "the" include plural referents unless the context clearly dictates otherwise. By way of example, "a compound" means one compound or more than one compound.

The terms described above and others used in the specification are well understood to those in the art.

In a further embodiment, the present invention provides compounds of formula (I), wherein X is selected to be N and/or Y is selected to by O and wherein the other substituents are selected from the same lists as mentioned herein with respect to formula (I). Compounds wherein X is N and Y is O are generally referred to as compounds of formula (Ia)

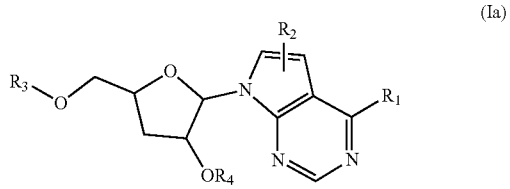

(Ia)

In yet a further embodiment, the present invention provides compounds of formula (I), wherein $R_1$ is selected to be —$NH_2$ and wherein the other substituents are selected from the same lists as mentioned herein with respect to formula (I). Preferably, this further limitation is included in the limitations already defined for formula (Ia); thereby resulting in compounds corresponding to formula (Ib):

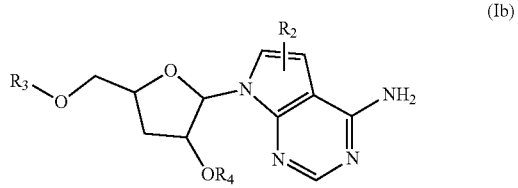

(Ib)

In another specific embodiment, the present invention provides compounds of formula (I), wherein $R_3$ is selected to be —H and wherein the other substituents are selected from the same lists as mentioned herein with respect to formula (I). Preferably, this further limitation is included in the limitations already defined for formula (Ib); thereby resulting in compounds corresponding to formula (Ic):

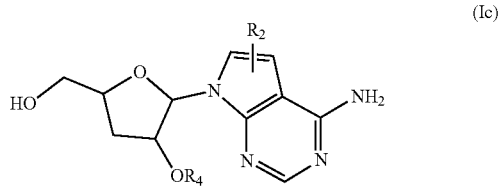

(Ic)

In yet a further specific embodiment, the present invention provides compounds of formula (I), wherein $R_2$ is selected to be —$C_{1-6}$alkynyl, optionally further substituted with one or more —$Ar_2$, or —$C_{1-6}$alkyl; and wherein the other substituents are selected from the same lists as mentioned herein with respect to formula (I). Preferably, this further limitation is included in the limitations already defined for formula (Ib); thereby resulting in compounds corresponding to formula (Ic).

In a further specific embodiment, the present invention provides compounds of formula (I), wherein $R_2$ is selected to be —$Ar_1$; and wherein the other substituents are selected from the same lists as mentioned herein with respect to formula (I). Preferably, this further limitation is included in the limitations already defined for formula (Ib); thereby resulting in compounds corresponding to formula (Ic).

In a very specific embodiment, in the compounds of the present invention, the ribose moiety has the D-stereochemistry as defined in formula (Id):

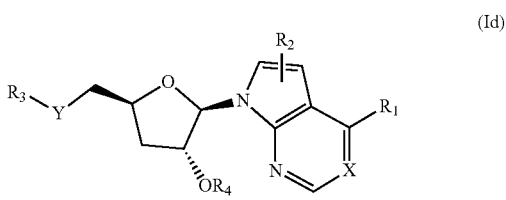

(Id)

In a particular embodiment, the present invention provides compounds of formula (I), wherein $R_4$ is selected to be —H.

While each of the above-defined embodiments specifically mention compounds of formula (I), (Ia), (Ib), (Ic) and (Id), the present invention also provides the use thereof in human or veterinary medicine.

In such use, the compounds are referred to as compounds of formula (II), (IIa), (IIb), (IIc) and (IId).

It should be noted that compounds in accordance with formula (I); more specifically (Ic) or (Ic); wherein $R_2$ is selected to be —$C_{2-10}$alkynyl or $C_{2-10}$alkenyl, optionally further substituted with one or more —$Cy_2$, or —$Ar_2$; where found to be particularly suitable in the treatment of *T. brucei*.

Furthermore, compounds in accordance with formula (I); more specifically (Ic) or (IIc); wherein $R_2$ is selected to be —$Ar_1$; where found to be particularly suitable in the treatment of *T. cruzi*.

The present invention also provides a compound according to formula III or a stereoisomer, tautomer, racemic, metabolite, pro-or-predrug, salt, hydrate, N—oxide form or solvate thereof

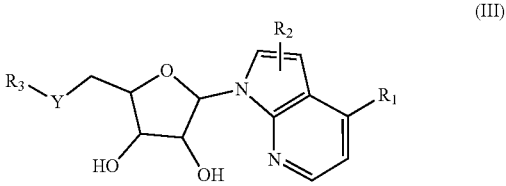

(III)

wherein
Y is selected from O and S;
$R_1$ is selected from —H, —$NR_5R_6$, halo, —OH, S—$C_{1-6}$alkyl and —O—$C_{1-6}$alkyl;

$R_2$ is selected from —$C_{1-6}$alkyl, —$C_{3-7}$cycloalkyl, —$C_{2-10}$alkenyl, —$C_{2-10}$alkynyl, halo, —$CF_3$, —S—$CF_3$, —$Cy_1$ and —$Ar_1$; wherein said —$C_{1-6}$alkyl, —$C_{2-10}$alkynyl, or —$C_{2-10}$alkenyl is optionally further substituted with one or more —$Cy_2$, or —$Ar_2$;

$R_3$ is selected from —H, —$C_{1-6}$alkyl, —$SO_2$—$NH_2$, and optionally substituted silyl; wherein said —$C_{1-6}$alkyl is optionally further substituted with one or more —OH; $R_5$, $R_6$ are each independently selected from —H, —$C_{3-7}$cycloalkyl and —$C_{1-6}$alkyl; or $R_5$ and R taken together with the N atom to which they are attached form a 5- to 6-membered heterocycle, further optionally comprising one or more heteroatoms selected from O, N and S;

$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, and —$OCF_3$; and $Ar_1$ and $Ar_2$ are each independently selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, and —$OCF_3$.

In a further aspect, the present invention provides a compound according to formula IV or a stereoisomer, tautomer, racemic, metabolite, pro-or-predrug, salt, hydrate, N—oxide form or solvate thereof

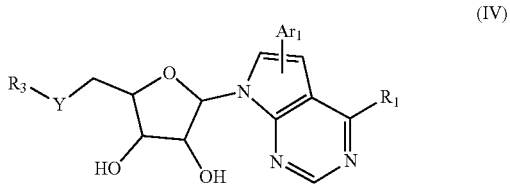

(IV)

wherein
Y is selected from O;
$R_1$ is selected from —H, —$NR_5R_6$, halo, —OH, S—$C_{1-6}$alkyl and —O—$C_{1-6}$alkyl;
$R_3$ is selected from —H, —$C_{1-6}$alkyl, —$SO_2$—$NH_2$, and optionally substituted silyl; wherein said —$C_{1-6}$alkyl is optionally further substituted with one or more —OH
$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N and S
$Ar_1$ is selected from a mono- or bicyclic aromatic cycle optionally containing one or heteroatoms, and optionally being further substituted with one or more halo, —$C_{1-6}$alkyl, —$CF_3$, —$NO_2$, —O—$C_{1-6}$alkyl, and —$OCF_3$;
for use in the diagnosis, prevention and/or treatment of a parasite infection in a subject in need thereof; more specifically for use in the diagnosis, prevention and/or treatment of a *Trypanosoma* infection in a subject in need thereof.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Uses

In one embodiment, the compounds of the present invention are useful as a medicament, specifically a human or veterinary medicine: in particular as anti-parasitic agents, more in particular as anti-protozoal agents. More in particular, compounds as provided herein are useful in the treatment of parasitic diseases such African trypanosomiasis and Chagas disease.

The present invention further provides a compound as defined herein or a (pharmaceutical) composition comprising said compound, for use as a human or veterinary medicine, in particular for use in the prevention and/or treatment of parasitic infections, more in particular for preventing and/or treating at least one infection, disease or disorder selected from the group comprising trypanosome infections (sleeping sickness; Chagas disease or American trypanosomiasis), Leishmaniasis, malaria, Trichomoniasis or Toxoplasmosis. A "trypanosome" refers to a protozoan parasite, which may infect host organisms, such as birds and mammals. In certain embodiments, a trypanosome is *Trypanosoma cruzi*. In certain embodiments, a trypanosome is *Trypanosoma brucei* spp. Exemplary trypanosomal parasites include, but are not limited to, *Trypanosoma brucei gambiense, Trypanosoma brucei* rhodesiense, and *Trypanosoma cruzi*.

In a preferred embodiment, the invention provides methods and uses of a compound as defined hereinbefore or of a composition comprising said compound(s) for the prevention and/or treatment of parasitic infections.

As used herein, "Chagas disease" refers to a parasitic disease associated with or caused by infection with the protozoan parasite *Trypanosoma cruzi*. Chagas disease can comprise an acute phase which typically lasts from weeks to months and is often symptom-free. When symptoms do occur they can include swelling at the infection site, fever, fatigue, rash, body aches, eyelid swelling, headache, loss of appetite, nausea, diarrhea, vomiting, swollen glands and enlargement of the liver or spleen. The disease can also include a chronic phase that typically occurs 10 to 20 years after initial infection. In the chronic stage symptoms can includes irregular heartbeat, congestive heart failure, sudden cardiac arrest, difficulty swallowing due to enlargement of the esophagus, and/or abdominal pain or constipation due to enlargement of the colon. The compounds of the present invention are particularly useful for treating the "chronic" stage" of Chagas disease.

Human African trypanosomiasis (HAT), also known as "sleeping sickness", is a vector-borne parasitic disease. It is caused by infection with protozoan parasites belonging to the genus *Trypanosoma* (*T. brucei* spp.). They are transmitted to humans by tsetse fly (*Glossina* genus) bites which have acquired their infection from human beings or from animals harbouring human pathogenic parasites. In the first stage, the trypanosomes multiply in subcutaneous tissues, blood and lymph. This is also called the haemo-lymphatic stage, which entails bouts of fever, headaches, joint pains and itching. In the second stage the parasites cross the blood-brain barrier to infect the central nervous system. This is known as the neurological or meningo-encephalic stage (stage II). In general this is when more obvious signs and symptoms of the disease appear: changes of behaviour, confusion, sensory disturbances and poor coordination. Disturbance of the sleep cycle, which gives the disease its name, is an important feature. Without treatment, sleeping sickness is considered fatal although cases of healthy carriers have been reported. The compounds of the present invention are particularly useful for treating said "stage II" of HAT disease or sleeping sickness.

Typically, disease management is made in 3 steps:
1. Screening for potential infection. This involves using serological tests and/or checking for clinical signs;
2. Diagnosing by establishing whether the parasite is present in body fluids;
3. Staging to determine the state of disease progression. This entails examining the cerebrospinal fluid obtained by lumbar puncture.

Diagnosis must be made as early as possible to avoid progressing to the neurological stage in order to elude complicated and risky treatment procedures.

The present invention further provides a method for the prevention and/or treatment of at least one parasitic infection or infestation in a mammalian subject (preferably human), the method comprising the step of administering to the subject a therapeutically or prophylactically effective amount of a compound in accordance with the present invention. A "parasitic infection" as used herein refers to an infection caused by any of the following parasites: *Plasmodium* spp., *P. falciparum*, *P. berghei*, *P. malariae*, *P. vivax*, *P. ovale*, *Cryptosporidium* spp., *Cryptosporidium parvum*, *C. hominis*, *Acanthanmoeba* spp., *Trypanosoma* spp. *Trypanosoma brucei brucei*, *T. b. rhodesiense*, *T. b. gambiense*, *T. b. evansi*, *T. b. equiperdum*, *T. simiae*, *T. vivax*, *T. congolense*, *T. cruzi*, *Leishmania* spp., *Leishmania donovani*, *L. major*, *L. mexicana*, *L. infantum*, *L. tropica*, *L. brazeliensis*, *Schistosoma* spp., *S. mansoni*, *S. haematobium*, *S. japonicum*, *Toxoplasma gondii*, *Trichomonas* spp., *Trichomonas vaginalis*, *Entamoeba invadens*, *Giardia* spp., *Giardia lamblia*; *Tritrichomonas* spp., *Histomonas meleagridis*, *Entamoeba* spp., *Limax* spp., *Acanthamoeba* spp., or *Eimeria* spp.

In a preferred embodiment, the invention provides a method for the prevention and/or treatment of *Trypanosoma* infections, in particular infections by *Trypanosoma brucei* and/or *Trypanosoma cruzi*.

Particularly preferred are the compounds of the invention having a nanomolar activity or having an IC50 value of less than 1 µM, in particular less than 0.5 µM, more in particular less than 0.1 µM, when tested in the in vitro assay as described herein, and e.g. as provided in Tables 1-4.

Compounds of the invention especially useful in the treatment of *T. brucei* infection are FH8446, FH9528, FH9529, FH9532, FH9531, FH9530, TH1008, FH5314, FH5278, FH5319, FH7429_U, FH7429_D, FH8470, FH8496, FH8517, FH8504, FH8505, FH9610, FH9611, FH8471, FH9591, FH9582, FH8522, FH9539, FH9552, FH9613, FH10628, FH10641, FH10649, FH10650, FH10659, FH10660, and/or FH10661. In a particular embodiment, the compound of the invention is selected from the group consisting of: FH5278, FH8446, FH9528, FH9529, FH9532, FH9531, FH9530, TH1008, FH7429_U, FH7429_D, FH8470, FH8496, FH8517, FH8504, FH9610, FH9611, FH9539, FH9552, FH10659, and FH10628.

Compounds of the invention especially useful in the treatment of *T. cruzi* infection are TH1012, FH3147, MS1001, FH5314, FH5278, FH5319, FH9530, FH7429_U, FH8470, FH8496, FH8512, FH8513, FH8517, FH8481, FH9581, FH9576, FH10641, FH10642, FH10644, FH10648, FH10649, FH10680, FH10681, FH10682 and/or FH10683. In a particular embodiment, the compound of the invention is selected from the group consisting of: TH1012, FH3147, MS1001, FH5314, FH5278, FH5319, FH9530, FH7429_U, FH8470, FH8496, FH8512, FH8513, FH8481, FH9581, FH9576, FH10641, FH10642, FH10644, FH10648, FH10649, FH10680, FH10681, FH10682 and FH10683.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N—methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

The present invention also relates to a pharmaceutical composition comprising one or more of the compounds as provided herein in admixture or in combination with a pharmaceutically acceptable carrier, diluent and/or excipient, and optionally an adjuvant or one or more further pharmaceutically active compounds.

The invention also provides a method of making a pharmaceutical composition comprising mixing one or more compounds of the invention with at least one pharmaceutically acceptable carrier, diluent or excipient and/or adjuvant, and optionally one or more further pharmaceutically active compounds (in particular anti-parasitic or anti-protozoal compounds).

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers.

In addition, co-solvents such as alcohols may improve the solubility and/or the stability of the compounds. In the preparation of aqueous compositions, addition of salts of the compounds of the invention can be more suitable due to their increased water solubility.

More in particular, the compositions may be formulated in a pharmaceutical formulation comprising a therapeutically effective amount of particles consisting of a solid dispersion of the compounds of the invention and one or more pharmaceutically acceptable water-soluble polymers. The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds or compositions can be administered by a variety of routes including the oral, rectal, ocular, transdermal, subcutaneous, intravenous, intramuscular or intranasal routes, depending mainly on the specific preparation used and the condition to be treated or prevented, and with oral administration being preferred. The at least one compound of the invention will generally be administered in an "effective amount", by which is meant any amount of a compound of the Formula I, II, III or IV, or any subgroup thereof that, upon suitable administration, is sufficient to achieve the desired prophylactic or therapeutic benefit in the treatment of a condition or to delay or minimize (the development of) one or more symptoms associated with the condition in the subject to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for treating a disease. In certain embodiments, a therapeutically effective amount is effective for treating an infectious disease. In certain embodiments, a therapeutically effective amount is effective for treating Chagas disease. In certain embodiments, a therapeutically effective amount is effective for treating sleeping sickness. In certain embodiments, a therapeutically effective amount is effective for treating malaria. In certain embodiments, a therapeutically effective amount is effective for treating a parasitic infection. In certain embodiments, a therapeutically effective amount is effective for treating a protozoan infection. In certain embodiments, a therapeutically effective amount is effective for treating a trypanosomal infection. In certain embodiments, a therapeutically effective amount is effective for treating a *T. cruzi* infection. In certain embodiments, a therapeutically effective amount is effective for treating a *T. brucei* infection.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compounds or compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof.

Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

In addition to a human application, the compounds and compositions of the present invention are also of value in the veterinary field, which for the purposes herein not only includes the prevention and/or treatment of diseases in animals, but also—for economically important animals such as chickens/turkeys/ducks/pigs/cattle and equine-species, etc.—enhancing the growth and/or weight of the animal and/or the amount and/or the quality of the meat or other products obtained from the animal.

Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. 3' Deoxyribofuranose Compounds

A1. General Synthesis Schemes

Carbohydrate Building Block Synthesis

Scheme A1

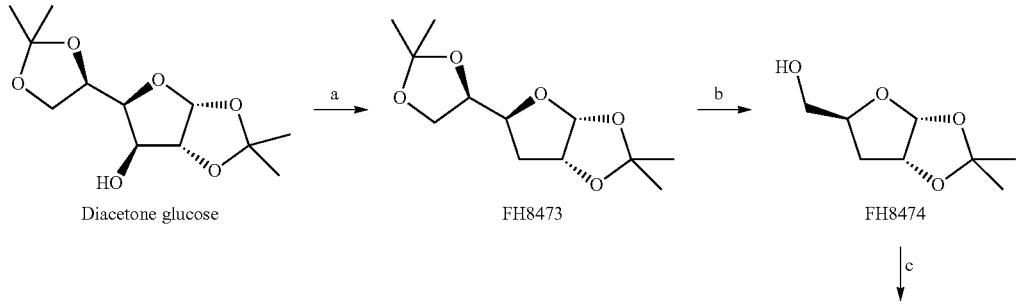

31

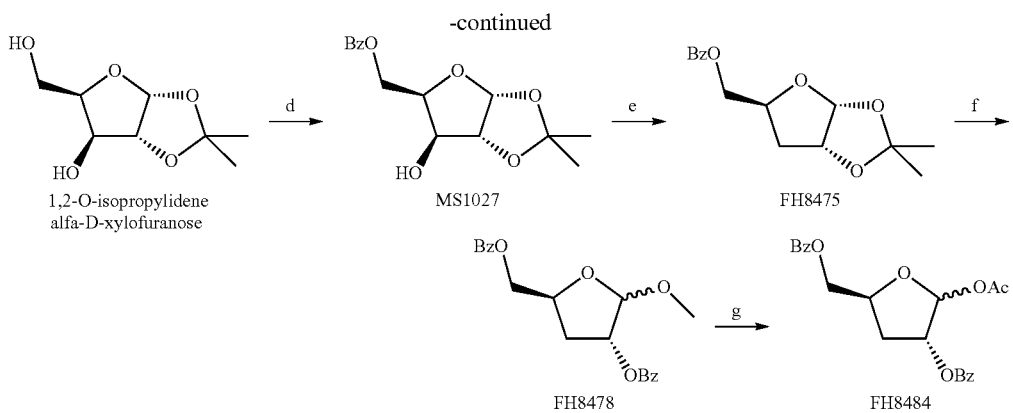

Reagents and conditions: a) 1. NaH, CS$_2$, MeI, THF; 2. (nBu)$_3$SnH, AIBN, toluene, reflux; b) 1. AcOH/water 80/20, overnight; 2. NaIO$_4$, water, 1H; 3. NaBH$_4$, EtOH, 0° C.-rt; c) BzCl, Et$_3$N, DCM, 0° C.; d) BzCl, Et$_3$N, DCM, 0° C., e) 1. TCDI, 1,2-dichloro-ethane; 2. (nBu)$_3$SnH, AIBN, toluene, reflux; f) 1. HCl, MeOH, 50° C.; 2. BzCl, Et$_3$N, DMAP, DCM, 0° C.-rt; g) Ac$_2$O, AcOH, H$_2$SO$_4$, rt.

The synthesis of glycosyl donor FH8484 started from commercially available diacetone-D-glucose or 1,2-O-isopropylidene-α-D-xylofuranose. Diacetone glucose was first deoxygenated employing classical Barton-McCombie deoxygenation, employing literature conditions, with the exception that the intermediate xanthate ester was not purified, but directly subjected to reductive conditions. Next, the distal isopropylidene was selectively cleaved under mild acidic conditions. Then, periodate mediated diol cleavage and subsequent one-pot aldehyde reduction furnished FH8474. FH8474 was further benzoylated, the remaining isopropylidene cleaved with c.HCl/MeOH and benzoylated to give FH8478. Transacetalization gave FH8484 which was the preferred coupling partner for the Vorbrüggen glycosylation. (the corresponding 1',2'-O-acetate was initially also prepared and used for glycosylation; but was found to give inferior glycosylation yields, despite the use of 2 eq. of glycosyl donor to allow for adequate conversion of the heterocyclic starting material)

Alternatively, protected xylofuranose was selectively protected at the 5—OH as a benzoate ester, by slow addition of BzCl at 0° C. Formation of the xanthate ester as for the above-mentioned sequence was sluggish, after which it was decided to employ TCDI and immediate reduction, which also furnished FH8475.

7-Substituted Analogues

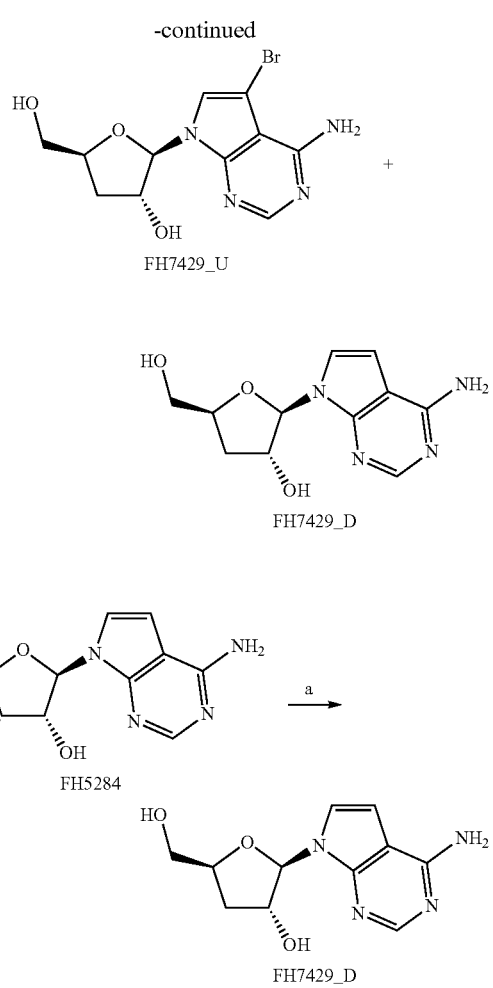

Scheme A2

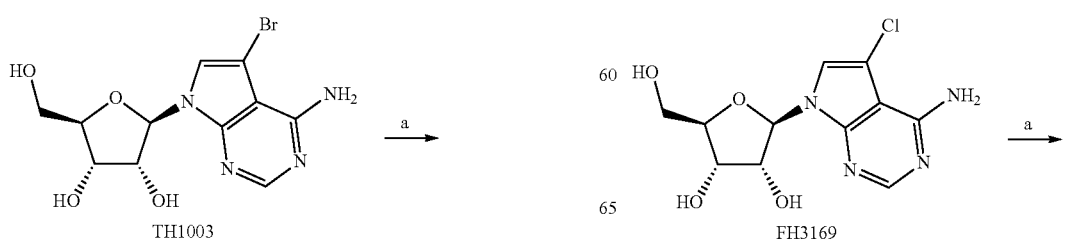

-continued

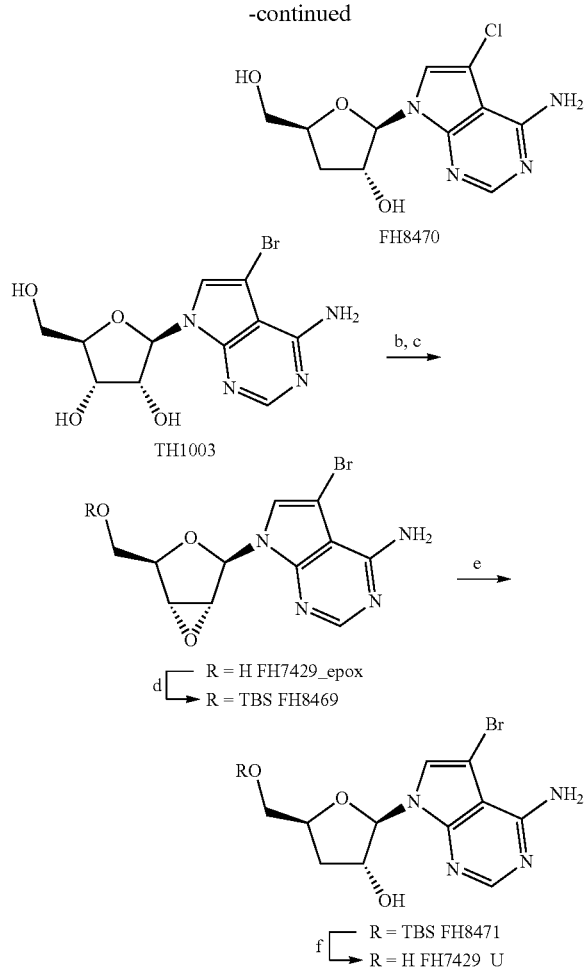

Reagents and conditions: a) 1. α-acetoxy-isobutyrylchloride, NaI, MeCN; 1. Pd/C, H₂ (balloon), aq. NaOAc, MeOH, overnight; 3. NH₃ 7N in MeOH, rt. or alternatively: a) 1. α-acetoxy-isobutyrylbromide, 'moist' MeCN; 2. Pd/C, H₂ (balloon), aq. NaOAc, MeOH, overnight; 3. NH₃ 7N in MeOH, rt.; b) 1. α-acetoxy-isobutyrylbromide, 'moist' MeCN; c) NaOMe 0.4M, MeOH, overnight; d) TBSCl, imidazole, DMF; e) LiEt₃BH (1M in THF), DMSO, 10° C.-rt, overnight (for C-5' unprotected analogues) or LiEt₃BH (1M in THF), THF, 0° C.-rt, overnight (for C-5' protected analogues); f) TFA/water (9/1).

Nucleoside analogs can be obtained by either modifying a pre-formed nucleoside analog, or by forging the glycosidic bond between two functionalized building blocks, in a glycosylation reaction. In Scheme A2 modification on an existing nucleoside is described (i.e. synthetic approaches to selectively deoxygenate the C-3' alcohol). In scheme A4 the second approach employing the glycosyl donor (scheme 3) and appropriate heterocycle are described.

C-3' deoxygenation can be achieved by reaction an appropriate ribo-nucleoside with α-acetoxy-isobutyrylbromide (Robins et al., 1984) or α-acetoxy-isobutyrylchloride (Jain et al., 1973; Robins et al., 1973) (in combination with NaI; Mattocks reagent), to give the intermediate 3'-halo derivative which is then subjected to dehalogenation by means of Pd/C and Hz. Alternatively, this halo intermediate is subjected to basic hydrolysis, furnishing the formation of a 2',3'-epoxide, that can be opened regioselectively by Li(Et)₃BH. (Hansske & Morris, 1985) Protection of the 5'—OH as a silyl ether provides an advantage, in that it avoids the use of DMSO in the reduction step, facilitating improved work-up and product isolated despite the two additional reaction steps.

Scheme A3

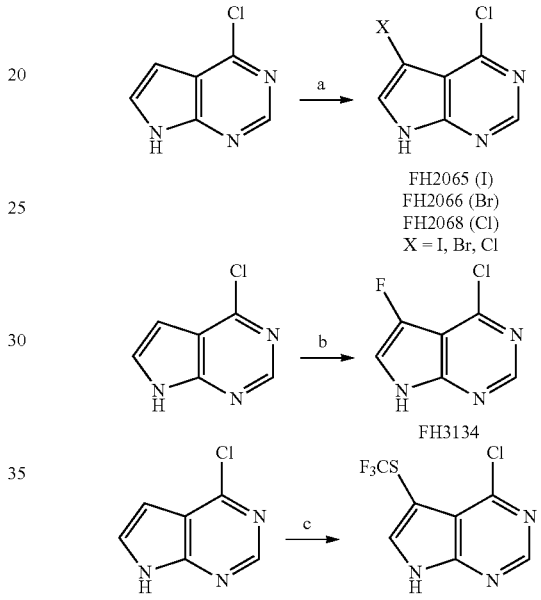

Reagents and conditions: a) NXS, DMF, overnight; b) Selectfluor®, AcOH, MeCN, 60° C., overnight; c) N-(triflurormethylthio)phtalimide, NaCl, DMF, 90° C., overnight.

Modified heterocycles are prepared according to literature procedures employing either a halo-succinimide or Selectfluor®. The synthesis of C-5 substituted trifluoromethylthio analog FH6335 was accomplished using N—(trifluoromethylthio)phthalimide and a catalytic amount of NaCl. (Honeker et al., 2015)

Scheme A4

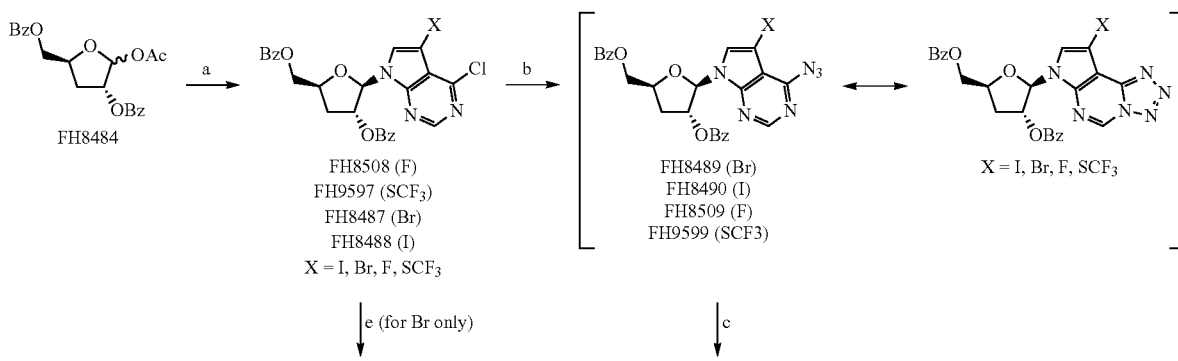

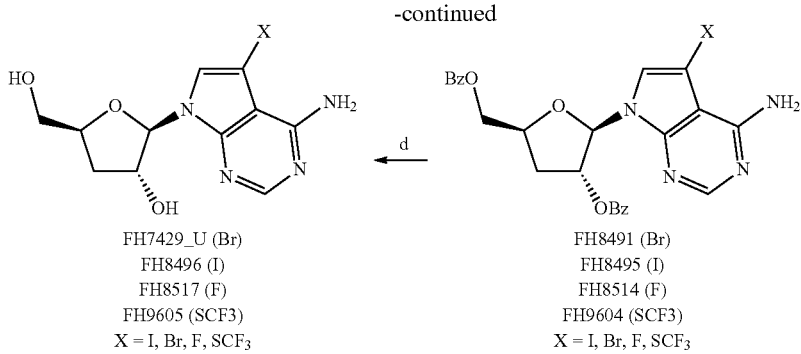

FH7429_U (Br)
FH8496 (I)
FH8517 (F)
FH9605 (SCF3)
X = I, Br, F, SCF3

FH8491 (Br)
FH8495 (I)
FH8514 (F)
FH9604 (SCF3)
X = I, Br, F, SCF3

Reagents and conditions: a) BSA, Heterocycle, TMSOTf, MeCN, 80° C., 1 H; b) NaN3, DMF, 65° C.; c) 1. PMe3 (1M in THF)/THF, 2. aq. HOAc (1M), MeCN, 65° C; d) NaOMe 0.2M, MeOH; e) NH3 7N in MeOH, 130° C., overnight.

Glycosylation of appropriate heterocycles with FH8484, furnished their corresponding nucleoside analogs (Scheme A4). Correct stereo-(β) and regio-(N7) isomer was verified by 2D NOESY and gHMBC experiments, respectively. Glycosylation reactions were performed under conditions as described. (Seela & Ming, 2007) Deprotection and subsequent amination with NH3/MeOH at 130° C. (for Bromo analog FH8487 only) gave FH7429_U. Nucleoside analogs FH8496, FH8517 and FH9605 were prepared by nucleophilic aromatic substitution with NaN3, followed by Staudinger reaction and iminophosphorane hydrolysis and final deprotection with NaOMe/MeOH.

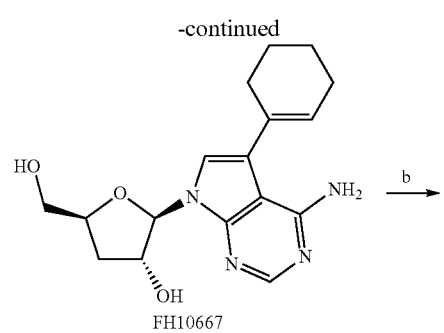

FH10667

Scheme A5

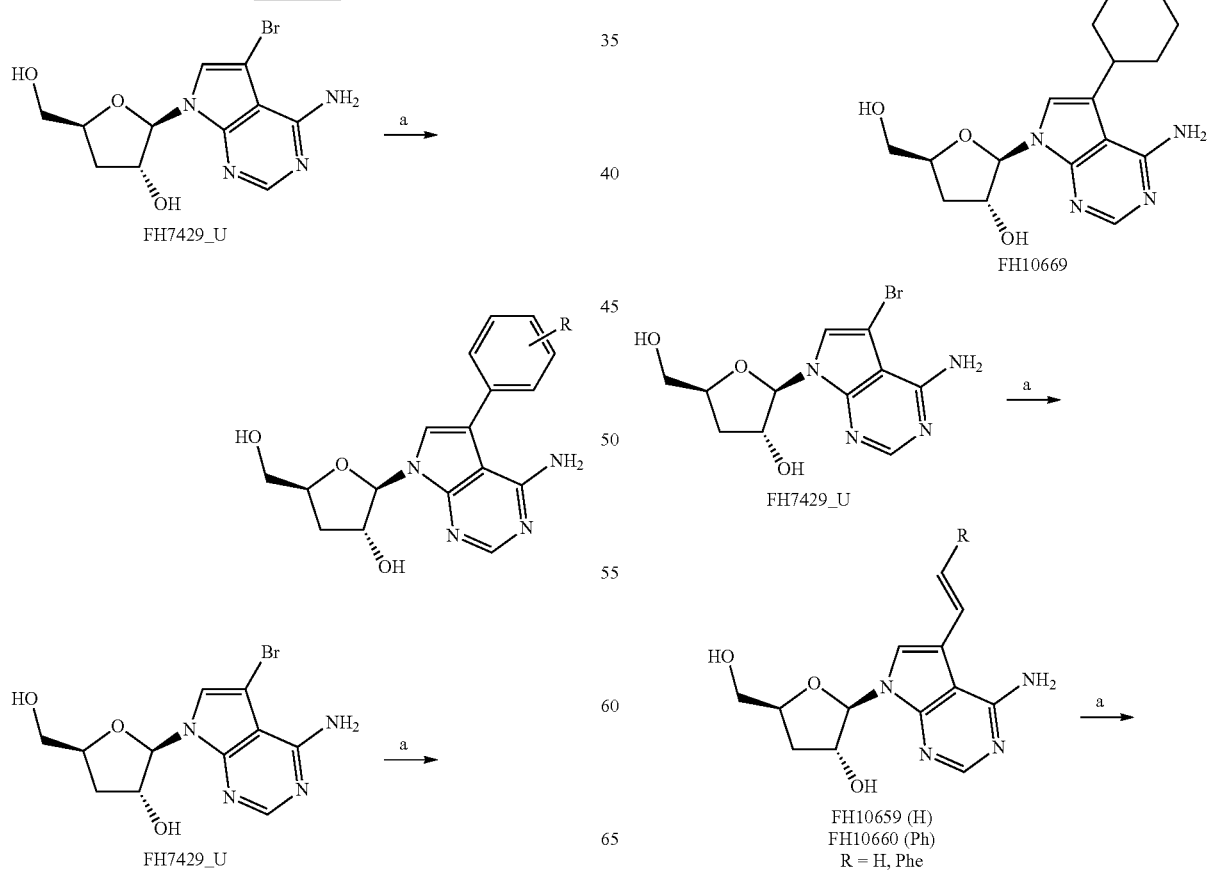

FH7429_U

FH10669

FH7429_U

FH7429_U

FH10659 (H)
FH10660 (Ph)
R = H, Phe

37
-continued
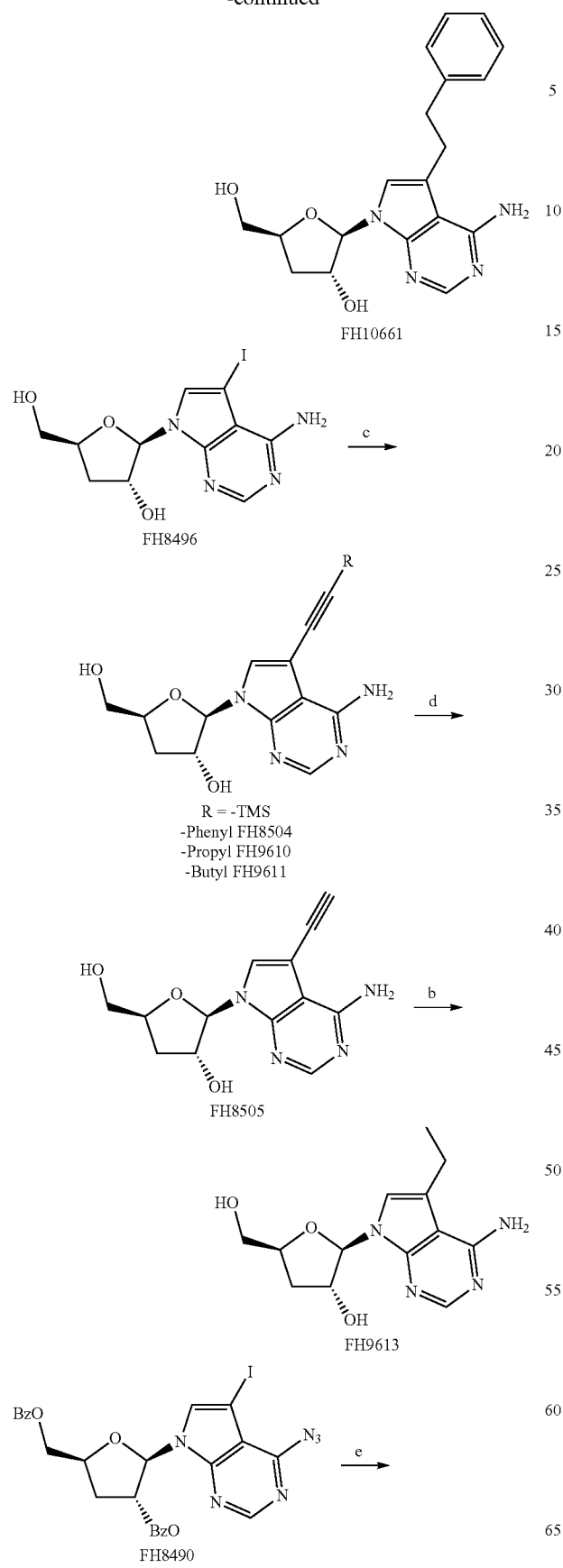
38
-continued
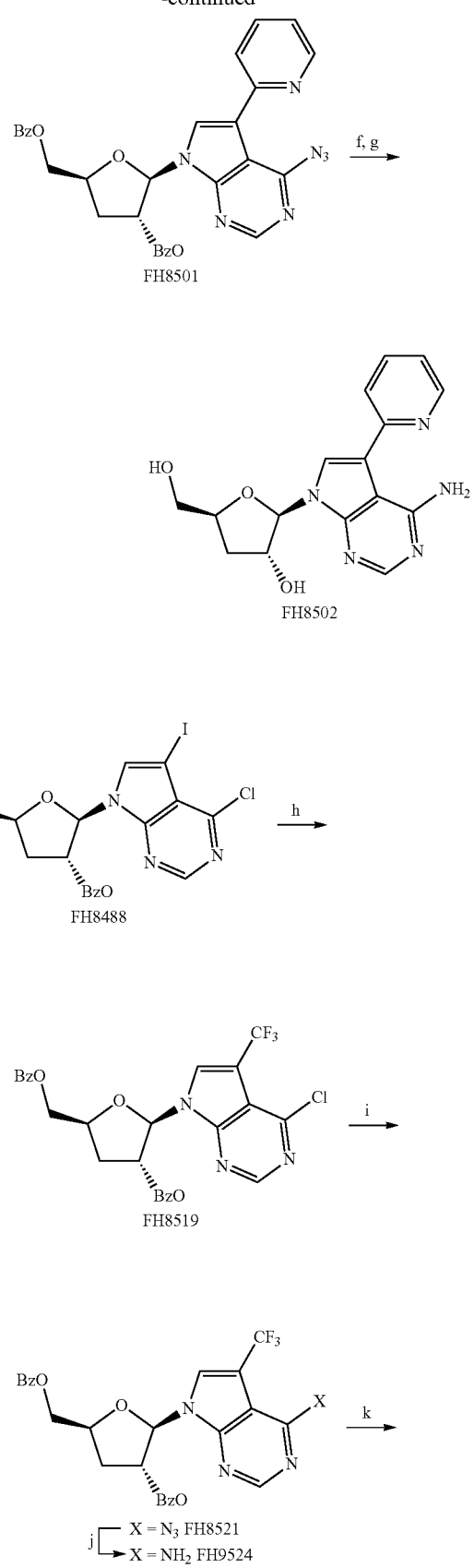

-continued

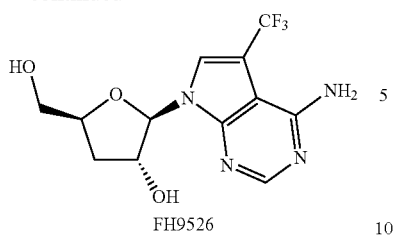

FH9526

Reagents and conditions: a) Aryl-boronic acid/R-vinylboronic acid/vinlyBF₃K, Pd(OAc)₂, Na₂CO₃ (Cs₂CO₃ for FH10667), TPPTS, MeCN/water (1:2), 100° C., 1-3H; b) Pd/C, H₂ (balloon), EtOH, 2-8 H; c) R—≡≡, Pd(Ph₃P)₂Cl₂, Cu(+1)I, Et₃N, DMF, overnight; d) K₂CO₃, MeOH, 3H; e) 1. iPrMgCl•LiCl (1.3M in THF), THF, -65° C.; 2. ZnCl₂ (0.5M in THF), -65° C. to rt, 30 min; 3. Pyridine-Br, Pd₂(dba)₃, RuPhos, THF, 60° C., overnight; f) 1. PMe₃ (1M in THF)/THF, 2. aq. HOAc (1M), MeCN, 65° C.; g) NaOMe 0.2M, MeOH; h) TMSCF₃, KF, Cu(+1)I, 1,10-Phenanthroline, B(OMe)₃, DMSO, 60° C., overnight; i) NaN₃, DMF, 65° C.; j) 1. PMe₃ (1M in THF)/THF, 2. aq. HOAc (1M), MeCN, 65° C.; k) NaOMe 0.2M, MeOH.

Synthesis of (substituted)aryl analogs was accomplished via an aqueous Suzuki reaction employing the nucleoside bromide FH7429_U, under conditions reported previously (Scheme A5).(Bourderioux et al., 2011) An overview of 3'-deoxy C-7 phenyl analogues analogs can be found below:

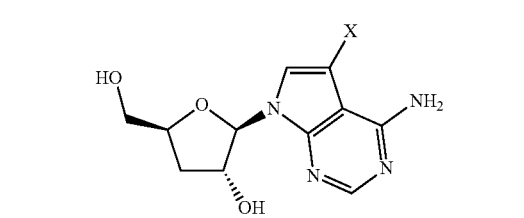

X =

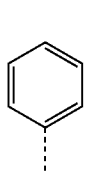 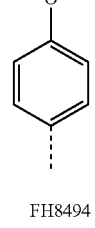 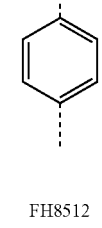

FH8480     FH8494     FH8512

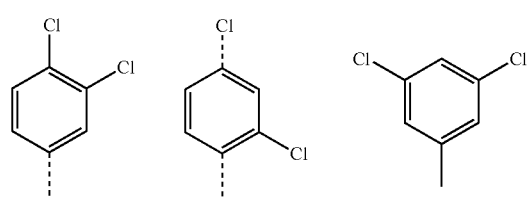

FH8513     FH9581     FH10642

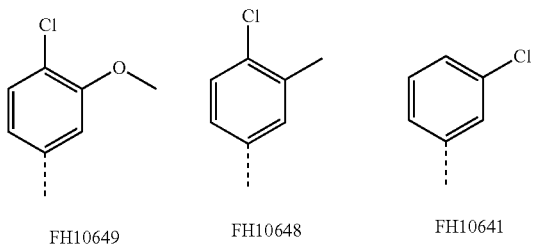

FH10649     FH10648     FH10641

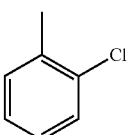 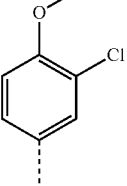 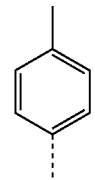

FH10644     FH10645     FH8481

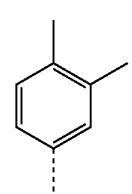 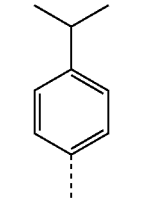 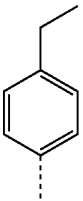

FH10653     FH9574     FH10647

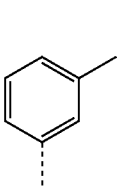 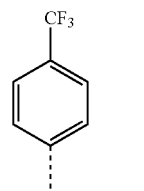 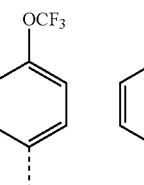 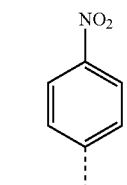

FH10639    FH9576    FH9577    FH9582

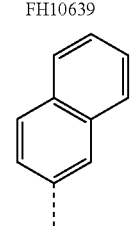 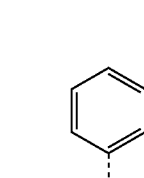 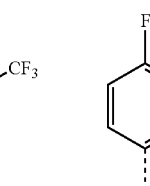

FH9575     FH10640     FH10680

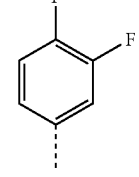 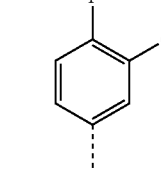 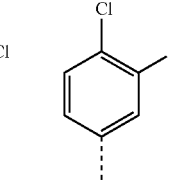

FH10682     FH10681     FH10683

Cyclohexenyl analog FH10667 was prepared analogously, except for the use of Cs₂CO₃ as the base instead of Na₂CO₃. Catalytic hydrogenation with Pd/C furnished cyclohexyl derivative FH10669. Ethenyl-substituted analogs were prepared in the same fashion. Sonogashira reaction (Bourderioux et al., 2011) with the appropriate terminal alkynes gave rise to FH8504, FH9610, FH9611 and FH8505 (after alkaline hydrolysis). 2-pyridyl derivative FH8502 was prepared, employing the conditions, described in detail for TH1008 (see below Section B). Introduction of a CF₃-substituent on derivative FH8488, employed the Ruppert-Prakash reagent under copper catalysis. (Gonda et al., 2014) Derivatization utilizing the same sequence as mentioned above, furnished FH9526.

8-Substituted Analogues

Scheme A6

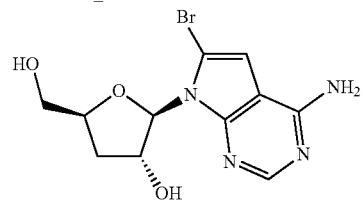

Reagents and conditions: NBS, KOAc, DMF, 10 min.

Bromination of FH7429_D under buffered conditions (KOAc) gave rise to the C-8 (C-6) bromo isomer FH10622, exclusively, in line with literature findings.

Pyrrolo[2,3-b]Pyridine Analogues

Scheme A7

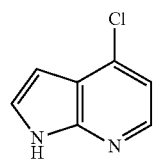

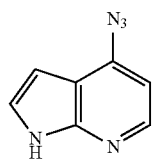

FH6353

FH9545

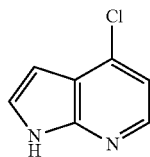

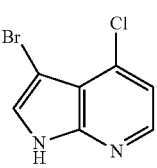

FH5295

Reagents and conditions: a) NaN$_3$, NH$_4$Cl, DMF, 110° C., 6H; b) NBS, DMF, overnight.

Scheme A8

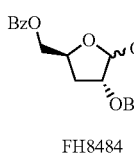 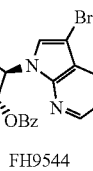 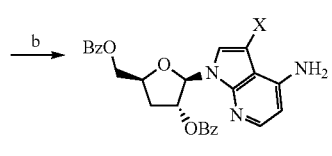

FH8484        FH9544

(X = Br) FH9548
(X = H)

FH9549 (Br)
FH9550 (H)

X = H, Br

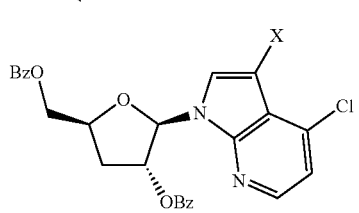 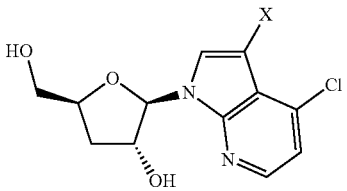

(X = Br) FH9538
(X = H)

X = H, Br

FH9540 (Br)
FH9541 (H)

X = H, Br

Reagents and conditions; a) BSA, Heterocycle, TMSOTf, MeCN, 80° C., 1 H; b) 1. PMe$_3$ (1M in THF) / THF, 2. aq. HOAc (1M), MeCN, 65° C.; c) Pd/C, H$_2$ (balloon), aq. NaOAc, EtOH; d) NaOMe 0.2M, MeOH.

Glycosylation of pyrrolo[2,3-b]pyridine analogs FH9545 and FH5295 with glycosyl donor FH8484 furnished the corresponding nucleosides, of which both stereo-(β) and regio-isomer (N1) was confirmed by 2D-NOESY and gHMBC (Scheme A8). Glycosylation conditions, employed for pyrrolo[2,3-d]pyrimidine derivatives were successfully translated to this class of heterocycle. Further derivatization (Staudinger reaction/iminophosphorane hydrolysis) and/or deprotection gave rise to the final nucleosides.

C-6 Substituted Derivatives

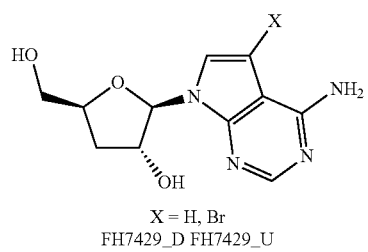

X = H, Br
FH7429_D FH7429_U a →

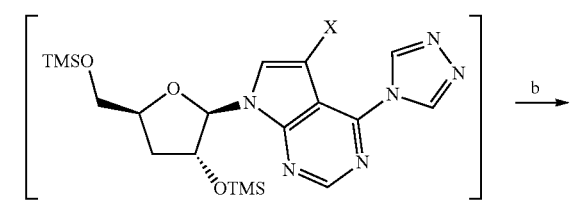

b →

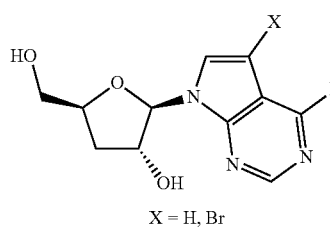

X = H, Br

R =
——NHMe   FH9554 FH8516
——NMe$_2$   FH9559 FH8522
——OH    FH9560
——OMe   FH9555
——SMe   FH9556

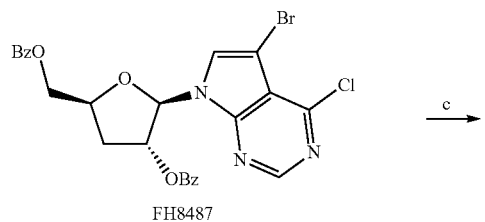

FH8487 c →

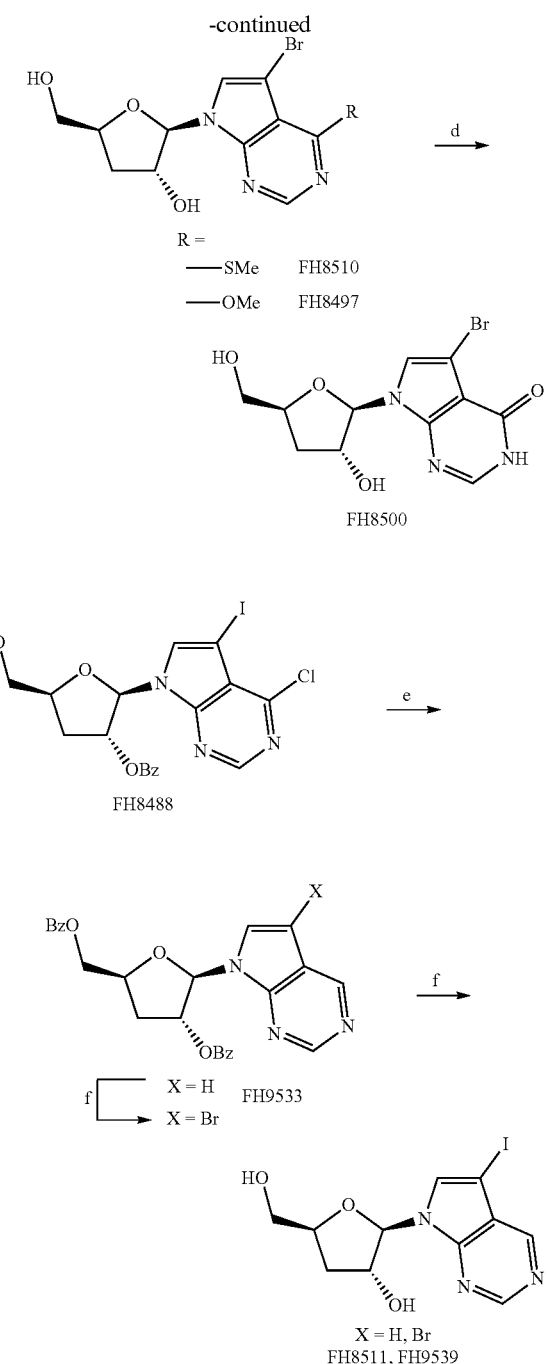

Scheme A9: Reagents and conditions: a) (E)-N'-((E)-(dimethylamino)methylene)-N,N-dimethylformohydrazonamide, TMSCl, pyridine, reflux; b) appropriate Nucleophile; c) NaSMe, EtOH, reflux//NaOMe, MeOH, 50° C.; d) NaI, TMSCl, MeCN, rt; e) Pd/C, H$_2$ (balloon), aq. NaOAc, EtOH; f) NBS, DMF, overnight; g) NaOMe 0.2M, MeOH.

Modification at the C-6 position of C-7 deaza purine nucleosides was accomplished using either one of two methods: direct nucleophilic displacement, or pre-derivatization of the C-6 exocyclic amino group into a 1,2,4-triazole (Miles et al. 1995) moiety and subsequent nucleophilic substitution (Scheme A9). Reductive dehalogenation with Pd/C and H$_2$ of FH8488 gave rise to FH9533, which was either directly deprotected to furnish FH8511 or halogenated with NBS and subsequently deprotected to give FH9539.

C-2' Ribofuranose Modification
Scheme A10
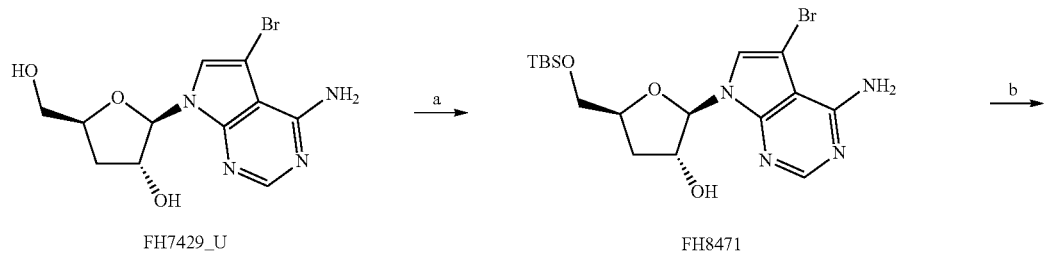
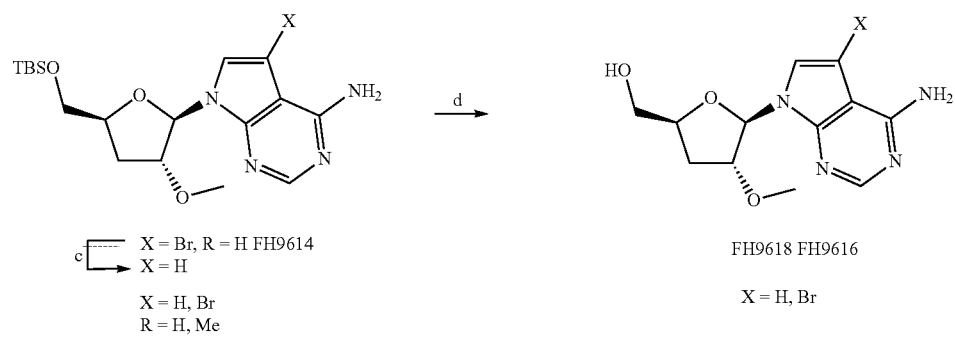
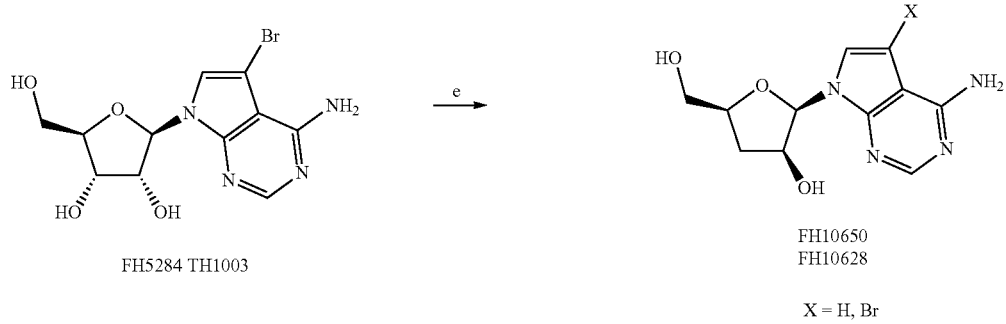
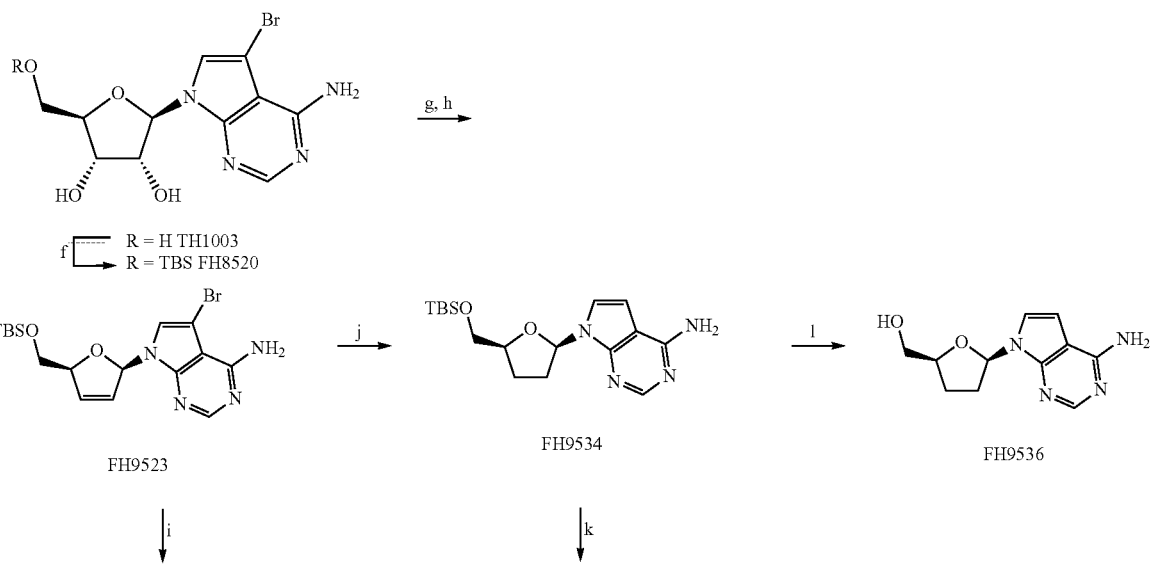

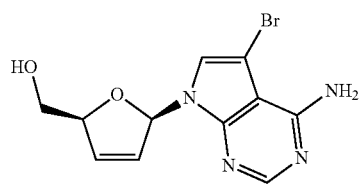

FH10632

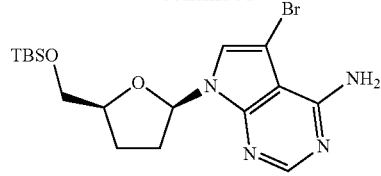

FH10635

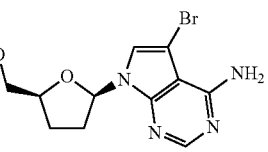

FH10638

Reagents and conditions: a) TBSCl, imidazole, DMF; b) NaH, MeI, THF, 0° C.; c) Pd/C, H$_2$ (balloon), aq. NaOAc, MeOH; d) NH$_4$F, MeOH, 50° C; e) 1. Pivaloylchloride, pyridine, -15° C.- 0° C.; 2. MsCl; 3. NaOMe, NaBH$_4$, MeOH, overnight; f) TBSCl, imidazole, DMF; g) TCDI, 1,2-DCE, reflux; h) P(OEt)$_3$, 160° C.; i) NH$_4$F, MeOH, 50° C.; j) Pd/C, H$_2$ (balloon), aq. NaOAc, EtOH; k) NBS, DMF; l) NH$_4$F, MeOH, 50° C.

Selective monosilylation of FH7429_U, followed by alkylation with MeI furnished derivative FH9614 in modest yield, due to overalkylation. Direct deprotection or dehalogenation followed by deprotection gave rise to final compounds FH9616 and FH9618, respectively. Arabino-nucleosides FH10650 and FH10628 were prepared, employing a three step, one-pot reaction, employing conditions described in literature, (Kawana et al. 1989) with the key step being a [1,2]-hydride shift and subsequent reduction, which has a clear advantage over the alternative, employing the 3'-tosylate and Li(Et)$_3$BH. Dideoxynucleosides were prepared in a similar way as described, employing a Corey-Winter olefination reaction as the key step.

C-4' Ribofuranose Modification

Scheme A11

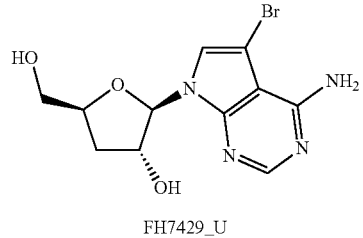

FH7429_U

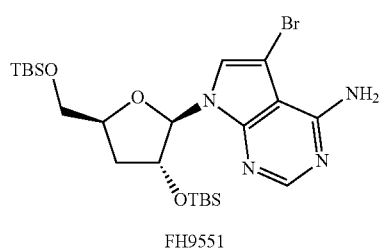

FH9551

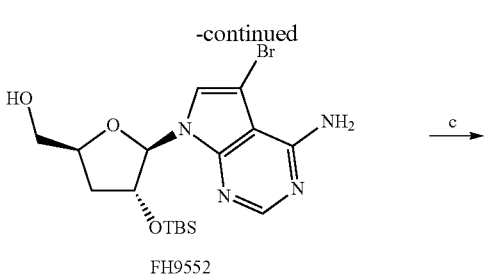

FH9552

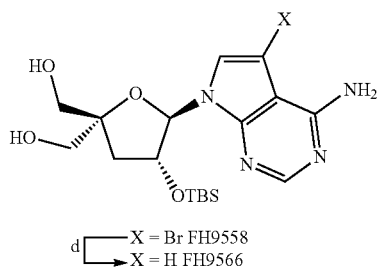

d ⎡ X = Br FH9558
  ⎣ X = H FH9566

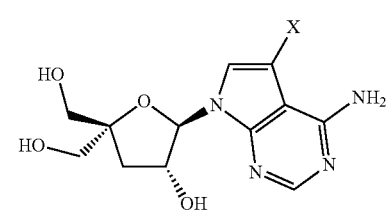

FH9569 FH9561

X = H, Br

Reagents and conditions: a) TBSCl, imidazole, DMF; b) TsOH, EA/MeOH, 5 H, 0° C.; c) 1. Dess-Martin periodinane, DCM, 0° C.-rt; 2. aq. CH$_2$O, NaOH; water/THF; 3. NaBH$_4$; d) Pd/C, H$_2$ (balloon), aq. NaOAc, EtOH; e) NH$_4$F, MeOH, 50° C.

FH7429_U was bis-silylated and subsequently the 5'-silyl group was selectively removed under acidic conditions. Oxidation to the corresponding aldehyde and direct aldol reaction with aq. formaldehyde, followed by NaBH$_4$ reduction furnished the corresponding 4'-CH$_2$OH derivative in modest yield. Final deprotection or dehalogenation followed by deprotection gave rise to the nucleoside derivatives FH9569 and FH9561.

49
C-5' Ribofuranose Modification
Scheme A12
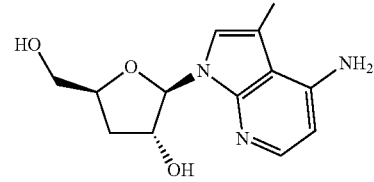
FH7429_U
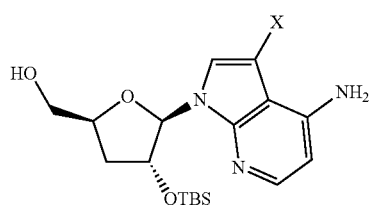
X = Br FH9552
X = H FH9594
X = H, Br
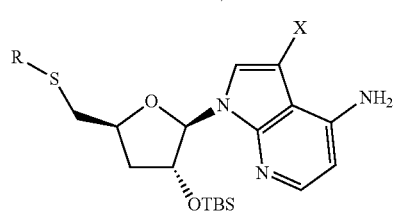
-Me  FH9595 FH9586
-Et   FH9585
-EtOH FH9596 FH9586
X = H, Br
R = Me, Et, EtOH
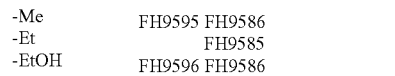
-Me  FH9600 FH9527
-Et   FH9590
-EtOH FH9601 FH9591
X = H, Br
R = Me, Et, EtOH
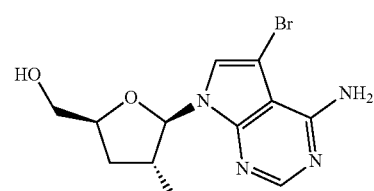
FH9552
50
-continued
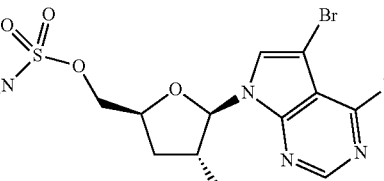
FH9589
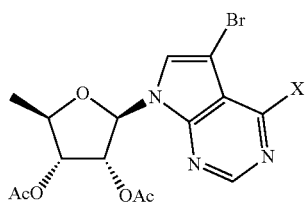
FH9608
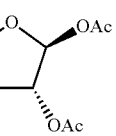
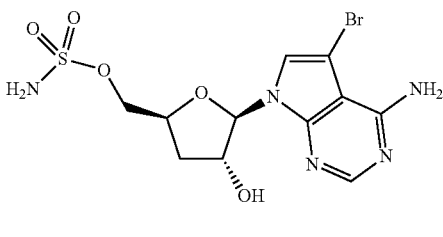
X = Cl  FH8476
X = N$_3$ FH8479
X = NH$_2$ FH8482
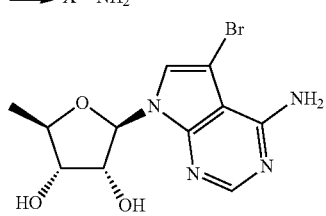
X = Br FH8485
X = H  FH8498
X = H, Br
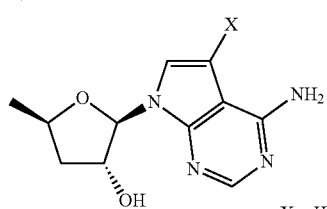
FH8499 FH8492

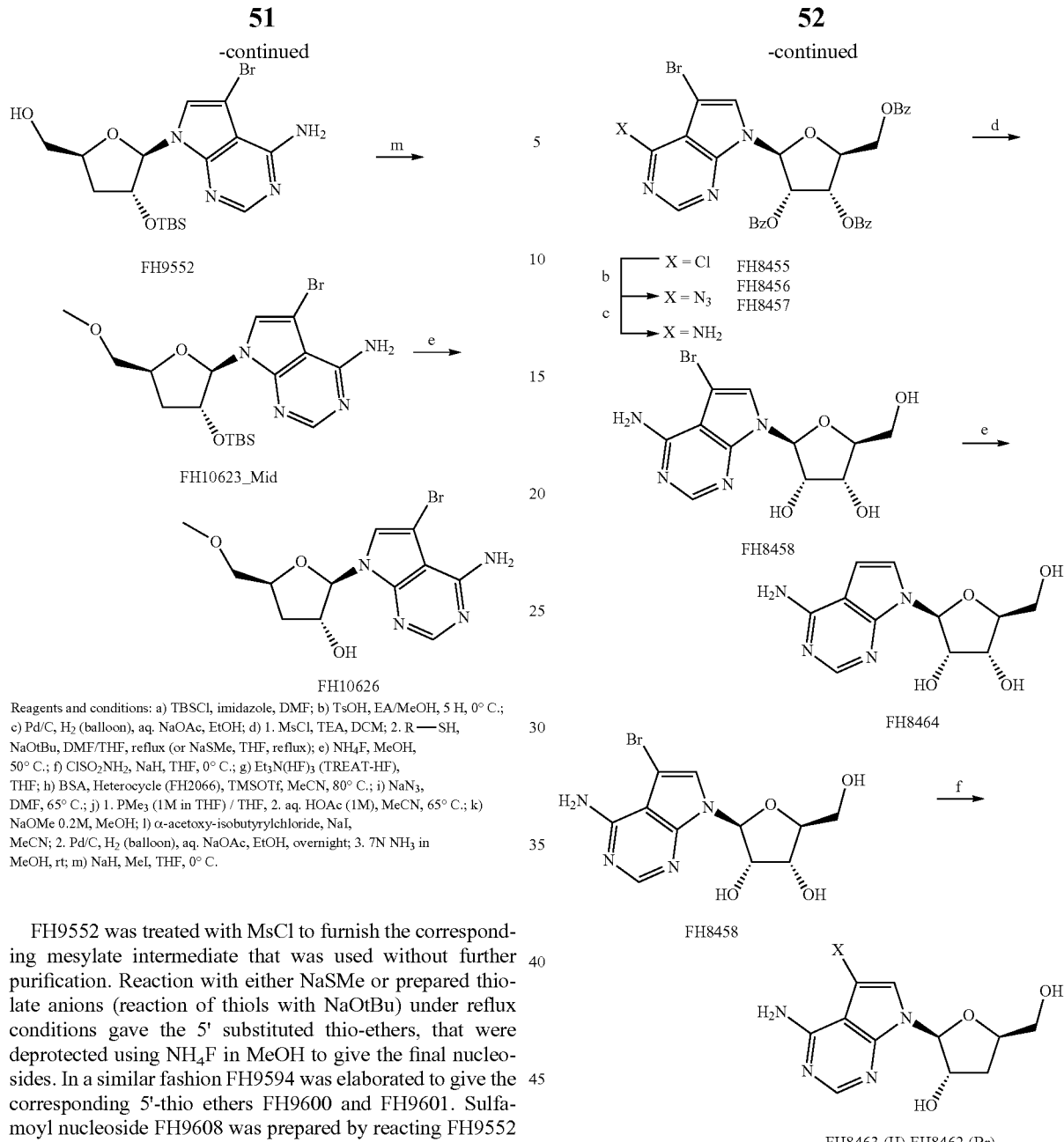

FH9552 was treated with MsCl to furnish the corresponding mesylate intermediate that was used without further purification. Reaction with either NaSMe or prepared thiolate anions (reaction of thiols with NaOtBu) under reflux conditions gave the 5' substituted thio-ethers, that were deprotected using $NH_4F$ in MeOH to give the final nucleosides. In a similar fashion FH9594 was elaborated to give the corresponding 5'-thio ethers FH9600 and FH9601. Sulfamoyl nucleoside FH9608 was prepared by reacting FH9552 with prepared sulfamoylchloride, and subsequent deprotection employing $Et_3N·3HF$. 5'-deoxy analogs were prepared by glycosylation with the commercially available glycosyl donor 5'-deoxy-1,2,3-O-acetyl-p-o-ribofuranose. 5'-methylation was achieved by reaction of FH9552 with MeI and subsequent deprotection to furnish FH10626.

L-Nucleosides

Scheme A13

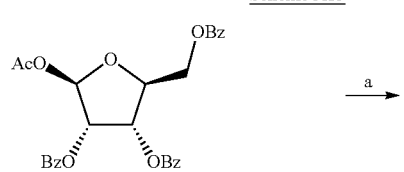

Synthesis of L-nucleosides employed the same conditions as described for their D-counterparts.

A2. Compound Synthesis

3'-Deoxyribofuranose Compounds

All reagents and solvents were obtained from standard commercial sources and were of analytical grade. Unless otherwise specified, they were used as received. All moisture sensitive reactions were carried out under argon atmosphere. Reactions were carried out at ambient temperature, unless otherwise indicated. Analytical TLC was performed on Machery-Nagel® precoated F254 aluminum plates and were visualized by UV followed by staining with basic aq. KMnat, Cerium-Molybdate, or sulfuric acid-anisaldehyde spray. Column chromatography was performed using Davisil® (40-63 μm) or on a Reverleris X2 (Grace/Büchi) automated Flash unit employing pre-packed silica columns. Exact mass measurements were performed on a Waters LCT Premier XE™ Time of Flight (ToF) mass spectrometer equipped with a standard electrospray (ESI) and modular Lockspray™ interface. Samples were infused in a MeCN/water (1:1)+0.1% formic acid mixture at 100 μL/min. NMR spectra were recorded on a Varian Mercury 300 MHz spectrometer. Chemical shifts (δ) are given in ppm and spectra are referenced to the residual solvent peak. Coupling constants are given in Hz. In $^{19}$F-NMR, signals were referenced to $CDCl_3$ or DMSO-$d_6$ lock resonance frequency according to IUPAC referencing with $CFCl_3$ set to 0 ppm. Melting points were determined on a Büchi-545 apparatus, and are uncorrected. Purity was assessed by means of analytical LC-MS employing either (1) Waters AutoPurification system (equipped with ACQUITY QDa (mass; 100-1000 amu)) and 2998 Photodiode Array (220-400 nm)) using a Waters Cortecs® C18 (2.7 μm 100×4.6 mm) column and a gradient system of HCOOH in $H_2O$ (0.05%, v/v)/MeCN at a flow rate of 1.44 mL/min, 100:00 to 00:100 in 6.5 minutes.

(2) Waters AutoPurification system (equipped with ACQUITY QDa (mass; 100-1000 amu)) and 2998 Photodiode Array (220-400 nm)) using a Waters Cortecs® C18 (2.7 μm 100×4.6 mm) column and a gradient system of HCOOH in $H_2O$ (0.2%, v/v)/MeCN at a flow rate of 1.44 mL/min, 95:05 to 00:100 in 6.5 minutes.

All obtained final compounds had purity >95%, as assayed by analytical HPLC (UV); unless otherwise indicated.

Carbohydrate Building Block Synthesis 3-deoxy-1,2:5,6-di-O-isopropylidene-α-D-ribo-hexofuranose (FH8473)

To a solution of diacetone glucose (26.0 g, 100 mmol), under nitrogen flow, was added imidazole (0.1 g, catalytic) and NaH (60% dispersion in mineral oil, 6.0 g, 150 mmol, 1.5 eq.) portionwise over a 5-10 min period. The resulting mixture was stirred for 20 min after which $CS_2$ (18.0 mL, 300 mmol, 3 eq.) was added in one portion. After stirring for 30 min, MeI (11.21 mL, 180 mmol, 1.8 eq.) was added in one portion. The reaction mixture was further stirred for 20 min, after which TLC indicated full conversion of the starting material. Next, 5 mL of acetic acid was added to quench residual NaH. The mixture was afterwards filtered, and the filtrate evaporated till a semi-solid. Diethylether and water were added, layers separated, and the diethylether layer sequentially washed with sat. aq. $NaHCO_3$ solution (2×), water (1×) and brine (1×). The organic layer was dried over $Na_2SO_4$, evaporated and used without further purification.

The residue was dissolved in anhydrous toluene (1000 mL, 10 mL/mmol), and to this was added AIBN (1.97 g, 12 mmol, 0.12 eq.), followed by $(nBu)_3SnH$ (32 mL, 120 mmol, 1.2 eq.) and the resulting solution refluxed till TLC analysis showed full conversion (~3 to 5H). Next, the mixture was cooled to room temperature and the solvent removed in vacuum and the residue partitioned between MeCN/hexanes. The MeCN layer was additionally washed with hexanes (2×) and then evaporated. Purification by column chromatography (gradient: 5→15% EA/PET), gave 15 g (61 mmol) of FH8473 as a yellowish oil (Yield=61%). $^1$H NMR (300 MHz, $CDCl_3$) δ: 1.32 (s, 3H, $CH_3$), 1.36 (s, 3H, $CH_3$), 1.43 (s, 3H, $CH_3$), 1.51 (s, 3H, $CH_3$), 1.72-1.81 (m, 1H, H-3'), 2.19 (dd, J=13.5, 4.2 Hz, 1H, H-3), 3.80-3.86 (m, 1H), 4.07-4.20 (m, 3H), 4.75 (t, J=4.2 Hz, 1H, H-2), 5.82 (d, J=3.6 Hz, 1H, H-1). HRMS (ESI): no corresponding signal detected.

1,2-O-Isopropylidene-3-Deoxy-α-D-Ribofuranose FH8474

FH8473 (15 g, 61 mmol, 1 eq.) was dissolved in a mixture of HOAc/water (80/20) (185 mL, 3 mL/mmol), and stirred overnight. The resulting mixture was next evaporated till near-dryness and co-evaporated with water 2×. The resulting oil was dissolved in water (150 mL, 10 mL/g SM), cooled to 0° C. in an ice bath and $NaIO_4$ (14.4 g, 67.1 mmol, 1.1 eq.) was added in portionwise. Following complete addition of $NaNIO_4$, the cooling was continued for approximately 10 min, and the ice baht was removed. after 30 min, TLC showed full conversion of the starting material. Next, EtOH (300 mL, 20 mL/g SM) was added and cooled in an ice bath. The resulting suspension was filtered and the filtrate cooled to 0° C. in an ice bath. To this solution was added $NaBH_4$ (2.31 g, 61 mmol, 1 eq.) portionwise. After complete addition, the ice bath was removed and stirring continued till full conversion of the intermediate aldehyde was observed by TLC (~1-2 h). Next, solid $NH_4Cl$ (16.32 g, 305 mmol, 5 eq.) was added. The resulting mixture was evaporated till near-dryness, after which EA and water were added. Layers were separated, and the organic layer washed once with sat. aq. $NaHCO_3$/sat. aq. $Na_2S_2O_3$ solution (1/1). The organic layer was separated, dried over $Na_2SO_4$, filtered and evaporated till dryness. Purification by column chromatography 25→75% EA/PET gave FH8474 as an oil that solidified upon standing (5.3 g, 30.5 mmol) in 50% yield. $^1$H NMR (300 MHz, $CDCl_3$) δ: 1.32 (s, 3H, $CH_3$), 1.51 (s, 3H, $CH_3$), 1.80 (br. s, 1H, OH), 1.85 (dd, J=13.2, 4.5 Hz, 1H, H-3'), 2.00 (dd, J=13.5, 4.5 Hz, 1H, H-3), 3.56 (dd, J=12.3, 4.5 Hz, 1H, H-5'), 3.89 (dd, J=12.3, 3.0 Hz, 1H, H-5), 4.31-4.38 (m, 1H, H-4), 4.76 (t, J=4.2 Hz, 1H, H-2), 5.82 (d, J=3.6 Hz, 1H, H-1). HRMS (ESI): no corresponding signal detected.

1,2-O-Isopropylidene-3-Deoxy-5-O-Benzoyl-α-D-Ribofuranose FH8475

Method 1

FH8474 (4.67 g, 26.8 mmol, 1 eq.) was dissolved in DCM (130 mL, 5 mL/mmol) under argon. To the stirring solution was added DMAP (cat.), $Et_3N$ (6.4 mL, 45.56 mmol, 1.7 eq.), after which the mixture was cooled to 0° C. in an ice bath. Next, BzCl (4.4 mL, 37.53 mmol, 1.4 eq.) was added slowly. After complete addition, the ice bath was removed and the mixture stirred till full conversion was observed by TLC (~2H). Next, water (5 mL) was added, stirred for 5 min, after which sat. aq. $NaHCO_3$ solution was added. The layers were separated and the organic layer washed once more with sat. aq. $NaHCO_3$ solution. The organic layer was dried over $Na_2SO_4$, filtered and evaporated till dryness. Purification by column chromatography 5→25% EA/PET gave FH8475 (7.0 g, 25.11 mmol) as a slightly yellow oil, in 94% yield.

Method 2:

MS1027 (15 g, 50 mmol, 1 eq.) was dissolved in 1,2-dichloroethane (260 mL, 5.2 mL/mmol SM). Next, TCDI was added (17 g, 95 mmol, 1.9 eq.). The resulting solution was refluxed for 2H, after which TLC analysis showed full conversion of the staring material. Next, water and DCM were added, and the layers separated. The water layer was washed with DCM two more times. Organic layers were combined, dried over Na$_2$SO$_4$, filtered and evaporated till dryness. Purification by column chromatography 10% EA/DCM gave 18 g of intermediate that was directly used. The intermediate (18 g, 46 mmol) was dissolved in toluene 1.25 L (27 mL/mmol SM). Next, AIBN (0.23 g, 1.38 mmol, 0.03 eq.) and (nBu)$_3$SnH (21 mL, 78.2 mmol, 1.7 eq.) were added. The resulting mixture was reflux, until TLC showed full conversion of the starting material (2-4H). After cooling to ambient temperature, the solvent was evaporated, and the resulting oil partitioned between MeCN/hexanes. The MeCN—layer was washed twice more with hexanes. Evaporation of the MeCN and purification by column chromatography 1→10% EA/PET gave FH8475 (7.5 g, 27 mmol) as a colourless oil, in 54% yield over two steps. $^1$H NMR (300 MHz, CDCl$_3$) δ: 1.34 (s, 3H, CH$_3$), 1.54 (s, 3H, CH$_3$), 1.76 (ddd, J=13.2, 10.5, 4.8 Hz, 1H, H-3'), 2.19 (dd, J=13.5, 4.2 Hz, 1H, H-3), 4.34-4.40 (m, 1H, H-5'), 4.61-4.51 (m, 2H, H-4, H-5), 4.79 (t, J=4.5 Hz, 1H, H-2), 5.88 (d, J=3.6 Hz, 1H, H-1), 7.41-7.47 (m, 2H, OBz (meta)), 7.54-7.60 (m, 1H, Bz (para)), 8.04-8.08 (m, 2H, OBz (ortho)). HRMS (ESI): calculated for C$_{15}$H$_{19}$O$_5$ ([M+H]$^+$): 279.1227, found: 279.1227.

1-O-Methyl-2,5-Di-O-Benzoyl-3-Deoxy-α/β-D-Ribofuranose FH8478

FH8475 (7 g, 25.11 mmol, 1 eq.) was dissolved in MeOH (250 mL, 10.8 mL/mmol SM). To the resulting solution was added water (12.6 mL, 0.5 mL/mmol SM), and cHCl (67.5 mL, 2.7 mL/mmol SM). The resulting solution was heated to 55° C. for ~30 min after which TLC showed full conversion of the starting material. The mixture was cooled to ambient temperature, and Et$_3$N (107 mL, 4.25 mL/mmol SM) was added to neutralize. The pH was checked to be ~7. The resulting solution was evaporated till near-dryness, after which it was partitioned between water and EA. Layers were separated and the water layer extracted once with EA. The organic layers were combined, dried over Na$_2$SO$_4$, filtered and evaporated till dryness. The resulting oil was dissolved in DCM (100 mL, 4 mL/mmol SM). Next, DMAP (cat.) and Et$_3$N (6.3 mL, 1.8 eq.) were added. The resulting solution was cooled to 0° C. in an ice bath, and BzCl (4.4 mL, 37.67 mmol, 1.5 eq.) added. Next, the mixture was allowed to come to room temperature. After TLC showed full conversion (~2H), water (5 mL) was added, stirred for 5 min, after which sat. aq. NaHCO$_3$ solution was added. The layers were separated and the organic layer washed once more with sat. aq. NaHCO$_3$ solution. The organic layer was dried over Na$_2$SO$_4$, filtered and evaporated till dryness. Purification by column chromatography 0→20% EA/PET, gave FH8478 (7.6 g, 21.3 mmol) as a colourless oil in 85% yield.

Some fractions contained only one anomer, which were collected separately once, for analytical purposes.
Spectral Data for the β-Anomer (FH8478-UP):
$^1$H NMR (300 MHz, CDCl$_3$) δ: 2.24-2.40 (m, 2H, H-3, H-3'), 3.40 (s, 3H, OCH$_3$), 4.36 (dd, J=11.7, 6.3 Hz, 1H, H-5'), 4.51 (dd, J=11.7, 3.9 Hz, 1H, H-5), 4.73-4.82 (m, 1H, H-4), 5.08 (s, 1H, H-1), 5.41 (dd, J=4.5, 1.5 Hz, 1H, H-2), 7.42-7.48 (m, 4H, OBz), 7.55-7.61 (m, 2H, OBz), 8.02-8.06 (m, 2H, OBz), 8.08-8.13 (m, 2H, OBz). $^{13}$C NMR (75 MHz, CDCl$_3$) δ: 32.16 (C-3), 54.83 (OCH$_3$), 67.34 (C-5), 77.57 (C-4), 78.32 (C-2), 107.17 (C-1), 128.53, 128.58, 129.77, 129.87, 130.09, 133.25, 133.48, 165.85 (C=O), 166.56 (C=O). HRMS (ESI): calculated for C$_{19}$H$_{17}$O$_5$ ([M-OAc]$^+$): 325.1071, found: 325.1058.

Spectral Data for the α-Anomer (FH8478-DOWN):
$^1$H NMR (300 MHz, CDCl$_3$) δ: 2.33-2.50 (m, 2H, H-3, H-3'), 3.42 (s, 3H, OCH$_3$), 4.38 (dd, J=11.7, 4.8 Hz, 1H, H-5'), 4.50 (dd, J=12.0, 3.6 Hz, 1H, H-5), 4.60-4.67 (m, 1H, H-4), 5.24-5.32 (m, 2H, H-1, H-2), 7.42-7.50 (m, 4H, OBz), 7.55-7.61 (m, 2H, OBz), 8.06-8.10 (m, 4H, OBz). $^{13}$C NMR (75 MHz, CDCl$_3$) δ: 30.33 (C-3), 55.53 (OCH$_3$), 66.51 (C-5), 73.50 (C-2), 73.60 (C-4), 102.09 (C-1), 128.54, 128.64, 129.86, 129.95, 133.35, 166.36 (C=O), 166.59 (C=O). HRMS (ESI): calculated for C$_{19}$H$_{17}$O$_5$ ([M-OAc]$^+$): 325.1071, found: 325.1069.

1-O-Acetyl-2,5-Di-O-Benzoyl-3-Deoxy-α/β-D-Ribofuranose FH8484

FH8478 (7.5 g, 21.0 mmol, 1 eq.) was dissolved in glacial AcOH (60 mL, 3 mL/mmol SM). Next, Ac$_2$O (7.9 mL, 84 mmol, 4.4 eq.) was added and the mixture cooled in an ice bath. As soon as solidification occurs, c.H$_2$SO$_4$ (4.0 mL, 79.8 mmol, 3.8 eq.) was added slowly. After complete addition, the ice bath was removed and the mixture stirred until TLC showed full conversion of the starting material (~30 min-1H). Then the mixture was transferred to a separatory funnel containing DCM. Slowly, an aq. sat. solution of Na$_2$CO$_3$ was added to neutralize the excess acid. After neutralization, the layers were separated, the water layer extracted once more with DCM. The organic layers were combined, dried over Na$_2$SO$_4$, filtered and evaporated till dryness. Purification by column chromatography 0→15% EA/PET, gave FH8484 (7.85 g, 20 mmol) as a colourless oil, in 97% yield. $^1$H NMR (300 MHz, CDCl$_3$) δ: 2.01 (s, 3H, OAc-β), 2.07 (s, 3H, OAc-α), 3.36-3.40 (m, 2H, H-3-γ, H-3'-β), 2.41-2.54 (m, 2H, H-3-α, H-3'-α), 4.38 (dd, J=12.0, 5.4 Hz, 1H, H-5'-β/H-5'-α), 4.51 (dd, J=12.0, 3.3 Hz, 1H, H-5-α), 4.59 (dd, J=12.0, 3.9 Hz, 1H, H-5-β), 4.78-4.86 (m, 1H, H-4-β/H-4-α), 5.49 (dd, J=3.9, 2.4 Hz, 1H, H-2-β), 5.53 (td, J=8.4, 4.5 Hz, 1H, H-2-α), 6.37 (s, 1H, H-1-β), 6.58 (d, J=4.5 Hz, 1H, H-1-α), 7.42-7.49 (m, 2H, OBz), 7.55-7.62 (m, 1H, OBz), 8.00-8.11 (m, 2H, OBz). Ratio (NMR-based): α/β=⅕. HRMS (ESI): calculated for C$_{19}$H$_{17}$O$_5$ ([M-OAc]$^+$): 325.1071, found: 325.1068.

C-7 Substituted Analogues

General Procedures
General Procedure 1 (Conversion of Ribo-Nucleoside into 3'-Deoxy Analogue)

NaI (10 eq.) was dissolved in anhydrous MeCN (10 mL/mmol SM), and stirred for 5 min under argon. Next, α-acetoxyisobutyrylchloride (3.5 eq.) was added, giving a white precipitate. The mixture was stirred vigorously for another 5-10 min, after which the appropriate ribonucleoside (1 eq.) was added in one portion. The resulting mixture was stirred for 1.5H after which TLC showed full conversion of SM. The mixture was poured in aq. sat. NaHCO$_3$/aq. sat. Na$_2$S$_2$O$_3$ solution. Next, CHCl$_3$ was added, and the layers separated. The water layer was extracted with CHCl$_3$ twice more. Organic layers were combined, dried over Na$_2$SO$_4$, filtered and evaporated. The resulting oil was dissolved in EtOH (7.5 mL/mmol SM) and 1 M aq. NaOAc solution (2.5 mL/mmol SM) was added. Next, the flask was purged with N2, after which a cat. amount of Pd/C was added. Next, the N$_2$-atmosphere was exchanged for H$_2$ (balloon; no bubbling) and the mixture stirred overnight. Next, the mixture was purged with N$_2$ to remover residual H$_2$-gas, and filtered over a pad of Celite®. The mixture was evaporated till dryness, and partitioned between EA and aq. sat. NaHCO$_3$/aq. sat. Na$_2$S$_2$O$_3$ solution. Layers were separated and the water layer extracted twice more with EA. Organic layers were combined, dried over $Na_2SO_4$, filtered and evaporated. The resulting oil was dissolved in 7N $NH_3$ in MeOH and stirred overnight. The solvent was removed, and the residue purified by column chromatography 0→15% MeOH/DCM.

General Procedure 2 Vorbrüggen Glycosylation

In a flame-dried two-neck round bottom flask under argon was added the appropriate heterocycle (1 eq.). Next, MeCN (7.5 mL/mmol SM) was added. To the stirring suspension was added BSA (1.1 eq.) in one portion. The resulting mixture was stirred at room temperature for ~10 min, after which the glycosyl donor (FH8484, 1.1 eq.) was added in one portion, immediately followed by TMSOTf (1.165 eq.). The resulting solution was stirred at ambient temperature for another 15 min, and then transferred to a pre-heated oil bath at 80° C. Heating was continued until full consumption of the glycosyl donor was observed by TLC (generally ~1H). Then, the mixture was cooled to ambient temperature. Next, EA was added and aq. sat. $NaHCO_3$. The layers were separated and the water layer extracted twice more with EA. Organic layers were combined, dried over $Na_2SO_4$, filtered and evaporated. The resulting oil was purified by column chromatography (generally isocratic with an eluent consisting of 12 to 20% EA/PET).

General Procedure 3 Nucleophilic Displacement with $NaN_3$

The appropriated nucleoside-CI (1 eq.) was dissolved in anhydrous DMF (10 mL/mmol SM). Next, $NaN_3$ (2.05 eq.) was added. The resulting mixture was heated in a pre-heated oil bath at 65° C. for 30 min. Next, the mixture was cooled to ambient temperature. Then, it was poured into half-saturated $NaHCO_3$ solution and EA (equal volumes). The layers were separated and the water layer extracted two more times with EA. The organic layers were combined, dried over $Na_2SO_4$, filtered and evaporated till dryness. The residue was purified by column chromatography (Generally a gradient of 10→35% EA/PET).

General Procedure 4 Staudinger Reduction and Iminophosphorane Hydrolysis

The appropriate azido-nucleoside (1 eq.) was dissolved in THF (10 mL/mmol). Then, $PMe_3$ solution (1 M in THF; 2 eq.) was added and the mixture stirred at ambient temperature until TLC analysis showed full conversion of starting material (generally 1H). Next, the solution was evaporated till dryness, and subsequently re-dissolved in MeCN (10 ml/mmol). To this solution was added a 1 M aq. HOAc solution (3.33 eq.), and the mixture heated in a pre-heated oil bath at 65° C. for 1H. Next, the mixture was cooled to ambient temperature and poured into sat. aq. $NaHCO_3$ solution. DCM was added, layers were separated and the water layer extracted two more times with DCM. The organic layers were combined, dried over $Na_2SO_4$, filtered and evaporated till dryness. Purification by column chromatography (generally gradient 30→75% EA/PET).

General Procedure 5 Sugar Deprotection—Ester Hydrolysis

The appropriate ester protected nucleoside (1 eq.) was dissolved in 0.2 M NaOMe/MeOH solution. The resulting mixture was stirred at ambient temperature until TLC showed full conversion of the starting material (typically 0.5-3H). Then, the mixture was neutralized by aq. 0.5 M HCl. Then, the mixture was evaporated till dryness and purified by column chromatography (1→15% MeOH/DCM).

General Procedure 6 Suzuki Coupling

FH7429_UP (1 eq.), boronic acid (1.5 eq.) or potassiumtrifluoroborate salt (1.5 eq.), $Na_2CO_3$ (9 eq.), $Pd(OAc)_2$ (0.05 eq.) and TPPTS (0.15 eq.) were added to a 10 mL round-bottom flask, equipped with a stir bar. Next, the flask was evacuated and refilled with argon. This procedure was repeated three times, in total. Next, degassed MeCN (2 mL/mmol SM) and $H_2O$ (4 mL/mmol SM) were added to the solids under argon. After 5 min of stirring, the mixture was heated to 100° C. in a pre-heated oil bath. When the starting material was fully consumed (usually 1-3 hours), the mixture was cooled to ambient temperature, and neutralized (pH ~7) with 0.5 M aq. HCl. The mixture was evaporated till dryness, resuspended in MeOH and evaporated (three times). Next, the mixture was adsorbed onto Celite® (from MeOH) and eluted over a short silica pad (~5 cm) with 20% MeOH/DCM. The liquid was evaporated in vacuo and purified by column chromatography (generally a gradient of 1→8% MeOH/DCM).

General Procedure 7 Sonogashira Coupling

FH8496 (1 eq.), $Cu^{+1}I$ (0.1 eq.), $Pd(Ph_3P)_2Cl_2$ (0.05 eq.) were added to a 10 mL round bottom flask, equipped with a stir bar. Next, the flask was evacuated and refilled with argon. This procedure was repeated three times, in total. Next, degassed DMF (4 mL/mmol SM) was added to the solids under argon. Next, degassed $Et_3N$ (0.40 mL/mmol SM) was added, followed by the corresponding alkyne (5 eq.). The resulting solution was stirred at ambient temperature overnight, after which it was evaporated till dryness. The resulting oil was dissolved in MeOH, pre-adsorbed onto Celite® and purified by column chromatography (generally a gradient of 1→8% MeOH/DCM).

General Procedure 8 Cyclization of Exocylic $NH_2$ into 1,2,4-Triazole Leaving Group To a 5-mL flame-dried round bottom flask, equipped with a stir bar, was added the appropriate nucleoside (1 eq.). Next, FH7442 (Garcia et al. 2008) (2 eq.) was added, followed by anhydrous pyridine (6 mL/mmol SM). After complete dissolution of the solids, TMSCI (1.91 eq.) was added and the mixture heated at 100° C. till full conversion of the starting material was observed (generally 24H for C-5 unsubstituted derivatives; 48H for C-5 halogenated derivatives). The mixture was cooled to ambient temperature and another portion of TMSCI (2 eq.) was added. After stirring for 15 min, the mixture was evaporated till dryness. Next, the residue was taken up in ice-cold DCM and successively washed with Brine/aq. sat. $NaHCO_3$ and twice Brine/aq. 1 M HCl. The organic layer was dried over $Na_2SO_4$, filtered and evaporated. The intermediate 1,2,4-triazol-4-yl nucleoside was directly used in nucleophilic displacement reactions without further purification.

General Procedure 9 Silyl Ether Deprotection

The appropriate nucleoside (1 eq.) was dissolved in MeOH (10-20 mL/mmol SM) and $NH_4F$ (20 eq.) was added.

The resulting solution was heated to 50° C. for 2 days, cooled to ambient temperature and DCM (20-40 mL) was added. The cloudy solution was filtered, and the filtrate evaporated till dryness. The residue was purified by column chromatography (generally 0→12% MeOH/DCM).

4-amino-5-bromo-N7-(3'-deoxy-β-D-ribofuranosyl)-pyrrolo[2,3-d]pyrimidine (FH7429_UP//FH7429_U)

Method 1:

According to general method 1, TH1003 (0.35 g, 1 mmol) was converted into FH7429_U (0.160 g, 0.49 mmol) in 49% yield as a white solid. Additionally, also FH7429_D was isolated (0.041 g, 0.164 mmol) in 16% yield.

Method 2:

FH7429_epox (0.15 g, 0.46 mmol, 1 eq.) was dissolved in anhydrous DMSO (11.5 mL, 25 mL/mmol SM) under argon. The solution was cooled in an ice bath. After the first appearance of solidification, LiEt$_3$BH (Superhydride®, 1 M in THF, 5.75 mL, 12.5 eq.) was added dropwise. After complete addition, the ice bath was removed and the remaining mixture stirred at ambient temperature overnight. Next, the reaction was carefully quenched by adding an aq. 0.5 M AcOH solution dropwise. After the gas evolution ceased, the mixture was evaporated till dryness and subjected to column chromatography (see method 1). FH7429_D (0.068 g, 0.207 mmol) was isolated in 45% yield.

Method 3:

FH8471 (0.5 g, 1.13 mmol) was dissolved in TFA/water (9/1; 9 mL, 8 mL/mmol SM) and stirred at ambient temperature till full conversion was observed (generally 30 min-1H). The resulting mixture was evaporated till dryness, co-evaporated with MeOH three times, and neutralized with 7N NH$_3$/MeOH, and evaporated again. Purification by column chromatography (see method 1) gave FH7429_D (0.22 g, 0.678 mmol) in 60% yield.

Method 4:

FH8487 (1.82 g, 3.3 mmol) was suspended in 7N NH$_3$/MeOH (100 mL) inside a stainless-steel pressure vessel. The vessel was carefully closed and heated to 130° C. overnight. After cooling to ambient temperature, the mixture was evaporated and purified by column chromatography 0→8% MeOH/DCM, to yield FH7429_U (0.65 g, 1.97 mmol) as a white solid in 60% yield.

Method 5:

FH7429_U was prepared according to general procedure 5. FH8491 (0.2 g, 0.372 mmol) gave rise to FH7429_U (0.071 g, 0.216 mmol) as a white solid in 58% yield. Purification by column chromatography (1→7.5% MeOH/DCM).

$^1$H NMR (300 MHz, DMSO-d$_6$) δ: 1.87 (ddd, J=13.2, 6.3, 3.3 Hz, 1H, H-3"), 2.14-2.23 (m, 1H, H-3'), 3.50 (ddd, J=12.0, 5.4, 4.2 Hz, 1H, H-5"), 3.66 (ddd, J=12.0, 5.4, 3.3 Hz, 1H, H-5'), 4.24-4.31 (m, 1H, H-4'), 4.34-4.39 (m, 1H, H-2'), 5.03 (t, J=5.7 Hz, 1H, OH-5'), 5.57 (d, J=4.5 Hz, 1H, OH-2'), 6.04 (d, J=2.7 Hz, 1H, H-1'), 6.76 (br. s, 2H, NH$_2$), 7.65 (s, 1H, H-6), 8.11 (s, 1H, H-2). $^{13}$C NMR (75 MHz, DMSO-d$_6$) δ: 34.25 (C-3'), 62.54 (C-5'), 74.98 (C-2'), 80.10 (C-4'), 86.32 (C-4), 90.08 (C-1'), 100.89 (C-4a), 121.41 (C-6), 148.99 (C-7a), 152.39 (C-2), 156.91 (C-4). HRMS (ESI): calculated for C$_{11}$H$_{14}$BrN$_4$O$_3$ ([M+H]$^+$): 329.0244, found: 329.0240.

4-amino-N7-(3'-deoxy-β-D-ribofuranosyl)-pyrrolo[2,3-d]pyrimidine (FH7429_DOWN)

FH7429_D was prepared according to general procedure 1. FH5284 (tubercidin) (0.16 g, 0.6 mmol) was converted into FH7429_D (0.065 g, 0.26 mmol) in 43% yield. $^1$H NMR (300 MHz, DMSO-d$_6$) δ: 1.91 (ddd, J=12.9, 6.6, 3.6 Hz, 1H, H-3"), 2.18 (ddd, J=12.9, 8.4, 6.3 Hz, 1H, H-3'), 3.49 (ddd, J=11.7, 5.7, 4.5 Hz, 1H, H-5"), 3.62 (ddd, J=11.7, 5.4, 3.6 Hz, 1H, H-5'), 4.24-4.29 (m, 1H, H-4'), 4.38-4.42 (m, 1H, H-2'), 5.05 (t, J=5.4 Hz, 1H, OH-5'), 5.51 (d, J=4.5 Hz, 1H, OH-2'), 6.00 (d, J=2.7 Hz, 1H, H-1'), 6.56 (d, J=3.6 Hz, 1H, H-5), 6.99 (br. s, 2H, NH$_2$), 7.32 (d, J=3.6 Hz, 1H, H-6), 8.05 (s, 1H, H-2). HRMS (ESI): calculated for C$_{11}$H$_{15}$N$_4$O$_3$ ([M+H]$^+$): 251.1139, found: 251.1136.

4-amino-5-chloro-N7-(3'-deoxy-β-D-ribofuranosyl)-pyrrolo[2,3-d]pyrimidine] (FH8470)

FH8470 was prepared according to general procedure 1. FH3169 (0.301 g, 1 mmol) was converted into FH8470 (0.050 g, 0.176 mmol) in 18% yield, as a white solid.

$^1$H NMR (300 MHz, DMSO-d$_6$) δ: 1.87 (ddd, J=12.9, 6.3, 3.0 Hz, 1H, H-3"), 2.18 (ddd, J=13.2, 8.7, 3.7 Hz, 1H, H-3'), 3.50 (ddd, J=12.0, 5.4, 3.9 Hz, 1H, H-5"), 3.66 (ddd, J=12.0, 5.4, 3.6 Hz, 1H, H-5'), 4.24-4.32 (m, 1H, H-4'), 4.33-4.38 (m, 1H, H-2'), 5.03 (t, J=5.4 Hz, 1H, OH-5'), 5.56 (d, J=4.5 Hz, 1H, OH-2'), 6.04 (d, J=2.4 Hz, 1H, H-1'), 6.84 (br. s, 2H, NH$_2$), 7.60 (s, 1H, H-6), 8.10 (s, 1H, H-2). $^{13}$C NMR (75 MHz, DMSO-d$_6$) δ: 24.28 (C-3'), 62.56 (C-5'), 74.98 (C-2'), 80.08 (C-4'), 89.99 (C-1'), 99.73 (C-4a), 102.28 (C-5), 118.86 (C-6), 148.55 (C-7a), 152.59 (C-2), 156.73 (C-4). HRMS (ESI): calculated for C$_{11}$H$_{14}$ClN$_4$O$_3$ ([M+H]$^+$): 285.0749, found: 285.0740. Melting point: 234° C.

4-amino-5-bromo-N7-(2',3'-anhydro-β-D-ribofuranosyl)-pyrrolo[2,3-d]pyrimidine (FH7429_epoxide)

TH1003 (0.35 g, 1 mmol) was suspended in anhydrous MeCN (20 mL, 20 mL/mmol SM), and 'moist' MeCN (2 mL, 2 mL/mmol SM; moist=1.98 mL MeCN+0.02 mL water) was added. Next, α-acetoxy-isobutyrylbromide (0.59 mL, 4 mmol, 4 eq.) was added and stirred at ambient temperature for approximately 1.5H. Next, the reaction was quenched by the addition of aq. sat. NaHCO$_3$/aq. sat. Na$_2$S$_2$O$_3$ solution and DCM. The water layer was extracted twice more with DCM, organic layers combined, dried over Na$_2$SO$_4$, filtered and evaporated. The residue was re-dissolved in 0.4 M NaOMe/MeOH (14 mL, 14 mL/mmol SM) and stirred overnight. Next, the mixture was neutralized by the addition of aq. 0.5 M HCl, evaporated and purified by column chromatography 1→6% MeOH/DCM. FH7429_epox (0.25 g, 0.77 mmol) was obtained as a white solid in 77% yield.

$^1$H NMR (300 MHz, DMSO-d$_6$) δ: 3.46-3.59 (m, 2H, H-5, H-5"), 4.12 (t, J=5.4 Hz, 1H, H-4'), 4.18 (d, J=3.0 Hz, 1H, H-3'), 4.30 (d, J=2.7 Hz, 1H, H-2'), 5.07 (t, J=4.8 Hz, 1H, OH-5'), 6.29 (s, 1H, H-1'), 6.82 (br. s, 2H, NH$_2$), 7.69 (s, 1H, H-6), 8.14 (s, 1H, H-2). $^{13}$C NMR (75 MHz, DMSO-d$_6$) δ: 57.96 (C-2'), 58.80 (C-3'), 61.12 (C-5'), 80.77 (C-4'), 81.71 (C-1'), 87.06 (C-5), 100.89 (C)-4a), 121.97 (C-6), 149.40 (C-7a), 152.68 (C-2), 156.97 (C-4).

4-amino-5-bromo-N7-(2',3'-O-anhydro-5'-O-t-butyl-dimethylsilyl)-pyrrolo[2,3-d]pyrimidine (FH8469)

FH7429_epox (0.354 g, 1.08 mmol) was dissolved in DMF (10 mL, 10 mL/mmol SM). Next, imidazole (0.111 g, 1.63 mmol, 1.5 eq.) and TBSCl (0.2 g, 1.3 mmol, 1.2 eq.) were added and the mixture stirred at ambient temperature overnight. Next, water and EA were added. The layers were separated and the water layer extracted with EA twice more. The organic layers were combined, dried over Na$_2$SO$_4$, filtered and evaporated. The residue was purified by column chromatography 50% EA/Hexanes to yield FH8469 (0.29 g, 0.65 mmol) as a white foam in 60% yield.

$^1$H NMR (300 MHz, CDCl$_3$) δ: 0.08 (s, 3H, CH$_3$), 0.09 (s, 3H, CH$_3$), 0.90 (s, 9H, CH$_3$), 3.80 (d, J=0.6 Hz, 1H, H-5"), 3.81 (d, J=0.9 Hz, 1H, H-5'), 4.07 (d, J=2.7 Hz, 1H, H-2'), 4.18 (dd, J=2.7, 0.3 Hz, 1H, H-3'), 4.31 (t, J=5.1 Hz, 1H, H-5'), 5.80 (br. s, 2H, NH$_2$), 6.38 (s, 1H, H-1'), 7.38 (s, 1H,

H-6), 8.27 (s, 1H, H-2). $^{13}$C NMR (75 MHz, CDCl$_3$) δ: −5.28 (CH$_3$), −5.21 (CH$_3$), 26.07 (t-Bu CH$_3$), 29.42 (C—(CH$_3$)$_3$), 59.07 (C-3'), 59.48 (C-2'), 63.51 (C-5'), 80.87 (C-2'), 83.53 (C-1'), 88.27 (C-5), 102.46 (C-4a), 122.01 (C-6), 149.67 (C-7a), 152.41 (C-2), 156.66 (C-4).

4-Amino-5-Bromo-N7-(3'-Deoxy-5'-O-t-Butyl-Dimethylsilyl)-β-D-Ribofuranosyl-Pyrrolo[2,3-d]pyrimidine (FH8471)

Method 1:
FH8469 (0.8 g, 1.81 mmol) was dissolved in anhydrous THF (20 mL, 10 mL/mmol SM) and cooled in an ice bath. Next, LiEt$_3$BH (Superhydride®, 1 M in THF, 18 mL, 10 eq.) was added dropwise. After complete addition, the ice bath was removed and the remaining mixture stirred at ambient temperature overnight. Next, the reaction was carefully quenched by adding an aq. 0.5 M AcOH solution dropwise. After the gas evolution ceased, aq. sat. NaHCO$_3$ was added together with EA. The layers were separated and the water layer extracted with EA twice more. The organic layers were combined, dried over Na$_2$SO$_4$, filtered and evaporated. The residue was purified by column chromatography 0→3% MeOH/DCM. FH8471 (0.44 g, 0.996 mmol) was isolated as a waxy solid in 55% yield.
Method 2:
FH7429_U (0.18 g, 0.547 mmol, 1 eq.) was dissolved in DMF and cooled to 0° C. Next, imidazole (0.095 g, 1.37 mmol, 2.5 eq.) and TBSCl (0.091 g, 0.602 mmol, 1.1 eq.) were added. The mixture was allowed to come to room temperature overnight, and aq. sat. NaHCO$_3$ was added together with EA.
The layers were separated and the water layer extracted with EA twice more. The organic layers were combined, dried over Na$_2$SO$_4$, filtered and evaporated. The residue was purified by column chromatography 0→3% MeOH/DCM. FH8471 (0.166 g, 0.375 mmol) was isolated as a waxy solid in 70% yield.

$^1$H NMR (300 MHz, CDCl$_3$) δ: 0.09 (s, 3H, CH$_3$), 0.01 (s, 3H, CH$_3$), 0.92 (s, 9H, t-Bu CH$_3$), 2.06 (ddd, J=13.2, 6.6, 4.5 Hz, 1H, H-3"), 2.33 (ddd, J=13.2, 7.5, 6.0 Hz, 1H, H-3'), 3.71 (dd, J=11.4, 2.7 Hz, 1H, H-5"), 4.02 (dd, J=11.4, 2.7 Hz, 1H, H-5'), 4.50-4.58 (m, 2H, H-4', H-2'), 5.86 (br. s, 2H, NH$_2$), 6.04 (d, J=2.7 Hz, 1H, H-1'), 7.54 (s, 1H, H-6), 8.22 (s, 1H, H-2). $^{13}$C NMR (75 MHz, CDCl$_3$) δ: −5.31 (CH$_3$), −5.21 (CH$_3$), 18.63 (Si—C(CH$_3$)$_3$), 26.11 (CH$_3$, t-Bu), 32.98 (C-3'), 64.17 (C-5'), 77.31 (C-2'), 81.43 (C-4'), 86.53 (C-5), 92.88 (C-1'), 102.61 (C-4a), 121.74 (C-6), 147.96 (C-7a), 151.49 (C-2), 156.60 (C-4).
7H-4-chloro-5-trifluoromethylthio-pyrrolo[2,3-d]pyrimidine] (FH6335)
To a flame-dried Schlenk tube under argon was added 6-chloro-7-deazapurine (0.077 g, 0.5 mmol, 1 eq.), N—(trifluoromethylthio)phthalimide (0.136 g, 0.55 mmol, 1.1 eq.) and NaCl (0.003 g, 0.05 mmol, 0.10 eq.). The flask was evacuated and backfilled with argon three times. Then, anhydrous DMF (2.5 mL, 5 mL/mmol SM) was added and the mixture heated in a pre-heated oil bath at 90° C. overnight.[31] After cooling to ambient temperature, water and EA were added. The layers were separated and the water layer extracted with EA twice more. The organic layers were combined, dried over Na$_2$SO$_4$, filtered and evaporated. The residue was purified by column chromatography 10% EA/DCM. FH6335 (0.043 g, 0.17 mmol) was isolated as a white solid in 34% yield. 1H NMR (300 MHz, DMSO-d$_6$) δ: 8.39 (s, 1H, H-6), 8.73 (s, 1H, H-2), 13.47 (br. s, 1H, NH). $^{19}$F-NMR (282 MHz, DMSO-d$_6$) δ: −44.66. HRMS (ESI): calculated for C$_7$H$_4$ClF$_3$N$_3$S ([M+H]$^+$): 253.9761, found: 253.9779. Melting point: 160° C.
4-chloro-5-bromo-N7-(2',5'-di-O-benzoyl-3'-deoxy-β-D-ribofuranosyl-pyrrolo[2,3-d]pyrimidine
(FH8487) FH8487 was prepared according to general procedure 2. FH2066 (1.53 g, 6.65 mmol) and FH8484 (2.81 g, 7.3 mmol) gave rise to FH8487 (2.96 g, 5.3 mmol) as a slight yellow foam in 80% yield. (Purification: 15% EA/PET) $^1$H NMR (300 MHz, CDCl$_3$) δ: 2.44 (ddd, J=14.1, 5.7, 1.8 Hz, 1H, H-3"), 2.74 (ddd, J=14.1, 10.2, 6.0 Hz, 1H, H-3'), 4.60 (dd, J=12.6, 4.5 Hz, 1H, H-5"), 4.75 (dd, J=12.6, 3.0 Hz, 1H, H-5'), 4.81-4.89 (m, 1H, H-4'), 5.91 (dt, J=6.0, 1.5 Hz, 1H, H-2'), 6.46 (d, J=1.5 Hz, 1H, H-1'), 7.45-7.52 (m, 4H, OBz (m-H)), 7.52 (s, 1H, H-6), 7.56-7.65 (m, 2H, OBz (p-H)), 8.01-8.09 (m, 4H, OBz (o-H)), 8.60 (s, 1H, H-2). $^{13}$C NMR (75 MHz, CDCl$_3$) δ: 33.20 (C-3'), 64.58 (C-5'), 78.64 (C-2'), 78.67 (C-4'), 89.51 (C-5), 90.26 (C-1'), 115.97 (C-4a), 126.80 (C-6), 128.76, 128.83, 129.16, 129.54, 129.80, 130.00, 133.61, 133.92, 150.07 (C$_7$a), 151.57 (C-2), 152.71 (C-4), 165.69 (C=O), 166.43 (C=O). HRMS (ESI): calculated for C$_{25}$H$_{20}$BrClN$_3$O$_5$ ([M+H]$^+$): 556.0269, found: 556.0278.
4-chloro-5-iodo-N7-(2',5'-di-O-benzoyl-3'-deoxy-β-D-ribofuranosyl)-pyrrolo[2,3-d]pyrimidine
(FH8488) FH8488 was prepared according to general procedure 2. FH2065 (1.4 g, 5.0 mmol) and FH8484 (2.11 g, 5.5 mmol) gave rise to FH8488 (2.3 g, 3.81 mmol) as a yellow foam in 76% yield. (Purification: 15% EA/PET) $^1$H NMR (300 MHz, CDCl$_3$) δ: 2.44 (ddd, J=14.1, 5.7, 1.8 Hz, 1H, H-3"), 2.76 (ddd, J=14.1, 10.2, 6.0 Hz, 1H, H-3'), 4.59 (dd, J=12.3, 4.5 Hz, 1H, H-5"), 4.75 (dd, J=12.3, 2.7 Hz, 1H, H-5'), 4.81-4.88 (m, 1H, H-4'), 5.91 (dt, J=6.0, 1.5 Hz, 1H, H-2'), 6.45 (d, J=1.5 Hz, 1H, H-1'), 7.46-7.51 (m, 4H, OBz), 7.57-7.65 (m, 2H, OBz), 7.60 (s, 1H, H-6), 8.01-8.09 (m, 4H, OBz), 8.59 (s, 1H, H-2). HRMS (ESI): calculated for C$_{25}$H$_{20}$ICIN$_3$O$_5$ ([M+H]$^+$): 604.0131, found: 604.0145.
4-chloro-5-fluoro-N7-(2',5'-di-O-benzoyl-3'-deoxy-β-D-ribofuranosyl)-pyrrolo[2,3-d]pyrimidine
(FH8508) FH8508 was prepared according to general procedure 2. FH3144 (0.26 g, 1.5 mmol) and FH8484 (0.64 g, 1.65 mmol) gave rise to FH8508 (0.32 g, 0.65 mmol) as a yellow foam in 43% yield. (Purification: 17% EA/PET) $^1$H NMR (300 MHz, CDCl$_3$) δ: 2.45 (ddd, J=14.1, 6.0, 1.8 Hz, 1H, H-3"), 2.72 (ddd, J=14.1, 10.2, 6.0 Hz, 1H, H-3'), 4.58 (dd, J=12.3, 4.8 Hz, 1H, H-5"), 4.72 (dd, J=12.3, 3.0 Hz, 1H, H-5'), 4.87-4.79 (m, 1H, H-4'), 5.91 (dt, J=6.0, 1.8 Hz, 1H, H-2'), 6.47 (t, J=1.5 Hz, 1H, H-1'), 7.23 (d, J=2.7 Hz, 1H, H-6), 7.43-7.51 (m, 4H, OBz), 7.57-7.65 (m, 2H, OBz), 7.99-8.09 (m, 4H, OBz), 8.60 (s, 1H, H-2). $^{19}$F-NMR (282 MHz, CDCl$_3$) δ: −166.81. HRMS (ESI): calculated for C$_{25}$H$_{20}$ClFN$_3$O$_5$ ([M+H]$^+$): 496.1070, found: 496.1075.
4-chloro-5-trifluoromethylthio-N7-(2'-5'-di-O-benzoyl-3'-deoxy-β-D-ribofuranosyl)-pyrrolo[2,3-d]pyrimidine
(FH9597) FH9597 was prepared according to General procedure 2. FH6335 (0.26 g, 1.02 mmol) and FH8484 (0.44 g, 1.13 mmol) gave rise to FH9597 (0.426 g, 0.764 mmol) as a white foam in 75% yield. (Purification: 15% EA/PET) $^1$H NMR (300 MHz, CDCl$_3$) δ: 2.47 (ddd, J=14.1, 5.7, 1.5 Hz, 1H, H-3"), 2.76 (ddd, J=14.1, 10.2, 6.0 Hz, 1H, H-3'), 4.63 (dd, J=12.6, 4.8 Hz, 1H, H-5"), 4.78 (dd, J=12.6, 3.0 Hz, 1H, H-5'), 4.84-4.92 (m, 1H, H-4'), 5.92 (dt, J=5.7, 1.5 Hz, 1H, H-2'), 6.46 (d, J=1.5 Hz, 1H, H-1'), 7.85 (s, 1H, H-6), 7.43-7.52 (m, 4H, OBz), 7.58-7.66 (m, 2H, OBz), 8.01-8.04 (m, 2H, OBz), 8.06-8.10 (m, 2H, OBz), 8.67 (s, 1H, H-2). $^{19}$F-NMR (282 MHz, CDCl$_3$) δ: −44.52. HRMS (ESI): calculated for C$_{26}$H$_{20}$ClF$_3$N$_3$O$_{5S}$ ([M+H]$^+$): 578.0759, found: 578.0748.

4-azido-5-bromo-N7-(2',5'-di-O-benzoyl-3'-deoxy-β-D-ribofuranosyl)-pyrrolo[2,3-d]pyrimidine (FH8489) FH8489 was prepared according to General procedure 3. FH8487 (0.356 g, 0.64 mmol) gave rise to FH8489 (0.230 g, 0.410 mmol) as a white foam in 64% yield. (Purification: 5→30% EA/PET) $^1$H NMR (300 MHz, DMSO-$d_6$) δ: 2.86 (ddd, J=14.1, 10.8, 6.3 Hz, 1H, H-3'), 4.54 (dd, J=12.0, 5.4 Hz, 1H, H-5"), 4.68 (dd, J=12.0, 3.0 Hz, 1H, H-3'), 4.82-4.90 (m, 1H, H-4'), 5.89 (d, J=6.0 Hz, 1H, H-2'), 6.66 (d, J=1.5 Hz, 1H, H-1'), 7.48-7.75 (m, 6H, OBz), 7.94-7.98 (m, 2H, OBz), 8.05-8.09 (m, 2H, OBz), 8.18 (s, 1H, H-6), 9.94 (s, 1H, H-2). 1H is missing; H-3" is located under the residual DMSO-peak. HRMS (ESI): calculated for $C_{25}H_{20}BrN_6O_5$ ([M+H]$^+$): 563.0673, found: 563.0709.

4-azido-5-iodo-N7-(2',5'-di-O-benzoyl-3'-deoxy-β-D-ribofuranosyl)-pyrrolo[2,3-d]pyrimidine (FH8490) FH8490 was prepared according to General procedure 3. FH8488 (0.181 g, 0.30 mmol) gave rise to FH8490 (0.146 g, 0.239 mmol) as a white foam in 80% yield. (Purification: 10→35% EA/PET) $^1$H NMR (300 MHz, DMSO-$d_6$) δ: 2.87 (ddd, J=14.4, 10.5, 6.3 Hz, 1H, H-3'), 4.54 (dd, J=12.3, 5.1 Hz, 1H, H-5"), 4.67 (dd, J=12.3, 3.0 Hz, 1H, H-5'), 4.81-4.90 (m, 1H, H-4'), 5.88 (d, J=6.0 Hz, 1H, H-2'), 6.63 (d, J=1.5 Hz, 1H, H-1'), 7.49-7.74 (m, 6H, OBz), 7.94-7.98 (m, 2H, OBz), 8.04-8.08 (m, 2H, OBz), 8.15 (s, 1H, H-6), 9.91 (s, 1H, H-2). 1H is missing; H-3 is located under the DMSO-residual signal. $^{13}$C NMR (75 MHz, DMSO-$d_6$) δ: 32.62 (C-3'), 55.38 (C-5), 64.85 (C-5'), 78.10 (C-4'), 78.81 (C-2'), 89.35 (C-1'), 106.81 (C-4a), 128.84 (OBz), 128.95 (OBz), 129.18 (OBz), 129.27 (OBz), 129.51 (OBz), 130.21 (OBz), 133.45 (OBz), 133.86 (OBz), 134.61 (C-2), 141.17 (C-7a), 145.95 (C-4), 165.02 (C=O), 165.52 (C=O). HRMS (ESI): calculated for $C_{25}H_{20}IN_6O_5$ ([M+H]$^+$): 611.0534, found: 611.0532.

4-azido-5-fluoro-N7-(2',5'-di-O-benzoyl-3'-deoxy-β-D-ribofuranosyl)-pyrrolo[2,3-d]pyrimidine (FH8509) FH8509 was prepared according to General procedure 3. FH8508 (0.300 g, 0.605 mmol) gave rise to FH8509 (0.187 g, 0.372 mmol) as a white foam in 62% yield. (Purification: 10→35% EA/PET) $^1$H NMR (300 MHz, DMSO-$d_6$) δ: 2.83 (ddd, J=14.4, 10.2, 6.3 Hz, 1H, H-3'), 4.52 (dd, J=12.0, 5.4 Hz, 1H, H-5"), 4.67 (dd, J=12.0, 3.0 Hz, 1H, H-3'), 4.80-4.87 (m, 1H, H-4'), 5.86 (d, J=6.3 Hz, 1H, H-2'), 6.69 (t, J=1.5 Hz, 1H, H-1'), 7.47-7.60 (m, 4H, OBz), 7.63-7.75 (m, 2H, OBz), 7.94-7.97 (m, 2H, OBz), 8.02 (d, J=2.1 Hz, 1H, H-6), 8.05-8.08 (m, 2H, OBz), 9.92 (s, 1H, H-2). 1H is missing; H-3" is located under the DMSO-residual signal. $^{19}$F-NMR (282 MHz, DMSO-$d_6$) δ: −164.98. HRMS (ESI): calculated for $C_{25}H_{20}FN_6O_5$ ([M+H]$^+$): 503.1474, found: 503.1468.

4-azido-5-trifluoromethylthio-N7-(2',5'-di-O-benzoyl-β-D-ribofuranosyl)-pyrrolo[2,3-d]pyrimidine (FH9599) FH9599 was prepared according to General procedure 3. FH9597 (0.333 g, 0.58 mmol) gave rise to FH9599 (0.323 g, 0.55 mmol) as a white foam in 95% yield. (Purification: 10→35% EA/PET) $^1$H NMR (300 MHz, DMSO-$d_6$) δ: 2.50-2.55 (m, 1H, H-3"), 2.89 (ddd, J=14.4, 10.8, 6.3 Hz, 1H, H-3'), 4.55 (dd, J=12.3, 5.4 Hz, 1H, H-5"), 4.71 (dd, J=12.3, 3.6 Hz, 1H, H-5'), 4.84-4.92 (m, 1H, H-4'), 5.95 (d, J=6.0 Hz, 1H, H-2'), 6.70 (d, J=1.2 Hz, 1H, H-1'), 7.45-7.51 (m, 2H, OBz), 7.55-7.75 (m, 4H, OBz), 7.92-7.95 (m, 2H, OBz), 8.05-8.09 (m, 2H, OBz), 8.51 (s, 1H, H-6), 10.02 (s, 1H, H-2). $^{19}$F-NMR (282 MHz, DMSO-$d_6$) δ: −43.60. HRMS (ESI): calculated for $C_{26}H_{20}F_3N_6O_5S$ ([M+H]$^+$): 585.1162, found: 585.1127.

4-amino-5-bromo-N7-(2',5'-di-O-benzoyl-3'-deoxy-β-D-ribofuranosyl)-pyrrolo[2,3-d]pyrimidine (FH8491) FH8491 was prepared according to General procedure 4. FH8489 (0.22 g, 0.39 mmol) gave rise to FH8491 (0.2 g, 0.37 mmol) in 95% yield. (Purification: 25→65% EA/PET) $^1$H NMR (300 MHz, CDCl$_3$) δ: 2.40 (ddd, J=14.1, 5.7, 1.8 Hz, 1H, H-3"), 2.73 (ddd, J=14.1, 10.5, 6.0 Hz, 1H, H-3'), 4.58 (dd, J=12.3, 4.8 Hz, 1H, H-5"), 4.71 (dd, J=12.3, 3.0 Hz, 1H, H-5'), 4.76-4.84 (m, 1H, H-4'), 5.61 (br. s, 2H, NH$_2$), 5.88 (dt, J=6.0, 1.5 Hz, 1H, H-2'), 6.44 (d, J=1.5 Hz, 1H, H-1'), 7.18 (s, 1H, H-6), 7.44-7.50 (m, 4H, OBz), 7.56-7.63 (m, 2H, OBz), 7.64-8.09 (m, 4H, OBz), 8.25 (s, 1H, H-2). HRMS (ESI): calculated for $C_{25}H_{22}BrN_4O_5$ ([M+H]$^+$): 537.0768, found: 537.0767.

4-amino-5-iodo-N7-(2'-5'-di-O-benzoyl-3'-deoxy-β-D-ribofuranosyl)-pyrrolo[2,3-d]pyrimidine (FH8495) FH8495 was prepared according to General procedure 4. FH8490 (0.135 g, 0.22 mmol) gave rise to FH8495 (0.128 g, 0.218 mmol) in 99% yield. (Purification: 25→65% EA/PET) $^1$H NMR (300 MHz, CDCl$_3$) δ: 2.40 (ddd, J=14.1, 5.7, 1.8 Hz, 1H, H-3"), 2.74 (ddd, J=14.1, 10.2, 6.0 Hz, 1H, H-3'), 4.57 (dd, J=12.3, 4.8 Hz, 1H, H-5"), 4.72 (dd, J=12.3, 3.0 Hz, 1H, H-5'), 4.76-4.84 (m, 1H, H-4'), 5.65 (br. s, 2H, NH$_2$), 5.88 (dt, J=5.7, 1.8 Hz, 1H, H-2'), 6.43 (d, J=1.8 Hz, 1H, H-1'), 7.25 (s, 1H, H-6), 7.44-7.51 (m, 4H, OBz), 7.57-7.63 (m, 2H, OBz), 7.64-8.09 (m, 4H, OBz), 8.25 (s, 1H, H-2). HRMS (ESI): calculated for $C_{25}H_{22}IN_4O_5$ ([M+H]$^+$): 585.0629, found: 585.0621.

4-amino-5-fluoro-N7-(2',5'-di-O-benzoyl-3'-deoxy-β-D-ribofuranosyl)-pyrrolo[2,3-d]pyrimidine (FH8514) FH8514 was prepared according to General procedure 4. FH8509 (0.180 g, 0.358 mmol) gave rise to FH8514 (0.164 g, 0.344 mmol) in 96% yield. (Purification: 35→70% EA/PET) $^1$H NMR (300 MHz, CDCl$_3$) δ: 2.40 (ddd, J=14.1, 5.7, 2.1 Hz, 1H, H-3"), 2.72 (ddd, J=14.1, 10.2, 6.3 Hz, 1H, H-3'), 4.55 (dd, J=12.3, 4.8 Hz, 1H, H-5"), 4.68 (dd, J=12.0, 3.0 Hz, 1H, H-5'), 4.74-4.82 (m, 1H, H-4'), 5.34 (br. s, 2H, NH$_2$), 5.89 (dt, J=6.0, 1.8 Hz, 1H, H-2'), 6.46 (t, J=1.8 Hz, 1H, H-1'), 6.88 (d, J=2.4 Hz, 1H, H-6), 7.43-7.50 (m, 4H, OBz), 7.56-7.63 (m, 2H, OBz), 8.03-8.09 (m, 4H, OBz), 8.26 (s, 1H, H-2). $^{19}$F-NMR (282 MHz, CDCl$_3$) δ: −167.80 (t, J=2.1 Hz, 1F). HRMS (ESI): calculated for $C_{25}H_{22}FN_4O_5$ ([M+H]$^+$): 477.1569, found: 477.1573.

4-amino-5-trifluoromethylthio-N7-(2'-5'-di-O-benzoyl-3'-deoxy-β-D-ribofuranosyl)-pyrrolo[2,3-d]pyrimidine (FH9604) FH9604 was prepared according to General procedure 4. FH9599 (0.310 g, 0.53 mmol) gave rise to FH9604 (0.256 g, 0.458 mmol) in 86% yield. (Purification: 35→50% EA/PET) $^1$H NMR (300 MHz, CDCl$_3$) δ: 2.42 (ddd, J=14.1, 5.4, 1.5 Hz, 1H, H-3"), 2.76 (ddd, J=14.1, 10.5, 6.0 Hz, 1H, H-3'), 4.61 (dd, J=12.3, 4.8 Hz, 1H, H-5"), 4.75 (dd, J=12.3, 3.0 Hz, 1H, H-5'), 4.81-4.87 (m, 1H, H-4'), 5.81 (br. s, 2H, NH$_2$), 5.91 (dt, J=5.7, 1.5 Hz, 1H, H-2'), 6.44 (d, J=1.5 Hz, 1H, H-1'), 7.43-7.51 (m, 4H, OBz), 7.55 (s, 1H, H-6), 7.57-7.64 (m, 2H, OBz), 8.03-8.10 (m, 4H, OBz), 8.30 (s, 1H, H-2). $^{19}$F-NMR (282 MHz, CDCl$_3$) δ: −44.99. HRMS (ESI): calculated for $C_{26}H_{22}F_3N_4O_5S$ ([M+H]$^+$): 559.1258, found: 559.1265.

4-amino-5-iodo-N7-(3'-deoxy-β-D-ribfuranosyl)-pyrrolo[2,3-d]pyrimidine (FH8496) FH8496 was prepared according to general procedure 5. FH8495 (0.12 g, 0.205 mmol) gave rise to FH8496 (0.042 g, 0.112 mmol) as a white solid in 54% yield. (Purification 5→7.5% MeOH/DCM) $^1$H NMR (300 MHz, DMSO-$d_6$) δ: 1.87 (ddd, J=12.9, 6.3, 3.3 Hz, 1H, H-3"), 2.18 (ddd, J=13.2, 8.7, 6.0 Hz, 1H, H-3'), 3.47-3.53 (m, 1H, H-5"), 3.63-3.68 (m, 1H, H-5'), 4.24-4.31 (m, 1H, H-4'), 4.37 (br. s, 1H, H-2'), 5.04 (br. s, 1H, OH-3'), 5.56 (br.

s, 1H, OH-2'), 6.01 (d, J=2.7 Hz, 1H, H-1'), 6.65 (br. s, 2H, NH$_2$), 7.68 (s, 1H, H-6), 8.11 (s, 1H, H-2). $^{13}$C NMR (75 MHz, DMSO-d$_6$) δ: 34.33 (C-3'), 51.38 (C-5), 62.59 (C-5'), 74.92 (C-2'), 80.02 (C-4'), 90.16 (C-1'), 103.09 (C-4a), 126.72 (C-6), 149.57 (C-7a), 151.89 (C-2), 157.14 (C-4). HRMS (ESI): calculated for C$_{11}$H$_{14}$IN$_4$O$_3$ ([M+H]$^+$): 377.0105, found: 377.0107. Melting point: 228° C.

4-amino-5-fluoro-N7-(3'-deoxy-β-D-ribofuranosyl)-pyrrolo[2,3-d]pyrimidine (FH8517) FH8517 was prepared according to general procedure 5. FH8514 (0.15 g, 0.315 mmol) gave rise to FH8517 (0.069 g, 0.257 mmol) as a white solid in 82% yield. (Purification 2→10% MeOH/DCM) $^1$H NMR (300 MHz, DMSO-d$_6$) δ: 1.87 (ddd, J=12.9, 6.3, 3.3 Hz, 1H, H-3"), 2.17 (ddd, J=13.2, 8.7, 6.0 Hz, 1H, H-3'), 3.49 (ddd, J=12.0, 5.4, 4.2 Hz, 1H, H-5"), 3.63 (ddd, J=12.0, 5.4, 3.6 Hz, 1H, H-5'), 4.22-4.29 (m, 1H, H-4'), 4.30-4.36 (m, 1H, H-2'), 4.99 (t, J=5.4 Hz, 1H, OH-5'), 5.53 (d, J=4.5 Hz, 1H, OH-2'), 6.07 (t, J=2.4 Hz, 1H, H-1'), 6.97 (br. s, 2H, NH$_2$), 7.34 (d, J=2.1 Hz, 1H, H-6), 8.07 (s, 1H, H-2). $^{19}$F-NMR (282 MHz, DMSO-d$_6$) δ: −167.99. $^{13}$C NMR (75 MHz, DMSO-d$_6$) δ: 35.46 (C-3'), 62.64 (C-5'), 74.81 (C-2'), 79.77 (C-4'), 89.51 (C-1'), 92.15 (d, J=16.0 Hz, 1C, C-4a), 103.94 (d, J=26.3 Hz, 1C, C-6), 142.36 (d, J=243.8 Hz, 1C, C-5), 145.49 (d, J=2.3 Hz, 1C, C-7a), 152.6 (C-2), 155.68 (d, J=3.5 Hz, 1C, C-4). HRMS (ESI): calculated for C$_{11}$H$_{14}$FN$_4$O$_3$ ([M+H]$^+$): 269.1044, found: 269.1044. Melting point: 204° C.

4-amino-5-trifluoromethylthio-N7-(3'-deoxy-β-D-ribofuranosyl)-pyrrolo[2,3-d]pyrimidine (FH9605) FH9605 was prepared according to general procedure 5. FH9604 (0.256 g, 0.458 mmol) gave rise to FH9605 (0.143 g, 0.408 mmol) as a white solid in 89% yield. (Purification 2.5→7.5% MeOH/DCM) $^1$H NMR (300 MHz, DMSO-d$_6$) δ:1.87 (ddd, J=13.2, 6.3, 3.0 Hz, 1H, H-3"), 2.18 (ddd, J=13.2, 9.0, 5.4 Hz, 1H, H-3'), 3.53 (ddd, J=12.0, 5.7, 3.9 Hz, 1H, H-5"), 3.73 (ddd, J=12.0, 5.4, 3.3 Hz, 1H, H-5'), 4.31-4.37 (m, 1H, H-4'), 4.39-4.44 (m, 1H, H-2'), 5.12 (t, J=5.4 Hz, 1H, OH-5'), 5.65 (d, J=4.2 Hz, 1H, OH-2'), 6.05 (d, J=2.1 Hz, 1H, H-1'), 6.91 (br. s, 2H, NH$_2$), 8.14 (s, 1H, H-6), 8.19 (s, 1H, H-2). $^{19}$F-NMR (282 MHz, DMSO-d$_6$) δ: −45.05. $^{13}$C NMR (75 MHz, DMSO-d$_6$) δ: 33.78 (C-3'), 62.23 (C-5'), 75.16 (C-2'), 80.68 (C-4'), 90.25 (q, J=2.25 Hz, 1C, C-5), 90.82 (C-1'), 103.08 (C-4a), 128.59 (q, J=307.95 Hz, 1C, SCF$_3$), 132.34 (C-6), 150.30 (C-7a), 152.73 (C-2), 157.22 (C-4). HRMS (ESI): calculated for C$_{12}$H$_{14}$F$_3$N$_4$O$_3$S ([M+H]$^+$): 351.0733, found: 351.0729. Melting point: 176° C.

4-amino-5-phenyl-N7-(3'-deoxy-β-D-ribofuranosyl)-pyrrolo[2,3-d]pyrimidine (FH8480) FH8480 was prepared according to General Procedure 6. FH7429_U (0.165 g, 0.5 mmol) gave rise to FH8480 (0.1 g, 0.306 mmol) as a white solid in 61% yield. $^1$H NMR (300 MHz, DMSO-d$_6$) δ: 1.91 (ddd, J=13.2, 6.3, 3.3 Hz, 1H, H-3"), 2.25 (ddd, J=13.2, 8.7, 6.0 Hz, 1H, H-3'), 3.51 (ddd, J=12.0, 5.7, 4.2 Hz, 1H, H-5"), 3.66 (ddd, J=12.0, 5.4, 3.6 Hz, 1H, H-5'), 4.27-4.34 (m, 1H, H-4'), 4.45-4.50 (m, 1H, H-2'), 5.02 (t, J=5.4 Hz, 1H, OH-5'), 5.57 (d, J=4.2 Hz, 1H, OH-2'), 6.10 (br. s, 2H, NH$_2$), 6.13 (d, J=2.4 Hz, 1H, H-1'), 7.34-7.41 (m, 1H, Ph-H), 7.41-7.52 (m, 4H, Ph-H), 7.54 (s, 1H, H-6), 8.16 (s, 1H, H-2). $^{13}$C NMR (75 MHz, DMSO-d$_6$) δ: 34.68 (C-3'), 62.80 (C-5'), 74.91 (C-2'), 79.93 (C-4'), 90.16 (C-1'), 100.25 (C-4a), 116.09 (C-5), 120.70 (C-6), 126.82 (C-Phenyl$_{ipso}$), 128.44 (2×C-Phenyl), 128.98 (2×C-Phenyl), 134.59 (C-Phenyl$_{para}$), 150.38 (C-7a), 151.69 (C-2), 157.26 (C-4). HRMS (ESI): calculated for C$_{17}$H$_{19}$N$_4$O$_3$ ([M+H]$^+$): 327.1452, found: 327.1448. Melting point: 109° C.

4-amino-5-(4-methylphenyl)-N7-(3'-deoxy-β-D-ribofuranosyl)-pyrrolo[2,3-d]pyrimidine (FH8481) FH8480 was prepared according to General Procedure 6. FH7429_U (0.165 g, 0.5 mmol) gave rise to FH8481 (0.066 g, 0.194 mmol) as a white solid in 39% yield. $^1$H NMR (300 MHz, DMSO-d$_6$) δ: 1.91 (ddd, J=13.2, 6.3, 3.3 Hz, 1H, H-3"), 2.24 (ddd, J=13.2, 8.4, 6.0 Hz, 1H, H-3'), 2.36 (s, 3H, CH$_3$), 3.47-3.54 (m, 1H, H-5"), 3.62-3.68 (m, 1H, H-5'), 4.26-4.33 (m, 1H, H-4'), 4.44-4.49 (m, 1H, H-2'), 5.02 (t, J=5.4 Hz, 1H, OH-5'), 5.57 (d, J=4.5 Hz, 1H, OH-2'), 6.09 (br. s, 2H, NH$_2$), 6.11 (d, J=2.7 Hz, 1H, H-1'), 7.28-7.30 (m, 2H, Ph-H), 7.35-7.37 (m, 2H, Ph-H), 7.49 (s, 1H, H-6), 8.15 (s, 1H, H-2). $^{13}$C NMR (75 MHz, DMSO-d$_6$) δ: 20.73 (CH$_3$), 34.70 (C-3'), 62.80 (C-5'), 74.86 (C-2'), 79.87 (C-4'), 90.11 (C-1'), 100.31 (C-4a), 116.00 (C-5), 120.35 (C-6), 128.37 (2×C-Phenyl), 129.53 (2×C-Phenyl), 131.62 (C-Phenyl$_{ipso}$), 136.06 (C-Phenyl$_{para}$), 150.26 (C-7a), 151.62 (C-2), 157.23 (C-2). HRMS (ESI): calculated for C$_{18}$H$_{21}$N$_4$O$_3$ ([M+H]$^+$): 341.1608, found: 341.1602. Melting point: 116° C.

4-amino-5-(4-methoxyphenyl)-N7-(3'-deoxy-β-D-ribofuranosyl)-pyrrolo[2,3-d]pyrimidine (FH8494) FH8494 was prepared according to General Procedure 6. FH7429_U (0.160 g, 0.5 mmol) gave rise to FH8494 (0.108 g, 0.303 mmol) as a white solid in 61% yield. $^1$H NMR (300 MHz, DMSO-d$_6$) δ: 1.91 (ddd, J=12.9, 6.3, 3.3 Hz, 1H, H-3"), 2.24 (ddd, J=13.2, 8.4, 6.0 Hz, 1H, H-3'), 3.50 (ddd, J=12.0, 5.1, 4.5 Hz, 1H, H-5"), 3.65 (ddd, J=12.0, 5.4, 3.9 Hz, 1H, H-5'), 4.25-4.33 (m, 1H, H-4'), 4.44-4.49 (m, 1H, H-2'), 5.01 (t, J=5.4 Hz, 1H, OH-5'), 5.56 (d, J=4.5 Hz, 1H, OH-2'), 6.06 (br. s, 2H, NH$_2$), 6.11 (d, J=2.7 Hz, 1H, H-1'), 7.02-7.07 (m, 2H, Ph-H), 7.36-7.41 (m, 2H, Ph-H), 7.44 (s, 1H, H-6), 8.14 (s, 1H, H-2). $^{13}$C NMR (75 MHz, DMSO-d$_6$) δ: 34.74 (C-3'), 55.17 (OCH$_3$), 62.83 (C-5'), 74.85 (C-2'), 79.84 (C-4'), 90.10 (C-1'), 100.45 (C-4a), 114.41 (2C, Ph-C), 115.73 (C-5), 120.08 (C-6), 126.73 (Ph-(C-1)), 129.69 (2C, Ph-C), 150.17 (C-7a), 151.60 (C-2), 157.28 (C-4), 158.38 (Ph-C—OCH$_3$). HRMS (ESI): calculated for C$_{18}$H$_{21}$N$_4$O$_4$ ([M+H]$^+$): 357.1557, found: 357.1550. Melting point: 163° C.

4-amino-5-(4-chlorophenyl)-N7-(3'-deoxy-β-D-ribofuranosyl)-pyrrolo[2,3-d]pyrimidine (FH8512)

FH8512 was prepared according to General Procedure 6. FH7429_U (0.160 g, 0.5 mmol) gave rise to FH8512 (0.062 g, 0.172 mmol) as a white solid in 35% yield. $^1$H NMR (300 MHz, DMSO-d$_6$) δ: 1.91 (ddd, J=12.9, 6.3, 3.3 Hz, 1H, H-3"), 2.24 (ddd, J=12.9, 8.4, 6.0 Hz, 1H, H-3'), 3.50 (ddd, J=11.7, 5.7, 4.2 Hz, 1H, H-5"), 3.66 (ddd, J=11.7, 5.4, 3.6 Hz, 1H, H-5'), 4.27-4.34 (m, 1H, H-4'), 4.44-4.49 (m, 1H, H-2'), 5.01 (t, J=5.7 Hz, 1H, OH-5'), 5.57 (d, J=4.2 Hz, 1H, OH-2'), 6.12 (d, J=2.7 Hz, 1H, H-1'), 6.19 (br. s, 2H, NH$_2$), 7.45-7.49 (m, 2H, Ph-H), 7.50-7.54 (m, 2H, Ph-H), 7.58 (s, 1H, H-6), 8.16 (s, 1H, H-2). $^{13}$C NMR (75 MHz, DMSO-d$_6$) δ: 34.64 (C-3'), 62.75 (C-5'), 74.89 (C-2'), 79.96 (C-4'), 90.13 (C-1'), 100.03 (C-4a), 114.92 (C-5), 121.02 (C-6), 128.84 (2C, Ph-C), 130.03 (2C, Ph-C), 131.42 (Ph-C), 133.40 (Ph-C), 150.52 (C-7a), 151.75 (C-2), 157.29 (C-4). HRMS (ESI): calculated for C$_{17}$H$_{18}$ClN$_4$O$_3$ ([M+H]$^+$): 361.1062, found: 361.1066. Melting point: 200° C.

4-amino-5-(3,4-dichlorophenyl)-N7-(3'-deoxy-D-ribofuranosyl-pyrrolo[2,3-d]pyrimidine (FH8513)

FH8513 was prepared according to General Procedure 6. FH7429_U (0.160 g, 0.5 mmol) gave rise to FH8513 (0.100 g, 0.253 mmol) as a white solid in 51% yield. $^1$H NMR (300 MHz, DMSO-d$_6$) δ: 1.91 (ddd, J=12.9, 6.3, 3.0 Hz, 1H, H-3"), 2.25 (ddd, J=13.2, 8.7, 6.0 Hz, 1H, H-3'), 3.51 (ddd, J=12.0, 5.7, 4.2 Hz, 1H, H-5"), 3.66 (ddd, J=12.0, 5.7, 3.6 Hz, 1H, H-5'), 4.26-4.34 (m, 1H, H-4'), 4.43-4.49 (m, 1H, H-2'), 5.01 (t, J=5.7 Hz, 1H, OH-5'), 5.58 (d, J=4.5 Hz, 1H, OH-2'), 6.12 (d, J=2.4 Hz, 1H, H-1'), 6.32 (br. s, 2H, NH$_2$), 7.42 (dd, J=8.1, 2.1 Hz, 1H, H-6$_{Phe}$), 7.66 (s, 1H, H-8), 7.68 (d, J=1.8 Hz, 1H, H-2$_{Phe}$), 7.69 (d, J=8.1 Hz, 1H, H-5$_{Phe}$), 8.17 (s, 1H, H-2). $^{13}$C NMR (75 MHz, DMSO-d$_6$) δ: 34.66 (C-3'), 62.78 (C-5'), 74.94 (C-2'), 80.07 (C-4'), 90.13 (C-1'), 99.87 (C-4a), 113.88 (C-5), 121.68 (C-6), 128.49 (C-6$_{Phe}$), 129.12 (C$_{Phe}$), 129.96 (C-2$_{Phe}$), 130.83 (C-5$_{Phe}$), 131.33, 135.22, 150.68 (C-7a), 151.87 (C-2), 157.35 (C-4). HRMS (ESI): calculated for C$_{17}$H$_{17}$Cl$_2$N$_4$O$_3$ ([M+H]$^+$): 395.0672, found: 395.0663. Melting point: 169° C.

4-amino-5-(4-isopropylphenyl)-N7-(3'-deoxy-β-D-ribofuranosyl)-pyrrolo[2,3-d]pyrimidine (FH9574) FH9574 was prepared according to General Procedure 6. FH7429_U (0.150 g, 0.45 mmol) gave rise to FH9574 (0.126 g, 0.343 mmol) as a white solid in 76% yield. $^1$H NMR (300 MHz, DMSO-d$_6$) δ: 1.24 (s, 3H, CH$_3$), 1.25 (s, 3H, CH$_3$), 1.91 (ddd, J=12.9, 6.3, 3.3 Hz, 1H, H-3"), 2.19-2.27 (m, 1H, H-3'), 2.94 (sept., J=6.9 Hz, 1H, C—H), 3.50 (ddd, J=11.7, 5.4, 4.2 Hz, 1H, H-5"), 3.65 (ddd, J=11.7, 5.4, 3.6 Hz, 1H, H-5'), 4.26-4.33 (m, 1H, H-4'), 4.43-4.49 (m, 1H, H-2'), 5.01 (t, J=5.7 Hz, 1H, OH-5'), 5.56 (d, J=4.5 Hz, OH-2'), 6.08 (br. s, 2H, NH$_2$), 6.11 (d, J=2.4 Hz, 1H, H-1'), 7.34-7.36 (m, 2H, Ph-H), 7.38-7.50 (m, 2H, Ph-H), 7.50 (s, 1H, H-6), 8.15 (s, 1H, H-2). $^{13}$C NMR (75 MHz, DMSO-d$_6$) δ: 23.89 (CH$_3$), 33.15 (CH), 34.69 (C-3'), 62.82 (C-5'), 74.91 (C-2'), 79.92 (C-4'), 90.12 (C-1'), 100.31 (C-4a), 116.00 (C-5), 120.48 (C-6), 126.92 (2C$_{Phe}$), 128.38 (2C$_{Phe}$), 132.03 (C-1$_{Phe}$), 147.00 (C-4$_{Phe}$), 150.26 (C-7a), 151.63 (C-2), 157.25 (C-4). HRMS (ESI): calculated for C$_{20}$H$_{25}$N$_4$O$_3$ ([M+H]$^+$): 369.1921, found: 369.1923. Melting point: 111-115° C.

4-amino-5-(2-naftyl)-N7-(3'-deoxy-β-D-ribfuranosyl)-pyrrolo[2,3-d]pyrimidine (FH9575)

FH9575 was prepared according to General Procedure 6. FH7429_U (0.150 g, 0.45 mmol) gave rise to FH9575 (0.113 g, 0.299 mmol) as a white solid in 66% yield. $^1$H NMR (300 MHz, DMSO-d$_6$) δ:1.93 (ddd, J=13.2, 6.3, 3.3 Hz, 1H, H-3"), 2.27 (ddd, J=13.2, 8.4, 6.0 Hz, 1H, H-3'), 3.52 (ddd, J=12.0, 5.4, 4.5 Hz, 1H, H-5"), 3.67 (ddd, J=11.7, 5.4, 3.3 Hz, 1H, H-5'), 4.28-4.36 (m, 1H, H-4'), 4.48-4.53 (m, 1H, H-2'), 5.04 (t, J=5.7 Hz, 1H, OH-5'), 5.60 (d, J=4.2 Hz, 1H, OH-2'), 6.16 (d, J=2.7 Hz, 1H, H-1'), 6.40 (br. s, 2H, NH$_2$), 7.49-7.58 (m, 2H, Ph-H-6$_{naph}$, H-7$_{naph}$), 7.65 (dd, J=8.7, 2.1 Hz, 1H, H-3$_{naph}$), 7.66 (s, 1H, H-6), 7.95-7.98 (m, 3H, H-1$_{naph}$, H-5$_{naph}$, H-8$_{naph}$), 8.02 (d, J=8.4 Hz, 1H, H-4$_{naph}$), 8.19 (s, 1H, H-2). $^{13}$C NMR (75 MHz, DMSO-d$_6$) δ: 34.74 (C-3'), 62.84 (C-5'), 74.93 (C-2'), 79.95 (C-4'), 90.18 (C-1'), 100.37 (C-4a), 116.16 (C-5), 121.09 (C-6), 125.88 (C-6$_{naph}$), 126.54 (C-7$_{naph}$), 126.60 (C-1$_{naph}$), 127.04 (C-3$_{naph}$), 127.65 (C$_{naph}$), 127.80 (C$_{naph}$), 128.46 (C-4$_{naph}$), 131.80 (C$_{naph}$), 132.06 (C$_{naph}$), 133.25 (C-8a$_{naph}$), 150.55 (C-7a), 151.77 (C-2), 157.38 (C-4). HRMS (ESI): calculated for C$_{21}$H$_{21}$N$_4$O$_3$ ([M+H]$^+$): 377.1608, found: 377.1614. Melting point: 132/185° C.

4-amino-5-(4-trifluoromethylphenyl)-N7-(3'-deoxy-β-D-ribofuranosyl)-pyrrolo[2,3-d]pyrimidine (FH9576) FH9576 was prepared according to General Procedure 6. FH7429_U (0.150 g, 0.45 mmol) gave rise to FH9576 (0.134 g, 0.340 mmol) as a white solid in 76% yield. $^1$H NMR (300 MHz, DMSO-d$_6$) δ: 1.91 (ddd, J=12.9, 6.3, 3.0 Hz, 1H, H-3"), 2.25 (ddd, J=13.2, 8.7, 6.0 Hz, 1H, H-3'), 3.52 (ddd, J=12.0, 5.7, 4.2 Hz, 1H, H-5"), 3.67 (ddd, J=11.7, 5.4, 3.6 Hz, 1H, H-5'), 4.28-4.35 (m, 1H, H-4'), 4.45-4.50 (m, 1H, H-2'), 5.03 (t, J=5.7 Hz, 1H, OH-5'), 5.59 (d, J=4.5 Hz, 1H, OH-2'), 6.13 (d, J=3.0 Hz, 1H, H-1'), 6.27 (br. s, 2H, NH$_2$), 7.66-7.69 (m, 2H, Ph-H), 7.70 (s, 1H, H-6), 7.80-7.82 (m, 2H, Ph-H), 8.18 (s, 1H, H-2). $^{19}$F-NMR (282 MHz, DMSO-d$_6$) δ: −60.72. $^{13}$C NMR (75 MHz, DMSO-d$_6$) δ: 34.57 (C-3'), 62.72 (C-5'), 74.97 (C-2'), 80.09 (C-4'), 90.21 (C-1'), 99.90 (C-4a), 114.89 (C-5), 121.91 (C-6), 124.54 (q, J=270.23 Hz, 1C, CF$_3$), 125.74 (q, J=3.45, 2C, C-3$_{Phe}$, C-5$_{Phe}$), 126.81 (q, J=32.1 Hz, 1C, C-4$_{Phe}$), 128.79 (2C, C-2$_{Phe}$, C-6$_{Phe}$), 138.76 (C-1$_{Phe}$), 150.76 (C-7a), 151.87 (C-2), 157.35 (C-4). HRMS (ESI): calculated for C$_{18}$H$_{18}$F$_3$N$_4$O$_3$ ([M+H]$^+$): 395.1326, found: 395.1309. Melting point: 223° C.

4-amino-5-(4-trifluoromethoxyphenyl)-N7-(3'-deoxy-β-D-ribofuranosyl)-pyrrolo[2,3-d]pyrimidine (FH9577) FH9577 was prepared according to General Procedure 6. FH7429_U (0.150 g, 0.45 mmol) gave rise to FH9577 (0.152 g, 0.37 mmol) as a white solid in 82% yield. $^1$H NMR (300 MHz, DMSO-d$_6$) δ: 1.91 (ddd, J=12.9, 6.3, 3.0 Hz, 1H, H-3"), 2.24 (ddd, J=13.2, 8.7, 5.7 Hz, 1H, H-3'), 3.51 (ddd, J=12.0, 5.7, 4.2 Hz, 1H, H-5"), 3.66 (ddd, J=11.7, 5.4, 3.6 Hz, 1H, H-5'), 4.27-4.34 (m, 1H, H-4'), 4.44-4.49 (m, 1H, H-2'), 5.01 (t, J=5.7 Hz, 1H, OH-5'), 5.58 (d, J=4.5 Hz, 1H, OH-2'), 6.13 (d, J=2.4 Hz, 1H, H-1'), 6.20 (br. s, 2H, NH$_2$), 7.44-7.47 (m, 2H, Ph-H), 7.55-7.59 (m, 2H, Ph-H), 7.60 (s, 1H, H-6), 8.17 (s, 1H, H-2). $^{19}$F-NMR (282 MHz, DMSO-d$_6$) δ: −56.72. $^{13}$C NMR (75 MHz, DMSO-d$_6$) δ: 34.66 (C-3'), 62.81 (C-5'), 74.96 (C-2'), 80.03 (C-4'), 90.16 (C-1'), 100.10 (C-4a), 114.80 (C-5), 120.19 (q, J=254.2 Hz, 1C, OCF$_3$), 121.29 (C-6), 121.53 (2C, Ph), 130.09 (2C, Ph), 133.95 (C-1$_{Phe}$), 147.22 (d, J=2.3 Hz, 1C, C-4$_{Phe}$), 150.53 (C-7a), 151.78 (C-2), 157.32 (C-4). HRMS (ESI): calculated for C$_{18}$H$_{18}$F$_3$N$_4$O$_4$ ([M+H]$^+$): 411.1275, found: 411.1262. Melting point: 194° C.

4-amino-5-(2,4-dichlorophenyl)-N7-(3'-deoxy-β-D-ribofuranosyl)-pyrrolo[2,3-d]pyrimidine (FH9581) FH9581 was prepared according to General Procedure 6. FH7429_U (0.150 g, 0.45 mmol) gave rise to FH9581 (0.056 g, 0.142 mmol) as a white solid in 31% yield. $^1$H NMR (300 MHz, DMSO-d$_6$) δ: 1.90 (ddd, J=13.2, 6.3, 3.3 Hz, 1H, H-3"), 2.21 (ddd, J=13.2, 8.4, 6.0 Hz, 1H, H-3'), 3.49 (ddd, J=12.3, 5.1, 4.5 Hz, 1H, H-5"), 3.64 (ddd, J=12.0, 5.1, 3.6 Hz, 1H, H-5'), 4.26-4.34 (m, 1H, H-4'), 4.42-4.48 (m, 1H, H-2'), 5.00 (t, J=5.4 Hz, 1H, OH-5'), 5.59 (d, J=4.5 Hz, 1H, OH-2'), 6.07 (br. s, 2H, NH$_2$), 6.10 (d, J=2.4 Hz, 1H, H-1'), 7.42 (d, J=8.1 Hz, 1H, Ph-H-6), 7.49 (dd, J=8.4, 2.1 Hz, 1H, Ph-H-5), 7.53 (s, 1H, H-6), 7.72 (d, J=2.1 Hz, 1H, Ph-H-3), 8.14 (s, 1H, H-2). $^{13}$C NMR (75 MHz, DMSO-d$_6$) δ:34.65 (C-3'), 62.80 (C-5'), 74.97 (C-4'), 80.06 (C-2'), 90.35 (C-1'), 101.40 (C-4a), 111.19 (C-5), 121.84 (C-6), 127.51 (C-5$_{Phe}$), 129.31 (C-3$_{Phe}$), 132.03 (C-Phe), 132.85 (C-Phe), 133.52 (C-6$_{Phe}$), 134.12 (C-Phe), 149.82 (C-7a), 151.79 (C-2), 157.17 (C-4). HRMS (ESI): calculated for C$_{17}$H$_{17}$Cl$_2$N$_4$O$_3$ ([M+H]$^+$): 395.0672, found: 395.0673. Melting point: 136° C.

4-amino-5-(4-nitrophenyl)-N7-(3'-deoxy-β-D-ribofuranosyl)-pyrrolo[2,3-d]pyrimidine (FH9582)

FH9582 was prepared according to General Procedure 6. FH7429_U (0.150 g, 0.45 mmol) gave rise to FH9582 (0.109 g, 0.293 mmol) as a yellow solid in 65% yield. 1H NMR (300 MHz, DMSO-d$_6$) δ: 1.91 (ddd, J=12.9, 6.3, 3.0 Hz, 1H, H-3"), 2.26 (ddd, J=13.2, 8.7, 6.0 Hz, 1H, H-3'), 3.52 (ddd, J=12.0, 5.7, 4.2 Hz, 1H, H-5"), 3.68 (ddd, J=12.0, 5.7, 3.6 Hz, 1H, H-5'), 4.29-4.36 (m, 1H, H-4'), 4.45-4.50 (m, 1H, H-2'), 5.04 (t, J=5.7 Hz, 1H, OH-5'), 5.61 (d, J=4.5 Hz, 1H, OH-2'), 6.14 (d, J=2.4 Hz, 1H, H-1'), 6.39 (br. s, 2H, NH$_2$), 7.69-7.74 (m, 2H, Ph-H (H-2, H-6)), 7.81 (s, 1H, H-6), 8.20 (s, 1H, H-2), 8.29-8.32 (m, 2H, Ph-H (H-3, H-5)). $^{13}$C NMR (75 MHz, DMSO-d$_6$) δ: 34.45 (C-3'), 62.63 (C-5'), 74.98 (C-2'), 80.17 (C-4'), 90.25 (C-1'), 99.73 (C-4a 114.51 (C-5), 122.70 (C-6), 124.09 (2 C-Ph$_{meta}$), 128.93 (2 C-Ph$_{ortho}$), 141.66 (C-Ph$_{ipso}$), 145.66 (C-Ph$_{para}$), 151.04 (C-7a), 152.03 (C-2), 157.39 (C-4). HRMS (ESI): calculated for C$_{17}$H$_{18}$N$_5$O$_5$ ([M+H]$^+$): 372.1302, found: 372.1299. Melting point: 254° C. (decomposed).

4-amino-5-(3-methylphenyl)-N7-(3'-deoxy-β-D-ribofuranosyl)-pyrrolo[2,3-d]pyrimidine (FH10639)

FH10639 was prepared according to General Procedure 6. FH7429_U (0.135 g, 0.4 mmol) gave rise to FH10639 (0.104 g, 0.306 mmol) as a white solid in 76% yield. $^1$H NMR (300 MHz, DMSO-d$_6$) δ: 1.91 (ddd, J=12.9, 6.3, 3.3 Hz, 1H, H-3"), 2.24 (ddd, J=13.2, 8.4, 6.0 Hz, 1H, H-3'), 2.37 (s, 3H, CH$_3$), 3.50 (ddd, J=12.0, 5.7, 4.5 Hz, 1H, H-5"), 3.65 (ddd, J=12.0, 5.4, 3.6 Hz, 1H, H-5'), 4.26-4.33 (m, 1H, H-4'), 4.40-4.49 (m, 1H, H-2'), 5.02 (t, J=5.7 Hz, 1H, OH-5'), 5.57 (d, J=4.5 Hz, 1H, OH-2'), 6.10 (br. s, 2H, NH$_2$), 6.12 (d, J=2.7 Hz, 1H, H-1'), 7.18 (d, J=7.5 Hz, 1H, Ph-H), 7.25 (d, J=7.5 Hz, 1H, Ph-H), 7.29 (s, 1H, H-Phenyl (H-2)), 7.37 (t, J=7.5 Hz, 1H, H-Phenyl (H-5)), 7.52 (s, 1H, H-6), 8.15 (s 1H, H-2). $^{13}$C NMR (75 MHz, DMSO-d$_6$) δ: 21.11 (CH$_3$), 34.71 (C-3'), 62.81 (C-5'), 74.87 (C-2'), 79.87 (C-4'), 90.09 (C-1'), 100.22 (C-4a), 116.16 (C-5), 120.52 (C-6), 125.48, 127.50, 128.81 (C-5$_{Phe}$), 129.12 (C-2$_{Phe}$), 134.49, 138.14, 150.30 (C-7a), 151.65 (C-2), 157.22 (C-4). HRMS (ESI): calculated for C$_{18}$H$_{21}$N$_4$O$_3$ ([M+H]$^+$): 341.1608, found: 341.1619. Melting point: 123° C.

4-amino-5-(3-trifluoromethylphenyl)-N7-(3'-deoxy-β-D-ribofuranosyl)-pyrrolo[2,3-d]pyrimidine (FH10640) FH10640 was prepared according to General Procedure 6. FH7429_U (0.135 g, 0.4 mmol) gave rise to FH10640 (0.136 g, 0.345 mmol) as a white solid in 86% yield. $^1$H NMR (300 MHz, DMSO-d$_6$) δ: 1.91 (ddd, J=13.2, 6.3, 3.3 Hz, 1H, H-3"), 2.26 (ddd, J=12.9, 8.7, 6.0 Hz, 1H, H-3'), 3.51 (ddd, J=12.0, 5.7, 4.2 Hz, 1H, H-5"), 3.66 (ddd, J=12.0, 5.4, 3.6 Hz, 1H, H-5'), 4.27-4.34 (m, 1H, H-4'), 4.46-4.51 (m, 1H, H-2'), 5.02 (t, J=5.7 Hz, 1H, OH-5'), 5.58 (d, J=4.5 Hz, 1H, OH-2'), 6.14 (d, J=2.7 Hz, 1H, H-1'), 6.24 (br. s, 2H, NH$_2$), 7.67-7.78 (m, 4H, Ph-H), 7.70 (s, 1H, H-6), 8.18 (s, 1H, H-2). $^{19}$F-NMR (282 MHz, DMSO-d$_6$) δ: −61.07. $^{13}$C NMR (75 MHz, DMSO-d$_6$) δ: 34.65 (C-3'), 62.73 (C-5'), 74.90 (C-2'), 80.00 (C-4'), 90.12 (C-1'), 99.98 (C-4a), 114.74 (C-5), 121.68 (C-6), 123.10 (q, J=3.45 Hz, 1C, C-Phe), 124.25 (d, J=271.28 Hz, 1C, CF$_3$), 124.62 (q, J=3.45 Hz, 1C, C-Phe), 129.52 (q, J=32.03 Hz, 1C, C-3$_{Phe}$), 129.86 (C-Phe), 132.20 (C-Phe), 135.53 (C-1$_{Phe}$), 150.70 (C-7a), 151.81 (C-2), 157.37 (C-4). HRMS (ESI): calculated for C$_{18}$H$_{18}$F$_3$N$_4$O$_3$ ([M+H]$^+$): 395.1326, found: 395.1322. Melting point: 125° C.

4-amino-5-(3-chlorophenyl)-N7-(3'-deoxy-β-D-ribofuranosyl)-pyrrolo[2,3-d]pyrimidine (FH10641)

FH10641 was prepared according to General Procedure 6. FH7429_U (0.135 g, 0.4 mmol) gave rise to FH10641 (0.081 g, 0.224 mmol) as a white solid in 56% yield. $^1$H NMR (300 MHz, DMSO-d$_6$) δ: 1.91 (ddd, J=13.2, 6.3, 3.3 Hz, 1H, H-3"), 2.25 (ddd, J=13.2, 8.7, 6.0 Hz, 1H, H-3'), 3.51 (ddd, J=11.7, 5.7, 4.2 Hz, 1H, H-5"), 3.66 (ddd, J=12.0, 5.4, 3.6 Hz, 1H, H-5'), 4.26-4.34 (m, 1H, H-4'), 4.44-4.49 (m, 1H, H-2'), 5.02 (t, J=5.7 Hz, 1H, OH-5'), 5.58 (d, J=4.5 Hz, 1H, OH-2'), 6.12 (d, J=2.7 Hz, 1H, H-1'), 6.21 (br. s, 2H, NH$_2$), 7.38-7.44 (m, 2H, Ph-H), 7.48 (d, J=7.5 Hz, 1H, Ph-H), 7.52 (t, J=1.5 Hz, 1H, Ph-H), 7.64 (s, 1H, H-6), 8.17 (s, 1H, H-2). $^{13}$C NMR (75 MHz, DMSO-d$_6$) δ: 34.66 (C-3'), 62.76 (C-5'), 74.93 (C-2'), 80.01 (C-4'), 90.12 (C-1'), 99.96 (C-4a), 114.75 (C-5), 121.45 (C-6), 126.46 (C$_{Phe}$), 126.95 (C$_{Phe}$), 127.96 (O$_{Phe}$), 130.64 (O$_{Phe}$), 133.47 (O$_{Phe}$), 136.69 (O$_{Phe}$), 150.58 (C-7a), 151.78 (C-2), 157.29 (C-4). HRMS (ESI): calculated for C$_{17}$H$_{18}$ClN$_4$O$_3$ ([M+H]$^+$): 361.1062, found: 361.1063. Melting point: 130° C./190° C.

4-amino-5-(3,5-dichlorophenyl)-N7-(3'-deoxy-β-D-ribofuranosyl)-pyrrolo[2,3-d]pyrimidine (FH10642) FH10642 was prepared according to General Procedure 6. FH7429_U (0.135 g, 0.4 mmol) gave rise to FH10642 (0.062 g, 0.157 mmol) as a white solid in 39% yield. $^1$H NMR (300 MHz, DMSO-d$_6$) δ: 1.90 (ddd, J=13.2, 6.3, 3.3 Hz, 1H, H-3"), 2.25 (ddd, J=13.2, 9.0, 5.7 Hz, 1H, H-3'), 3.51 (ddd, J=11.7, 5.7, 4.5 Hz, 1H, H-5"), 3.66 (ddd, J=11.7, 5.7, 3.6 Hz, 1H, H-5'), 4.26-4.34 (m, 1H, H-4'), 4.43-4.48 (m, 1H, H-2'), 5.01 (t, J=5.7 Hz, 1H, OH-5'), 5.58 (d, J=4.5 Hz, 1H, OH-2'), 6.12 (d, J=2.4 Hz, 1H, H-1'), 6.37 (br. s, 2H, NH$_2$), 7.47 (d, J=1.8 Hz, 2H, H-Phenyl (H-2, H-6)), 7.53 (t, J=2.1 Hz, 1H, H-Phenyl (H-4)), 7.71 (s, 1H, H-6), 8.17 (s, 1H, H-2). 13C NMR (75 MHz, DMSO-d$_6$) δ: 34.66 (C-3'), 62.75 (C-5'), 74.96 (C-2'), 80.10 (C-4'), 90.09 (C-1'), 99.73 (C-4a), 113.65 (C-5), 122.16 (C-6), 125.79 (C-4$_{Phe}$), 126.76 (20, C-2$_{Phe}$, C-6$_{Phe}$), 134.20 (20, C-3$_{Phe}$, C-5$_{Phe}$), 138.00 (0-1$_{Phe}$), 150.76 (C-7a), 151.90 (C-2), 157.35 (C-4). HRMS (ESI): calculated for C$_7$H$_{17}$Cl$_2$N$_4$O$_3$ ([M+H]$^+$): 395.0672, found: 395.0663. Melting point: 211° C.

4-amino-5-(3-chloro-4-methylphenyl)-N7-(3'-deoxy-β-D-ribofuranosyl)-pyrrolo[2,3-d]pyrimidine (FH10644) FH10644 was prepared according to General Procedure 6. FH7429_U (0.135 g, 0.4 mmol) gave rise to FH10644 (0.113 g, 0.301 mmol) as a white solid in 75% yield. $^1$H NMR (300 MHz, DMSO-d$_6$) δ: 1.91 (ddd, J=13.2, 6.3, 3.3 Hz, 1H, H-3"), 2.25 (ddd, J=12.9, 8.7, 6.0 Hz, 1H, H-3'), 2.37 (s, 3H, CH$_3$), 3.51 (ddd, J=12.0, 5.7, 4.5 Hz, 1H, H-5"), 3.66 (ddd, J=12.0, 5.4, 3.6 Hz, 1H, H-5'), 4.26-4.33 (m, 1H, H-4'), 4.43-4.49 (m, 1H, H-2'), 5.01 (t, J=5.7 Hz, 1H, OH-5'), 5.57 (d, J=4.5 Hz, 1H, OH-2'), 6.12 (d, J=2.7 Hz, 1H, H-1'), 6.18 (br. s, 2H, NH$_2$), 7.32 (dd, J=7.8, 1.8 Hz, 1H, H-6$_{Phe}$), 7.44 (d, J=8.1 Hz, 1H, H-5$_{Phe}$), 7.50 (d, J=1.8 Hz, 1H, H-2$_{Phe}$), 7.59 (s, 1H, H-6), 8.16 (s, 1H, H-2). $^{13}$C NMR (75 MHz, DMSO-d$_6$) δ:19.26 (CH$_3$), 34.66 (C-3'), 62.76 (C-5'), 74.90 (C-2'), 79.95 (C-4'), 90.09 (C-1'), 100.04 (C-4a), 114.63 (C-5), 121.06 (C-6), 127.02 (C$_{Phe}$), 128.38 (C$_{Phe}$), 131.59 (2C$_{Phe}$), 133.60 (C$_{Phe}$), 134.05 (C$_{Phe}$), 150.45 (C-7a), 151.72 (C-2), 157.26 (C-4). HRMS (ESI): calculated for C$_{18}$H$_{20}$ClN$_4$O$_3$ ([M+H]$^+$): 375.1218, found: 375.1213. Melting point: 135° C.

4-amino-5-(3-chloro-4-methoxyphenyl)-N7-(3'-deoxy-β-D-ribofuranosyl-pyrrolo[2,3-d]pyrimidine (FH10645) FH10645 was prepared according to General Procedure 6. FH7429_U (0.135 g, 0.4 mmol) gave rise to FH10645 (0.089 g, 0.228 mmol) as a white solid in 57% yield. $^1$H NMR (300 MHz, DMSO-d$_6$) δ: 1.91 (ddd, J=12.9, 6.6, 3.3 Hz, 1H, H-3"), 2.25 (ddd, J=13.2, 8.4, 6.0 Hz, 1H, H-3'), 3.50 (ddd, J=11.7, 5.7, 4.2 Hz, 1H, H-5"), 3.65 (ddd, J=12.0, 5.7, 3.6 Hz, 1H, H-5'), 3.90 (s, 3H, OCH$_3$), 4.25-4.33 (m, 1H, H-4'), 4.43-4.48 (m, 1H, H-2'), 5.01 (t, J=5.7 Hz, 1H, OH-5'), 5.56 (d, J=4.2 Hz, 1H, OH-2'), 6.11 (d, J=2.7 Hz, 1H, H-1'), 6.16 (br. s, 2H, NH$_2$), 7.25 (d, J=8.4 Hz, 1H, H-5$_{Phe}$), 7.38 (dd, J=8.4, 2.1 Hz, 1H, H-6$_{Phe}$), 7.50 (d, J=2.1 Hz, 1H, H-2$_{Phe}$), 7.52 (s, 1H, H-6), 8.15 (s, 1H, H-2). $^{13}$C NMR (75 MHz, DMSO-d$_6$) δ: 34.74 (C-3'), 56.18 (OCH$_3$), 62.81 (C-5'), 74.90 (C-2'), 79.92 (C-4'), 90.07 (C-1'), 100.21 (C-4a), 113.23 (C-5$_{Phe}$), 114.55 (C-5), 120.64 (C$_{Phe}$), 121.32 (C-6), 127.83 (C$_{Phe}$), 128.80 (C-6$_{Phe}$), 129.66 (C-2$_{Phe}$), 150.32 (C-7a), 151.69 (C-2), 153.48 (OCH$_3$), 157.29 (C-4). HRMS (ESI): calculated for C$_{18}$H$_{20}$ClN$_4$O$_4$ ([M+H]$^+$): 391.1168, found: 391.1163. Melting point: 249° C. (decomposed).

4-amino-5-(4-ethylphenyl)-N7-(3'-deoxy-β-D-ribofuranosyl)-pyrrolo[2,3-d]pyrimidine (FH10647)

FH10647 was prepared according to General Procedure 6. FH7429_U (0.135 g, 0.4 mmol) gave rise to FH10647 (0.101 g, 0.285 mmol) as a white solid in 71% yield. $^1$H NMR (300 MHz, DMSO-d$_6$) δ: 1.22 (t, J=7.8 Hz, 3H, CH$_3$), 1.91 (12.9, 6.3, 3.3 Hz, 1H, H-3"), 2.24 (ddd, J=12.9, 8.7, 6.0 Hz, 1H, H-3'), 2.66 (q, J=7.8 Hz, 2H, CH$_2$), 3.50 (ddd, J=12.0, 5.7, 4.5 Hz, 1H, H-5"), 3.65 (ddd, J=12.0, 5.4, 3.3 Hz, 1H, H-5'), 4.26-4.33 (m, 1H, H-4'), 4.44-4.49 (m, 1H, H-2'), 5.02 (t, J=5.7 Hz, 1H, OH-5'), 5.57 (d, J=4.5 Hz, 1H, OH-2'), 6.08 (br. s, 2H, NH$_2$), 6.12 (d, J=2.4 Hz, 1H, H-1'), 7.30-7.33 (m, 2H, Ph-H), 7.38-7.40 (m, 2H, Ph-H), 7.50 (s, 1H, H-6), 8.15 (s, 1H, H-2). $^{13}$C NMR (75 MHz, DMSO-d$_6$) δ:15.57 (CH$_3$), 27.84 (CH$_2$), 34.69 (C-3'), 62.79 (C-5'), 74.88 (C-2'), 79.89 (C-4'), 90.12 (C-1'), 100.30 (C-4a), 116.00 (C-5), 120.40 (C-6), 128.35 (2C$_{Phe}$), 128.40 (2C$_{Phe}$), 131.88 (C$_{Phe}$), 142.36 (C$_{Phe}$), 150.26 (C-7a), 151.60 (C-2), 157.23 (C-4). HRMS (ESI): calculated for C$_{19}$H$_{23}$N$_4$O$_3$ ([M+H]$^+$): 355.1765, found: 355.1772. Melting point: 114° C.

4-amino-5-(3-methyl-4-chlorophenyl)-N7-(3'-deoxy-β-D-ribofuranosyl)-pyrrolo[2,3-d]pyrimidine (FH10648) FH10648 was prepared according to General Procedure 6. FH7429_U (0.135 g, 0.4 mmol) gave rise to FH10648 (0.092 g, 0.245 mmol) as a white solid in 61% yield. $^1$H NMR (300 MHz, DMSO-d$_6$) δ: 1.91 (ddd, J=12.9, 6.3, 3.3 Hz, 1H, H-3"), 2.24 (ddd, J=13.2, 8.4, 6.0 Hz, 1H, H-3'), 2.39 (s, 3H, CH$_3$), 3.51 (ddd, J=12.0, 5.7, 4.5 Hz, 1H, H-5"), 3.65 (ddd, J=12.0, 5.7, 3.6 Hz, 1H, H-5'), 4.26-4.34 (m, 1H, H-4'), 4.43-4.49 (m, 1H, H-2'), 5.04 (t, J=5.7 Hz, 1H, OH-5'), 5.57 (d, J=4.5 Hz, 1H, OH-2'), 6.12 (d, J=2.7 Hz, 1H, H-1'), 6.18 (br. s, 2H, NH$_2$), 7.29 (dd, J=8.1, 2.4 Hz, 1H, H-6$_{Phe}$), 7.44 (d, J=1.8 Hz, 1H, H-2$_{Phe}$), 7.49 (d, J=8.1 Hz, 1H, H-5$_{Phe}$), 7.55 (s, 1H, H-6), 8.16 (s, 1H, H-2). $^{13}$C NMR (75 MHz, DMSO-d$_6$) δ:19.72 (CH$_3$), 34.68 (C-3'), 62.78 (C-5'), 74.88 (C-2'), 79.92 (C-4'), 90.10 (C-1'), 100.07 (C-4a), 115.03 (C-5), 120.86 (C-6), 127.47 (C$_{Phe}$), 129.22 (C$_{Phe}$), 131.10 (C$_{Phe}$), 131.74 (C$_{Phe}$), 133.45 (C$_{Phe}$), 135.85 (C$_{Phe}$), 150.44 (C-7a), 151.71 (C-2), 157.25 (C-4). HRMS (ESI): calculated for C$_{18}$H$_{20}$ClN$_4$O$_3$ ([M+H]$^+$): 375.1218, found: 375.1212. Melting point: 125° C.

4-amino-5-(3-methoxy-4-chlorophenyl)-N7-(3'-deoxy-β-D-ribofuranosyl)-pyrrolo[2,3-d]pyrimidine (FH10649) FH10649 was prepared according to General Procedure 6. FH7429_U (0.135 g, 0.4 mmol) gave rise to FH10649 (0.122 g, 0.312 mmol) as a white solid in 78% yield. $^1$H NMR (300 MHz, DMSO-d$_6$) δ: 1.91 (ddd, J=12.9, 6.3, 3.0 Hz, 1H, H-3"), 2.25 (ddd, J=12.9, 8.4, 6.0 Hz, 1H, H-3'), 3.51 (ddd, J=12.0, 5.7, 4.2 Hz, 1H, H-5"), 3.67 (ddd, J=12.0, 5.4, 3.6 Hz, 1H, H-5'), 3.91 (s, 3H, OCH$_3$), 4.27-4.34 (m, 1H, H-4'), 4.44-4.49 (m, 1H, H-2'), 5.03 (t, J=5.7 Hz, 1H, OH-5'), 5.58 (d, J=4.5 Hz, 1H, OH-2'), 6.12 (d, J=2.7 Hz, 1H, H-1'), 6.25 (br. s, 2H, NH$_2$), 7.04 (dd, J=8.1, 1.8 Hz, 1H, H-6$_{Phe}$), 7.17 (d, J=1.8 Hz, 1H, H-2$_{Phe}$), 7.49 (d, J=8.1 Hz, 1H, H-5$_{Phe}$), 7.62 (s, 1H, H-6), 8.16 (s, 1H, H-2). $^{13}$C NMR (75 MHz, DMSO-d$_6$) δ: 34.63 (C-3'), 55.99 (OCH$_3$), 62.72 (C-5'), 74.88 (C-2'), 79.95 (C-4'), 90.13 (C-1'), 100.02 (C-4a), 112.87, 115.32, 119.41, 121.00, 121.09, 130.09, 134.76, 150.45 (C-7a), 151.72 (C-2), 154.58 (C—OCH$_3$), 157.26 (C-4). HRMS (ESI): calculated for C$_{18}$H$_{20}$ClN$_{404}$ ([M+H]$^+$): 391.1168, found: 391.1163. Melting point: 208° C.

4-amino-5-(3,4-dimethylphenyl)-N7-(3'-deoxy-β-D-ribofuranosyl)-pyrrolo[2,3-d]pyrimidine (FH10653) FH10653 was prepared according to General Procedure 6. FH7429_U (0.135 g, 0.4 mmol) gave rise to FH10653 (0.103 g, 0.291 mmol) as a white solid in 73% yield. $^1$H NMR (300 MHz, DMSO-d$_6$) δ: 1.91 (ddd, J=12.9, 6.3, 3.3 Hz, 1H, H-3"), 2.19-2.28 (m, 1H, H-3'), 2.27 (s, 3H, CH$_3$), 2.28 (s, 3H, CH$_3$), 3.50 (ddd, J=12.0, 5.4, 4.5 Hz, 1H, H-5"), 3.65 (ddd, J=12.0, 5.4, 3.6 Hz, 1H, H-5'), 4.25-4.33 (m, 1H, H-4'), 4.44-4.49 (m, 1H, H-2'), 5.01 (t, J=5.7 Hz, 1H, OH-5'), 5.56 (d, J=4.5 Hz, 1H, OH-2'), 6.06 (br. s, 2H, NH$_2$), 6.11 (d, J=2.7 Hz, 1H, H-1'), 7.17 (dd, J=7.5, 1.5 Hz, 1H, H-2$_{Phe}$), 7.24 (d, J=6.9 Hz, 2H, H-5$_{Phe}$, H-6$_{Phe}$), 7.46 (s, 1H, H-6), 8.14 (s, 1H, H-2). $^{13}$C NMR (75 MHz, DMSO-d$_6$) δ:19.05 (CH$_3$), 19.49 (CH$_3$), 34.74 (C-3'), 62.82 (C-5'), 74.84 (C-2'), 79.83 (C-4'), 90.09 (C-1'), 100.33 (C-4a), 116.10 (C-5), 120.19 (C-6), 125.80 (C$_{Phe}$), 129.63 (C$_{Phe}$), 129.70 (C$_{Phe}$), 131.99 (C$_{Phe}$), 134.85 (C$_{Phe}$), 136.78 (C$_{Phe}$), 150.19 (C-7a), 151.60 (C-2), 157.23 (C-4). HRMS (ESI): calculated for C$_{19}$H$_{23}$N$_4$O$_3$ ([M+H]$^+$): 355.1765, found: 355.1767. Melting point: 125° C.

4-amino-5-(4-fluorophenyl)-N7-(3'-deoxy-β-D-ribofuranosyl)-pyrrolo[2,3-d]pyrimidine (FH10680)

FH10680 was prepared according to general procedure 6. FH7429_U (0.135 g, 0.4 mmol) gave rise to FH10680 (0.096 g, 0.247 mmol) as a white solid. Yield=69%. Melting point: 186-187° C. $^1$H NMR (300 MHz, DMSO-d$_6$) δ: 1.91 (ddd, J=12.9, 6.3, 3.3 Hz, 1H, H-3"), 2.24 (ddd, J=13.2, 8.7, 4.2 Hz, 1H, H-3'), 3.50 (ddd, J=12.0, 5.7, 4.5 Hz, 1H, H-5"), 3.65 (ddd, J=12.0, 5.4, 3.6 Hz, 1H, H-5'), 4.26-4.33 (m, 1H, H-4'), 4.43-4.49 (m, 1H, H-2'), 5.01 (t, J=5.7 Hz, 1H, OH-5'), 5.57 (d, J=4.2 Hz, 1H, OH-2'), 6.11 (d, J=2.7 Hz, 1H, H-1'), 6.14 (br. s, 2H, NH$_2$), 7.26-7.34 (m. 2H, H-3$_{Phe}$, H-5$_{Phe}$), 7.45-7.51 (m, 2H, H-2$_{Phe}$, H-6$_{Phe}$), 7.53 (s, 1H, H-6), 8.15 (s, 1H, H-2). $^{19}$F-NMR (282 MHz, DMSO-d$_6$) δ: −116.18−−116.08 (m, 1F). $^{13}$C NMR (75 MHz, DMSO-d$_6$) δ: 34.7 (C-3'), 62.8 (C-5'), 74.9 (C-2'), 79.9 (C-4'), 90.1 (C-1'), 100.2 (C-4a), 115.0 (C-5), 115.7 (d, J=21.8 Hz, 2C, C-3$_{Phe}$, C-5$_{Phe}$), 120.7 (C-6), 130.3 (d, J=8.3 Hz, 2C, C-2$_{Phe}$, C-6$_{Phe}$), 130.9 (C-1$_{Phe}$), 150.3 (C-7a), 151.7 (C-2), 157.3 (C-4), 161.4 (d, J=241.5 Hz, 1C, C-4$_{Phe}$). HRMS (ESI): calculated for C$_{17}$H$_{18}$FN$_4$O$_3$ ([M+H]$^+$): 345.1357, found: 345.1363.

4-amino-5-(3-chloro-4-fluorophenyl)-N7-(3'-deoxy-β-D-ribofuranosyl)-pyrrolo[2,3-d]pyrimidine (FH10681) FH10681 was prepared according to general procedure 6. FH7429_U (0.135 g, 0.4 mmol) gave rise to FH10681 (0.098 g, 0.259 mmol) as a white solid. Yield=65%. Melting point: 178° C. $^1$H NMR (300 MHz, DMSO-d$_6$) δ:1.91 (ddd, J=12.9, 6.3, 3.3 Hz, 1H, H-3"), 2.25 (ddd, J=13.2, 8.4, 6.0 Hz, 1H, H-3'), 3.51 (ddd, J=11.7, 5.7, 4.8 Hz, 1H, H-5"), 3.65 (ddd, J=12.0, 5.4, 3.9 Hz, 1H, H-5'), 4.26 (m, 1H, H-4'), 4.43-4.48 (m, 1H, H-2'), 5.00 (t, J=5.7 Hz, 1H, OH-5'), 5.57 (d, J=4.2 Hz, 1H, OH-2'), 6.12 (d, J=2.4 Hz, 1H, H-1'), 6.26 (br. s, 2H, NH$_2$), 7.42 (ddd, J=8.4, 5.1, 2.1 Hz, 1H, H-6$_{Phe}$), 7.49 (q, J=9.0 Hz, 1H, H-5$_{Phe}$), 7.60 (s, 1H, H-6), 7.63 (dd, J=7.2, 2.1 Hz, 1H, H-2$_{Phe}$), 8.16 (s, 1H, H-2). $^{19}$F-NMR (282 MHz, DMSO-d$_6$) δ: −119.95−−119.87 (m, 1F). $^{13}$C NMR (75 MHz, DMSO-d$_6$) δ: 34.7 (C-3'), 62.8 (C-5'), 74.9 (C-2'), 80.0 (C-4'), 90.1 (C-1'), 100.0 (C-4a), 114.0 (C-5), 117.1 (d, J=21.8 Hz, 1C, C-5$_{Phe}$), 119.7 (d, J=18.0 Hz, 1C, C-3$_{Phe}$), 121.3 (C-6), 128.9 (d, J=6.8 Hz, 1C, C-6$_{Phe}$), 130.2 (C-2$_{Phe}$), 132.3 (d, J=3.8 Hz, 1C, C-1$_{Phe}$), 150.5 (C-7a), 151.8 (C-2), 156.3 (d, J=245.3 Hz, 1C, C-4$_{Phe}$), 157.3 (C-4). HRMS (ESI): calculated for C$_{17}$H$_{17}$ClFN$_4$O$_3$ ([M+H]$^+$): 379.0968, found: 379.0974.

4-amino-5-(3,4-difluorophenyl)-N7-(3'-deoxy-β-D-ribofuranosyl)-pyrrolo[2,3-d]pyrimidine (FH10682) FH10682 was prepared according to general procedure 6. FH7429_U (0.135 g, 0.4 mmol) gave rise to FH10682 (0.11 g, 0.304 mmol) as a white solid. Yield=76%.

Melting point: 218° C. ¹H NMR (300 MHz, DMSO-d₆) δ:1.91 (ddd, J=12.9, 6.3, 3.3 Hz, 1H, H-3"), 2.24 (ddd, J=13.2, 9.0, 6.0 Hz, 1H, H-3'), 3.51 (ddd, J=12.0, 6.0, 4.5 Hz, 1H, H-5"), 3.66 (ddd, J=12.0, 5.4, 3.6 Hz, 1H, H-5"), 4.26-4.34 (m, 1H, H-4'), 4.43-4.48 (m, 1H, H-2'), 5.01 (t, J=5.7 Hz, 1H, OH-5'), 5.58 (d, J=4.5 Hz, 1H, OH-2'), 6.12 (d, J=2.4 Hz, 1H, H-1'), 6.27 (br. s, 2H, NH₂), 7.24-7.30 (m, 1H, H$_{Phe}$), 7.43-7.56 (m, 2H, H$_{Phe}$, H$_{Phe}$), 7.59 (s, 1H, H-6), 8.16 (s, 1H, H-2). ¹⁹F-NMR (282 MHz, DMSO-d₆) δ: −142.14–−141.97 (m, 1F), −138.31–−138.16 (m, 1F). ¹³C NMR (75 MHz, DMSO-d₆) δ: 34.7 (C-3'), 62.8 (C-5'), 74.9 (C-2'), 80.0 (C-4'), 90.1 (C-1'), 100.0 (C-4a), 114.2 (C-5), 117.2-117.9 (m, 2C, C$_{Phe}$), 121.3 (C-6), 125.0-125.2 (m, 1C, C$_{Phe}$), 132.1 (m, 1C, C-1$_{Phe}$), 147.4 (dd, J=65.3, 12.8 Hz, 1C, C$_{Phe}$), 150.5 (C-7a), 150.7 (dd, J=66.8, 12.8 Hz, 1C, C$_{Phe}$), 151.8 (C-2), 157.3 (C-4). HRMS (ESI): calculated for C₁₇H₁₇F₂N₄O₃ ([M+H]⁺): 363.1263, found: 363.1277.

4-amino-5-(3'-fluoro-4-chlorophenyl)-N7-(3'-deoxy-β-D-ribofuranosyl)-pyrrolo[2,3-d]pyrimidine (FH10683) FH10683 was prepared according to general procedure 6. FH7429_U (0.135 g, 0.4 mmol) gave rise to FH10683 (0.068 g, 0.18 mmol) as a white solid. Yield=45%. Melting point: 206° C. ¹H NMR (300 MHz, DMSO-d₆) δ: 1.91 (ddd, J=12.9, 6.3, 3.3 Hz, 1H, H-3"), 2.24 (ddd, J=13.2, 8.7, 6.0 Hz, 1H, H-3'), 3.51 (ddd, J=12.0, 5.7, 4.5 Hz, 1H, H-5"), 3.66 (ddd, J=11.7, 5.4, 3.6 Hz, 1H, H-5'), 4.27-4.34 (m, 1H, H-4'), 4.43-4.48 (m, 1H, H-2'), 5.01 (t, J=5.7 Hz, 1H, OH-5'), 5.58 (d, J=4.5 Hz, 1H, OH-2'), 6.12 (d, J=2.4 Hz, 1H, H-1'), 6.33 (br. s, 2H, NH₂), 7.30 (dd, J=8.4, 2.1 Hz, 1H, H-5$_{Phe}$), 7.45 (dd, J=10.5, 2.1 Hz, 1H, H-2$_{Phe}$), 7.65 (s, 1H, H-6), 7.65 (app. d, J=16.2 Hz, 1H, H-6$_{Phe}$), 8.17 (s, 1H, H-2). ¹⁹F-NMR (282 MHz, DMSO-d₆) δ: −115.99–−115.93 (m, 1F). ¹³C NMR (75 MHz, DMSO-d₆) δ: 34.6 (C-3'), 62.7 (C-5'), 74.9 (C-2'), 80.1 (C-1'), 90.1 (C-1'), 99.8 (C-4a), 114.2 (C-5), 116.5 (d, J=20.3 Hz, 1C, C-2$_{Phe}$), 117.47 (d, 1C, J=16.5 Hz, 1C, C-4$_{Phe}$), 121.6 (C-6), 125.4 (d, J=2.3 Hz, 1C, C-5$_{Phe}$), 130.82 (C-6$_{Phe}$), 135.7 (d, J=7.5 Hz, 1C, C-1$_{Phe}$), 150.6 (C-7a), 151.8 (C-2), 157.29 (d, J=244.5 Hz, 1C, C-3$_{Phe}$), 157.30 (C-4). HRMS (ESI): calculated for C₁₇H₁₇ClFN₄O₃ ([M+H]⁺): 379.0968, found: 379.0982.

4-amino-5-cyclohex-1-en-1-yl-N7-(3'-deoxy-β-D-ribofuranosyl)-pyrrolo[2,3-d]pyrimidine (FH10667) FH10667 was prepared according to General Procedure 6, except that Cs₂CO₃ was used instead of Na₂CO₃. FH7429_U (0.140 g, 0.425 mmol) gave rise to FH10667 (0.127 g, 0.384 mmol) as a white solid in 80% yield. ¹H NMR (300 MHz, DMSO-d₆) δ:1.59-1.67 (m, 2H, CH₂), 1.69-1.77 (m, 2H, CH₂), 1.89 (ddd, J=12.9, 6.3, 3.3 Hz, 1H, H-3"), 2.15-2.24 (m, 3H, CH₂, H-3'), 2.29-2.35 (m, 2H, CH₂), 3.49 (ddd, J=11.7, 5.1, 4.8 Hz, 1H, H-5"), 3.63 (ddd, J=12.0, 5.1, 3.9 Hz, 1H, H-5'), 4.22-4.30 (m, 1H, H-4'), 4.37-4.42 (m, 1H, H-2'), 5.02 (t, J=5.7 Hz, 1H, OH-5'), 5.51 (d, J=4.5 Hz, 1H, OH-2'), 5.72 (t, J=3.6 Hz, 1H, H-2$_{cyclohex}$), 6.04 (d, J=2.7 Hz, 1H, H-1'), 6.31 (br. s, 2H, NH₂), 7.36 (s, 1H, H-6), 8.09 (s, 1H, H-2). ¹³C NMR (75 MHz, DMSO-d₆) δ: 21.55 (CH₂), 22.51 (CH₂), 25.05 (CH₂), 29.55 (CH₂), 34.77 (C-3'), 62.92 (C-5'), 74.67 (C-2'), 79.65 (C-4'), 89.99 (C-1'), 99.99 (C-4a), 118.16 (C-5), 119.35 (C-6), 125.68 (C$_{olefin}$), 131.63 (C$_{olefin}$), 149.80 (C-7a), 151.39 (C-2), 157.26 (C-4). HRMS (ESI): calculated for C₁₇H₂₃N₄O₃ ([M−H]⁻): 331.1765, found: 331.1765.

4-amino-5-cyclohexyl-N7-(3'-deoxy-β-D-ribofuranosyl)-pyrrolo[2,3-d]pyrimidine (FH10669)

FH10667 (0.084 g, 0.253 mmol) was dissolved in EtOH (10 mL). Next, the flask was purged with N₂, after which a cat. amount of Pd/C was added. Then, the N₂-atmosphere was exchanged for H₂ (balloon; bubbling), and the mixture stirred until TLC showed full conversion of the SM (approx. 8H). Then, the H₂-balloon was removed, the mixture purged again with N₂ and filtered over Celite®. The filtrate was evaporated till dryness and purified by column chromatography 1→8% MeOH/DCM to give FH10669 (0.072 g, 0.217 mmol) as a white solid in 86% yield. ¹H NMR (300 MHz, DMSO-d₆) δ: 1.15-1.33 (m, 3H, CH₂), 1.44-1.58 (m, 2H, CH₂), 1.71-1.75 (m, 3H, CH₂), 1.88 (ddd, J=12.9, 6.6, 3.6 Hz, 1H, H-3'), 1.93-1.98 (m, 2H, CH₂), 2.18 (ddd, J=12.9, 8.1, 6.0 Hz, 1H, H-3'), 2.87-2.96 (m, 1H, CH), 3.47 (ddd, J=12.0, 6.0, 4.3 Hz, 1H, H-5"), 3.61 (ddd, J=11.7, 5.1, 3.6 Hz, 1H, H-5'), 4.20-4.28 (m, 1H, H-4'), 4.36-4.41 (m, 1H, H-2'), 5.04 (t, J=5.7 Hz, 1H, OH-5'), 5.47 (d, J=4.5 Hz, 1H, OH-2'), 5.99 (d, J=3.0 Hz, 1H, H-1'), 6.44 (br. s, 2H, NH₂), 7.08 (s, 1H, H-6), 8.02 (s, 1H, H-2). ¹³C NMR (75 MHz, DMSO-d₆) δ: 25.78, 25.85, 34.14, 34.30, 34.95, 63.04 (C-5'), 74.46 (C-2'), 79.39 (C-4'), 90.13 (C-1'), 101.49 (C-4a), 116.92 (C-5), 121.47 (C-6), 150.06 (C-7a), 151.05 (C-2), 157.38 (C-4). HRMS (ESI): calculated for C₁₇H₂₅N₄O₃ ([M−H]⁻): 333.1921, found: 333.1931. Melting point: 117° C.

4-amino-5-vinyl-N7-(3'-deoxy-β-D-ribfuranosyl)-pyrrolo[2,3-d]pyrimidine (FH10659)

FH10659 was prepared according to General Procedure 6. FH7429_U (0.135 g, 0.4 mmol), vinylBF₃K (0.081 g, 0.6 mmol) gave rise to FH10659 (0.036 g, 0.130 mmol) as a white solid in 33% yield. ¹H NMR (300 MHz, DMSO-d₆) δ: 1.90 (ddd, J=12.9, 6.6, 3.3 Hz, 1H, H-3"), 2.21 (ddd, J=13.2, 8.7, 6.0 Hz, 1H, H-3'), 3.51 (ddd, J=11.4, 4.8, 4.5 Hz, 1H, H-5"), 3.66 (ddd, J=11.7, 4.8, 3.6 Hz, 1H, H-5'), 4.24-4.32 (m, 1H, H-4'), 4.37-4.43 (m, 1H, H-2'), 5.06 (t, J=5.4 Hz, 1H, OH-5'), 5.11 (dd, J=11.1, 1.8 Hz, 1H, H-vinyl), 5.54 (d, J=4.2 Hz, 1H, OH-2'), 5.55 (dd, J=17.1, 1.8 Hz, 1H, H-vinyl), 6.04 (d, J=2.4 Hz, 1H, H-1'), 7.00 (br. s, 2H, NH₂), 7.10 (dd, J=17.4, 10.8 Hz, 1H, H-vinyl), 7.67 (s, 1H, H-6), 8.06 (s, 1H, H-2). ¹³C NMR (75 MHz, DMSO-d₆) δ: 34.65 (C-3'), 62.82 (C-5'), 74.79 (C-2'), 79.83 (C-4'), 90.12 (C-1'), 100.56 (C-4a), 112.81 (C-5), 113.85 (C-vinyl), 118.66 (C-6), 129.12 (C-vinyl), 150.24 (C-7a), 151.49 (C-2), 157.60 (C-4). HRMS (ESI): calculated for C₁₃H₁₇N₄O₃ ([M+H]⁺): 277.1295, found: 277.1287. Melting point: >250° C. (decomposed).

4-amino-5-(E-styryl)-N7-(3'-deoxy-β-D-ribfuranosyl)-pyrrolo[2,3-d]pyrimidine (FH10660)

FH10660 was prepared according to General Procedure 6. FH7429_U (0.135 g, 0.4 mmol) gave rise to FH10660 (0.087 g, 0.247 mmol) as a white solid in 62% yield. 1H NMR (300 MHz, DMSO-d₆) δ: 1.92 (ddd, J=13.2, 6.6, 3.3 Hz, 1H, H-3"), 2.21-2.30 (m, 1H, H-3'), 3.54 (ddd, J=12.0, 5.4, 4.5 Hz, 1H, H-5"), 3.69 (ddd, J=11.7, 5.4, 3.6 Hz, 1H, H-5'), 4.27-4.34 (m, 1H, H-4'), 4.42-4.47 (m, 1H, H-2'), 5.09 (t, J=5.7 Hz, 1H, OH-5'), 5.56 (d, J=4.5 Hz, 1H, OH-2'), 6.07 (d, J=2.7 Hz, 1H, H-1'), 6.90 (br. s, 2H, NH₂), 6.99 (d, J=16.2 Hz, 1H, vinyl-H), 7.19-7.24 (m, 1H, H$_{Phe}$), 7.33-7.38 (m, 2H, H$_{Phe}$), 7.53 (d, J=16.1 Hz, 1H, vinyl-H), 7.65-7.67 (m, 2H, H$_{Phe}$), 7.84 (s, 1H, H-6), 8.08 (s, 1H, H-2). ¹³C NMR (75 MHz, DMSO-d₆) δ: 34.75 (C-3'), 62.90 (C-5'), 74.81 (C-2'), 79.87 (C-4'), 90.10 (C-1'), 100.76 (C-4a), 113.74 (C-5), 118.63 (C-6), 120.49 (C$_{vinyl}$), 126.40 (2×C$_{Phe}$), 126.87 (C-4$_{phe}$), 127.34 (C$_{vinyl}$), 128.43 (2×C$_{Phe}$), 137.51 (C-1$_{Phe}$), 150.44 (C-7a), 151.52 (C-2), 157.69 (C-4). Melting point: 170° C. HRMS (ESI): calculated for C₁₉H₂₁N₄O₃ ([M+H]⁺): 353.1608, found: 353.1610.

4-amino-5-(phenylethyl)-N7-(3'-deoxy-β-D-ribfuranosyl)-pyrrolo[2,3-d]pyrimidine (FH10661)

FH10660 (0.047 g, 0.133 mmol) was dissolved in EtOH (8 mL). Next, the flask was purged with N₂, after which a cat. amount of Pd/C was added. Then, the $N_2$-atmosphere was exchanged for $H_2$ (balloon; bubbling), and the mixture stirred until TLC showed full conversion of the SM (approx. 5H). Then, the $H_2$-balloon was removed, the mixture purged again with $N_2$ and filtered over Celite®. The filtrate was evaporated till dryness and purified by column chromatography 1→8% MeOH/DCM to give FH10661 (0.036 g, 0.1 mmol) as a white solid in 76% yield. $^1$H NMR (300 MHz, DMSO-d$_6$) δ: 1.88 (ddd, J=13.2, 6.3, 3.3 Hz, 1H, H-3″), 2.11 (ddd, J=13.2, 8.4, 6.3 Hz, 1H, H-3′), 2.86-2.92 (m, 2H, CH$_2$), 3.04-3.13 (m, 2H, CH$_2$), 3.43-3.50 (m, 1H, H-5″), 3.59 (ddd, J=11.7, 5.4, 3.9 Hz, 1H, H-5′), 4.20-4.28 (m, 1H, H-4′), 4.30-4.35 (m, 1H, H-2′), 5.00 (t, J=5.7 Hz, 1H, OH-5′), 5.48 (d, J=4.2 Hz, 1H, OH-2′), 6.00 (d, J=2.7 Hz, 1H, H-1′), 6.55 (br. s, 2H, NH$_2$), 7.07 (s, 1H, H-6), 7.15-7.22 (m, 1H, Ph-H), 7.26-7.28 (m, 4H, Ph-H), 8.03 (s, 1H, H-2). $^{13}$C NMR (75 MHz, DMSO-d$_6$) δ:27.55 (CH$_2$), 35.12 (C-3′), 35.87 (CH$_2$), 63.16 (C-5′), 74.67 (C-2′), 79.57 (C-4′), 89.98 (C-1′), 102.02 (C-4a), 114.42 (C-5), 118.77 (C-6), 125.73 (C$_{Phe}$), 128.09 (2 C$_{Phe}$), 128.47 (2 C$_{Phe}$), 141.56 (C$_{Phe}$), 150.23 (C-7a), 151.28 (C-2), 157.70 (C-4). HRMS (ESI): calculated for $C_{19}H_{21}N_4O_3$ ([M+H]$^+$): 355.1765, found: 355.1741. Melting point: 76° C.

4-amino-5-phenylethynyl-N7-(3′-deoxy-β-D-ribofuranosyl)-pyrrolo[2,3-d]pyrimidine (FH8504)

FH8504 was prepared according to General procedure 6. FH8496 (0.140 g, 0.372 mmol) give rise to FH8504 (0.124 g, 0.354 mmol) as a slightly yellow solid in 95% yield. $^1$H NMR (300 MHz, DMSO-d$_6$) δ: 1.90 (ddd, J=12.9, 6.3, 3.0 Hz, 1H, H-3″), 2.22 (ddd, J=12.9, 9.0, 5.7 Hz, 1H, H-3′), 3.50-3.57 (m, 1H, H-5″), 3.66-3.73 (m, 1H, H-5′), 4.28-4.36 (m, 1H, H-4′), 4.38-4.43 (m, 1H, H-2′), 5.07 (t, J=5.4 Hz, 1H, OH-5′), 5.61 (d, J=4.2 Hz, 1H, OH-2′), 6.06 (d, J=2.4 Hz, 1H, H-1′), 6.70 (br. s, 2H, NH$_2$), 7.37-7.46 (m, 3H, Ph-H), 7.55-7.61 (m, 2H, Ph-H), 7.90 (s, 1H, H-6), 8.17 (s, 1H, H-2). $^{13}$C NMR (75 MHz, DMSO-d$_6$) δ: 34.27 (C-3′), 62.54 (C-5′), 75.12 (C-2′), 80.34 (C-4′), 83.18 (C5-$\underline{C}$≡C), 90.34 (C-1′), 91.00 (C-5-C≡$\underline{C}$), 94.35 (C-5), 102.65 (C-4a), 122.55 (Ph-C), 126.70 (C-6), 128.46 (Ph-C), 128.69 (2×Ph-C), 131.08 (2×Ph-C), 149.26 (C-7a), 152.76 (C-2), 157.60 (C-4). HRMS (ESI): calculated for $C_{19}H_{19}N_4O_3$ ([M+H]$^+$): 351.1452, found: 351.1448. Melting point: 120° C.

4-amino-5-ethynyl-N7-(3′-deoxy-β-D-ribofuranosyl)-pyrrolo[2,3-d]pyrimidine (FH8505)

FH8505 was prepared according to General procedure 7. FH8496 (0.140 g, 0.372 mmol) was transformed into the intermediate TMS-protected FH8505. The resulting solid was dissolved in MeOH (5 mL) and $K_2CO_3$ (0.026 g, 0.185 mmol, 0.5 eq.) added. The resulting suspension was stirred at ambient temperature for 5H, after which it was evaporated till dryness. The resulting oil was purified by column chromatography 1→8% MeOH/DCM, to give FH8505 (0.061 g, 0.222 mmol) as a white solid in 60% yield. $^1$H NMR (300 MHz, DMSO-d$_6$) δ: 1.87 (ddd, J=12.9, 6.3, 3.3 Hz, 1H, H-3″), 2.19 (ddd, J=12.9, 8.7, 5.7 Hz, 1H, H-3′), 3.48-3.56 (m, 1H, H-5″), 3.63-3.71 (m, 1H, H-5′), 4.26 (s, 1H, ethynyl-H), 4.28-4.34 (m, 1H, H-4′), 4.38 (br. s, 1H, H-2′), 5.07 (br. s, 1H, OH-5′), 5.59 (br. s, 1H, OH-2′), 6.01 (d, J=2.4 Hz, 1H, H-1′), 6.64 (br. s, 2H, NH$_2$), 7.84 (s, 1H, H-6), 8.13 (s, 1H, H-2). $^{13}$C NMR (75 MHz, DMSO-d$_6$) δ: 34.15 (C-3′), 62.46 (C-5′), 75.06 (C-2′), 77.48 (C$_5$—$\underline{C}$≡C), 80.29 (C-4′), 82.92 (C$_5$—C≡$\underline{C}$), 90.32 (C-1′), 93.58 (C-5), 102.27 (C-4a), 126.99 (C-6), 148.94 (C-7a), 152.75 (C-2), 157.47 (C-4). HRMS (ESI): calculated for $C_{13}H_{15}N_4O_3$ ([M+H]$^+$): 275.1139, found: 275.1140. Melting point: 192° C.

4-amino-5-pent-1-yn-N7-(3′-deoxy-β-D-ribofuranosyl)-pyrrolo[2,3-d]pyrimidine (FH9610)

FH9610 was prepared according to General procedure 7. FH8496 (0.09 g, 0.24 mmol) give rise to FH9610 (0.069 g, 0.218 mmol) as a white solid in 91% yield. $^1$H NMR (300 MHz, DMSO-d$_6$) δ: 0.99 (t, J=7.5 Hz, 3H, C≡C—CH$_2$—CH$_2$-$\underline{CH_3}$), 1.57 (sext, J=7.2 Hz, 2H, C≡C—CH$_2$-$\underline{CH_2}$—CH$_3$), 1.87 (ddd, J=13.2, 6.3, 3.0 Hz, 1H, H-3″), 2.19 (ddd, J=13.2, 8.7, 6.0 Hz, 1H, H-3′), 2.45 (t, J=7.2 Hz, 2H, C≡C-$\underline{CH_2}$—CH$_2$—CH$_3$), 3.50 (ddd, J=12.0, 5.4, 4.2 Hz, 1H, H-5″), 3.66 (ddd, J=12.0, 5.4, 3.6 Hz, 1H, H-5′), 4.24-4.31 (m, 1H, H-4′), 4.32-4.38 (m, 1H, H-2′), 5.06 (t, J=5.7 Hz, 1H, OH-5′), 5.58 (d, J=4.2 Hz, 1H, OH-2′), 6.01 (d, J=3.0 Hz, 1H, H-1′), 6.63 (br. s, 2H, NH$_2$), 7.67 (s, 1H, H-6), 8.11 (s, 1H, H-2). $^{13}$C NMR (75 MHz, DMSO-d$_6$) δ: 13.43 (≡—CH$_2$CH$_2$$\underline{CH_3}$), 20.85 (≡—CH$_2$$\underline{CH_2}$CH$_3$), 21.71 (≡—$\underline{CH_2}$CH$_2$CH$_3$), 34.31 (C-3′), 62.57 (C-5′), 73.90 (C-6-$\underline{C}$≡C—CH$_2$), 75.03 (C-2′), 80.14 (C-4′), 90.20 (C-1′), 92.29, 95.21, 125.36 (C-6), 148.88 (C-2), 152.53 (C-7a), 157.57 (C-4). (1C missing) HRMS (ESI): calculated for $C_{16}H_{21}N_4O_3$ ([M+H]$^+$): 317.1608, found: 317.1598. Melting point: 127-129° C.

4-amino-5-hex-1-yn-N7-(3′-deoxy-β-D-ribofuranosyl)-pyrrolo[2,3-d]pyrimidine (FH9611)

FH9611 was prepared according to General procedure 7. FH8496 (0.09 g, 0.24 mmol) give rise to FH9611 (0.075 g, 0.227 mmol) as a white solid in 95% yield. $^1$H NMR (300 MHz, DMSO-d$_6$) δ: 0.91 (t, J=7.2 Hz, 3H, C≡C—H$_2$—CH$_2$—CH$_2$-$\underline{CH_3}$), 1.36-1.47 (m, 2H, C≡C—CH$_2$—CH$_2$-$\underline{CH_2}$—CH$_3$), 1.48-1.59 (m, 2H, C≡C—CH$_2$-$\underline{CH_2}$—CH$_2$—CH$_3$), 1.87 (ddd, J=13.2, 6.6, 3.3 Hz, 1H, H-3″), 2.19 (ddd, J=12.9, 8.7, 5.7 Hz, 1H, H-3′), 2.45 (t, J=7.2 Hz, 2H, C≡C-$\underline{CH_2}$—CH$_2$—CH$_2$—CH$_3$), 3.50 (ddd, J=12.0, 5.4, 4.2 Hz, 1H, H-5″), 3.66 (ddd, J=12.0, 5.4, 3.6 Hz, 1H, H-5′), 4.24-4.32 (m, 1H, H-4′), 4.33-4.38 (m, 1H, H-2′), 5.05 (t, J=5.7 Hz, 1H, OH-5′), 5.57 (d, J=4.5 Hz, 1H, OH-2′), 6.00 (d, J=2.4 Hz, 1H, H-1′), 6.63 (br. s, 2H, NH$_2$). 7.66 (s, 1H, H-6). 8.11 (s, 1H, H-2). $^{13}$C NMR (75 MHz, DMSO-d$_6$) δ: 13.46 (≡—CH$_2$CH$_2$CH$_2$$\underline{CH_3}$), 18.54 (≡—CH$_2$CH$_2$$\underline{CH_2}$CH$_3$), 21.49 (≡—CH$_2$$\underline{CH_2}$CH$_2$CH$_3$), 30.31 (≡—$\underline{CH_2}$CH$_2$CH$_2$CH$_3$), 34.31 (C-3′), 62.59 (C-5′), 73.76, 75.01, 80.14, 90.19, 92.40, 95.22, 125.33 (C-6), 148.87 (C-2), 152.53 (C-7a), 157.57 (C-4). (1C missing) HRMS (ESI): calculated for $C_{17}H_{23}N_4O_3$ ([M+H]$^+$): 331.1765, found: 331.1745. Melting point: 161-163° C.

4-amino-5-ethyl-N7-(3′-deoxy-β-D-ribofuranosyl)-pyrrolo[2,3-d]pyrimidine (FH9613)

FH8505 (0.05 g, 0.182 mmol) was dissolved in EtOH (5 mL). Next, the flask was purged with N2, after which a cat. amount of Pd/C was added. Then, the N2-atmosphere was exchanged for $H_2$ (balloon; bubbling), and the mixture stirred until TLC showed full conversion of the SM (approx. 2H). Then, the $H_2$-balloon was removed, the mixture purged again with N2 and filtered over Celite®. The filtrate was evaporated till dryness and purified by column chromatography 1→10% MeOH/DCM to give FH9613 as a white solid (0.043 g, 0.155 mmol) in 85% yield. $^1$H NMR (300 MHz, DMSO-d$_6$) δ: 1.19 (t, J=7.2 Hz, 3H, CH$_3$), 1.90 (ddd, J=12.9, 6.6, 3.6 Hz, 1H, H-3″), 2.18 (ddd, J=12.9, 8.4, 6.3 Hz, 1H, H-3′), 2.76 (t, J=7.2 Hz, 2H, CH$_2$), 3.48 (ddd, J=11.7, 6.0, 4.8 Hz, 1H, H-5″), 3.61 (ddd, J=11.7, 5.4, 3.9 Hz, 1H, H-5′), 4.20-4.26 (m, 1H, H-4′), 4.28-4.41 (m, 1H, H-2′), 5.02 (t, J=5.7 Hz, 1H, OH-5′), 5.47 (d, J=4.5 Hz, 1H, OH-2′), 5.99 (d, J=2.7 Hz, 1H, H-1′), 6.52 (br. s, 2H, NH$_2$), 7.08 (s, 1H, H-6), 8.02 (s, 1H, H-2). $^{13}$C NMR (75 MHz, DMSO-d$_6$) δ: 14.94 (CH$_3$), 19.19 (CH$_2$), 35.06 (C-3′), 63.14 (C-5′), 74.52 (C-2′), 79.39 (C-4′), 89.97 (C-1′), 101.91 (C-4a), 116.76 (C-5), 117.99 (C-6), 150.36 (C-7a), 151.33

(C-2), 157.62 (C-4). HRMS (ESI): calculated for $C_{13}H_{19}N_4O_3$ ([M+H]$^+$): 279.1452, found: 279.1448. Melting point: 200° C.

4-azido-5-(pyrid-2-yl)-N7-(2',5'-di-O-benzoyl-3'-deoxy-β-D-ribofuranosyl)-pyrrolo[2,3-d]pyrimidine (FH8501)

FH8490 (0.46 g, 0.75 mmol, 1 eq.) was dissolved in anhydrous toluene (10 mL) and evaporated till dryness. This procedure was repeated 3 times. Next, the residue was dissolved in anhydrous THF (6.5 mL, 8.5 mL/mmol SM) under argon. The solution was cooled to −65° C. iPrMgCl·LiCl solution (0.64 mL, 0.83 mmol, 1.3 M in THF 1.1 eq.) was added in one portion. The resulting solution was stirred at −65° C. for 30 min, after which a small sample was quenched with sat. NH$_4$Cl solution and used for TLC analysis. Generally, full conversion was then observed. Next, ZnCl$_2$ solution (0.5 M in THF) (1.8 mL, 0.9 mmol, 1.2 eq.) was added in one portion, and the mixture stirred for another 5-10 min at −65° C. Then, the cooling was removed and the mixture stirred at ambient temperature for 20 min. Next, to a flame-dried Schlenk-tube (5 mL) containing a stir bar, was added Pd$_2$(dba)$_3$ (0.014 g, 0.015 mmol, 0.02 eq.), RuPhos (0.028 g, 0.06 mmol, 0.08 eq.). The tube was evacuated and refilled with argon three times. Then, anhydrous THF (2.3 mL, 3 mL/mmol SM) was added as well as the pyridine-Br (0.1 mL, 1.05 mmol, 1.4 eq.). The mixture was stirred for approximately 5 min and the resulting solution was then transferred via syringe to the flask containing the nucleoside-zinc reagent. An additional 0.5-1 mL of anhydrous THF was used to rinse the Schlenk tube and added to the mixture as well. The resulting solution was stirred at 60° C. overnight. After cooling to room temperature, the mixture was then quenched by adding water (~5 mL) and transferred to a separatory funnel. EA and aq. 1 M EDTA (pH=8) solution were added. The layers were separated and the water layer was extracted with EA 2 more times. The organic layers were combined, dried over Na$_2$SO$_4$, filtered and evaporated in vacuo. The resulting mixture was purified by column chromatography 35→40% EA/PET. FH8501 (0.24 g, 0.427 mmol) was isolated as a yellow solid in 57% yield. $^1$H NMR (300 MHz, DMSO-d$_6$) δ: 2.50-2.57 (m, 1H, H-3"), 2.90 (ddd, J=14.1, 10.2, 6.3 Hz, 1H, H-3'), 4.57 (dd, J=12.3, 5.1 Hz, 1H, H-5"), 4.71 (dd, J=12.0, 3.0 Hz, 1H, H-5'), 4.85-4.92 (m, 1H, H-4'), 6.03 (d, J=6.3 Hz, 1H, H-2'), 6.75 (d, J=1.8 Hz, 1H, H-1'), 7.33-7.39 (m, 3H, OBz, Pyr-H), 7.54-7.60 (m, 3H, OBz), 7.69-7.75 (m, 1H, OBz), 7.92-7.95 (m, 2H, OBz), 8.01 (dd, J=7.8, 2.1 Hz, 1H, Pyr-H), 8.05-8.09 (m, 2H, OBz), 8.59 (s, 1H, H-6), 8.60 (ddd, J=4.8, 1.8, 0.9 Hz, 1H, H-Pyr), 9.02 (dt, J=8.1, 0.9 Hz, 1H, H-Pyr), 9.98 (s, 1H, H-2). HRMS (ESI): calculated for $C_{30}H_{24}N_7O_5$ ([M+H]$^+$): 562.1833, found: 562.1854.

4-amino-5-(pyrid-2-yl)-N7-(3'-deoxy-β-D-ribfuranosyl)-pyrrolo[2,3-d]pyrimidine (FH8502)

FH8501 (0.22 g, 0.392 mmol, 1 eq.) was dissolved in THF (5 mL, 10 mL/mmol SM) and PMe$_3$ (1.0 M in THF) (0.8 mL, 0.8 mmol, 2 eq.) was added. The resulting solution was stirred overnight, after which it was evaporated till dryness. The residue was taken up into MeCN (5 mL, 10 mL/mmol SM), and aq. 1 M HOAc (1.3 mL, 1.3 mmol, 3.3 eq.) was added. The mixture was then heated to 65° C. in a pre-heated oil bath for 1H. After cooling to ambient temperature, it was poured into sat. aq. NaHCO$_3$ solution. DCM was added, layers were separated and the water layer extracted two more times with DCM. The organic layers were combined, dried over Na$_2$SO$_4$, filtered and evaporated till dryness. Purification by column chromatography gave rise to the intermediate purine-amine derivative, which was directly (deprotection). To a solution of the purine-amine derivative in MeOH (15 mL/mmol) was added NaOMe/MeOH solution (5.4 M, 0.2 eq.), and the mixture was stirred at ambient temperature until TLC analysis showed full conversion (generally between 30 min to 1H). Next, the mixture was neutralized (pH ~7) with 0.5 M aq. HCl and evaporated till dryness. The residue was taken up in MeOH, and co-evaporated with Celite®, and subjected to column chromatography, to give FH8502 (0.057 g, 0.174 mmol) as a white solid in 44% yield. $^1$H NMR (300 MHz, DMSO-d$_6$) δ: 1.91 (ddd, J=12.9, 6.3, 3.0 Hz, 1H, H-3"), 2.23-2.33 (m, 1H, H-3'), 3.56 (ddd, J=12.0, 5.4, 4.2 Hz, 1H, H-5"), 3.74 (ddd, J=12.0, 5.4, 3.6 Hz, 1H, H-5'), 4.30-4.37 (m, 1H, H-4'), 4.44-4.49 (m, 1H, H-2'), 5.15 (t, J=5.7 Hz, 1H, OH-5'), 5.60 (d, J=4.2 Hz, 1H, OH-2'), 6.09 (d, J=2.4 Hz, 1H, H-1'), 7.24 (br. s, 1H, NH), 7.24 (ddd, J=7.2, 5.1, 1.2 Hz, 1H, H-5$_{pyridine}$), 7.84 (ddd, J=8.1, 7.2, 1.8 Hz, 1H, H-4$_{pyridine}$), 7.95 (dt, J=8.1, 0.9 Hz, 1H, H-3$_{pyridine}$), 8.08 (s, 1H, H-2), 8.28 (s, 1H, H-6), 8.54 (ddd, J=5.1, 1.8, 0.9 Hz, 1H, H-6$_{pyridine}$), 9.84 (br. s, 1H, NH). $^{13}$C NMR (75 MHz, DMSO-d$_6$) δ: 14.30 (C-3'), 62.60 (C-5'), 74.92 (C-2'), 80.20 (C-4'), 90.31 (C-1'), 100.37 (C-4a), 115.73 (C-5), 120.26 (C-3$_{pyridine}$), 120.96 (C-5$_{pyridine}$), 122.72 (C-6), 137.65 (C-4$_{pyridine}$), 147.88 (C-6$_{pyridine}$), 150.96 (C-7a), 152.50 (C-2), 153.22 (C-2$_{pyridine}$), 158.68 (C-4). HRMS (ESI): calculated for $C_{16}H_{18}N_5O_3$ ([M+H]$^+$): 328.1404, found: 328.1411. Melting point: 227° C.

4-azido-5-trifluoromethyl-N7-(2',5'-di-O-benzoyl-3'-deoxy-β-D-ribofuranosyl)-pyrrolo[2,3-d]pyrimidine (FH8519)

In a flame-dried culture tube equipped with a stir bar was added under argon FH8488 (0.54 g, 0.9 mmol, 1 eq.), Cu$^{+1}$I (0.035 g, 0.18 mmol, 0.2 eq.), 1,10-phenanthroline (0.033 g, 0.18 mmol, 0.2 eq.) and KF (0.157 g, 2.7 mmol, 3 eq.). The tube was closed with an inverted septum, evacuated and refilled with argon three times. Then, DMSO (2 mL, 2 mL/mmol SM) was added followed by B(OMe)$_3$ (0.301 mL, 2.7 mmol, 3 eq.). Then, TMSCF$_3$ (0.405 mL, 2.7 mmol, 3 eq.) was carefully added (dropwise).[35] Next, the entirety of the reaction mixture was immersed in a pre-heated oil bath at 60° C. and stirred for approximately 20H. Then, the mixture was cooled to ambient temperature, and EA was added, followed by water. The layers were separated and the water layer extracted once more with EA. The organic layers were combined, dried over Na$_2$SO$_4$, filtered and evaporated till dryness. The residue was purified by column chromatography 10→25% EA/PET, to yield FH8519 as a yellowish foam (0.35 g, 0.641 mmol) in 71% yield. [note: the obtained product did contain a small fraction of unreacted SM~5-10%; which was taken forth to the next step, without further purification] $^1$H NMR (300 MHz, CDCl$_3$) δ: 2.46 (ddd, J=14.4, 5.7, 1.5 Hz, 1H, H-3"), 2.72 (ddd, J=14.1, 10.5, 6.0 Hz, 1H, H-3'), 4.63 (dd, J=12.3, 4.5 Hz, 1H, H-5"), 4.76 (dd, J=12.6, 3.0 Hz, 1H, H-5'), 4.84-4.92 (m, 1H, H-4'), 5.96 (dt, J=4.5, 1.5 Hz, 1H, H-2'), 6.44 (d, J=1.5 Hz, 1H, H-1'), 7.41-7.52 (m, 4H, OBz), 7.57-7.66 (m, 2H, OBz), 7.88 (d, J=1.2 Hz, 1H, H-6), 7.99-8.10 (m, 4H, OBz), 8.69 (s, 1H, H-2). $^{19}$F-NMR (282 MHz, CDCl$_3$) δ: −55.84. HRMS (ESI): calculated for $C_{26}H_{20}F_3N_3O_5$ ([M+H]$^+$): 546.1038, found: 546.1041.

4-azido-5-trifluoromethyl-N7-(2',5'-di-O-benzoyl-3'-deoxy-β-D-ribofuranosyl)-pyrrolo[2,3-d]pyrimidine (FH8521)

FH8521 was prepared according to General procedure 3. FH8519 (0.34 g, 0.623 mmol) gave rise to FH8521 (0.25 g, 0.453 mmol) as a white foam in 73% yield. (purification: 10→25% EA/PET) $^1$H NMR (300 MHz, DMSO-d$_6$) δ: 2.50-2.55 (m, 1H, H-3"), 2.91 (ddd, J=14.4, 10.8, 6.3 Hz, 1H, H-3'), 4.56 (dd, J=12.3, 5.4 Hz, 1H, H-5"), 4.70 (dd, J=12.3, 3.0 Hz, 1H, H-5'), 4.84-4.92 (m, 1H, H-4'), 5.97 (d, J=6.0 Hz, 1H, H-2'), 6.70 (d, J=1.5 Hz, 1H, H-1'), 7.45-7.75 (m, 6H, OBz), 7.93-7.97 (m, 2H, OBz), 8.04-8.09 (m, 2H, OBz), 8.56 (d, J=1.2 Hz, 1H, H-6), 10.06 (s, 1H, H-2). $^{19}$F-NMR (282 MHz, DMSO-d$_6$) δ: −56.68. HRMS (ESI): calculated for C$_{26}$H$_{20}$F$_3$N$_6$O$_5$ ([M+H]$^+$): 553.1442, found: 553.1440.

4-amino-5-trifluoromethyl-N7-(2',5'-di-O-benzoyl-3'-deoxy-β-D-ribofuranosyl)-pyrrolo[2,3-d]pyrimidine (FH9524)

FH9524 was prepared according to General procedure 4. FH8521 (0.24 g, 0.434 mmol) gave rise to FH9524 (0.191 g, 0.363 mmol) as a white foam in 84% yield. (purification: 20→50% EA/PET) $^1$H NMR (300 MHz, CDCl$_3$) δ: 2.42 (ddd, J=14.1, 5.7, 1.8 Hz, 1H, H-3"), 2.77 (ddd, J=14.1, 10.5, 6.0 Hz, 1H, H-3'), 4.61 (dd, J=12.3, 4.8 Hz, 1H, H-5"), 4.73 (dd, J=12.3, 3.0 Hz, 1H, H-5'), 4.79-4.87 (m, 1H, H-4'), 5.47 (br. s, 2H, NH$_2$), 5.93 (dt, J=6.0, 1.5 Hz, 1H, H-2'), 6.43 (d, J=1.5 Hz, 1H, H-1'), 7.42-7.51 (m, 4H, OBz), 7.56-7.64 (m, 3H, H-6, OBz), 8.02-8.10 (m, 4H, OBz), 8.33 (s, 1H, H-2). $^{19}$F-NMR (282 MHz, CDCl$_3$) δ: −55.29. HRMS (ESI): calculated for C$_{26}$H$_{22}$F$_3$N$_4$O$_5$ ([M+H]$^+$): 527.1537, found: 527.1543.

4-amino-5-trifluoromethyl-N7-(3'-deoxy-β-D-ribofuranosyl)-pyrrolo[2,3-d]pyrimidine (FH9526)

FH9526 was prepared according to general procedure 5. FH9524 (0.18 g, 0.342 mmol) gave rise to FH9526 (0.102 g, 0.32 mmol) as a white powder in 93% yield. (Purification 2→8% MeOH/DCM) $^1$H NMR (300 MHz, DMSO-d$_6$) δ:1.86 (ddd, J=13.2, 6.0, 3.0 Hz, 1H, H-3"), 2.21 (ddd, J=13.2, 9.0, 5.7 Hz, 1H, H-3'), 3.54 (ddd, J=12.0, 5.4, 3.6 Hz, 1H, H-5"), 3.75 (ddd, J=12.0, 5.4, 3.3 Hz, 1H, H-5'), 4.31-4.37 (m, 1H, H-4'), 4.30-4.43 (m, 1H, H-2'), 5.14 (t, J=5.4 Hz, 1H, OH-5'), 5.64 (d, J=4.5 Hz, 1H, OH-2'), 6.08 (d, J=2.1 Hz, 1H, H-1'), 6.57 (br. s, 2H, NH$_2$), 8.24 (s. 1H, H-2), 8.26 (q, J=1.5 Hz, 1H, H-6). $^{19}$F-NMR (282 MHz, DMSO-d$_6$) δ: −53.48. $^{13}$C NMR (75 MHz, DMSO-d$_6$) δ: 33.55 (C-3'), 62.00 (C-5'), 75.16 (C-2'), 80.61 (C-4'), 90.56 (C-1'), 97.98 (C-4a), 102.75 (q, J=36.7 Hz, 1C, C-5), 123.60 (q, J=264.5 Hz, 1C, CF$_3$), 123.80 (q, J=5.7 Hz, 1C, C-6), 150.67 (C-7a), 152.99 (C-2), 156.18 (C-4). HRMS (ESI): calculated for C$_{12}$H$_{14}$F$_3$N$_4$O$_3$ ([M+H]$^+$): 319.1013, found: 319.1012. Melting point: 167° C.

C-8 Substituted Analogues
4-amino-6-bromo-N7-(3'-deoxy-β-D-ribfuranosyl)-pyrrolo[2,3-d]pyrimidine (FH10622)

FH7429_D (0.106 g, 0.423 mmol) and KOAc (0.083 g, 0.846 mmol, 2 eq.) were dissolved in anhydrous DMF (1.7 mL, 4 mL/mmol SM). Then, a solution of NBS (0.151 g, 0.846 mmol, 2 eq.) in anhydrous DMF (0.85 mL, 2 mL/mmol SM) was added dropwise. After the addition was complete the resulting solution was stirred at ambient temperature for another 10 min. Next, the solution was evaporated till dryness and purified by column chromatography 2→10% MeOH/DCM. FH10622 (0.02 g, 0.061 mmol) was isolated a slightly yellow solid in 14% yield. $^1$H NMR (300 MHz, DMSO-d$_6$) δ: 1.98 (ddd, J=12.6, 7.5, 5.1 Hz, 1H, H-3'), 2.40-2.46 (m, 1H, H-3"), 3.39-3.45 (m, 1H, H-5"), 3.53-3.59 (m, 1H, H-5'), 4.20-4.28 (m, 1H, H-4'), 5.08 (br. s, 1H, H-2'), 5.34 (br. s, 1H, OH-5'), 5.49 (br. s, 1H, OH-2'), 5.78 (d, J=4.8 Hz, 1H, H-1'), 6.79 (s, 1H, H-5), 7.22 (br. s, 2H, NH$_2$), 8.30 (s, 1H, H-2). $^{13}$C NMR (75 MHz, DMSO-d$_6$) δ: 35.84 (C-3'), 63.98 (C-5'), 71.94 (C-2'), 79.19 (C-4'), 92.82 (C-1'), 102.91 (C-4a), 103.69 (C-7), 108.54 (C-6), 149.74 (C-7a), 151.69 (C-2), 156.50 (C-4). HRMS (ESI): calculated for C$_{11}$H$_{14}$BrN$_4$O$_3$ ([M+H]$^+$): 329.0244, found: 329.0242. Melting point: 130° C. (decomposed).

Pyrrolo[2,3-b]Pyridine Analogues
1H-4-azido-pyrrolo[2,3-b]pyridine] (FH6353)
1H-4-chloro-pyrrolo[2,3-b]pyridine (0.765 g, 5 mmol, 1 eq.) was dissolved in DMF (15 mL, 3 mL/mmol SM), and NH$_4$Cl (1.34 g, 25 mmol, 5 eq.) were added, followed by NaN$_3$ (1.63 g, 25 mmol, 5 eq.). The mixture was heated to 110° C. After 7H, the mixture was allowed to cool to ambient temperature, diluted with EA, and poured into half-sat. aq. NaHCO$_3$ solution. The layers were separated and the water layer washed twice with EA. The organic layers were combined, dried over Na$_2$SO$_4$, filtered and evaporated till dryness. The residue was purified by column chromatography (30% EA/PET) to give FH6353 (0.53 g, 3.32 mmol) as a white solid in 66% yield. $^1$H NMR (300 MHz, DMSO-d$_6$) δ: 6.46 (dd, J=3.3, 1.8 Hz, 1H, H-3), 6.88 (d, J=5.4 Hz, 1H, H-5), 7.46 (dd, J=3.6, 2.4 Hz, 1H, H-2), 8.18 (d, J=5.1 Hz, 1H, H-6), 11.86 (br. s, 1H, NH). $^{13}$C NMR (75 MHz, DMSO-d$_6$) δ: 96.94 (C-3), 105.03 (C-5), 111.99 (C-3a), 125.89 (C-2), 139.45 (C-7a), 143.72 (C-6), 149.94 (C-4). HRMS (ESI): calculated for C$_7$H$_6$N5 [M+H]$^+$): 160.0618, found: 160.0585. Melting point: 180° C. (decomposed).

1H-3-bromo-4-azido-pyrrolo[2,3-b]pyridine (FH9545)
FH6353 (0.56 g, 3.5 mmol) was dissolved in DMF (5.5 mL, 1.5 mL/mmol SM). Next, NBS (0.654 g, 3.68 mmol) was added and the resulting solution was stirred at ambient temperature overnight, protected from light. Then, the solution was poured into ice-cold water (18 mL, 5 mL/mmol SM) and cooled into an ice bath. After ~10 min the remaining suspension was filtered and the solid washed four times with 5 mL ice-cold water. Then the solid was collected and dried under high vacuum to give FH9545 as a dark yellow solid (0.709 g, 2.98 mmol) in 85% yield. $^1$H NMR (300 MHz, DMSO-d$_6$) δ: 7.05 (d, J=5.1 Hz, 1H, H-5), 7.63 (d, J=1.8 Hz, 1H, H-2), 8.24 (d, J=5.1 Hz, 1H, H-6), 12.19 (br. s, 1H, NH). HRMS (ESI): calculated for C$_7$H$_4$BrN$_5$ ([M+H]$^+$): 237.9723, found: 237.9725. Melting point: 200° C.

1H-3-bromo-4-chloro-pyrrolo[2,3-b]pyridine (FH5295)
1H-4-chloro-pyrrolo[2,3-b]pyridine (0.765 g, 5 mmol, 1 eq.) was dissolved in DMF (7.5 mL, 1.5 mL/mmol SM). NBS (0.935 g, 5.25 mmol) was added and the resulting solution was stirred at ambient temperature overnight, protected from light. Then, the solution was poured into ice-cold water (25 mL, 5 mL/mmol SM) and cooled into an ice bath. After ~10 min the remaining suspension was filtered and the solid washed four times with 10 mL ice-cold water. Then the solid was collected and dried under high vacuum to give FH5295 as a yellow solid (1.12 g, 4.8 mmol) in 96% yield. $^1$H NMR (300 MHz, DMSO-d$_6$) δ: 7.23 (d, J=5.1 Hz, 1H, H-5), 7.81 (d, J=2.7 Hz, 1H, H-2), 8.21 (d, J=5.1 Hz, 1H, H-6), 12.44 (br s, 1H, N—H). $^{13}$C NMR (75 MHz, DMSO-d$_6$) δ: 85.03 (C-3), 114.58 (C-3a), 117.13 (C-5), 127.71 (C-2), 134.17 (C-4), 144.18 (C-6), 147.98 (C-7a). HRMS (ESI): calculated for C$_7$H$_5$BrClN$_2$ ([M+H]$^+$): 230.9319, found: 230.9332. Melting point: 210° C. (decomposed).

3-bromo-4-azido-N1-(2',5'-di-O-benzoyl-3'-deoxy-β-D-ribofuranosyl)-pyrrolo[2,3-b]pyridine
(FH9544) FH9544 was prepared according to General procedure 2. FH9545 (0.595 g, 2.5 mmol) and FH8484 (1.06 g, 2.75 mmol) gave rise to FH9544 (0.834 g, 1.48 mmol) as a yellowish foam in 59% yield. [Purification: 10→35% EA/PET). $^1$H NMR (300 MHz, CDCl$_3$) δ: 2.40 (ddd, J=14.1, 5.4, 1.5 Hz, 1H, H-3"), 2.71 (ddd, J=14.1, 10.5, 6.0 Hz, 1H, H-3'), 4.60 (dd, J=12.3, 4.5 Hz, 1H, H-5"), 4.71 (dd, J=12.3, 3.0 Hz, 1H, H-5'), 4.79-4.85 (m, 1H, H-4'), 5.88 (dt, J=4.5, 1.5 Hz, 1H, H-2'), 6.57 (d, J=1.5 Hz, 1H, H-1'), 6.88 (d, J=5.4 Hz, 1H, H-5), 7.40 (s, 1H, H-2), 7.44-7.51 (m, 4H, OBz), 7.56-7.64 (m, 2H, OBz), 8.04-8.10 (m, 4H, OBz), 8.24 (d, J=5.1 Hz, 1H, H-6). $^{13}$C NMR (75 MHz, CDCl$_3$) δ: 33.50 (C-3'), 64.89 (C-5'), 78.09 (C-4'), 78.78 (C-2'), 87.98

(C-3), 89.74 (C-1'), 106.64 (C-5), 111.54 (C-3a), 124.88 (C-2), 128.67 (2C, OBz), 128.77 (2C, OBz), 129.41 (OBz), 129.66 (OBz), 129.86 (2C, OBz), 129.98 (2C, OBz), 133.45 (OBz), 133.74 (OBz), 142.13 (C-4), 145.21 (C-6), 147.87 (C-7a), 165.66 (C=O), 166.51 (C=O). HRMS (ESI): calculated for $C_{26}H_{21}BrN_5O_5$ ([M+H]$^+$): 562.0721, found: 562.0714.

3-bromo-4-amino-N1-(2'-5'-di-O-benzoyl-3'-deoxy-β-D-ribofuranosyl)-pyrrolo[2,3-b]pyridine (FH9548) FH9548 was prepared according to General procedure 4. FH9544 (0.803 g, 1.43 mmol) gave rise to FH9548 (0.7 g, 1.3 mmol) as a slightly yellow foam in 91% yield. (purification: 15→50% EA/PET) $^1$H NMR (300 MHz, CDCl$_3$) δ: 2.37 (ddd, J=14.1, 5.7, 1.8 Hz, 1H, H-3"), 2.69 (ddd, J=14.1, 10.5, 6.0, 1H, H-3'), 4.58 (dd, J=12.3, 4.8 Hz, 1H, H-5"), 4.69 (dd, J=12.0, 3.0 Hz, 1H, H-5'), 4.74-4.82 (m, 1H, H4'), 4.95 (br. s, 2H, NH$_2$), 5.87 (dt, J=4.2, 1.5 Hz, 1H, H-2'), 6.25 (d, J=5.4 Hz, 1H, H-5), 6.58 (d, J=1.8 Hz, 1H, H-1'), 7.20 (s, 1H, H-6), 7.43-7.50 (m, 4H, OBz), 7.56-7.62 (m, 2H, OBz), 7.94 (s, 1H, H-2), 8.05-8.10 (m, 4H, OBz). HRMS (ESI): calculated for $C_{26}H_{23}BrN_3O_5$ ([M+H]$^+$): 536.0816, found: 536.0812.

3-bromo-4-amino-N1-(3'-deoxy-β-D-ribofuranosyl)-pyrrolo[2,3-b]pyridine (FH9549)

FH9549 was prepared according to General procedure 5. FH9548 (0.22 g, 0.41 mmol) gave rise to FH9549 (0.13 g, 0.396 mmol) as a white solid in 96% yield. (Purification 1→8% MeOH/DCM) $^1$H NMR (300 MHz, DMSO-d$_6$) δ:1.87 (ddd, J=12.9, 6.3, 3.6 Hz, 1H, H-3"), 2.18 (ddd, J=12.9, 8.4, 6.0 Hz, 1H, H-3'), 3.49 (ddd, J=11.7, 5.7, 3.9 Hz, 1H, H-5"), 3.65 (ddd, J=11.7, 5.1, 3.6 Hz, 1H, H-5'), 4.23-4.30 (m, 1H, H-4'), 4.35-4.41 (m, 1H, H-2'), 5.13 (t, J=5.4 Hz, 1H, OH-5'), 5.50 (d, J=4.2 Hz, 1H, OH-2'), 6.07 (d, J=2.7 Hz, 1H, H-1'), 6.11 (br. s, 2H, NH$_2$), 6.29 (d, J=5.4 Hz, 1H, H-5), 7.58 (s, 1H, H-2), 7.79 (d, J=5.7 Hz, 1H, H-6). $^{13}$C NMR (75 MHz, DMSO-d$_6$) δ: 34.44 (C-3'), 62.77 (C-5'), 74.63 (C-2'), 79.68 (C-4'), 85.50 (C-3), 90.31 (C-1'), 101.42 (C-5), 104.77 (C-3a), 121.50 (C-2), 144.62 (C-6), 147.23 (C-7a), 148.44 (C-4). HRMS (ESI): calculated for $C_{12}H_{15}BrN_3O_3$ ([M+H]$^+$): 328.0291, found: 328.0290. Melting point: 250° C. (decomposed).

4-amino-N1-(3'-deoxy-β-D-ribofuranosyl)-pyrrolo[2,3-b]pyridine (FH9550)

FH9548 (0.45 g, 0.84 mmol) was dissolved in EtOH (15 mL). Next, aq. 1 M NaOAc (3 mL) was added. Then, the flask was purged with N2, after which a cat. amount of Pd/C was added. Next, the N$_2$-atmosphere was exchanged for H$_2$ (balloon; bubbling), and the mixture stirred until TLC showed full conversion of the SM (approx. 2H). Then, the H$_2$-balloon was removed, the mixture purged again with N$_2$ and filtered over Celite®. The filtrate was evaporated till dryness and taken up in water/EA. The layers were separated and the organic layer washed once with aq. sat. Na$_2$S$_2$O$_3$. The organic layer was collected, dried over Na$_2$SO$_4$, filtered and evaporated till dryness. Next the intermediate was immediately deprotected using General procedure 5, to yield FH9550 (0.162 g, 0.65 mmol) as a white solid in 77% yield. (Purification: 2→8% MeOH/DCM) $^1$H NMR (300 MHz, DMSO-d$_6$) δ: 1.92 (ddd, J=12.6, 6.6, 4.2 Hz, 1H, H-3"), 2.19 (ddd, J=12.9, 7.8, 6.3 Hz, 1H, H-3'), 3.47 (dd, J=11.7, 4.2 Hz, 1H, H-5"), 3.61 (dd, J=12.0, 3.6 Hz, 1H, H-5'), 4.22-4.29 (m, 1H, H-4'), 4.48 (dt, J=3.9, 3.0 Hz, 1H, H-2'), 5.45 (br. s, 2H, OH-2', OH-5'), 6.00 (d, J=3.3 Hz, 1H, H-1'), 6.19 (d, J=5.4 Hz, 1H, H-5), 6.23 (br. s, 2H, NH$_2$), 6.54 (d, J=3.6 Hz, 1H, H-3), 7.27 (d, J=3.9 Hz, 1H, H-2), 7.72 (d, J=5.4 Hz, 1H, H-6). $^{13}$C NMR (75 MHz, DMSO-d$_6$) δ: 35.12 (C-3'), 63.45 (C-5'), 74.17 (C-2'), 79.25 (C-4'), 91.08 (C-1'), 98.31 (C-3), 100.13 (C-5), 108.11 (C-3a), 121.80 (C-2), 143.40 (C-6), 148.03 (C-7a), 148.41 (C-4). HRMS (ESI): calculated for $C_{12}H_{16}N_3O_3$ ([M+H]$^+$): 250.1186, found: 250.1175. Melting point: 164° C.

3-bromo-4-chloro-N1-(2',5'-di-O-benzoyl-3'-deoxy-β-D-ribofuranosyl)-pyrrolo[2,3-b]pyridine (FH9538)

FH9538 was prepared according to General procedure 2. FH5295 (0.631 g, 2.73 mmol) and FH8484 (1.15 g, 3.0 mmol) gave rise to FH9538 (0.937 g, 1.7 mmol) as a slightly yellow foam in 62% yield. (Purification: 13→15% EA/PET) $^1$H NMR (300 MHz, CDCl$_3$) δ: 2.41 (ddd, J=14.1, 5.4, 1.5 Hz, 1H, H-3"), 2.72 (ddd, J=14.1, 10.5, 6.0 Hz, 1H, H-3'), 4.60 (dd, J=12.3, 4.8 Hz, 1H, H-5"), 4.72 (dd, J=12.3, 3.0 Hz, 1H, H-5'), 4.79-4.86 (m, 1H, H-4'), 5.90 (dt, J=5.7, 1.5 Hz, 1H, H-2'), 6.57 (d, J=1.5 Hz, 1H, H-1'), 7.12 (d, J=5.4 Hz, 1H, H-5), 7.45-7.51 (m, 4H, OBz), 7.57 (s, 1H, H-2), 7.57-7.64 (m, 2H, OBz), 8.03-8.10 (m, 4H, OBz), 8.16 (d, J=5.1 Hz, 1H, H-6). $^{13}$C NMR (75 MHz, CDCl$_3$) δ: 33.45 (C-3'), 64.85 (C-5'), 78.21 (C-4'), 78.77 (C-2'), 88.80 (C-3), 89.93 (C-1'), 117.13 (C-3a), 118.65 (C-5), 126.06 (C-2), 128.68 (OBz), 128.79 (OBz), 129.39 (OBz), 129.63 (OBz), 129.84 (OBz), 129.98 (OBz), 133.48 (OBz), 133.75 (OBz), 136.82 (C-4), 144.42 (C-6), 147.00 (C-7a), 165.64 (C=O), 166.51 (C=O). HRMS (ESI): calculated for $C_{26}H_{21}BrClN_2O_5$ ([M+H]$^+$): 555.0317, found: 555.0314.

3-bromo-4-chloro-N1-(3'-deoxy-β-D-ribofuranosyl)-pyrrolo[2,3-b]pyridine (FH9540)

FH9540 was prepared according to General procedure 5. FH9538 (0.15 g, 0.27 mmol) gave rise to FH9540 (0.081 g, 0.232 mmol) as a white foam in 86% yield. (Purification: 1→10% MeOH/DCM) $^1$H NMR (300 MHz, DMSO-d$_6$) δ:1.89 (ddd, J=13.2, 6.3, 3.0 Hz, 1H, H-3"), 2.22 (ddd, J=12.9, 9.0, 5.7 Hz, 1H, H-3'), 3.53 (ddd, J=12.0, 5.1, 3.9 Hz, 1H, H-5"), 3.71 (ddd, J=12, 5.4, 3.3 Hz, 1H, H-5'), 4.30-4.37 (m, 1H, H-4'), 4.38-4.43 (m, 1H, H-2'), 5.06 (t, J=5.4 Hz, 1H, OH-5'), 5.61 (d, J=4.5 Hz, 1H, OH-2'), 6.23 (d, J=2.4 Hz, 1H, H-1'), 7.32 (d, J=5.4 Hz, 1H, H-5), 8.16 (s, 1H, H-2), 8.26 (s, 1H, H-6). $^{13}$C NMR (75 MHz, DMSO-d$_6$) δ: 34.01 (C-3'), 62.28 (C-5'), 75.15 (C-2'), 80.37 (C-4'), 85.88 (C-3), 90.42 (C-1'), 115.34 (C-3a), 118.00 (C-5), 127.39 (C-2), 134.59 (C-4), 144.18 (C-6), 146.60 (C-7a). HRMS (ESI): calculated for $C_{12}H_{13}BrClN_2O_3$ ([M+H]$^+$): 346.9793, found: 346.9797. Melting point: 171° C.

4-chloro-N1-(3'-deoxy-β-D-ribofuranosyl)-pyrrolo[2,3-b]pyridine (FH9541)

FH9538 (0.2 g, 0.35 mmol) was dissolved in EtOH (8 mL). Next, aq. 1 M NaOAc (2 mL) was added. Then, the flask was purged with N2, after which a cat. amount of Pd/C was added. Next, the N2-atmosphere was exchanged for H$_2$ (balloon; bubbling), and the mixture stirred until LC/MS showed full conversion of the SM (partial hydrogenation of the bromide; approx. 45 min-1H). Then, the H$_2$-balloon was removed, the mixture purged again with N2 and filtered over Celite®. The filtrate was evaporated till dryness and taken up in water/EA. The layers were separated and the organic layer washed once with aq. sat. Na$_2$S$_2$O$_3$. The organic layer was collected, dried over Na$_2$SO$_4$, filtered and evaporated till dryness. Next the intermediate was immediately deprotected using General procedure 5. FH9541 (0.03 g, 0.112 mmol) was obtained as a white solid in 32% yield. (Purification 1→5% MeOH/DCM) $^1$H NMR (300 MHz, DMSO-d$_6$) δ:1.92 (ddd, J=12.9, 6.3, 3.8 Hz, 1H, H-3"), 2.22 (ddd, J=13.2, 9.0, 6.0 Hz, 1H, H-3'), 3.53 (ddd, J=12.0, 5.4, 4.2 Hz, 1H, H-5"), 3.67 (ddd, J=11.7, 5.4, 3.6 Hz, 1H, H-5'), 4.28-4.36 (m, 1H, H-4'), 4.41-4.46 (m, 1H, H-2'), 5.00 (t, J=5.4 Hz, 1H, OH-5'), 5.58 (d, J=4.2 Hz, 1H, OH-2'), 6.22 (d, J=2.4 Hz, 1H, H-1'), 6.59 (d, J=3.6 Hz, 1H, H-3), 7.28 (d, J=5.1 Hz, 1H, H-5), 7.91 (d, J=3.6 Hz, 1H, H-2), 8.23 (d, J=5.1 Hz, 1H, H-6). $^{13}$C NMR (75 MHz, DMSO-d$_6$) δ: 34.62 (C-3'), 62.71 (C-5'), 75.04 (C-2'), 80.04 (C-4'), 90.54 (C-1'), 98.31 (C-3), 116.17 (C-5), 119.36 (C-3a), 127.44 (C-2), 134.32 (C-4), 143.59 (C-6), 147.59 (C-7a). HRMS (ESI): calculated for $C_{12}H_{14}ClN_2O_3$ ([M+H]$^+$): 269.0687, found: 269.0685. Melting point: 125° C.

C-6 Substituted Analogues 4-methylamino-5-bromo-N7-(3'-deoxy-β-D-ribofuranosyl)-pyrrolo[2,3-d]pyrimidine (FH8516) FH8516 was prepared according to General procedure 8. FH7429_U (0.08 g, 0.243 mmol) was derivatized and the intermediate reacted with 3 mL of 40% aq. MeNH$_2$, which yielded FH8516 (0.06 g, 0.174 mmol) as a white solid in 72% yield. (Purification: 1→8% MeOH/DCM). $^1$H NMR (300 MHz, DMSO-d$_6$) δ: 1.87 (ddd, J=12.9, 6.3, 3.3 Hz, 1H, H-3"), 2.19 (ddd, J=12.9, 8.7, 6.0 Hz, 1H, H-3'), 3.00 (d, J=4.8 Hz, 3H, NHCH$_3$), 3.50 (dd, J=12.0, 3.9 Hz, 1H, H-5"), 3.66 (dd, J=12.0, 3.3 Hz, 1H, H-5'), 4.24-4.32 (m, 1H, H-4'), 4.34-4.38 (m, 1H, H-2'), 5.03 (br. s, 1H, OH-5'), 5.57 (br. s, 1H, OH-2'), 6.05 (d, J=2.4 Hz, 1H, H-1'), 6.63 (q, J=4.5 Hz, 1H, NH), 7.64 (s, 1H, H-6), 8.20 (s, 1H, H-2). $^{13}$C NMR (75 MHz, DMSO-d$_6$) δ: 27.67 (NHCH$_3$), 34.25 (C-3'), 62.53 (C-5'), 75.01 (C-2'), 80.11 (C-4'), 85.82 (C-5), 90.10 (C-1'), 101.21 (C-4a), 121.10 (C-6), 148.29 (C-7a), 152.30 (C-2), 156.13 (C-4). HRMS (ESI): calculated for $C_{12}H_{16}BrN_4O_3$ ([M+H]$^+$): 343.0400, found: 343.0407. Melting point: 209° C.

4-dimethylamino-5-bromo-N7-(3'-deoxy-β-D-ribofuranosyl)-pyrrolo[2,3-d]pyrimidine (FH8522) FH8522 was prepared according to General procedure 8. FH7429_U (0.08 g, 0.243 mmol) was derivatized and the intermediate reacted with 3 mL of 40% aq. Me$_2$NH, which yielded FH8522 (0.013 g, 0.036 mmol) as a white solid in 15% yield. (Purification: 1→8% MeOH/DCM). $^1$H NMR (300 MHz, DMSO-d$_6$) δ: 1.87 (ddd, J=13.2, 6.3, 3.0 Hz, 1H, H-3"), 2.19 (ddd, J=13.2, 9.0, 5.7 Hz, 1H, H-3'), 3.19 (s, 6H, NMe$_2$), 3.52 (ddd, J=12.0, 5.4, 4.2 Hz, 1H, H-5"), 3.68 (ddd, J=12.0, 5.4, 3.6 Hz, 1H, H-5'), 4.25-4.34 (m, 1H, H-4'), 4.35-4.40 (m, 1H, H-2'), 5.04 (t, J=5.4 Hz, 1H, OH-5'), 5.58 (d, J=4.5 Hz, 1H, OH-2'), 6.12 (d, J=2.4 Hz, 1H, H-1'), 7.82 (s, 1H, H-6), 8.24 (s, 1H, H-2). $^{13}$C NMR (75 MHz, DMSO-d$_6$) δ: 34.13 (C-3'), 41.86 (2C, N(CH$_3$)$_2$), 62.40 (C-5'), 75.03 (C-2'), 80.20 (C-4'), 86.95 (C-5), 90.08 (C-1'), 103.28 (C-4a), 123.22 (C-6), 150.43 (2C, C-2, C-7a), 158.99 (C-4). HRMS (ESI): calculated for $C_{13}H_{18}BrN_4O_3$ ([M+H]$^+$): 357.0557, found: 357.0559. Melting point: 80° C.

4-thiomethyl-5-bromo-N7-(3'-deoxy-β-D-ribofuranosyl)-pyrrolo[2,3-d]pyrimidine (FH8510)

FH8487 (0.19 g, 0.341 mmol) was suspended in EtOH (7 mL, 20 mL/mmol SM), and NaSMe (0.05 g, 0.682 mmol, 2 eq.) was added. The resulting suspension was heated till reflux, until LC/MS showed full conversion of the starting material (approx. 2H). The mixture was cooled to ambient temperature and evaporated. Purification by column chromatography (1→6% MeOH/DCM) gave FH8510 (0.08 g, 0.222 mmol) as a slightly yellow solid in 65% yield. $^1$H NMR (300 MHz, DMSO-d$_6$) δ: 1.88 (ddd, J=13.2, 6.3, 3.0 Hz, 1H, H-3"), 2.21 (ddd, J=13.2, 9.0, 5.7 Hz, 1H, H-3'), 2.63 (s, 3H, SCH$_3$), 3.52 (ddd, J=12.0, 5.1, 3.9 Hz, 1H, H-5"), 3.69 (ddd, J=12.0, 5.4, 3.3 Hz, 1H, H-5'), 4.30-4.36 (m, 1H, H-4'), 4.37-4.43 (m, 1H, H-2'), 5.05 (t, J=5.4 Hz, 1H, OH-5'), 5.63 (d, J=4.2 Hz, 1H, OH-2'), 6.14 (d, J=2.4 Hz, 1H, H-1'), 8.00 (s, 1H, H-6), 8.65 (s, 1H, H-2). $^{13}$C NMR (75 MHz, DMSO-d$_6$) δ: 11.61 (SCH$_3$), 33.98 (C-3'), 62.27 (C-5'), 75.18 (C-2'), 80.51 (C-4'), 86.84 (C-5), 90.20 (C-1'), 114.22 (C-4a), 125.21 (C-6), 147.01 (C-7a), 150.93 (C-2), 161.42 (C-4). HRMS (ESI): calculated for $C_{12}H_{15}BrN_3O_3S$ ([M+H]$^+$): 360.0012, found: 360.0012. Melting point: 195° C.

4-methoxy-5-bromo-N7-(3'-deoxy-β-D-ribofuranosyl)-pyrrolo[2,3-d]pyrimidine (FH8497)

FH8486 (0.16 g, 0.323 mmol) was suspended in 0.5 M NaOMe/MeOH solution (7 mL) and heated at 50° C. for 1.5H, after which the solution was cooled to ambient temperature and neutralized with aq. 0.5 M HCl. Then, the mixture was evaporated till dryness and purified by column chromatography (1→5% MeOH/DCM) to give FH8497 (0.077 g, 0.224 mmol) as a white solid in 69% yield. $^1$H NMR (300 MHz, DMSO-d$_6$) δ: 1.89 (ddd, J=12.9, 6.0, 3.0 Hz, 1H, H-3"), 2.22 (ddd, J=12.9, 8.7, 6.0 Hz, 1H, H-3'), 3.44-3.54 (m, 1H, H-5"), 3.66-3.72 (m, 1H, H-5'), 4.06 (s, 3H, OCH$_3$), 4.28-4.35 (m, 1H, H-4'), 4.40 (br. s, 1H, H-2'), 5.04 (br. s, 1H, OH-5'), 5.62 (br. s, 1H, OH-2'), 6.13 (d, J=2.1 Hz, 1H, H-1'), 7.89 (s, 1H, H-6), 8.46 (s, 1H, H-2). $^{13}$C NMR (75 MHz, DMSO-d$_6$) δ: 34.12 (C-3'), 53.82 (OCH$_3$), 62.37 (C-5'), 75.15 (C-2'), 80.39 (C-4'), 86.13 (C-5), 90.35 (C-1'), 104.00 (C-4a), 124.00 (C-6), 150.36 (C-7a), 151.33 (C-2), 162.18 (C-4). HRMS (ESI): calculated for $C_{12}H_{15}BrN_3O_4$ ([M+H]$^+$): 344.0240, found: 344.0231. Melting point: 164-166° C.

4-oxo-5-bromo-N7-(3'-deoxy-β-D-ribofuranosyl)-pyrrolo[2,3-d]pyrimidine (FH8500)

FH8497 (0.05 g, 0.145 mmol) was suspended in anhydrous MeCN (5 mL, 30 mL/mmol SM) and NaI (0.087 g, 0.58 mmol, 4 eq.) was added. Next, TMSCl (0.075 mL, 0.58 mmol, 4 eq.) was added and the mixture stirred at ambient temperature till full conversion was observed by LC/MS (~approx. 1.5H). The mixture was evaporated till dryness and co-evaporated with MeOH. Purification by column chromatography (1→15% MeOH/DCM) gave FH8500 (0.01 g, 0.03 mmol) as a white solid in 21% yield. $^1$H NMR (300 MHz, DMSO-d$_6$) δ:1.86 (ddd, J=12.9, 6.3, 3.0 Hz, 1H, H-3"), 2.18 (ddd, J=13.2, 8.7, 5.7 Hz, 1H, H-3'), 3.51 (ddd, J=12.0, 5.1, 4.2 Hz, 1H, H-5"), 3.66 (ddd, J=12.0, 5.4, 3.3 Hz, 1H, H-5'), 4.25-4.75 (m, 2H, H-4', H-2'), 5.00 (t, J=5.4 Hz, 1H, OH-5'), 5.59 (d, J=4.5 Hz, 1H, OH-2'), 5.99 (d, J=2.4 Hz, 1H, H-1'), 7.56 (s, 1H, H-6), 7.94 (s, 1H, H-2), 12.09 (br. s, 1H, NH). $^{13}$C NMR (75 MHz, DMSO-d$_6$) δ: 34.16 (C-3'), 62.37 (C-5'), 75.35 (C-2'), 80.37 (C-4'), 89.99 (C-1'), 90.31 (C-5), 105.96 (C-4a), 120.40 (C-6), 144.78 (C-2), 146.47 (C-7a), 157.23 (C-4). HRMS (ESI): calculated for $C_{11}H_{13}BrN_3O_4$([M+H]$^+$): 330.0084, found: 330.0080. Melting point: 268° C.

N7-(2',5'-di-O-benzoyl-3'-deoxy-β-D-ribofuranosyl)-pyrrolo[2,3-d]pyrimidine (FH9533)

FH8488 (0.211 g, 0.35 mmol) was dissolved in EtOH (5 mL). Next, aq. 1 M NaOAc (2 mL) was added. Then, the flask was purged with N2, after which a cat. amount of Pd/C was added. Next, the N2-atmosphere was exchanged for H$_2$ (balloon; bubbling), and the mixture stirred until TLC showed full conversion of the SM (approx. 2H). Then, the H$_2$-balloon was removed, the mixture purged again with N$_2$ and filtered over Celite®. The mixture was evaporated till dryness, and partitioned between EA and aq. sat. NaHCO$_3$/aq. sat. Na$_2$S$_2$O$_3$ solution. Layers were separated and the water layer extracted twice more with EA. Organic layers were combined, dried over Na$_2$SO$_4$, filtered and evaporated. Purification (15→50% EA/PET) gave FH9533 (0.13 g, 0.295 mmol) as a white foam in 84% yield. $^1$H NMR (300 MHz, CDCl$_3$) δ: 2.46 (ddd, J=14.1, 6.0, 1.8 Hz, 1H, H-3"), 2.85 (ddd, J=14.1, 10.2, 6.3 Hz, 1H, H-3'), 4.57 (dd, J=12.3, 5.1 Hz, 1H, H-5"), 4.72 (dd, J=12.3, 3.3 Hz, 1H, H-5'), 4.80-4.88 (m, 1H, H-4'), 6.00 (dt, J=6.0, 1.8 Hz, 1H, H-2'), 6.52 (d, J=2.1 Hz, 1H, H-1'), 6.57 (d, J=3.9 Hz, 1H, H-5), 7.40 (d, J=3.9 Hz, 1H, H-6), 7.41-7.50 (m, 4H, OBz), 7.51-7.64 (m, 2H, OBz), 8.01-8.10 (m, 4H, OBz), 8.86 (s, 1H), 8.96 (s, 1H). HRMS (ESI): calculated for $C_{25}H_{22}N_3O$ ([M+H]$^+$): 444.1554, found: 444.1562.

5-bromo-N7-(2'-5'-di-O-benzoyl-3'-deoxy-β-D-ribofuranosyl)-pyrrolo[2,3-d]pyrimidine (FH9537)

FH9533 (0.128 g, 0.289 mmol, 1 eq.) was dissolved in DMF (3 mL, 10 mL/mmol SM) and NBS (0.054 g, 0.303 mmol, 1.05 eq.) was added. The resulting solution was stirred at ambient temperature overnight, protected from light. Next, the mixture was poured in to aq. sat. NaHCO$_3$/EA. The layers were separated and the organic layer washed with aq. sat. Na$_2$S$_2$O$_3$. Next, the organic layer was dried over Na$_2$SO$_4$, filtered, and evaporated till dryness. Purification by column chromatography (0→50% EA/PET) gave rise to FH9537 (0.125 g, 0.239 mmol) in 83% yield. $^1$H NMR (300 MHz, CDCl$_3$) δ: 2.45 (ddd, J=14.1, 5.7, 1.8 Hz, 1H, H-3"), 2.79 (ddd, J=14.1, 10.5, 6.0 Hz, 1H, H-3'), 4.60 (dd, J=12.3, 4.5 Hz, 1H, H-5"), 4.74 (dd, J=12.3, 3.0 Hz, 1H, H-5'), 4.81-4.88 (m 1H, H-4'), 5.95 (dt, J=5.7, 1.8 Hz, 1H, H-2'), 6.50 (d, J=1.5 Hz, 1H, H-1'), 7.44-7.57 (m, 4H, OBz), 7.45 (s, 1H, H-6), 7.57-7.65 (m, 2H, OBz), 8.01-8.10 (m, 4H, OBz), 8.90 (s, 1H), 8.90 (s, 1H).

5-bromo-N7-(3'-deoxy-β-D-ribofuranosyl)-pyrrolo[2,3-d]pyrimidine (FH9539)

FH9539 was prepared according to General procedure 5. FH9537 (0.11 g, 0.21 mmol) gave rise to FH9539 (0.055 g, 0.176 mmol) as a white solid in 84% yield. (Purification: 1→6% MeOH/DCM) $^1$H NMR (300 MHz, DMSO-d$_6$) δ:1.91 (ddd, J=13.2, 6.3, 3.3 Hz, 1H, H-3"), 2.25 (ddd, J=13.2, 8.7, 6.0 Hz, 1H, H-3'), 3.53 (ddd, J=12.0, 5.1, 3.9 Hz, 1H, H-5"), 3.70 (ddd, J=12.0, 5.7, 3.6 Hz, 1H, H-5'), 4.30-4.38 (m, 1H, H-4'), 4.33-4.48 (m, 1H, H-2'), 5.05 (t, J=5.4 Hz, 1H, OH-5'), 5.63 (d, J=4.2 Hz, 1H, OH-2'), 6.20 (d, J=2.4 Hz, 1H, H-1'), 8.15 (s, 1H, H-6), 8.91 (s, 1H, H-2), 8.94 (s, 1H, H-4). $^{13}$C NMR (75 MHz, DMSO-d$_6$) δ: 34.10 (C-3'), 62.36 (C-5'), 75.09 (C-2'), 80.46 (C-4'), 87.58 (C-5), 90.03 (C-1'), 118.09 (C-4a), 126.72 (C-6), 148.30 (C-4), 149.28 (C-7a), 151.98 (C-2). HRMS (ESI): calculated for $C_{11}H_{13}BrN_3O_3$ ([M+H]$^+$): 314.0135, found: 314.0138. Melting point: 186° C.

C-2' Substituted Analogues 4-amino-5-bromo-N7-(2'-O-methyl-3'-deoxy-5-O-t-butyldimethylsilyl-β-D-ribofuranosyl)-pyrrolo[2,3-d]pyrimidine (FH9614_Mi) FH8471 (0.111 g, 0.251 mmol) was dissolved in anhydrous THF (3 mL, 10 mL/mmol SM), and cooled to 0° C. in an ice-bath. Then, NaH (60% dispersion in mineral oil) (0.012 g, 0.301 mmol, 1.2 eq.) was added, directly followed by MeI (0.018 mL, 0.276 mmol, 1.1 eq.). The mixture was kept at 0° C. for approximately 2H, after which it was quenched by the addition of aq. 0.5 M HCl. Then, water and EA were added, layers separated and the water layer extracted twice more with EA. Organic layers were combined, dried over Na$_2$SO$_4$, filtered and evaporated. Purification by column chromatography 10→75% EA/PET yielded FH9614_Mid (0.039 g, 0.085 mmol) as a colourless oil in 34% yield. Additionally, another fraction contained FH9614_UP (0.048 g, 0.100 mmol) in 40% yield. (NMR data for FH9614_UP, see below) $^1$H NMR (300 MHz, CDCl$_3$) δ: 0.14 (s, 3H, CH$_3$), 0.15 (s, 3H, CH$_3$), 0.97 (s, 9H, t-Bu), 1.97 (ddd, J=13.5, 5.7, 2.1 Hz, 1H, H-3"), 2.29 (ddd, J=13.2, 10.2, 5.4 Hz, 1H, H-3'), 3.75 (dd, J=11.7, 2.4 Hz, 1H, H-5"), 3.97 (d, J=5.7 Hz, 1H, H-4'), 4.10 (dd, J=11.7, 2.7 Hz, 1H, H-5'), 4.39-4.46 (m, 1H, H-2'), 5.61 (br. s, 2H, NH$_2$), 6.37 (d, J=1.2 Hz, 1H, H-1'), 7.56 (s, 1H, H-6), 8.26 (s, 1H, H-2). HRMS (ESI): calculated for $C_{18}H_{30}BrN_4O_3Si$ ([M+H]$^+$): 457.1265, found: 457.1259. Melting point: 164-166° C.

4-amino-5-bromo-N7-(2'-O-methyl-3'-deoxy-β-D-ribofuranosyl)-pyrrolo[2,3-d]pyrimidine (FH9616) FH9616 was prepared according to general procedure 9. FH9614_Mid (0.075 g, 0.164 mmol) gave rise to FH9616 (0.033 g, 0.096 mmol) as a white powder in 58% yield. (Purification: 0→6% MeOH/DCM) $^1$H NMR (300 MHz, DMSO-d$_6$) δ: 2.08 (ddd, J=13.5, 6.0, 2.4 Hz, 1H, H-3"), 2.21 (ddd, J=13.5, 9.6, 6.0 Hz, 1H, H-3'), 3.31 (s, 3H, OCH$_3$), 3.49-3.56 (m, 1H, H-5"), 3.69 (ddd, J=12.0, 5.4, 3.3 Hz, 1H, H-5'), 4.06 (dt, J=5.7, 2.1 Hz, 1H, H-2'), 4.18-4.26 (m, 1H, H-4'), 5.08 (t, J=5.4 Hz, 1H, OH-5'), 6.19 (d, J=2.1 Hz, 1H, H-1'), 6.80 (br. s, 2H, NH$_2$), 7.69 (s, 1H, H-6), 8.12 (s, 1H, H-2). $^{13}$C NMR (75 MHz, DMSO-d$_6$) δ: 31.20 (C-3'), 55.64 (OCH$_3$), 62.09 (C-5'), 80.53 (C-4'), 85.08 (C-5), 86.51 (C-2'), 87.66 (C-1'), 100.94 (C-4a), 121.24 (C-6), 148.70 (C-7a), 152.52 (C-2), 156.91 (C-4). HRMS (ESI): calculated for $C_{12}H_{16}BrN_4O_3$ ([M+H]$^+$): 343.0400, found: 343.0405. Melting point: 160° C.

4-amino-5-bromo-N7-(2'-arabino-3'-deoxy-β-D-ribofuranosyl)-pyrrolo[2,3-d]pyrimidine (FH10628) TH1003 (0.125 g, 0.362 mmol) was dissolved in anhydrous pyridine (1 mL, 2.7 mL/mmol) and cooled to −15° C. in an isopropanol-dry ice bath. Then, pivaloylchloride (0.136 mL, 1.1 mmol, 3.04 eq.) was added dropwise. After complete addition, the mixture was kept at −15° C. for 1 hour. Then, the mixture was transferred to an ice-bath (0° C.) and stirred for another 2 hours. At that time, mesylchloride (0.084 mL, 1.08 mmol, 2.97 eq.) was added at 0° C. Next, the ice bath was removed and the mixture stirred at ambient temperature for 3 hours. Then, water was added, together with diethylether. The layers were separated, and the water layer extracted with diethylether twice more. The organic layers were combined, washed with brine and dried over Na$_2$SO$_4$, filtered and evaporated till dryness. Next, the mixture was re-dissolved in MeOH (3 mL, 8 mmol/mmol SM) and NaOMe (5.4 M in MeOH) (0.54 mL, 2.9 mmol, 8 eq.) was added, followed by NaBH$_4$ (0.05 g, 1.28 mmol, 3.54 eq.). The resulting mixture was stirred at ambient temperature overnight. Then acetone (5 mL) was added and stirred for approximately 20 min, after which the mixture was quenched with aq. 0.5 M HCl. The mixture was evaporated till dryness and purified by column chromatography (2→10% MeOH/DCM) to yield FH10628 (0.075 g, 0.229 mmol) as a white solid in 63% yield. $^1$H NMR (300 MHz, DMSO-d$_6$) δ: 1.93 (dt, J=12.6, 8.1 Hz, 1H, H-3"), 2.23 (dt, J=12.9, 6.6 Hz, 1H, H-3'), 3.55 (dt, J=11.7, 5.4 Hz, 1H, H-5"), 3.64 (ddd, J=11.7, 5.4, 3.6 Hz, 1H, H-5'), 3.99-4.06 (m, 1H, H-4'), 4.40-4.48 (m, 1H, H-2'), 5.10 (t, J=5.4 Hz, 1H, OH-5'), 5.26 (d, J=5.7 Hz, 1H, OH-2'), 6.30 (d, J=5.4 Hz, 1H, H-1'), 6.70 (s, 1H, NH$_2$), 7.58 (s, 1H, H-6), 8.08 (s, 1H, H-2). $^{13}$C NMR (75 MHz, DMSO-d$_6$) δ: 33.81 (C-3'), 62.63 (C-5'), 70.30 (C-2'), 77.45 (C-4'), 84.00 (C-1'), 85.35 (C-5), 100.51 (C-4a), 123.27 (C-6), 149.40 (C-7a), 152.10 (C-2), 156.77 (C-4). HRMS (ESI): calculated for $C_{11}H_{14}BrN_4O_3$ ([M+H]$^+$): 329.0244, found: 329.0249. Melting point: 178° C.

4-amino-N7-(2'-arabino-3'-deoxy-β-D-ribofuranosyl)-pyrrolo[2,3-d]pyrimidine (FH10650)

FH10650 was prepared according to the procedure reported for FH10628. FH5284 (tubercidin) (0.21 g, 0.78 mmol) gave rise to FH10650 (0.064 g, 0.256 mmol) in 33% yield. (purification: 2→12% MeOH/DCM). $^1$H NMR (300 MHz, DMSO-d$_6$) δ:1.87-1.96 (m, 1H, H-3"), 2.24-2.33 (m, 1H, H-3'), 3.54 (dd, J=11.4, 4.8 Hz, 1H, H-5"), 3.61 (dd, J=11.7, 3.9 Hz, 1H, H-5'), 3.98-4.06 (m, 1H, H-4'), 4.38-4.45 (m, 1H, H-2'), 5.04 (br. s, 1H, OH-5'), 5.19 (d, J=5.1 Hz, 1H, OH-2'), 6.28 (d, J=5.1 Hz, 1H, H-1'), 6.51 (d, J=3.6 Hz, 1H, H-5), 6.91 (br. s, 2H, $NH_2$), 7.35 (d, J=3.9 Hz, 1H, H-6), 8.03 (s, 1H, H-2). $^{13}$C NMR (75 MHz, DMSO-$d_6$) δ: 34.69 (C-3'), 63.21 (C-5'), 70.26 (C-2'), 77.00 (C-4'), 83.98 (C-1'), 98.39 (C-4a), 102.27 (C-5), 123.51 (C-6), 150.09 (C-7a), 151.31 (C-2), 157.29 (C-4). Melting point: 166° C.

4-amino-5-bromo-N7-(5'-O-t-butyldimethylsilyl-β-D-ribofuranosyl)-pyrrolo[2,3-d]pyrimidine (FH8520) TH1003 (0.345 g, 1 mmol) was dissolved in anhydrous DMF (4 mL, 4 mL/mmol SM) and cooled to 0° C. Then, imidazole (0.17 g, 2.5 mmol, 2.5 eq.) and TBSCl (0.16 g, 1.05 mmol, 1.05 eq.) were sequentially added. The resulting solution was stirred at 0° C. until TLC showed full conversion of the starting material. Then the mixture was quenched with water, and EA was added. The layers were separated, the water layer extracted twice more with EA. The organic layers were combined, dried over $Na_2SO_4$, filtered and evaporated till dryness. Purification by column chromatography (2→8% MeOH/DCM) gave rise to FH8520 (0.36 g, 0.784 mmol) as a waxy white solid in 78% yield. $^1$H NMR (300 MHz, DMSO-$d_6$) δ: 0.09 (s, 3H, $CH_3$), 0.09 (s, 3H, $CH_3$), 0.91 (s, 9H, tBu), 3.73 (dd, J=11.4, 3.6 Hz, 1H, H-5"), 3.83 (dd, J=11.4, 3.6 Hz, 1H, H-5'), 3.92 (q, J=3.6 Hz, 1H, H-4'), 4.07 (dd, J=9.0, 5.1 Hz, 1H, H-3'), 4.26 (q, J=5.4 Hz, 1H, OH-2'), 5.14 (d, J=5.1 Hz, 1H, OH-3'), 5.43 (d, J=6.0 Hz, 1H, OH-2'), 6.10 (d, J=5.4 Hz, 1H, H-1'), 6.78 (br. s, 2H, $NH_2$), 7.54 (s, 1H, H-6), 8.11 (s, 1H, H-2). HRMS (ESI): calculated for $C_{17}H_{28}BrN_4O_4Si$ ([M+H]$^+$): 459.1058, found: 459.1058.

4-amino-5-bromo-N7-(2'-3'-anhydro-5'-O-t-butyidimethylsilyl-β-D-ribofuranosyl)-pyrrolo[2,3-d]pyrimidine (FH9523) FH8520 (0.35 g, 0.762 mmol, 1 eq.) was dissolved in 1,2-dichloroethane (7 mL, 10 mL/mmol) and TCDI (0.272 g, 1.52 mmol, 2 eq.) was added. The resulting solution was heated till reflux for 2H. It was cooled to ambient temperature and evaporated till dryness. The resulting oil was re-dissolved in P(OEt)$_3$ (10 mL) and heated till reflux. After 2.5H, LCMS showed full conversion of the starting material and the mixture was cooled to ambient temperature and evaporated till dryness. The residue was purified by column chromatography (0→2.5% MeOH/DCM) to yield FH9523 (0.1 g, 0.235 mmol) as a colourless oil in 31% yield. $^1$H NMR (300 MHz, CDCl$_3$) δ: 0.08 (s, 3H, Si—CH$_3$), 0.08 (s, 3H, Si—CH$_3$), 0.91 (s, 9H, tBu-CH$_3$), 3.79 (dd, J=11.1, 3.9 Hz, 1H, H-5"), 3.83 (dd, J=11.1, 3.9 Hz, 1H, H-5'), 4.89-4.94 (m, 1H, H-4'), 5.66 (br. s, 2H, $NH_2$), 5.92 (ddd, J=6.0, 2.4, 1.5 Hz, 1H, H-2'), 6.33 (dt, J=6.0, 1.8 Hz, 1H, H-1'), 7.29 (s, 1H, H-6), 7.29-7.31 (m, 1H, H-3'), 8.28 (s, 1H, H-2). HRMS (ESI): calculated for $C_{17}H_{26}BrN_4O_2Si$ ([M+H]$^+$): 425.1003, found: 425.1013.

4-amino-5-bromo-N7-(2',3'-anhydro-2',3'-dideoxy-β-D-ribofuranosyl)-pyrrolo[2,3-d]pyrimidine (FH10632) FH10632 was prepared according to General procedure 9. FH9523 (0.057 g, 0.134 mmol) gave rise to FH10632 (0.025 g, 0.08 mmol) as a white solid in 60% yield. (Purification: 0→5% MeOH/DCM) $^1$H NMR (300 MHz, DMSO-$d_6$) δ: 3.56 (dd, J=5.4, 4.2 Hz, 2H, H-5', H-5"), 4.80-4.93 (m, 1H, H-4'), 4.95 (t, J=5.7 Hz, 1H, OH-5'), 6.02 (ddd, J=6.0, 2.4, 1.5 Hz, 1H, H-2'), 6.43 (dt, J=6.0, 1.8 Hz, 1H, H-3'), 6.77 (br. s, 2H, $NH_2$), 7.12 (dt, J=3.0, 1.8 Hz, 1H, H-1'), 7.43 (s, 1H, H-6), 8.13 (s, 1H, H-2). $^{13}$C NMR (75 MHz, DMSO-$d_6$) δ: 62.97 (C-5'), 86.72 (C-5), 87.45 (C-4'), 87.50 (C-1'), 100.84 (C-4a), 121.43 (C-6), 125.89 (C-2'), 134.13 (C-3'), 149.18 (C-7a), 152.56 (C-2), 156.94 (C-4). HRMS (ESI): calculated for $C_{11}H_{12}BrN_4O_2$ ([M+H]$^+$): 311.0138, found: 311.0141. Melting point: 192° C.

4-amino-5-bromo-N7-(2',3'-dideoxy-5'-O-t-butyldimethylsilyl-β-D-ribofuranosyl)-pyrrolo[2,3-d]pyrimidine (FH10635) FH9534 (0.107 g, 0.307 mmol, 1 eq.) was dissolved in DMF (1.6 mL, 5 mL/mmol SM). Next, NBS (0.055 g, 0.307 mmol, 1 eq.) in DMF (1.6 mL, 5 mL/mmol SM) was added dropwise. After complete addition the resulting solution was stirred for 30 min, and then evaporated till dryness. The residue was taken up in aq. sat. $NaHCO_3$ and EA. The organic layer was washed with aq. sat. $Na_2S_2O_3$ once, dried over $Na_2SO_4$, filtered and evaporated till dryness. The residue was purified by column chromatography (0→3% MeOH/DCM) to give FH10635 (0.054 g, 0.126 mmol) as a slightly yellow oil in 41% yield. $^1$H NMR (300 MHz, CDCl$_3$) δ: 0.11 (s, 3H, Si-Me), 0.12 (s, 3H, Si-Me), 0.94 (s, 9H, tBu), 1.95-2.06 (m, 1H, H-3"), 2.08-2.26 (m, 2H, H-3', H-2"), 2.37-2.50 (m, 1H, H-2'), 3.74 (dd, J=11.1, 3.0 Hz, 1H, H-5"), 3.96 (dd, J=11.1, 3.3 Hz, 1H, H-5'), 4.14-4.21 (m, 1H, H-4'), 5.76 (br. s, 2H, $NH_2$), 6.51 (dd, J=6.6, 3.3 Hz, 1H, H-1'), 7.49 (s, 1H, H-6), 8.24 (s, 1H, H-2). HRMS (ESI): calculated for $C_{17}H_{18}BrN_4O_2Si$ ([M+H]$^+$): 427.1159, found: 427.1176.

4-amino-5-bromo-N7-(2',3'-dideoxy-β-D-ribofuranosyl)-pyrrolo[2,3-d]pyrimidine (FH10638) FH10638 was prepared according to general procedure 9. FH10635 (0.054 g, 0.126 mmol, 1 eq.) gave rise to FH10638 (0.035 g, 0.112 mmol) as a white solid in 89% yield. (Purification: 0→6% MeOH/DCM) $^1$H NMR (300 MHz, DMSO-$d_6$) δ: 1.96-2.04 (m, 2H, H-3', H-3"), 2.13-2.23 (m, 1H, H-2"), 2.30-2.42 (m, 1H, H-2'), 3.49 (ddd, J=11.7, 5.4, 4.5 Hz, 1H, H-5"), 3.60 (ddd, J=11.7, 5.7, 4.2 Hz, 1H, H-5'), 4.00-4.08 (m, 1H, H-4'), 4.95 (t, J=5.7 Hz, 1H, OH-5'), 6.37 (dd, J=6.9, 4.5 Hz, 1H, H-1'), 6.75 (br. s, 2H, $NH_2$), 7.64 (s, 1H, H-6), 8.09 (s, 1H, H-2). $^{13}$C NMR (75 MHz, DMSO-$d_6$) δ: 25.82 (C-3'), 31.79 (C-2'), 62.95 (C-5'), 81.03 (C-4'), 83.55 (C-1'), 86.30 (C-5), 100.85 (C-4a), 121.24 (C-6), 148.85 (C-7a), 152.35 (C-2), 156.87 (C-4). HRMS (ESI): calculated for $C_{11}H_{14}BrN_4O_2$ ([M+H]$^+$): 313.0295, found: 313.0300. Melting point: 156° C.

C-4' Substituted Analogues 4-amino-5-bromo-N7-(2'-O-t-butyldimethylsilyl-3'-deoxy-β-D-ribofuranosyl)-pyrrolo[2,3-d]pyrimidine (FH9551) FH7429_U (0.703 g, 2.14 mmol, 1 eq.), imidazole (0.88 g, 12.84 mmol, 6 eq.) and DMAP (0.04 g, 0.321 mmol, 0.15 eq.) were dissolved in DMF (11 mL, 5 mL/mmol SM). Next, TBSCl (0.805 g, 5.34 mmol, 2.5 eq.) was added, and the resulting mixture stirred at ambient temperature till full conversion was observed (generally overnight). Then, water and EA were added. The layers were separated, and the water layer extracted with EA twice more. The organic layers were combined, dried over $Na_2SO_4$, filtered and evaporated till dryness. The residue was purified by column chromatography (10→40% EA/PET) to give FH9551 (1.0 g, 1.79 mmol) as a white solid in 84% yield. $^1$H NMR (300 MHz, CDCl$_3$) δ: 0.03 (s, 3H, Si—CH$_3$), 0.08 (s, 3H, Si—CH$_3$), 0.15 (s, 3H, Si—CH$_3$), 0.16 (s, 3H, Si—CH$_3$), 0.87 (s, 9H, t-BuSi), 0.97 (s, 9H, t-BuSi), 1.83 (ddd, J=12.9, 5.7, 2.7 Hz, 1H, H-3"), 2.25 (ddd, J=12.9, 9.0, 5.1 Hz, 1H, H-3'), 3.75 (dd, J=11.7, 2.7 Hz, 1H, H-5"), 4.10 (dd, J=11.7, 2.4 Hz, 1H, H-5'), 4.41-4.44 (m, 1H, H-4'), 4.46-4.52 (m, 1H, H-2'), 5.56 (br. s, 2H, $NH_2$), 6.19 (d, J=1.8 Hz, 1H, H-1'), 7.57 (s, 1H, H-6), 8.24 (s, 1H, H-2). $^{13}$C NMR (75 MHz, CDCl$_3$) δ: −5.26 (CH$_3$), −5.11 (CH$_3$), −5.01 (CH$_3$), −4.63 (CH$_3$), 18.11 (tBu-C), 18.75 (tBu-C), 25.84 (tBu (CH$_3$)$_3$), 26.23 (tBu(CH$_3$)$_3$), 34.07 (C-3'), 63.99 (C-5'), 77.92 (C-4'), 80.70 (C-2'), 91.31 (C-1' & C-5), 102.50

(C-4a), 121.32 (C-6), 149.31 (C-7a), 152.57 (C-2), 156.71 (C-4). HRMS (ESI): calculated for $C_{23}H_{42}BrN_4O_3Si_2$ ([M+H]$^+$): 557.1973, found: 557.1965.

4-amino-5-bromo-N7-(2'-O-t-butyldimethylsilyl-3'-deoxy-β-D-ribofuranosyl)-pyrrolo[2,3-d]pyrimidine (FH9552) FH9551 (1.0 g, 1.79 mmol, 1 eq.) was dissolved in MeOH (24.5 mL 12.5 mL/mmol) and EA (24.5 mL, 12.5 mL/mmol) and the solution cooled to 0° C. in an ice bath. Then pTsOH·1H$_2$O (0.96 g, 5.01 mmol, 2.8 eq.) was added and the resulting solution stirred at 0° C. until full conversion of the starting material was observed by TLC (generally between 5 to 7 hours). Then, K$_2$CO$_3$ (1.37 g, 1.43 g/g pTSOH·1H$_2$O) was added and stirred for 30 min at ambient temperature. The resulting suspension was filtered and the filtrate evaporated till dryness. The residue was purified by column chromatography (1→5% MeOH/DCM) to give FH9552 (0.586 g, 1.32 mmol) as a white foam in 74% yield. $^1$H NMR (300 MHz, CDCl$_3$) δ: −0.26 (s, 3H, Si—CH$_3$), −0.15 (s, 3H, Si—CH$_3$), 0.78 (s, 9H, t-BuSi), 2.15 (ddd, J=12.3 8.7, 3.6 Hz, 1H, H-3"), 2.50 (ddd, J=12.3, 7.5.3.6 Hz, 1H, H-3'), 3.48-3.56 (m, 1H, H-5"), 3.95 (dd, J=12.6, 1.5 Hz, 1H, H-5'), 4.46 (ddt, J=12.6, 3.3, 1.8 Hz, 1H, H-4'), 5.02 (td, J=7.8, 6.0 Hz, 1H, H-2'), 5.47 (d, J=6.0 Hz, 1H, H-1'), 5.73 (br. s, 2H, NH$_2$), 5.91 (d, J=10.8 Hz, 1H, OH-5'), 7.01 (s, 1H, H-6), 8.25 (s, 1H, H-2). HRMS (ESI): calculated for $C_{17}H_{28}BrN_{43}Si$ ([M+H]$^+$): 473.1214, found: 443.1109.

4-amino-5-bromo-N7-(2'-O-t-butyldimethylsilyl-3'-deoxy-4'-hydroxymethyl-β-D-ribofuranosyl)-pyrrolo[2,3-d]pyrimidine (FH9558) FH9552 (0.225 g, 0.5 mmol, 1 eq.) was dissolved in DCM (5 mL, 10 mL/mmol SM) and cooled to 0° C. Then, Dess-Martin periodinane (0.254 g, 0.6 mmol, 1.2 eq.) was added. The resulting solution was stirred at ambient temperature until full conversion of the starting material was observed (between 3 to 5H). Then, aq. sat. NaHCO$_3$ and DCM were added. The layers were separated and the water layer extracted twice more with DCM. The organic layers were combined, dried over Na$_2$SO$_4$, filtered and evaporated till dryness. The residue was taken up in THF (5 mL, 10 mL/mmol SM), and aq. formaldehyde (37% WV) (0.8 mL, 0.278 mmol) was added together with aq. 1 M NaOH solution (1 mL). the resulting mixture was stirred at ambient temperature overnight, after which NaBH$_4$ (0.1 g, 2.5 mmol, 5 eq.) was added, and stirred for 1H at ambient temperature. Then the mixture was quenched by the addition of aq. 0.5 M HCl, and EA added. The layers were separated, and the water layer extracted with EA twice more. The organic layers were combined, dried over Na$_2$SO$_4$, filtered and evaporated till dryness. The residue was purified by column chromatography (0→5% MeOH/DCM) to give FH9558 (0.046 g, 0.097 mmol) as an oil in 20% yield. $^1$H NMR (300 MHz, CDCl$_3$) δ: −0.31 (s, 3H, Si—CH$_3$), −0.18 (s, 3H, Si—CH$_3$), 0.77 (s, 9H, tBu-CH$_3$), 2.09 (dd, J=12.3, 9.0 Hz, 1H, H-3"), 2.55 (dd, J=12.6, 8.1 Hz, 1H, H-3'), 3.45 (d, J=12.3 Hz, 1H, H-5"), 3.59 (s, 2H, H-5", H-5'), 3.82 (d, J=12.3 Hz, 1H, H-5'), 5.14-5.22 (m, 1H, H-2'), 5.44 (d, J=6.9 Hz, 1H, H-1'), 5.77 (br. s, 2H, NH$_2$), 6.99 (s, 1H, H-6), 8.25 (s, 1H, H-2). HRMS (ESI): calculated for $C_{18}H_{30}BrN_4O_4Si$ ([M+H]$^+$): 473.1214, found: 473.1220.

4-amino-5-bromo-N7-(3'-deoxy-4'-hydroxymethyl-β-D-ribofuranosyl)-pyrrolo[2,3-d]pyrimidine (FH9561) FH9561 was prepared according to General procedure 9. FH9558 (0.046 g, 0.0978 mmol, 1 eq.) gave rise to FH9561 (0.026 g, 0.072 mmol) as a white solid in 74% yield. (Purification: 2→12% MeOH/DCM). $^1$H NMR (300 MHz, DMSO-d$_6$) δ: 1.94 (dd, J=12.6, 7.8 Hz, 1H, H-3"), 2.28 (dd, J=12.6, 7.8 Hz, 1H, H-3"), 3.47-3.56 (m, 4H, H-5', H-5"), 4.52-4.62 (m, 1H, H-2'), 4.94 (t, J=5.7 Hz, 1H, OH-5'), 5.16 (t, J=5.7 Hz, 1H, OH-5'), 5.44 (d, J=5.7 Hz, 1H, OH-2'), 5.97 (d, J=6.0, 1H, H-1'), 6.79 (br. s, 2H, NH$_2$), 7.64 (s, 1H, H-6), 8.09 (s, 1H, H-2). $^{13}$C NMR (75 MHz, DMSO-d$_6$) δ: 36.06 (C-3'), 64.63 (2C, C-5', C-5"), 74.05 (C-2'), 86.37, 86.51, 89.19 (C-1'), 101.02 (C-4a), 122.01 (C-6), 149.49 (C-7a), 152.30 (C-2), 156.95 (C-4). HRMS (ESI): calculated for $C_{12}H_{16}BrN_4O_4$ ([M+H]$^+$): 359.0349, found: 359.0385. Melting point: 228° C.

C-5' Substituted Analogues 4-amino-N7-(2'-O-t-butyldimethylsilyl-3'-deoxy-β-D-ribofuranosyl)-pyrrolo[2,3-d]pyrimidine (FH9594) FH9552 (0.477 g, 1.08 mmol) was dissolved in EtOH (20 mL) and aq. 1 M NaOAc (5 mL) was added. Then, the flask was purged with N$_2$, after which a cat. amount of Pd/C was added. Next, the N$_2$-atmosphere was exchanged for H$_2$ (balloon; bubbling), and the mixture stirred until LC/MS showed full conversion of the SM (approx. 2H). Then, the H$_2$-balloon was removed, the mixture purged again with N2 and filtered over Celite®. The mixture was evaporated till dryness, and partitioned between EA and aq. sat. NaHCO$_3$/aq. sat. Na$_2$S$_2$O$_3$ solution. Layers were separated and the water layer extracted twice more with EA. Organic layers were combined, dried over Na$_2$SO$_4$, filtered and evaporated till dryness. Purification by column chromatography (5% MeOH/DCM) gave rise to FH9594 (0.357 g, 0.98 mmol) as a white waxy solid in 91% yield. $^1$H NMR (300 MHz, CDCl$_3$) δ: −0.33 (s, 3H, CH$_3$), −0.21 (s, 3H, CH$_3$), 0.76 (s, 9H, tBu), 2.19 (dt, J=12.0, 9.0 Hz, 1H, H-3"), 2.54 (ddd, J=12.3, 7.8, 2.7 Hz, 1H, H-3'), 3.51 (br. s, 1H, H-5"), 3.98 (dd, J=12.6, 1.5 Hz, 1H, H-5'), 4.44-4.49 (m, 1H, H-4'), 5.08-5.15 (m, 1H, H-2'), 5.23 (br. s, 2H, NH$_2$), 5.49 (d, J=6.3 Hz, 1H, H-1'), 6.32 (d, J=3.6 Hz, 1H, H-5), 6.55 (br. s, 1H, OH-5'), 6.99 (d, J=3.6 Hz, 1H, H-6), 8.29 (s, 1H, H-2). $^{13}$C NMR (75 MHz, CDCl$_3$) δ: −5.31 (CH$_3$), −5.15 (CH$_3$), 18.01 (Si—C(CH$_3$)$_3$), 25.73 (3C, t-Bu), 35.13 (C-3'), 65.38 (C-5'), 73.57 (C-2'), 79.73 (C-4'), 95.91 (C-1'), 97.71 (C-5), 105.42 (C-4a), 126.04 (C-6), 149.06 (C-7a), 151.47 (C-2), 157.23 (C-4). HRMS (ESI): calculated for $C_{17}H_{29}N_4O_3Si$ ([M+H]$^+$): 365.2003, found: 365.1994.

4-amino-5-bromo-N7-(2'-O-t-butyldimethylsilyl-3'-deoxy-5'-thiomethyl-β-D-ribofuranosyl)-pyrrolo[2,3-d]pyrimidine (FH9583) FH9552 (0.111 g, 0.25 mmol) was dissolved in DCM (4 mL, 15 mL/mmol SM) and cooled to 0° C. in an ice bath. Next, Et$_3$N (0.084 mL, 0.6 mmol, 2.4 eq.) was added, followed by MsCl (0.023 mL, 0.3 mmol, 1.2 eq.). Then, the reaction was allowed to stir at ambient temperature for 30 min-1H, after which full conversion of the SM was observed by TLC analysis. Next, aq. sat. NH$_4$Cl was added, and the layers were separated. The water layer was extracted twice more with DCM. The organic layers were combined, dried over Na$_2$SO$_4$, filtered and evaporated till dryness. The resulting foam was re-dissolved in anhydrous THF (2.5 mL, 10 mL/mmol SM). Next, NaSMe (0.044 g, 0.625 mmol, 2.5 eq.) was added and the mixture refluxed for approximately 2 hours. The solution was then cooled to ambient temperature and neutralized with aq. 0.5 M HCl. Then, DCM was added, layers separated, and the water layer extracted once more with DCM. The organic layers were combined, dried over Na$_2$SO$_4$, filtered and evaporated till dryness. The residue was purified by column chromatography (10→30% EA/PET) to give FH9583 (0.052 g, 0.11 mmol) as an oil in 44% yield. $^1$H NMR (300 MHz, CDCl$_3$) δ: 0.03 (s, 3H, CH$_3$), 0.07 (s, 3H, CH$_3$), 0.88 (s, 9H, t-Bu), 2.04-2.10 (m, 2H, H-3', H-3"), 2.19 (s, 3H, SCH$_3$), 4.55-4.66 (m, 2H, H-2', H-4'), 5.58 (br. s, 2H, NH$_2$), 6.13 (d, J=1.8 Hz, 1H, H-1'), 7.19 (s, 1H, H-6), 8.25 (s, 1H, H-2). HRMS (ESI): calculated for $C_{18}H_{30}BrN_4O_2SSi$ ([M+H]$^+$): 473.1037, found: 473.1037.

4-amino-5-bromo-N7-(2'-O-t-butyldimethylsilyl-3'-deoxy-5'-thio-ethyl-β-D-ribofuranosyl)-pyrrolo[2,3-d]pyrimidine (FH9585) FH9585 was prepared as described for FH9583, except that NaSEt (5 eq.) was used. NaSEt was prepared by addition of EtSH (5 eq.) to a stirring solution of NaOtBu (5 eq.) in anhydrous THF (10 mL/mmol SM). FH9552 (0.155 g, 0.35 mmol) gave rise to FH9585 (0.097 g, 0.199 mmol) as an oil in 57% yield. (Purification: 5→30% EA/PET). $^1$H NMR (300 MHz, CDCl$_3$) δ: 0.03 (s, 3H, SiCH$_3$), 0.06 (s, 3H, SiCH$_3$), 0.88 (s, 9H, t-Bu), 1.27 (t, J=7.5 Hz, 3H, CH$_3$), 2.04-2.10 (m, 2H, H-3', H-3"), 2.62 (q, J=7.5 Hz, 2H, CH$_2$), 2.86 (dd, J=13.8, 6.0 Hz, 1H, H-5"), 2.92 (dd, J=13.8, 5.4 Hz, 1H, H-5'), 4.54-4.64 (m 2H, H-2', H-4'), 5.59 (br. s, 2H, NH$_2$), 6.13 (d, J=1.8 Hz, 1H, H-1'), 7.22 (s, 1H, H-6), 8.25 (s, 1H, H-2). HRMS (ESI): calculated for $C_{19}H_{32}BrN_4O_2SSi$ ([M+H]$^+$): 487.1193, found: 487.1203.

4-amino-5-bromo-N7-(2'-O-t-butyldimethylsilyl-3'-deoxy-5'—S-thio-ethan-2-ol-β-D-ribofuranosyl)-pyrrolo[2,3-d]pyrimidine (FH9586) FH9586 was prepared as described for FH9583, except that NaSEtOH (5 eq.) was used. NaSEtOH was prepared by addition of HSEtOH (5 eq.) to a stirring solution of NaOtBu (5 eq.) in anhydrous THF (10 mL/mmol SM). FH9552 (0.155 g, 0.35 mmol) gave rise to slightly impure FH9586 (0.188 g, 0.37 mmol). (Purification: 0→3% MeOH/DCM) $^1$H NMR (300 MHz, CDCl$_3$) δ: 0.02 (s, 3H, CH$_3$), 0.06 (s, 3H, CH$_3$), 0.87 (s, 9H, t-Bu), 2.04-2.14 (m, 2H, H-3', H-3"), 2.25 (br. s, 1H, OH), 2.77-2.80 (m, 2H, SCH$_2$), 2.90-2.93 (m, 2H, H-5', H-5"), 3.74 (t, J=5.4 Hz, 1H, CH$_2$H), 4.64-4.56 (m, 2H, H-2', H-4'), 5.60 (br. s, 2H, NH$_2$), 6.13 (d, J=1.8 Hz, 1H, H-1'), 7.20 (s, 1H, H-6), 8.25 (s, 1H, H-2). HRMS (ESI): calculated for $C_{19}H_{32}BrN_4O_3SSi$ ([M+H]$^+$): 503.1142, found: 503.1168.

4-amino-N7-(2'-O-t-butyldimethylsilyl-3'-deoxy-5'-thiomethyl-β-D-ribofuranosyl)-pyrrolo[2,3-d]pyrimidine (FH9595) FH9595 was prepared according to the procedure described for FH9583. FH9594 (0.128 g, 0.35 mmol) was transformed into FH9595 (0.067 g, 0.17 mmol) as an oil in 49% yield. $^1$H NMR (300 MHz, CDCl$_3$) δ: 0.00 (s, 3H, Si—CH$_3$), 0.01 (s, 3H, Si—CH$_3$), 0.85 (s, 9H, t-Bu), 2.07 (ddd, J=12.9, 6.0, 2.7 Hz, 1H, H-3"), 2.10-2.16 (m, 1H, H-3'), 2.17 (s, 3H, SCH$_3$), 2.82 (dd, J=13.8, 6.0 Hz, 1H, H-5"), 2.88 (dd, J=13.8, 5.4 Hz, 1H, H-5'), 4.56-4.65 (m, 2H, H-4', H-2'), 5.31 (br. s, 2H, NH$_2$), 6.14 (d, J=2.1 Hz, 1H, H-1'), 6.37 (d, J=3.6 Hz, 1H, H-5), 7.17 (d, J=3.6 Hz, 1H, H-6), 8.29 (s, 1H, H-2). HRMS (ESI): calculated for $C_{18}H_{31}N_4O_2SSi$ ([M+H]$^+$): 395.1931, found: 395.1920.

4-amino-N7-(2'-O-t-butyldimethylsilyl-3'-deoxy-5'—S-thio-ethan-2-ol-β-D-ribofuranosyl)-pyrrolo[2,3-d]pyrimidine (FH9596) FH9595 was prepared according to the procedure described for FH9583, except that NaSEtOH (5 eq.) was used. NaSEtOH was prepared by addition of HSEtOH (5 eq.) to a stirring solution of NaOtBu (5 eq.) in anhydrous THF (10 mL/mmol SM). FH9594 (0.128 g, 0.35 mmol) gave rise to FH9596 (0.072 g, 0.17 mmol) as an oil in 48% yield. (Purification: 2→8% MeOH/DCM) $^1$H NMR (300 MHz, CDCl$_3$) δ: −0.01 (s, 3H, Si—CH$_3$), 0.00 (s, 3H, Si—CH$_3$), 0.85 (s, 9H, t-Bu), 2.06 (ddd, J=12.9, 6.0, 2.7 Hz, 1H, H-3"), 2.19 (ddd, J=12.9, 9.3, 5.7 Hz, 1H, H-5'), 2.63 (br. s, 1H, OH), 2.77 (td, J=6.0, 2.1 Hz, 2H, H-5', H-5"), 2.91 (d, J=5.4 Hz, 2H, S—CH$_2$CH$_2$OH), 3.71 (t, J=5.7 Hz, 2H, S—CH$_2$CH$_2$), 4.54-4.61 (m, 1H, H-4'), 4.64 (dt, J=5.7, 2.4 Hz, 1H, H-2'), 5.25 (br. s, 2H, NH$_2$), 6.14 (d, J=2.4 Hz, 1H, H-1'), 6.36 (d, J=3.6 Hz, 1H, H-5), 7.15 (d, J=3.6 Hz, 1H, H-6), 8.29 (s, 1H, H-2). HRMS (ESI): calculated for $C_{19}H_{33}N_4O_3SSi$ ([M+H]$^+$): 425.2037, found: 425.2007.

4-amino-5-bromo-N7-(3'-deoxy-5'-thiomethyl-β-D-ribofuranosyl)-pyrrolo[2,3-d]pyrimidine (FH9527)

FH9527 was prepared according to General procedure 9. FH9583 (0.052 g, 0.11 mmol) gave rise to FH9527 (0.026 g, 0.072 mmol) as a white solid in 66% yield. (Purification: 0.4→4% MeOH/DCM) $^1$H NMR (300 MHz, DMSO-d$_6$) δ:2.04 (ddd, J=13.2, 6.0, 3.0 Hz, 1H, H-3"), 2.07 (s, 3H, SCH$_3$), 2.18 (ddd, J=13.2, 9.0, 6.0 Hz, 1H, H-3'), 2.78 (d, J=6.3 Hz, 2H, H-5', H-5"), 4.34-4.39 (m, 1H, H-4'), 4.40-4.46 (m, 1H, H-2'), 5.61 (d, J=4.2 Hz, 1H, OH-2'), 6.06 (d, J=2.4 Hz, 1H, H-1'), 6.78 (br. s, 2H, NH$_2$), 7.52 (s, 1H, H-6), 8.12 (s, 1H, H-2). $^{13}$C NMR (75 MHz, DMSO-d$_6$) δ: 15.69 (SCH$_3$), 37.78 (C-5'), 38.39 (C-3'), 74.69 (C-2'), 78.52 (C-4'), 87.06 (C-5), 89.91 (C-1'), 100.81 (C-4a), 121.16 (C-6), 149.31 (C-7a), 152.58 (C-2), 156.93 (C-4). HRMS (ESI): calculated for $C_{12}H_{16}N_4O_2S$ ([M+H]$^+$): 359.0172, found: 359.0184. Melting point: 205° C.

4-amino-5-bromo-N7-(3'-deoxy-5'-thio-ethyl-β-D-ribofuranosyl)-pyrrolo[2,3-d]pyrimidine (FH9590) FH9590 was prepared according to General procedure 9. FH9585 (0.097 g, 0.199 mmol) gave rise to FH9590 (0.048 g, 0.129 mmol) as a white solid in 65% yield. (Purification: 0.5→4% MeOH/DCM) $^1$H NMR (300 MHz, DMSO-d$_6$) δ:1.15 (t, J=7.5 Hz, 3H, CH$_3$), 2.04 (ddd, J=13.2, 6.0, 2.7 Hz, 1H, H-3"), 2.18 (ddd, J=13.2, 9.0, 6.0 Hz, 1H, H-3'), 2.54 (t, J=7.2 Hz, 2H, SCH$_2$), 2.81 (d, J=6.0 Hz, 2H, H-5', H-5"), 4.32-4.39 (m, 1H, H-4'), 4.41-4.46 (m, 1H, H-2'), 5.60 (d, J=4.2 Hz, 1H, OH-2'), 6.06 (d, J=2.4 Hz, 1H, H-1'), 6.79 (br. s, 2H, NH$_2$), 7.53 (s, 1H, H-6), 8.12 (s, 1H, H-2). $^{13}$C NMR (75 MHz, DMSO-d$_6$) δ: 14.79 (CH$_3$), 25.93 (SCH$_2$), 35.32 (C-5'), 38.36 (C-3'), 74.72 (C-2'), 78.83 (C-4'), 87.07 (C-5), 89.91 (C-1'), 100.80 (C-4a), 121.19 (C-6), 149.31 (C-7a), 152.59 (C-2), 156.94 (C-4). HRMS (ESI): calculated for $C_{13}H_{18}BrN_4O_2S$ ([M+H]$^+$): 373.0328, found: 373.0337. Melting point: 191° C.

4-amino-5-bromo-N7-(3'-deoxy-5'-thio-ethan-2-ol-β-D-ribofuranosyl)-pyrrolo[2,3-d]pyrimidine (FH9591) FH9591 was prepared according to General procedure 9. FH9586 (0.188, 0.373 mmol) gave rise to FH9591 (0.09 g, 0.232 mmol) as a white solid in 62% yield. (Purification: 2→10% MeOH/DCM) $^1$H NMR (300 MHz, DMSO-d$_6$) δ:2.04 (ddd, J=13.2, 6.0, 3.0 Hz, 1H, H-3"), 2.17 (ddd, J=13.2, 9.0, 6.0 Hz, 1H, H-3'), 2.59 (t, J=6.9 Hz, 2H, SCH$_2$CH$_2$OH), 2.78-2.89 (m, 2H, H-5', H-5"), 3.51 (dt, J=6.9, 5.7 Hz, 2H, SCH$_2$CH$_2$OH), 4.31-4.37 (m, 1H, H-4'), 4.38-4.45 (m, 1H, H-2'), 4.75 (t, J=5.7 Hz, 1H, SCH$_2$CH$_2$OH), 5.60 (d, J=4.2 Hz, 1H, OH-2'), 6.06 (d, J=2.4 Hz, 1H, H-1'), 6.80 (br. s, 2H, NH$_2$), 7.52 (s, 1H, H-6), 8.12 (s, 1H, H-2). $^{13}$C NMR (75 MHz, DMSO-d$_6$) δ: 34.71 (SCH$_2$CH$_2$OH), 35.96 (C-5'), 38.30 (C-3'), 60.89 (SCH$_2$CH$_2$OH), 74.71 (C-2'), 78.77 (C-4'), 87.06 (C-5), 89.91 (C-1'), 100.80 (C-4a), 121.18 (C-6), 149.28 (C-7a), 152.56 (C-2), 156.93 (C-4). HRMS (ESI): calculated for $C_{13}H_{18}BrN_4O_3S$ ([M+H]$^+$): 389.0278, found: 389.0276. Melting point: 164° C.

4-amino-5-bromo-N7-(2'-O-t-butyldimethylsilyl-3'-deoxy-5'-sulfamoyl-β-D-ribofuranosyl)-pyrrolo[2,3-d]pyrimidine (FH9589)

Preparation of Sulfamoylchloride:

In a flame-dried Schlenk tube equipped with a stir bar, was added under argon chlorosulfonyl isocyanate (87 μL), and the tube cooled to 0° C. in an ice-bath. Then, formic acid (39 μL) was added, and the mixture was allowed to reach ambient temperature gradually. Next, 1 mL of anhydrous THF was added and the resulting solution used.

FH9552 (0.22 g, 0.5 mmol, 1 eq.) was dissolved in anhydrous THF (7.5 mL, 15 mL/mmol SM) and cooled to 0° C. in an ice-bath. Next, NaH (60% dispersion in mineral oil) (0.024 g, 0.06 mmol, 1.5 eq.) was added, immediately followed by 0.83 mL of the prepared sulfamoylchloride solution. This mixture was stirred at 0° C. for approximately 3 hours, after which MeOH was added to quench the mixture. The resulting mixture was then evaporated till dryness, and partitioned between EA and water. The organic layer was washed with $NH_4Cl$, dried over $Na_2SO_4$, filtered and evaporated till dryness. Purification by column chromatography 0→4% MeOH/DCM gave FH9589 (0.132 g, 0.253 mmol) as an oil in 51% yield. $^1$H NMR (300 MHz, MeOH-$d_4$) δ: −0.05 (s, 3H, $CH_3$), 0.01 (s, 3H, $CH_3$), 0.84 (s, 9H, tBu), 2.13 (ddd, J=13.2, 6.9, 4.5 Hz, 1H, H-3"), 2.33 (ddd, J=13.2, 7.2, 6.3 Hz, 1H, H-3'), 4.26 (dd, J=11.1, 4.2 Hz, 1H, H-5"), 4.37 (dd, J=11.1, 3.3 Hz, 1H, H-5'), 4.58-4.70 (m, 2H, H-2', H-4'), 6.13 (d, J=3.3 Hz, 1H, H-1'), 7.46 (s, 1H, H-8), 8.11 (s, 1H, H-2). HRMS (ESI): calculated for $C_{17}H_{29}N_5O_4SSi$ ($[M+H]^+$): 522.0837, found: 522.0835.

4-amino-N7-(3'-deoxy-5'-O-sulfamoyl-β-D-ribofuranosyl)-pyrrolo[2,3-d]pyrimidine (FH9608)

FH9589 (0.13 g, 0.249 mmol, 5 eq.) was dissolved in anhydrous THF (10 mL, 40 mL/mmol SM). Next, $Et_3N\cdot3HF$ (0.205 mL, 1.245 mmol, 5 eq.) was added, and the resulting solution stirred at ambient temperature overnight. Then, another portion of $Et_3N\cdot3HF$ (0.205 mL, 1.245 mmol, 5 eq.) was added and stirring continued for 24 hours. Then, the resulting mixture was filtered and evaporated till dryness. $Et_3N$ was added and evaporated once more. The resulting mixture was purified by column chromatography 5→15% MeOH/DCM. The resulting solid was dissolved in MeOH and aq. 1 M NaOH was added till pH 10. The mixture was then evaporated till dryness and purified by column chromatography again (5→15% MeOH/DCM) to give FH9608 (0.053 g, 0.129 mmol) as a white solid in 52% yield. $^1$H NMR (300 MHz, MeOH-$d_4$) δ: 2.12 (ddd, J=13.5, 6.6, 3.3 Hz, 1H, H-3"), 2.32 (ddd, J=13.5, 9.0, 6.0 Hz, 1H, H-3'), 4.26 (dd, J=11.1, 4.2 Hz, 1H, H-5"), 4.38 (dd, J=11.3, 3.0 Hz, 1H, H-5'), 4.50-4.54 (m, 1H, H-2'), 4.61-4.68 (m, 1H, H-4'), 6.16 (d, J=2.7 Hz, 1H, H-1'), 7.45 (s, 1H, H-6), 8.12 (s, 1H, H-2). $^1$H NMR (300 MHz, MeOH-$d_4$+2 drops $D_2O$) δ: 2.15 (ddd, J=13.5, 6.6, 3.3 Hz, 1H, H-3"), 2.33 (ddd, J=13.5, 8.7, 6.0 Hz, 1H, H-3'), 4.27 (dd, J=11.1, 4.2 Hz, 1H, H-5"), 4.41 (dd, J=11.1, 3.0 Hz, 1H, H-5'), 4.51-4.55 (m, 1H, H-2'), 4.64-4.70 (m, 1H, H-4'), 6.16 (d, J=2.4 Hz, 1H, H-1'), 7.45 (s, 1H, H-6), 8.12 (s, 1H, H-2). $^{13}$C NMR (75 MHz, MeOH-$d_4$+2 drops $D_2O$) δ: 35.09 (C-3'), 71.18 (C-5'), 76.69 (C-2'), 78.62 (C-4'), 89.06 (C-5), 92.14 (C-1'), 122.54 (C-6), 150.12 (C-7a), 153.26 (C-2), 158.55 (C-4). Melting point: 260° C. (decomposed).

4-chloro-5-bromo-N7-(2',3'-di-O-acetyl-5'-deoxy-β-D-ribofuranosyl)-pyrrolo[2,3-d]pyrimidine (FH8476) In a 25 mL flame-dried 2-neck round-bottom flask, equipped with a stir bar was added FH2066 (0.691 g, 3 mmol, 1 eq.) under argon. Next, anhydrous MeCN (12 mL, 4 mL/mmol SM) was added, followed by BSA (0.88 mL, 3.6 mmol, 1.2 eq.). After 10 min stirring at ambient temperature, 1,2,3-tri-O-acetyl-5-deoxy-D-ribofuranose (1.56 g, 6 mmol, 2 eq.) was added, immediately followed by TMSOTf (1.09 mL, 6 mmol, 2 eq.) and the resulting mixture stirred at ambient temperature for another 15 min. Then, the mixture was heated at 80° C. in a pre-heated oil bath for approximately 1.5H. Next, it was cooled to ambient temperature, and EA and aq. sat. $NaHCO_3$ were added. The layers were separated and the water layer extracted with EA twice more. The organic layers were combined, dried over $Na_2SO_4$, filtered and evaporated till dryness. The residue was purified by column chromatography (3→4% EA/DCM) to give FH8476 (0.42 g, 0.968 mmol) as a white foam in 32% yield. $^1$H NMR (300 MHz, $CDCl_3$) δ: 1.48 (d, J=6.3 Hz, 3H, $CH_3$), 2.04 (s, 3H, OAc), 2.14 (s, 3H, OAc), 4.30 (dd, J=6.6, 5.1 Hz, 1H, H-4'), 5.24 (t, J=5.4 Hz, 1H, H-3'), 5.67 (t, J=5.4 Hz, 1H, H-2'), 6.35 (d, J=5.4 Hz, 1H, H-1'), 7.41 (s, 1H, H-6), 8.65 (s, 1H, H-2).

4-azido-5-bromo-N7-(2',3'-di-O-acetyl-5'-deoxy-β-D-ribofuranosyl)-pyrrolo[2,3-d]pyrimidine (FH8479) FH8479 was prepared according to General procedure 3. FH8476 (0.419 g, 0.968 mmol) give rise to FH8479 (0.326 g, 0.744 mmol) as a white foam in 77% yield. (Purification: 10→35% EA/HEX) $^1$H NMR (300 MHz, DMSO-$d_6$) δ: 1.44 (d, J=6.3 Hz, 1H, $CH_3$), 2.02 (s, 3H, OAc), 2.14 (s, 3H, OAc), 4.24-4.32 (m, 1H, H-4'), 5.29 (dd, J=6.0, 4.8 Hz, 1H, H-3'), 5.82 (t, J=6.0 Hz, 1H, H-2'), 6.45 (d, J=6.0 Hz, 1H, H-1'), 8.33 (s, 1H, H-6), 10.00 (s, 1H, H-2).

4-amino-5-bromo-N7-(2',3'-di-O-acetyl-5'-deoxy-β-D-ribofuranosyl)-pyrrolo[2,3-d]pyrimidine (FH8482) FH8482 was prepared according to General procedure 4. FH8479 (0.3 g, 0.683 mmol) gave rise to FH8482 (0.279 g, 0.676 mmol) in 99% yield. (Purification: 35→75% EA/HEX) $^1$H NMR (300 MHz, $CDCl_3$) δ: 1.47 (d, J=6.6 Hz, 1H, $CH_3$), 2.05 (s, 3H, OAc), 2.13 (s, 3H, OAc), 4.27 (ddd, J=12.9, 6.3, 4.8 Hz, 1H, H-4'), 5.22 (dd, J=5.7, 5.1 Hz, 1H, H-3'), 5.62 (t, J=5.7 Hz, 1H, H-2'), 5.82 (br. s, 2H, $NH_2$), 6.34 (d, J=5.7 Hz, 1H, H-1'), 7.11 (s, 1H, H-6), 8.28 (s, 1H, H-2). HRMS (ESI): calculated for $C_{15}H_{18}BrN_4O_5$ ($[M+H]^+$): 413.0455, found: 413.0465.

4-amino-5-bromo-N7-(5'-deoxy-β-D-ribofuranosyl)-pyrrolo[2,3-d]pyrimidine (FH8485)

FH8485 was prepared according to General procedure 5. FH8482 (0.27 g, 0.653 mmol) gave rise to FH8485 (0.193 g, 0.586 mmol) in 90% yield. (Purification: 5→7.5% MeOH/DCM) $^1$H NMR (300 MHz, DMSO-$d_6$) δ: 1.27 (d, J=6.3 Hz, 1H, $CH_3$), 3.82-3.94 (m, 2H, H-3', H-4'), 4.38 (q, J=5.4 Hz, 1H, H-2'), 5.09 (d, J=5.1 Hz, 1H, OH-3'), 5.32 (d, J=6.0 Hz, 1H, OH-2'), 6.02 (d, J=5.1 Hz, 1H, H-1'), 6.78 (br. s, 2H, $NH_2$), 7.59 (s, 1H, H-6), 8.11 (s, 1H, H-2). HRMS (ESI): calculated for $C_{11}H_{14}BrN_4O_3$ ($[M+H]^+$): 329.0244, found: 329.0246.

4-amino-5-bromo-N7-(3'-5'-dideoxy-β-D-ribofuranosyl)-pyrrolo[2,3-d]pyrimidine (FH8492)

FH8492 was prepared according to General procedure 1 (except for the use of 2.5 eq. of acyl chloride instead of 3.5). FH8485 gave rise to FH8492 (0.074 g, 0.236 mmol) as a white solid in 49% yield. $^1$H NMR (300 MHz, DMSO-$d_6$) δ: 1.29 (d, J=6.0 Hz, 3H, $CH_3$), 1.96-2.00 (m, 2H, C-3", C-3'), 4.28-4.37 (m, 1H, H-4'), 4.39-4.43 (m, 1H, H-2'), 4.39-4.43 (m, 1H, H-2'), 5.55 (d, J=4.2 Hz, 1H, OH-2'), 6.01 (d, J=2.1 Hz, 1H, H-1'), 6.58 (br. s, 2H, $NH_2$), 7.44 (s, 1H, H-6), 8.12 (s, 1H, H-2). $^{13}$C NMR (75 MHz, DMSO-$d_6$) δ: 20.61 ($CH_3$), 40.70 (C-3'), 75.07 (C-4'), 75.47 (C-2'), 86.90 (C-5), 90.20 (C-1'), 100.84 (C-4a), 121.13 (C-6), 149.20 (C-7a), 152.55 (C-2), 156.93 (C-4). HRMS (ESI): calculated for $C_{11}H_{14}BrN_4O_2$ ($[M+H]^+$): 313.0295, found: 313.0293. Melting point: 226° C.

4-amino-5-bromo-N7-(2'-O-t-butyldimethylsilyl-3'-deoxy-5'-O-methyl-β-D-ribofuranosyl)-pyrrolo[2,3-d]pyrimidine (FH10623_Mid)

FH9552 (0.156 g, 0.35 mmol, 1 eq.) was dissolved in anhydrous THF (4 mL, 10 mL/mmol SM), and cooled to 0° C. in an ice-bath. Next, NaH (60% dispersion in mineral oil) (0.017 g, 0.42 mmol, 1.2 eq.) was added, directly followed by MeI (0.024 mL, 0.385 mmol, 1.1 eq.). The resulting solution was stirred at 0° C. for 1 hour and then at ambient temperature overnight. Then, it was quenched by the addition of aq. 0.5 M HCl; water and EA were added, layers separated and the water layer extracted twice more with EA. Organic layers were combined, dried over $Na_2SO_4$, filtered and evaporated. Purification by column chromatography (10→40% EA/PET) gave FH10623_Mid (0.04 g, 0.087 mmol) as an oil in 25% yield. $^1$H NMR (300 MHz, $CDCl_3$) δ: 0.03 (s, 3H, $SiCH_3$), 0.07 (s, 3H, $SiCH_3$), 0.87 (s, 9H, tBu), 1.89 (ddd, J=12.9, 6.0, 2.4 Hz, 1H, H-3"), 2.17 (ddd, J=12.9, 9.9, 5.4 Hz, 1H, H-3'), 3.45 (s, 3H, $OCH_3$), 3.56 (dd, J=10.5, 3.9 Hz, 1H, H-5"), 3.75 (dd, J=10.8, 3.0 Hz, 1H, H-5'), 4.44-4.47 (m 1H, H-4'), 4.51-4.59 (m 1H, H-2'), 5.73 (br. s, 2H, $NH_2$), 6.17 (d, J=1.5 Hz, 1H, H-1'), 7.40 (s, 1H, H-6), 8.22 (s, 1H, H-2). HRMS (ESI): calculated for $CH_{30}BrN_4O_3Si$ ($[M+H]^+$): 457.1265, found: 457.1268.

4-amino-5-bromo-N7-(3'-deoxy-5'-O-methyl-β-D-ribofuranosyl)-pyrrolo[2,3-d]pyrimidine (FH10626) FH10626 was prepared according to General procedure 9. FH10623_Mid (0.04 g, 0.087 mmol) gave rise to FH10626 (0.02 g, 0.058 mmol) as a white solid in 67% yield. (Purification: 0→6% MeOH/DCM) $^1$H NMR (300 MHz, DMSO-$d_6$) δ: 1.92 (ddd, J=13.2, 6.3, 2.7 Hz, 1H, H-3"), 2.16 (ddd, J=13.2, 9.3, 5.7 Hz, 1H, H-3'), 3.29 (s, 3H, $OCH_3$), 3.47 (dd, J=10.8, 5.1 Hz, 1H, H-5"), 3.56 (dd, J=10.8, 3.6 Hz, 1H, H-5'), 4.33-4.41 (m, 2H, H-2', H-4'), 5.61 (d, J=4.2 Hz, 1H, OH-2'), 6.06 (d, J=2.4 Hz, 1H, H-1'), 6.78 (br. s, 2H, $NH_2$), 7.52 (s, 1H, H-6), 8.11 (s, 1H, H-2). $^{13}$C NMR (75 MHz, DMSO-$d_6$) δ: 34.95 (C-3'), 58.46 ($OCH_3$), 73.72 (C-5'), 74.76 (C-2'), 78.09 (C-4'), 86.70 (C-5), 89.95 (C-1'), 100.82 (C-4a), 121.09 (C-6), 149.17 (C-7a), 152.52 (C-2), 156.91 (C-4). HRMS (ESI): calculated for $C_{12}H_{16}BrN_4O_3$ ($[M+H]^+$): 343.0400, found: 343.0403. Melting point: 198° C.

A3. Biological Evaluation

All trypanosome strains were cultured in the standard HMI-9 medium supplemented with 10% fetal bovine serum (FBS) at 37° C. in a 5% $CO_2$ atmosphere.

*Trypanosoma brucei*

Drug susceptibility tests with Lister 427WT, TbAT1-KO, B48 and ISMR1 were performed exactly as described by Omar et al. (2016) using an assay based on the viability indicator dye resazurin (Alamar blue) in 96-well plates, each well containing $2\times10^4$ cells. The plates were incubated for 48 h with a doubling dilution series of the test compounds in HMI-9/FBS at 37° C./5% $CO_2$ (23 dilutions starting at 100 μM, except for the pentamidine control (50 μM)), after which resazurin was added to each well and the plates incubated for another 24 h. Fluorescence was determined using a FLUOstar Optima (BMG Labtech, Durham, N.C.) and the results fitted to a sigmoid curve with variable slope using Prism 5.0 (GraphPad, San Diego, Ca).

Susceptibility assays with *T. brucei* Squib 427 (suramin-sensitive) or *T. b. rhodesiense* STIB-900 were performed under similar conditions as above but using 10 concentrations of a 4-fold compound dilution series starting at 64 μM. *T. brucei* Squib 427 was seeded at $1.5\times10^4$ parasites/well and *T. b. rhodesiense* at $4\times10^3$ parasites/well, followed by addition of resazurin after 24 hours (*T. brucei*) or 6 hours (*T. b. rhodesiense*).

*Trypanosoma cruzi*

Drug activity against *T. cruzi* was tested with the nifurtimox-sensitive Tulahuen CL2 β galactosidase strain (Buckner et al., 1996). This strain was maintained on MRC-5$_{SV2}$ (human lung fibroblast) cells in MEM medium, supplemented with 200 mM L-glutamine, 16.5 mM $NaHCO_3$ and 5% inactivated fetal calf serum. All cultures and assays were conducted at 37° C./5% $CO_2$. Assays were with 4.103 MRC-5 cells/well and 4.104 parasites/well. Impact of test compound dilution series (10 concentrations of a 4-fold compound dilution series starting at 64 μM) on parasite growth was analyzed after 7 days incubation by adding the substrate CPRG (chlorophenolred β-D-galactopyranoside). The change in color was measured spectrophotometrically at 540 nm after 4 hours incubation at 37° C. The results were expressed as % reduction in parasite burdens compared to control wells from which an $EC_{50}$ was calculated.

*Trichomonas vaginalis*—In Vitro Assay

*T. vaginalis* trophozoites (metronidazole susceptible G3 strain) were grown in vitro in modified Diamond's media (MDM) with 10% heat inactivated horse serum (HIHS) acquired from Gibco Life Technologies. After medium preparation, the pH was adjusted to 6.3-6.4 employing 1.0 M aq. HCl. Parasites cultures were passaged every day by taking 1 mL of cell culture into a 25 mL bottle of fresh media to ensure the cells were kept at the appropriate concentration of ~$2\times10^6$ cells/mL. The culture flasks were filled completely and tightly capped to provide the cells with an anaerobic environment. The parasites were maintained in incubation at 37° C. When culturing in multiwell plates, the plates were sealed with Nescofilm® and inserted in BD GasPak EZ pouches (BD Diagnostics, UK) in order to create anaerobic conditions. Assays were performed with $5\times10^4$ trophozoites/well (100 μL) to which compound dilutions were added (100 μL). Outside wells of columns and rows were filled with 200 μL of sterile water. Plates were sealed with Nescofilm® and incubated under anaerobic conditions as described above. After 24 h, 30 μL of assay dye solution (resorufin) was added, and incubated for 1-2 h before being read using Fluostar Optima (BMG Labtech, UK) at an excitation wavelength of 544 nm and an emission wavelength of 620 nm.

In Vivo Antiparasitic Activity Analysis in Mice (*T. brucei*; Acute Model)

Female Swiss mice (BW 20-24 g; Janvier France) were allocated randomly to groups of 3 animals and infected intraperitoneally (IP) with $10^4$ *T. b. brucei* Squib 427 derived from a heavily infected donor mouse. Drinking water and food were available ad libitum throughout the experiment. The test compound of the invention was formulated in 10% (V/V) PEG400 in water at 2 mg/mL and was freshly prepared at every administration. The test compound was administered orally (PO) b.i.d. for 5 days at 25 mg/kg. The reference drug suramin was formulated in PBS at 2.5 mg/mL and administered s.i.d. IP for 5 days at 10 mg/kg. Treatment was initiated ½ hour prior to the IP infection. Animals were observed for the occurrence/presence of clinical or adverse effects during the course of the experiment and were weighed daily. Parasitemia analysis was performed by microscopic evaluation of tail vein blood samples at 4, 7, 10, 14 and 21 dpi (pre-set endpoint). As a test of cure, blood samples (250 μL) were collected from treated mice at 21 dpi and were sub-inoculated IP in naive Swiss mice followed by parasitemia follow-up.

In Vivo Antiparasitic Activity Analysis in Mice (*T. brucei*; Stage-II Disease Model)

Female Swiss mice (BW~20-24 g; Janvier Labs, France) were allocated randomly to groups of 4 animals and infected intraperitoneally (IP) with $10^4$ *T. brucei*(*T. brucei* AnTAR1$^{PPYRE9}$), originating from a heavily infected donor mouse, in a 0.25 mL inoculum volume. Drinking water and food were available ad libitum throughout the experiment. The test compound, FH7429_D was formulated in 5% (V/V)

Tween80 at 4 mg/mL and administered according to body weight (25 mg/kg bid., oral gavage) for 5 days. Treatment commenced at 21 dpi, in mice which had positive CNS involvement (BLI). Two reference groups: vehicle control as well as melarsoprol (120 mg/kg, s.i.d. topical for 3 days) were included. Topical melarsoprol formulation was prepared as following: 3.6% melarsprol in propylene glycol was used to prepare a 1.5% hydroxypropylcellulose (HPC) gel.

Animals were observed for the occurrence of clinical or adverse effects during the course of the experiment and were weighed twice weekly. Parasitemia analysis was performed by microscopic evaluation of tail vein blood samples at 21 (before treatment initiation), 25, 28, 32 and 35 dpi. Bioluminescent imaging (BLI) was performed at 7, 14, 21, 28, 35, 43, 50 and 53 dpi. BLI experiments were performed as following: D-luciferin (15 mg/kg) was injected intraperitoneally, and mice were subsequently anaesthetized using isoflurane. The luminescent signal was measured over a 5 second as well as 5-minute exposure time, both for the ventral as well as the dorsal side of the animals.

In Vivo Antiparasitic Activity Analysis in Mice (*T. cruzi*)

Male Swiss Webster mice (18-20 g; 4-5 weeks of age) were housed at a maximum of 6 per cage, kept in a specific-pathogen-free (SPF) room at 20 to 24° C. under a 12-h light and 12-h dark cycle, and provided sterilized water and chow ad libitum. The animals were allowed to acclimate for 7 days before starting the experiments. Infection was performed by intraperitoneal (i.p.) injection of 104 bloodstream trypomastigotes (Y-strain). Age-matched non-infected mice were maintained under identical conditions. The animals were divided into the following groups (n=6): uninfected (non-infected and non-treated), untreated (infected but treated only with vehicle), and treated (infected and treated with the compounds). The *T. cruzi* (Y-strain) infected mice were treated for five consecutive days, starting at the $5^{th}$ day post-infection (dpi), which in this experimental model corresponds to the time of parasitemia onset, using 25 mg/kg (oral gavage, b.i.d.) of the tested compound FH8512, and 100 mg/kg/day BZ administered orally (oral gavage, s.i.d.). Nucleoside test compound FH8512 was formulated in 10% (v/v) EtOH, 0.1 M aq. citrate buffer (pH=3.02) at 1.8 mg/mL, respectively and dosed according to body weight. Formulations were prepared freshly before each administration. Only mice with positive parasitemia were used in the infected groups. Parasitemia was individually checked by direct microscopic counting of the number of parasites in 5 μl of blood (Panel A—FIG. 5), and mice were checked for mortality daily until 30 days post-treatment (corresponding to 40 dpi). Mortality is expressed as the percent cumulative mortality (CM; Panel B—FIG. 5).

TABLE 1

In vitro anti-trypanosomal (*T. brucei brucei* and *T. brucei rhodesiense*) activity of prepared nucleosides analogues. $EC_{50}$ values are given in μM and are the average of 2-4 independent determinations. Suramin was used as a reference drug and gave $EC_{50}$ values of 0.05 μM and 0.04 μM for *T. b. brucei* and *T. b. rhodesiense*, respectively. N.D.: Not determined.

| Compound | T. brucei brucei (μM) | T. brucei rhod. (μM) | MRC-5 (μM) |
|---|---|---|---|
| FH7429_U | 0.002 | <0.0005 | 16.14 |
| FH7429_D | 0.05 | 0.0005 | >64 |
| FH8470 | 0.002 | 0.0004 | 9.9 |
| FH8496 | 0.01 | 0.001 | 3.4 |
| FH8517 | 0.002 | 0.0003 | 3.6 |
| FH9605 | 27.2 | 21 | 18.6 |
| FH8480 | 7.9 | 1.2 | 61.8 |
| FH8481 | 33.2 | 18.4 | 21 |
| FH8494 | 3.7 | 1.2 | 24.3 |
| FH8512 | 2.3 | 1.8 | 19.1 |
| FH8513 | 1.8 | 1.5 | 13.6 |
| FH9581 | 19.6 | 7.3 | 19.6 |
| FH9582 | 2.1 | 0.32 | >64 |
| FH9576 | 19.5 | 6.6 | 40 |
| FH9577 | 24.5 | 9.8 | 40.4 |
| FH9575 | 18.6 | 2 | 5 |
| FH9574 | >64 | 55.9 | 24.9 |
| FH10667 | N.D. | N.D. | N.D. |
| FH10669 | N.D. | N.D. | N.D. |
| FH10659 | 0.04 | 0.005 | 25.55 |
| FH10660 | 1.76 | 0.17 | 49.43 |
| FH10661 | 8.26 | 0.67 | >64 |
| FH8504 | 0.3 | 0.12 | 9.6 |
| FH9610 | 0.32 | 0.04 | >64 |
| FH9611 | 0.32 | 0.06 | >64 |
| FH8505 | 0.005 | 0.0005 | 1.29 |
| FH9613 | 1.78 | 0.65 | >64 |
| FH8502 | 7.6 | 37.3 | 33.7 |
| FH9526 | 0.94 | 1.88 | 0.66 |
| FH10622 | 4.97 | 1.02 | >64 |
| FH9549 | 35.2 | >64 | >64 |
| FH9550 | >64 | 30.8 | >64 |
| FH9540 | 14.8 | 28.9 | 27.2 |
| FH9541 | 31.2 | 7.97 | >64 |
| FH10639 | 30.49 | 11.17 | >64 |
| FH10641 | 7.13 | 0.55 | 36.09 |
| FH10644 | 4.74 | 5.99 | 17.95 |
| FH10647 | 7.58 | 1.5 | 18.37 |

TABLE 1-continued

In vitro anti-trypanosomal (*T. brucei brucei* and *T. brucei rhodesiense*) activity of prepared nucleosides analogues. $EC_{50}$ values are given in μM and are the average of 2-4 independent determinations. Suramin was used as a reference drug and gave $EC_{50}$ values of 0.05 μM and 0.04 μM for *T. b. brucei* and *T. b. rhodesiense*, respectively. N.D.: Not determined.

| Compound | *T. brucei brucei* (μM) | *T. brucei rhod.* (μM) | MRC-5 (μM) |
|---|---|---|---|
| FH10649 | 2.01 | 0.54 | 17.16 |
| FH8471 | 1.21 | 0.08 | 5.31 |
| FH9554 | 26.7 | 15 | >64 |
| FH9559 | >64 | >64 | >64 |
| FH9560 | 29.6 | 2.86 | >64 |
| FH9555 | >64 | >64 | >64 |
| FH9556 | >64 | 58 | >64 |
| FH8516 | 6.21 | 8.25 | >64 |
| FH8522 | 1.88 | 0.79 | >64 |
| FH8510 | 1.68 | 4.34 | 0.29 |
| FH8497 | 2.62 | 3.7 | 2.7 |
| FH8500 | 8.09 | 2.26 | >64 |
| FH8511 | 28.5 | 23.1 | >64 |
| FH9539 | 0.51 | 0.91 | 21 |
| FH9618 | 49 | 30.9 | >64 |
| FH9616 | 32.5 | 25.4 | >64 |
| FH10650 | 6.62 | 0.6 | >64 |
| FH10628 | 0.13 | 0.03 | 45.6 |
| FH9536 | >64 | >64 | >64 |
| FH10632 | >64 | 59.85 | 45.6 |
| FH10638 | 57.85 | 24.42 | 16.45 |
| FH9569 | >64 | >64 | >64 |
| FH9561 | 26.8 | 5.6 | >64 |
| FH9600 | 43.6 | 31.8 | >64 |
| FH9601 | 51.5 | 26.5 | >64 |
| FH9527 | 32.5 | 22.3 | 15.3 |
| FH9590 | 32.9 | 10.6 | 25.8 |
| FH9591 | 5.05 | 0.71 | 26.5 |
| FH9608 | 4.6 | 0.87 | 5.09 |
| FH8499 | >64 | >64 | >64 |
| FH8492 | 33.5 | 20.1 | 10.2 |
| FH10626 | 32 | 18.7 | 22.7 |
| FH8458 | >64 | >64 | >64 |
| FH8464 | >64 | >64 | >64 |
| FH8463 | >64 | >64 | >64 |
| FH8462 | >64 | >64 | >64 |
| FH10640 | 8.6 | 1.77 | 49.58 |
| FH10642 | 7.7 | 5.45 | 30.24 |
| FH10645 | 7.13 | 2.51 | >64 |
| FH10648 | 6.4 | 2.09 | 16.66 |
| FH10653 | 8.81 | 2.17 | 22.26 |
| FH9552 | 0.63 | 0.27 | >64 |

TABLE 2

Activity of prepared analogues against *T. cruzi*. $EC_{50}$ values are given in μM as average of 2-3 independent replicates. Benznidazole was included as a reference compound and gave an $EC_{50}$ of 2.40 μM.

| Compound | *T. cruzi* (μM) | MRC-5 (μM) |
|---|---|---|
| FH7429_U | 0.02 | 16.14 |
| FH7429_D | >64 | >64 |
| FH8470 | 0.05 | 9.9 |
| FH8496 | 0.03 | 3.4 |
| FH8517 | 1.22 | 3.6 |
| FH9605 | 25.97 | 18.6 |
| FH8480 | 2.57 | 61.8 |
| FH8481 | 0.46 | 21 |
| FH8494 | 2.4 | 24.3 |
| FH8512 | 0.05 | 19.1 |
| FH8513 | 0.06 | 13.6 |
| FH9581 | 0.5 | 19.6 |
| FH9582 | 1.2 | >64 |
| FH9576 | 0.53 | 40 |
| FH9577 | 1.39 | 40.4 |
| FH9554 | >64 | >64 |
| FH9559 | >64 | >64 |
| FH9560 | >64 | >64 |
| FH9555 | >64 | >64 |
| FH9556 | >64 | >64 |
| FH8516 | >64 | >64 |
| FH8522 | 20.9 | >64 |
| FH8510 | 35.8 | 0.29 |
| FH8497 | >64 | 2.7 |
| FH8500 | >64 | >64 |
| FH8511 | >64 | >64 |
| FH9539 | 36.8 | 21 |
| FH9618 | >64 | >64 |
| FH9616 | >64 | >64 |
| FH10650 | >64 | >64 |
| FH9575 | 0.72 | 5 |
| FH9574 | 8.5 | 24.9 |
| FH10667 | N.D. | N.D. |
| FH10669 | N.D. | N.D. |
| FH10659 | 9.44 | 25.55 |
| FH10660 | 6.28 | 49.43 |
| FH10661 | >64 | >64 |
| FH8504 | 3.7 | 9.6 |
| FH9610 | 4.1 | >64 |
| FH9611 | 9.7 | >64 |
| FH8505 | 1.66 | 1.29 |
| FH9613 | 19.73 | >64 |
| FH8502 | 40.8 | 33.7 |
| FH9526 | 2.33 | 0.66 |
| FH10622 | >64 | >64 |
| FH10628 | 1.47 | 45.6 |
| FH9536 | >64 | >64 |
| FH10632 | >64 | 45.6 |
| FH10638 | 43.28 | 16.45 |
| FH9569 | >64 | >64 |
| FH9561 | >64 | >64 |
| FH9600 | >64 | >64 |
| FH9601 | 23.7 | >64 |
| FH9527 | 25 | 15.3 |
| FH9590 | 35.7 | 25.8 |
| FH9591 | 33.8 | 26.5 |
| FH9608 | 9.91 | 5.09 |
| FH8499 | >64 | >64 |
| FH8492 | 12 | 10.2 |
| FH8626 | 50.4 | 22.7 |

TABLE 2-continued

Activity of prepared analogues against *T. cruzi*.
EC$_{50}$ values are given in µM as average
of 2-3 independent replicates. Benznidazole was included
as a reference compound and gave an EC$_{50}$ of 2.40 µM.

| Compound | T. cruzi (µM) | MRC-5 (µM) | Compound | T. cruzi (µM) | MRC-5 (µM) |
|---|---|---|---|---|---|
| FH9549 | >64 | >64 | FH8458 | >64 | >64 |
| FH9550 | >64 | >64 | FH8464 | >64 | >64 |
| FH9540 | 15 | 27.2 | FH8463 | >64 | >64 |
| FH9541 | >64 | >64 | FH8462 | >64 | >64 |
| FH10639 | 5.15 | >64 | FH10640 | 11.21 | 49.56 |
| FH10641 | 0.97 | 36.09 | FH10642 | 0.55 | 30.24 |
| FH10644 | 0.27 | 17.95 | FH10645 | 3.3 | >64 |
| FH10647 | 1.04 | 18.37 | FH10648 | 0.21 | 16.66 |
| FH10649 | 0.06 | 17.16 | FH10653 | 1.37 | 22.26 |
| FH10680 | 0.64 | >64 | FH10681 | 0.30 | 45.47 |
| FH10682 | 0.33 | >64 | FH10683 | 0.07 | 18.64 |

TABLE 3

Activity of prepared analogues
against *T. vaginalis*. EC$_{50}$ values
are given in µM as average
of 2-5 independent replicates.

| Compound Code | T. vaginalis EC$_{50}$ (µM) |
|---|---|
| FH8494 | 0.73 |
| FH8512 | 0.17 |
| FH8513 | 0.33 |
| FH9577 | 0.79 |
| FH9576 | 0.26 |
| Metronidazole | 0.53 |

In Vivo Evaluation

Figure 3:
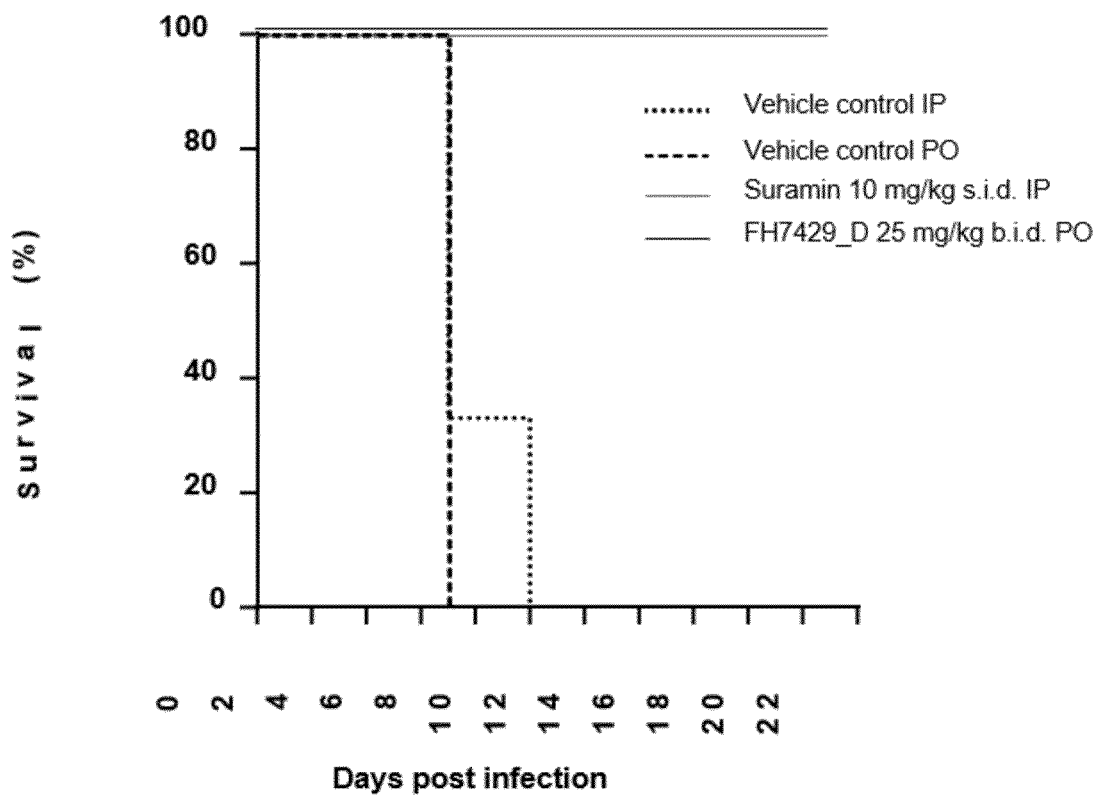
FIG. 3: Survival analysis of *T. brucei* Squib 427 infected mice orally treated for 5 days with FH7429_D, suramin and vehicle. Presented data are obtained from 3 mice per group.

To extend the in vitro observations into an in vivo setting, the anti-trypanosomal activity of FH7429_D was evaluated in a *T. brucei* infection model in mice (FIG. 3). All mice in the vehicle control groups developed severe clinical trypanosomiasis and died by day 7, except for one mouse in the IP vehicle control group that succumbed by day 10 of infection. In the suramin-treated reference group (10 mg/kg for 5 consecutive days), no symptoms nor parasitemia developed and all mice survived until day 21. FH7429_D administration at 25 mg/kg PO b.i.d. or 10 mg/kg s.i.d. IP for 5 consecutive days resulted in excellent activity given that no clinical symptoms of trypanosomiasis were observed. All FH7429_D treated mice (both PO and IP groups) survived until day 21. Sub-inoculations in naive mice were carried and ascertained total parasitological cure in the animals surviving until day 21 post infection without detectable parasitemia levels following treatment. These results are indicative of sterile cure in the surviving animals by the oral treatment with FH7429_D. No signs of adverse drug effects were observed.

Next, the efficacy of FH7429_D was assayed in a mouse model of stage-II HAT (CNS involvement).

Figure 4:
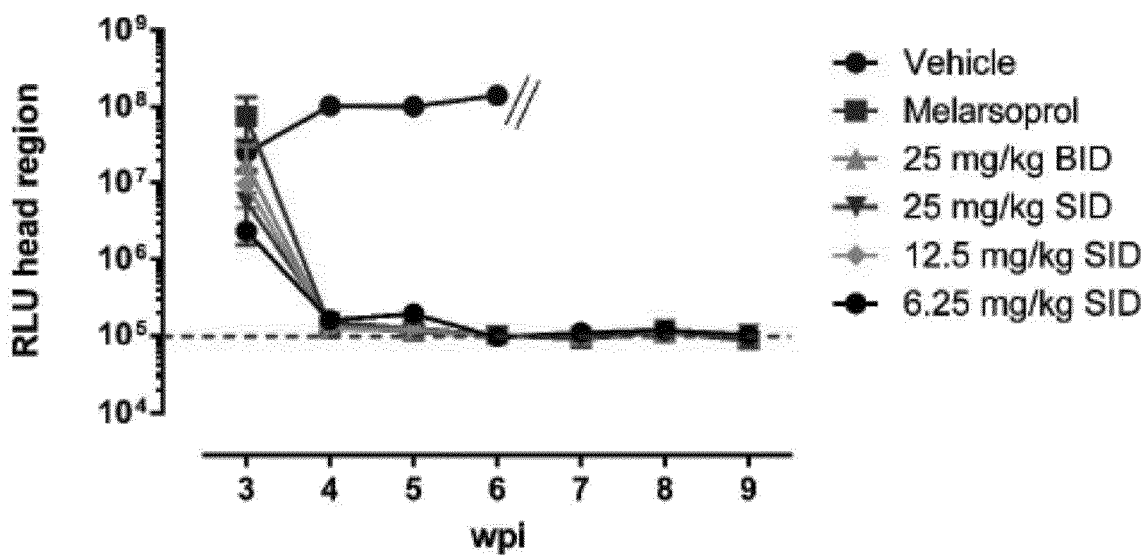
FIG. 4: Analysis of parasitemia within the head region of *T. brucei* AnTAR1$^{PPYRE9}$ infected animals. Treatment was with either vehicle, melarsoprol or FH7429_D (different dosing regimes).

Treatment was initiated at 21 dpi and given for 5 consecutive days (25 mg/kg PO, b.i.d. or 25 mg/kg PO, s.i.d. or 12.5 mg/kg, s.i.d. or 6.25 mg/kg, s.i.d.). All treated animals did not show any signs of parasitemia from 28 dpi onwards (either by means of bioluminescence imaging (BLI) or tail vain blood analysis) and were considered cured. (FIG. 4) 3'-deoxy-7-deaza-purine nucleosides represent a novel class of bioactive nucleoside analogs with specific activity against certain protozoan pathogens, particularly those which lack a functioning de novo purine synthesis pathway. FH7429_D has proven to be able cure an acute infection of *T. brucei* in mice; after both oral and IP administration. This contrasts with the use of 3'-deoxy-adenosine (cordycepin), which, as a monotherapy, is unable to clear the infection. Additionally, it was found that the addition of C-7 halogens and other functional groups is in certain cases able to greatly improve the anti-trypanosomal activity (low to sub-nM), without also becoming overtly cytotoxic, which contrasts literature findings in that halogenated derivatives generally attribute to cytotoxicity. Furthermore, some analogues have shown a favourable 'mixed' P1/P2 adenosine transporter profile in *T. brucei*, which is especially beneficial with regard to the development of transporter-mediated resistance. This mixed P1/P2 transporter profile is by any means surprising, given the vast amount of binding data present in literature for these transporters.

Figure 5:
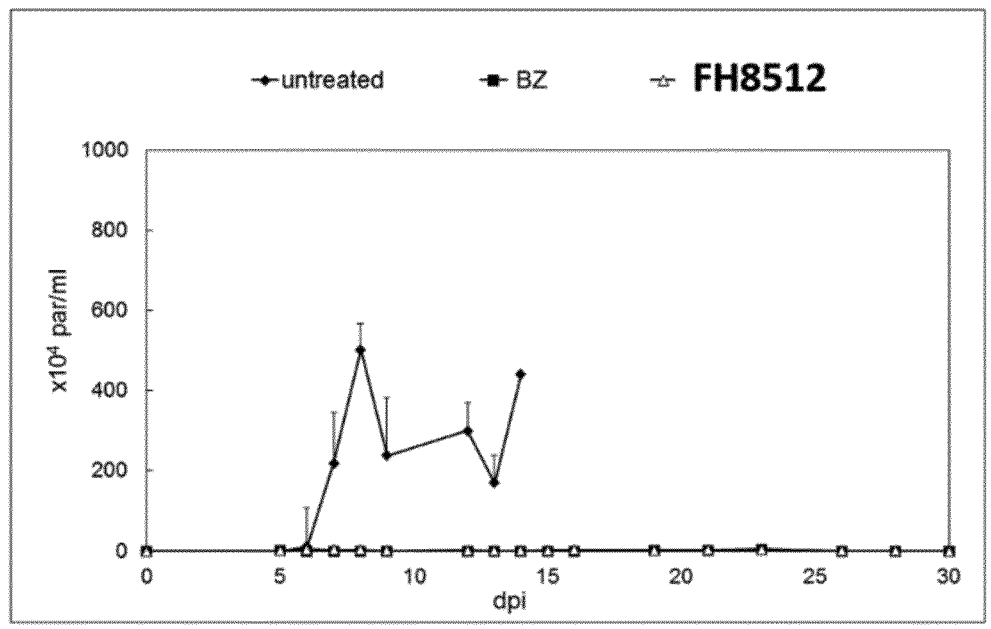
FIG. 5: Parasitemia (A) and survival analysis (B) of *T. cruzi* (Y-strain) infected mice orally treated with FH8512, benznidazole (BZ) and vehicle for 5 days.
Figure 5:
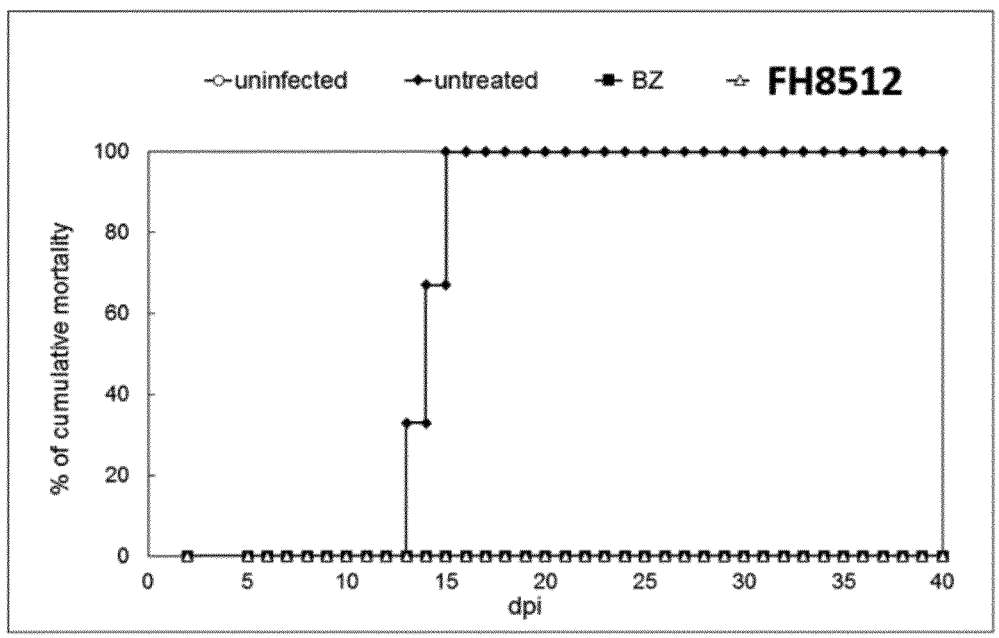

Aryl-substituted derivatives appear to be preferred when regarding activity against *T. cruzi*, which is a parasite not frequently targeted by nucleoside analogs. One analog (FH8512) displayed potent antitrypanosomal activity when assayed at 25 mg/kg PO b.i.d. for five days in a *T. cruzi* model of infection (Y-strain; FIG. 5). FH8512 was able to suppress blood parasitemia and protect animals from mortality caused by the infection.

B. Ribofuranose Compounds

B1. General Synthesis Schemes

The synthesis of C-7 substituted phenyl analogues was accomplished via an aqueous Suzuki reaction, employing the known nucleoside bromide, under similar conditions as reported previously. (Bourderioux et al., 2011) (Scheme B1) The 3-pyridyl analogue (FH4185) was successfully obtained, employing its pinacol boronic ester via the same protocol, albeit with a prolonged reaction time. Similar conditions afforded the 4-pyridinyl isomer (FH4187) and 5-pyrimidyl derivative (FH4184), in non-practical yields only (<5%), consistent with inherent pyridine/pyrimidine reactivity. Instead, reaction conditions reported by Fu (Kudo et al. 2006) were used, giving FH4187 and FH4184 in modest yields.

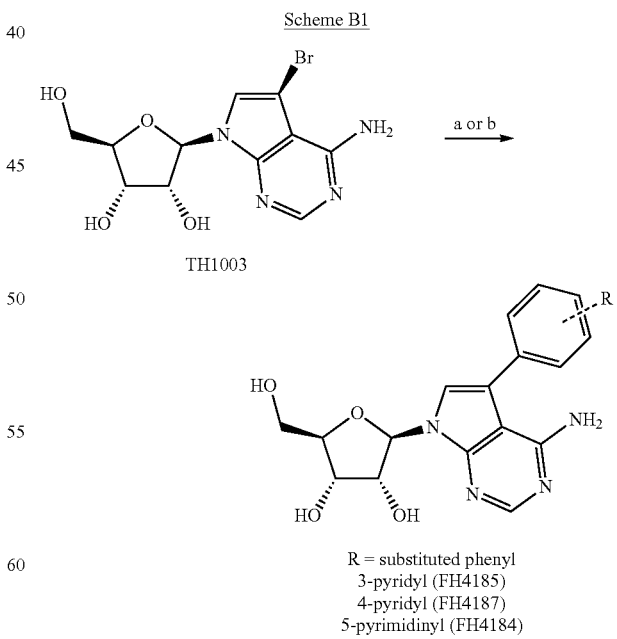

Scheme B1

R = substituted phenyl
3-pyridyl (FH4185)
4-pyridyl (FH4187)
5-pyrimidinyl (FH4184)

reagents and conditions: a) aryl-B(OH)$_2$ or aryl-B pinacol ester, Na$_2$CO$_3$, Pd(OAc)$_2$, TPPTS, MeCN/H$_2$O (1/2 ratio), 100° C., yield: 22-65% ; b) aryl-B(OH)$_2$, K$_3$PO$_4$, Pd$_2$(dba)$_3$, P(c-Hex)$_3$, water/dioxane, 100° C., yield: 26% (FH4187) , 35% (FH4184).

For certain heterocycles for which the boronic acid or corresponding ester derivative are not commercially available or are notoriously unstable, a Stille coupling was used. Halide coupling partners were obtained by nucleophilic aromatic displacement on FH3133 with sodium azide, giving rise to the corresponding tetrazolo[1,5-c]pyrimidine, followed by Staudinger reaction and iminophosphorane hydrolysis (Scheme B2).

Scheme B2

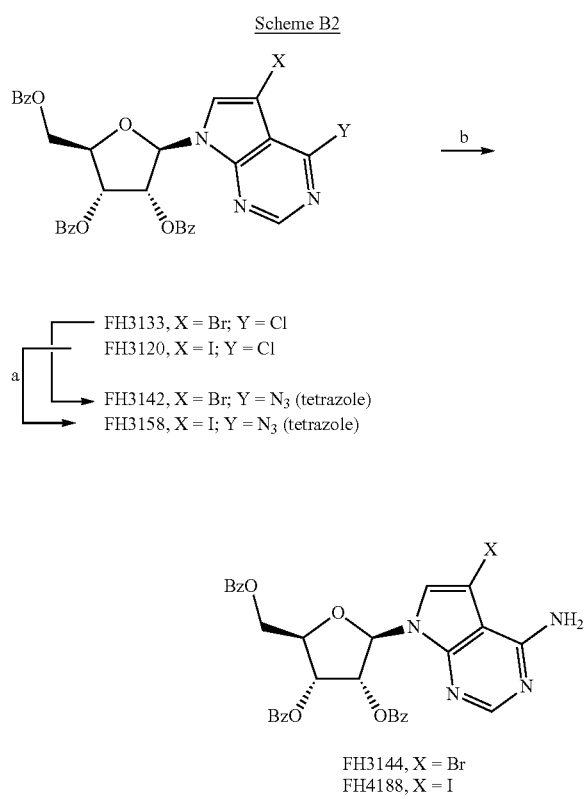

FH3133, X = Br; Y = Cl
FH3120, X = I; Y = Cl a

FH3142, X = Br; Y = N$_3$ (tetrazole)
FH3158, X = I; Y = N$_3$ (tetrazole)

FH3144, X = Br
FH4188, X = I reagent and conditions: a) NaN$_3$, DMF, 65° C., yield: 90% (FH3142), 86% (FH3158); b) 1. PMe$_3$ (1M in THF), THF // 2. aq. HOAc (1M), MeCN, 65° C., yield: 81% (FH3144), 93% (FH4188).

Stille couplings were performed by using either commercial (2-pyridyl, 2-pyrazinyl and 2-pyrimidinyl) or prepared (methyl-imidazolyl) organostannanes, employing literature conditions (Bourderioux et al., 2011). In all cases except one (FH3172), protected intermediates were immediately deprotected after Stille coupling, using 7N NH$_3$ in MeOH.

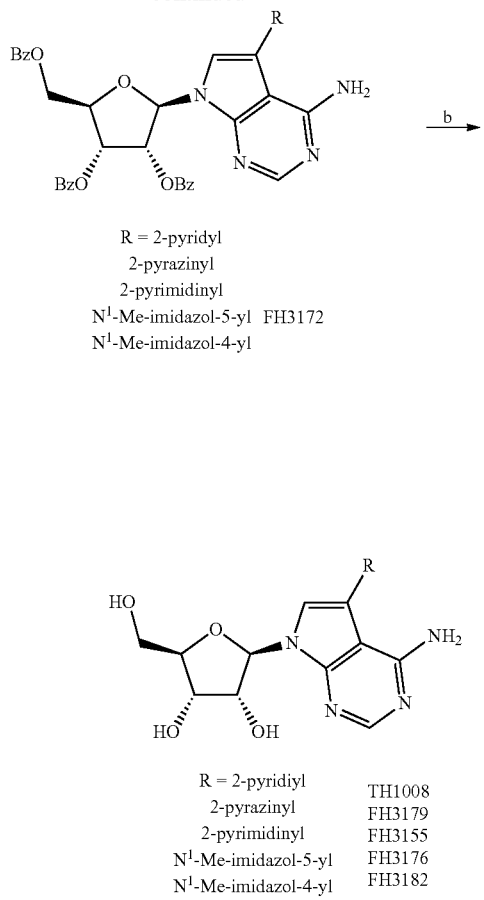

R = 2-pyridyl
2-pyrazinyl
2-pyrimidinyl
N$^1$-Me-imidazol-5-yl  FH3172
N$^1$-Me-imidazol-4-yl R = 2-pyridiyl    TH1008
2-pyrazinyl       FH3179
2-pyrimidinyl     FH3155
N$^1$-Me-imidazol-5-yl  FH3176
N$^1$-Me-imidazol-4-yl  FH3182 reagents and conditions: a) Ar—Sn(nBu)$_3$, Pd(Ph$_3$P)$_2$Cl$_2$, DMF, 100° C.; b) 7N NH$_3$/MeOH.

To obtain substituted pyridine analogues (TH1008, FH3179, FH3155, FH3176 & FH3182), a different synthetic strategy was devised. A Suzuki reaction with altered coupling partner polarity could be used. Therefore, pinacol boronic ester nucleoside FH7423 was synthesized. Alternatively, a Negishi coupling strategy, is also an attractive alternative. The nucleoside zinc derivative was prepared by magnesium-iodine exchange with Knochel's Turbo Grignard reagent, followed by transmetallation with ZnCl$_2$ and subsequent Negishi coupling using Pd$_2$(dba)$_3$ and RuPhos (Milne et al., 2004). Final compounds were obtained by employing the above-mentioned sequence of Staudinger reduction, iminophosphorane hydrolysis and immediate deprotection using NaOMe/MeOH.

Scheme B3

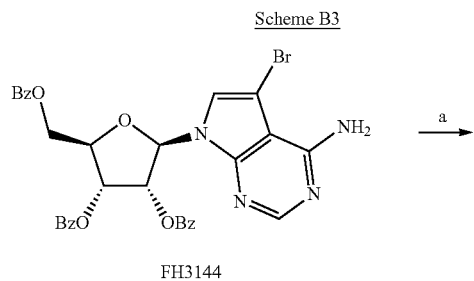

FH3144

Scheme B4

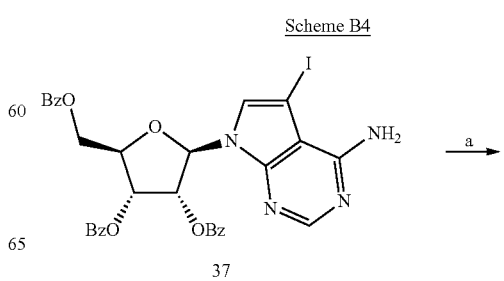

37

105

-continued

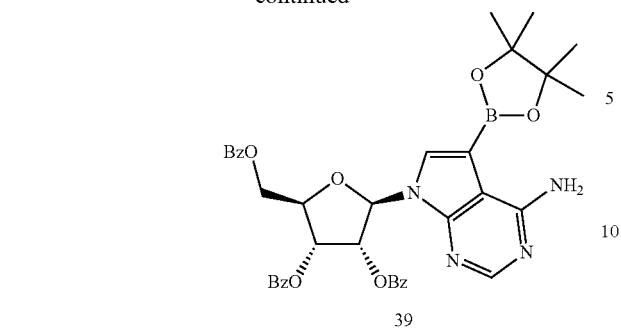

39

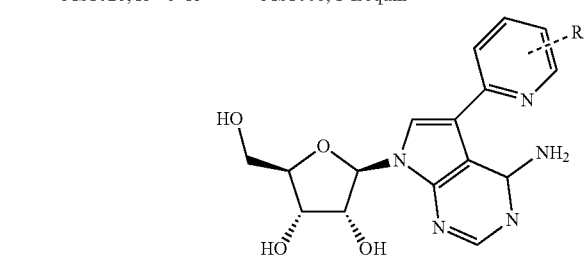

35

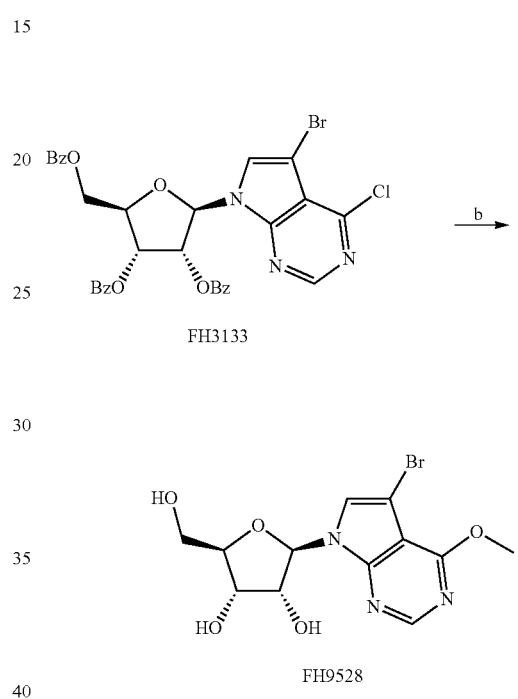

FH8451, R = H          MS1005, R = 5-Cl
MS1008, R = 4-Me       MS1031, R = 5-F
MS1009, R = 4-OMe      MS1010, 2-Quin
MS1029, R = 6-Cl       MS1024, 3-Isoquin
MS1028, R = 5 Cl       MS1006, 1-Isoquin Reagents and conditions: a) B$_2$pin$_2$, KOAc, PdCl$_2$dppf•DCM, DMSO, 100° C., yield: 37%; b) 1. iPrMgCl•LiCl (1.3M in THF), THF, -65° C. // 2. ZnCl$_2$ (0.5M in THF), -65° C. to rt // 3. Pyridine ((iso-)Quinoline-Br), Pd$_2$(dba)$_3$, RuPhos, THF, 60° C., yield: 16 – 51%; c) 1. PMe$_3$ (1M in THF), THF // 2. aq. HOAc (1M), MeCN, 65° C. // 3. NaOMe, MeOH, yield: 22–66%.

Alkoxy-Substituted Ribofuranose Nucleosides

Scheme B3

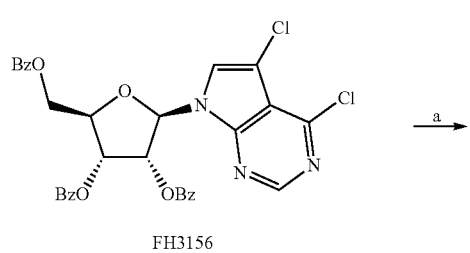

FH3156

106

-continued

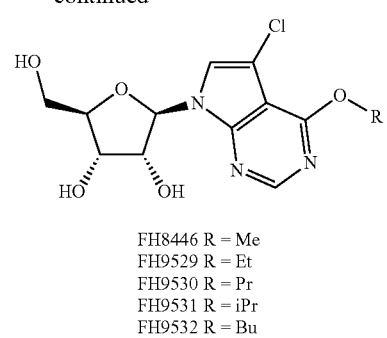

FH8446 R = Me
FH9529 R = Et
FH9530 R = Pr
FH9531 R = iPr
FH9532 R = Bu

FH3133

FH9528

Reagents and conditions: a) Na, alcohol (or NaOMe/MeOH; NaOEt/EtOH), 50° C.

Alkoxy-substituted analogs were obtained by heating the corresponding chloride in a solution of the alkoxide base/alcohol, which also furnished deprotection.

Pyrrolo[2,3-b]Pyridine Ribofuranose Nucleosides

Scheme B4

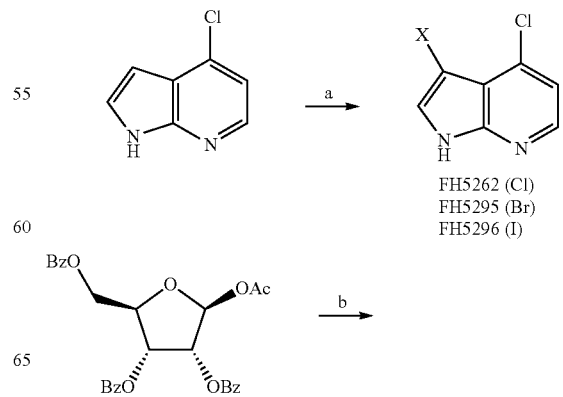

FH5262 (Cl)
FH5295 (Br)
FH5296 (I)

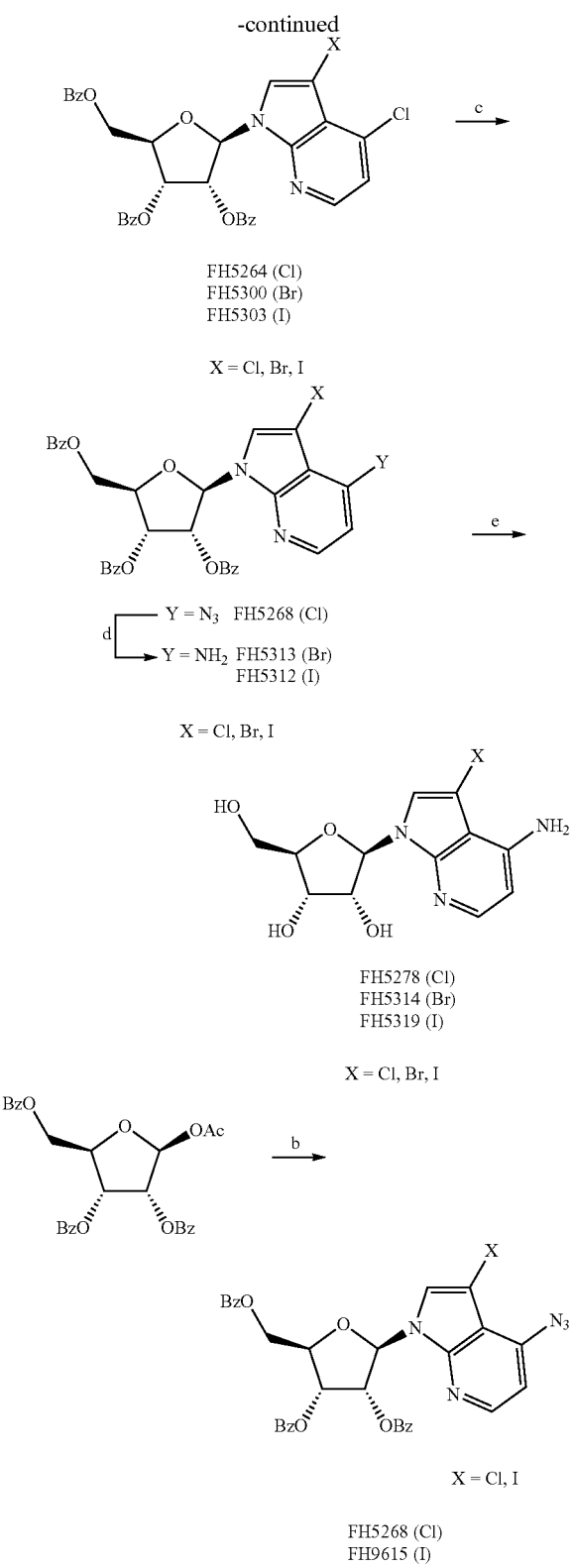

FH5264 (Cl)
FH5300 (Br)
FH5303 (I)

X = Cl, Br, I

Y = N₃ FH5268 (Cl)
Y = NH₂ FH5313 (Br)
   FH5312 (I)

X = Cl, Br, I

FH5278 (Cl)
FH5314 (Br)
FH5319 (I)

X = Cl, Br, I

X = Cl, I

FH5268 (Cl)
FH9615 (I)

Reagents and conditions: a) NXS, DMF; b) Heterocycle, BSA, TMSOTf, MeCN, 80° C.; c) NaN₃, 15-crown-5, DMF, 110° C.; d) 1. PMe₃ in THF, THF; 2. aq. HOAc, MeCN, 65° C.; e) 7N NH₃/MeOH.

Pyrrolo[2,3-b]pyridine analogs have been obtained employing the same methodology as described for the 3'-deoxy nucleosides, described in Section A.

B.2. Compound Synthesis

Following the above defined general reaction schemes, the below mentioned more specific conditions were used in the preparation of the Ribofuranose compounds of the invention.

Chemistry

All reagents and solvents were obtained from standard commercial sources and were of analytical grade. Unless otherwise specified, they were used as received. Compounds TH1003, FH3133, FH3120, FH5284, 1-methyl-5-(tributylstannyl)-1H-imidazole, 1-methyl-4-(tributylstannyl)-1H-imidazole were prepared as described in literature. All moisture sensitive reactions were carried out under argon atmosphere. Reactions were carried out at ambient temperature, unless otherwise indicated. Analytical TLC was performed on Machery-Nagel® precoated F254 aluminum plates and were visualized by UV followed by staining with basic aq. $KMnO_4$, Cerium-Molybdate, or sulfuric acid-anisaldehyde spray. Column chromatography was performed using Davisil® (40-63 μm) or on a Reverleris X2 (Grace/Büchi) automated Flash unit employing pre-packed silica columns. Exact mass measurements were performed on a Waters LCT Premier XE™ Time of Flight (ToF) mass spectrometer equipped with a standard electrospray (ESI) and modular Lockspray™ interface. Samples were infused in a MeCN/water (1:1)+0.1% formic acid mixture at 100 μL/min. NMR spectra were recorded on a Varian Mercury 300 MHz spectrometer. Chemical shifts (δ) are given in ppm and spectra are referenced to the residual solvent peak. Coupling constants are given in Hz. In $^{19}$F-NMR, signals were referenced to $CDCl_3$ or DMSO-$d_6$ lock resonance frequency according to IUPAC referencing with $CFCl_3$ set to 0 ppm. Melting points were determined on a Büchi-545 apparatus, and are uncorrected. Purity was assessed by means of analytical LC-MS employing either (3) Waters Alliance 2695 XE separation Module using a Phenomenex Luna® reversed-phase C18 (2) column (3 μm, 100×2.00 mm) and a gradient system of HCOOH in $H_2O$ (0.1%, v/v)/HCOOH in MeCN (0.1%, v/v) at a flow rate of 0.4 mL/min, 10:90 to 0:100 in 9 minutes. High-resolution MS spectra were recorded on a Waters LCT Premier XE Mass spectrometer.

(4) Waters AutoPurification system (equipped with ACQUITY QDa (mass; 100-1000 amu)) and 2998 Photodiode Array (220-400 nm)) using a Waters Cortecs® C18 (2.7 μm 100×4.6 mm) column and a gradient system of HCOOH in $H_2O$ (0.2%, v/v)/MeCN at a flow rate of 1.44 mL/min, 95:05 to 00:100 in 6.5 minutes.

All obtained final compounds had purity >95%, as assayed by analytical HPLC (UV); unless otherwise indicated.

General Procedure A (Suzuki Coupling):

TH1003 (1 eq.), boronic acid (1.5 eq.) or pinacol ester [for compound FH4185 (1.5 eq.)], $Na_2CO_3$ (9 eq.), Pd(OAc)₂ (0.05 eq.) and TPPTS (0.15 eq.) were added to a 10 mL round-bottom flask, equipped with a stir bar. Next, the flask was evacuated and refilled with argon. This procedure was repeated three times in total. Next, degassed MeCN (2 mL/mmol SM) and $H_2O$ (4 mL/mmol SM) were added to the solids under argon. After 5 min of stirring, the mixture was heated to 100° C. in a pre-heated oil bath. When the starting material was fully consumed (usually 1-3 hours), the mixture was cooled to ambient temperature, and neutralized (pH ~7) with 0.5 M aq. HCl. The mixture was evaporated till dryness, resuspended in MeOH and evaporated (three times). Next, the mixture was adsorbed onto Celite® (from MeOH) and eluted over a short silica pad (~5 cm) with 20%

MeOH/DCM. The liquid was evaporated in vacuo and purified by column chromatography.

General Procedure B (Stille Coupling):

FH3144 (1 eq.) and Pd(Ph$_3$P)$_2$Cl$_2$ (0.10 eq.) were added to a flame-dried 5 mL round bottom flask, equipped with a stir bar, under argon. Next, the flask was evacuated and refilled with argon. This procedure was repeated three times in total. Next, degassed anhydrous DMF (4 mL/mmol SM) was added under argon. The resulting solution was stirred at for ~5 min after which the organostannane (2 eq.) was added via syringe. The mixture was then heated to 100° C. in a pre-heated oil bath overnight. Next, the mixture was cooled to ambient temperature and evaporated to dryness. The resulting oil was partitioned between MeCN/Hexanes. The MeCN—layer was extracted twice more with hexanes, and then evaporated. The resulting mixture was purified by column chromatography. In most cases, the obtained product was immediately used in the next step (deprotection).

General Procedure C (Negishi Coupling):

FH3158 was dissolved in anhydrous toluene (10 mL) and evaporated till dryness. This procedure was repeated 3 times. Next, the residue was dissolved in anhydrous THF (8.5 mL/mmol SM) under argon. The solution was cooled to −65° C. iPrMgCl·LiCl solution (1.3 M in THF; 1.1 eq.) was added in one portion. The resulting solution was stirred at −65° C. for 30 min, after which a small sample was quenched with sat. NH$_4$Cl solution and used for TLC analysis. Generally, full conversion was then observed. Next, ZnCl$_2$ solution (0.5 M in THF, 1.2 eq.) was added in one portion, and the mixture stirred for another 5-10 min at −65° C. Then, the cooling was removed and the mixture stirred at ambient temperature for 20 min. Next, to a flame-dried Schlenk-tube (5 mL) containing a stir bar, were added Pd$_2$(dba)$_3$ (0.02 eq.), RuPhos (0.08 eq.) and the appropriate pyridine-Br or (iso-)quinoline-Br (1.4 eq.) (when solid) under argon. The tube was evacuated and refilled with argon three times. Then, anhydrous THF (3 mL/mmol SM) was added as well as the pyridine-Br or (iso-)quinoline-Br (1.4 eq.) (when liquid). The mixture was stirred for approximately 5 min and the resulting solution was then transferred via syringe to the flask containing the nucleoside-zinc reagent. An additional 0.5-1 mL of anhydrous THF was used to rinse the Schlenk tube and added to the mixture as well. The resulting solution was stirred at 60° C. overnight. After cooling to ambient temperature, the mixture was then quenched by adding water (~5 mL) and transferred to a separatory funnel. EA and aq. 1 M EDTA (pH=8) solution were added. The layers were separated and the water layer was extracted with EA two more times. The organic layers were combined, dried over Na$_2$SO$_4$, filtered and evaporated in vacuo. The resulting mixture was purified by column chromatography.

General Procedure D (Staudinger Reduction/Iminophosphorane Hydrolysis and Subsequent Deprotection of 7-Deaza-7-Pyridyl/(Iso-)Quinolinyl Derivatives):

The appropriate azido-nucleoside (1 eq.) was dissolved in THF (10 mL/mmol). Then, PMe$_3$ solution (1 M in THF; 2 eq.) was added and the mixture stirred at ambient temperature until TLC analysis showed full conversion of starting material (generally overnight). Next, the solution was evaporated till dryness, and subsequently re-dissolved in MeCN (10 ml/mmol). To this solution was added a 1 M aq. HOAc solution (3.33 eq.), and the mixture heated in a pre-heated oil bath at 65° C. for 1H. Next, the mixture was cooled to ambient temperature and poured into sat. aq. NaHCO$_3$ solution. DCM was added, layers were separated and the water layer extracted two more times with DCM. The organic layers were combined, dried over Na$_2$SO$_4$, filtered and evaporated till dryness. Purification by column chromatography gave rise to the intermediate purine-amine derivative, which was used directly (deprotection). To a solution of the purine-amine derivative in MeOH (15 mL/mmol) was added NaOMe/MeOH solution (5.4 M, 0.2 eq.), and the mixture was stirred at ambient temperature until TLC analysis showed full conversion (generally between 30 min to 1H). Next, the mixture was neutralized (pH ~7) with 0.5 M aq. HCl and evaporated till dryness. The residue was taken up in MeOH, and co-evaporated with Celite®, and subjected to column chromatography.

General Procedure E (Glycosylation of Pyrrolo[2,3-b] Pyridine Analogues

In a flame-dried two-neck round bottom flask under argon was added the appropriate heterocycle (1 eq.). Next, MeCN (7.5 mL/mmol SM) was added. To the stirring suspension was added BSA (1.1 eq.) in one portion. The resulting mixture was stirred at room temperature for ~10 min, after which the glycosyl donor (1-O-acetyl-2,3,5-tri-O-benzoyl-β-D-ribofuranose, 1.1 eq.) was added in one portion, immediately followed by TMSOTf (1.2 eq.). The resulting solution was stirred at ambient temperature for another 15 min, and then transferred to a pre-heated oil bath at 80° C. Heating was continued until full consumption of the glycosyl donor was observed by TLC (generally ~1H). Then, the mixture was cooled to ambient temperature. Next, EA was added and aq. sat. NaHCO$_3$. The layers were separated and the water layer extracted twice more with EA. Organic layers were combined, dried over Na$_2$SO$_4$, filtered and evaporated. The resulting oil was purified by column chromatography (generally isocratic with an eluent consisting of 12 to 20% EA/PET).

B.3. Ribofuranose Compounds

Using the above defined reaction procedures, the compounds as depicted herein below were prepared. Chemical characterization data for each of the prepared compounds can be found further on.

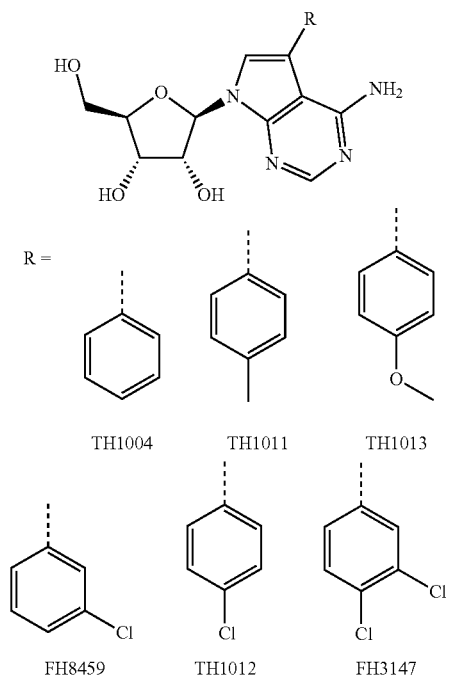

-continued

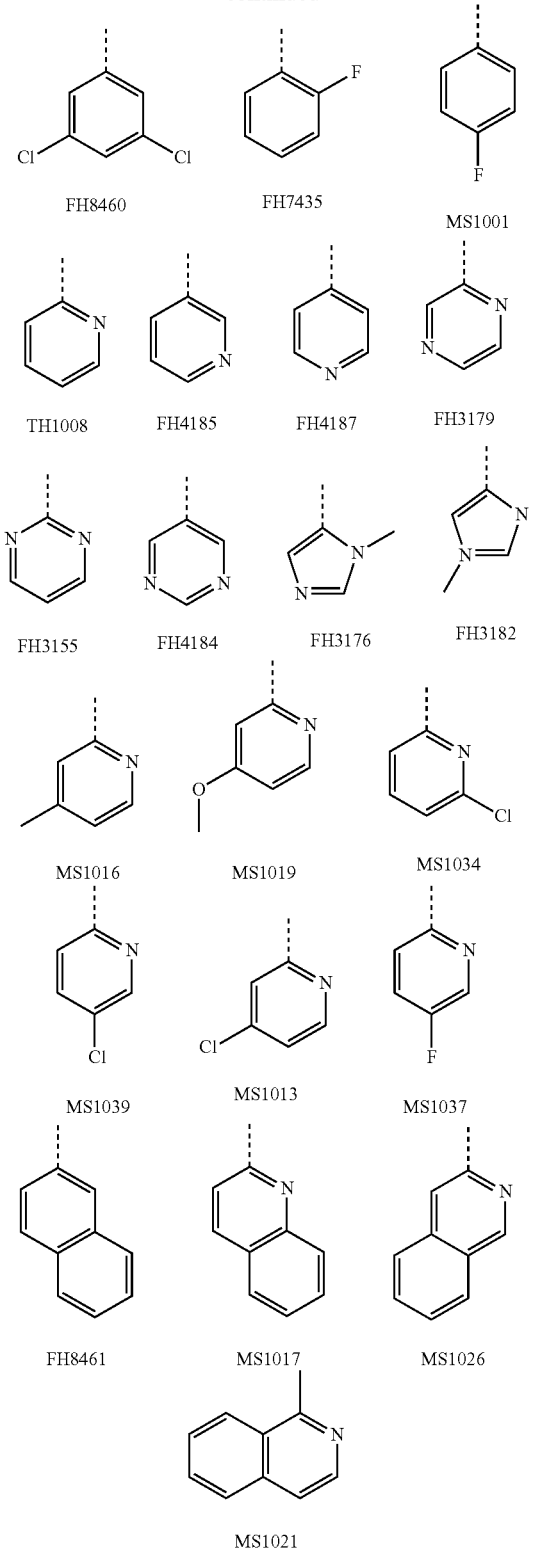

4-amino-5-phenyl-N7-(β-D-ribofuranosyl)-pyrrolo[2,3-d]pyrimidine (TH1004) TH1004 was prepared according to General Procedure A (reaction time: 2H). TH1003 (0.172 g, 0.5 mmol) gave rise to TH1004 as a white solid (0.106 g, 0.310 mmol). Column chromatography: 1→10% MeOH/DCM. Yield=62%. $^1$H NMR (300 MHz, DMSO-d$_6$) δ: 3.53 (ddd, J=12.0, 6.3, 3.9 Hz, 1H, H-5″), 3.63 (dt, J=12.0, 4.5 Hz, 1H, H-5′), 3.91 (q, J=3.6 Hz, 1H, H-4′), 4.08-4.13 (m, 1H, H-3′), 4.46 (q, J=6.0 Hz, 1H, H-2′), 5.11 (d, J=4.8 Hz, 1H, OH-3′), 5.18 (dd, J=6.0, 5.1 Hz, 1H, OH-5′), 5.32 (d, J=6.6 Hz, 1H, OH-2′), 6.10 (br. s, 2H, NH$_2$), 6.12 (d, J=6.0 Hz, 1H, H-1′), 7.35-7.52 (m, 5H, H$_{Phe}$), 7.54 (s, 1H, H-6), 8.15 (s, 1H, H-2). HRMS (ESI): calculated for C$_{17}$H$_{19}$N$_4$O$_4$ ([M+H]$^+$): 343.1401, found: 343.1418. Spectral data are in accordance with literature values.

4-amino-5-(4-methylphenyl)-N7-(β-D-ribofuranosyl)-pyrrolo[2,3-d]pyrimidine (TH1011) TH1011 was prepared according to General Procedure A (reaction time: 2H). TH1003 (0.172 g, 0.5 mmol) gave rise to TH1011 as a white solid (0.080 g, 0.224 mmol). Column chromatography: 1→10% MeOH/DCM. Yield=45%. Melting point: 165° C. $^1$H NMR (300 MHz, DMSO-d$_6$) δ: 2.36 (s, 3H, CH$_3$), 3.50-3.57 (m, 1H, H-5″), 3.61-3.66 (m, 1H, H-5′), 3.90 (q, J=3.6 Hz, 1H, H-4′), 4.10 (br. s, 1H, H-3′), 4.46 (br. s, 1H, H-2′), 5.12 (br. s, 1H, OH-3′), 5.18 (t, J=5.4 Hz, 1H, OH-5′), 5.31 (br. s, 1H, OH-2′), 6.10 (br. s, 2H, NH$_2$), 6.11 (d, J=6.3 Hz, 1H, H-1′), 7.28-7.31 (m, 2H, H$_{Phe}$), 7.35-7.38 (m, 2H, H$_{Phe}$), 7.49 (s, 1H, H-6), 8.14 (s, 1H, H-2). $^{13}$C NMR (75 MHz, DMSO-d$_6$) δ: 20.74 (CH$_3$), 61.67 (C-5′), 70.62 (C-3′), 73.76 (C-2′), 85.09 (C-4′), 87.03 (C-1′), 100.58 (C-4a), 116.18 (C-5), 120.81 (C-6), 128.37 (2C$_{Phe}$), 128.56 (2C$_{Phe}$), 131.51 (C-1$_{Phe}$), 136.14 (C-4$_{Phe}$), 150.75 (C-7a), 151.63 (C-2), 157.31 (C-4). HRMS (ESI): calculated for C$_{18}$H$_{21}$N$_4$O$_4$ ([M+H]$^+$): 357.1557, found: 357.1575.

4-amino-5-(4-chlorophenyl)-N7-(β-D-ribofuranosyl)-pyrrolo[2,3-d]pyrimidine (TH1012) TH1012 was prepared according to the General Procedure A (reaction time: 3H). TH1003 (0.172 g, 0.5 mmol) gave rise to TH1012 as a white solid (0.084 g, 0.223 mmol). Column chromatography: 1→10% MeOH/DCM. Yield=45%. Melting point: 130-132° C. $^1$H NMR (300 MHz, DMSO-d$_6$) δ: 3.53 (ddd, J=11.7, 6.0, 3.9 Hz, 1H, H-5″), 3.60-3.67 (m, 1H, H-5′), 3.90 (q, J=3.6 Hz, 1H, H-4′), 4.08-4.13 (m, 1H, H-4′), 4.42-4.48 (m, 1H, H-2′), 5.11 (d, J=4.8 Hz, 1H, OH-3′), 5.17 (t, J=5.7 Hz, 1H, OH-5′), 5.32 (d, J=6.6 Hz, 1H, OH-2′), 6.12 (d, J=6.0 Hz, 1H, H-1′), 6.21 (br. s, 2H, NH$_2$), 7.46-7.49 (m, 2H, Ph-CH), 7.52-7.55 (m, 2H, Ph-CH), 7.58 (s, 1H, H-6), 8.15 (s, 1H, H-2). $^{13}$C NMR (75 MHz, DMSO-d$_6$) δ:61.64 (C-5′), 70.59 (C-3′), 73.78 (C-2′), 85.12 (C-4′), 87.01 (C-1′), 100.28 (C-4a), 115.15 (C-5), 121.48 (C-6), 128.85 (2C$_{Ph}$), 130.06 (2C$_{Ph}$), 131.50 (C$_{Ph}$), 133.30 (C$_{Ph}$), 151.02 (C-7a), 151.75 (C-2), 157.34 (C-4). HRMS (ESI): calculated for C$_{17}$H$_{18}$ClN$_4$O$_4$ ([M+H]$^+$): 377.1011, found: 377.1028.

4-amino-5-(3,4-dichlorophenyl)-N7-(β-D-ribofuranosyl)-pyrrolo[2,3-d]pyrimidine (FH3147) FH3147 was prepared according to General Procedure A (reaction time: 3H). TH1003 (0.172 g, 0.5 mmol) gave rise to FH3147 as a white solid (0.060 g, 0.146 mmol). Column chromatography: 1→10% MeOH/DCM. Yield=29%. Melting point: 221-223° C. $^1$H NMR (300 MHz, DMSO-d$_6$) δ: 3.53 (dd, J=11.7, 3.3 Hz, 1H, H-5″), 3.64 (dd, J=11.7, 3.6 Hz, 1H, H-5′), 3.90 (q, J=3.6 Hz, 1H, H-4′), 4.42-4.47 (m, 1H, H-2′), 5.13 (br. s, 2H, OH-3′, OH-5′), 5.33 (d, J=6.0 Hz, 1H, OH-2′), 6.12 (d, J=6.3 Hz, 1H, H-1′), 6.41 (br. s, 2H, NH$_2$), 7.43 (dd, J=8.4, 2.1 Hz, 1H, H-6$_{Phe}$), 7.68-7.72 (m, 3H, H-6, H-2$_{Phe}$, H-5$_{Phe}$), 8.17 (s, 1H, H-2). $^{13}$C NMR (75 MHz, DMSO-d$_6$) δ: 61.61 (C-5′), 70.52 (C-3′), 73.79 (C-2′), 85.12 (C-4′), 86.98 (C-1′), 100.03 (C-4a), 114.18 (C-5), 122.18 (C-6), 128.49 (C$_{Phe}$), 129.21 (C$_{Phe}$), 129.94 (C$_{Phe}$), 130.85 (C$_{Phe}$), 131.34 (C$_{Phe}$), 135.04 (C$_{Phe}$), 151.10 (C-7a), 151.59 (C-2), 157.19 (C-4). HRMS (ESI): calculated for C$_{17}$H$_{17}$Cl$_2$N$_4$O$_5$ ([M+H]$^+$): 411.0621, found: 411.0627.

4-amino-5-(3-chlorophenyl)-N7-(β-D-ribofuranosyl)-pyrrolo[2,3-d]pyrimidine (FH8459) FH8459 was prepared according to General Procedure A (reaction time: 1H). TH1003 (0.241 g, 0.7 mmol) gave rise to FH8459 as a white solid (0.056 g, 0.151 mmol). Column chromatography: 1→10% MeOH/DCM. Yield=22%. Melting point: 135° C. $^1$H NMR (300 MHz, DMSO-$d_6$) δ: 3.53 (ddd, J=12.0, 6.0, 4.2 Hz, 1H, H-5"), 3.64 (ddd, J=12.0, 4.8, 4.2 Hz, 1H, H-5'), 3.90 (q, J=3.6 Hz, 1H, H-4'), 4.09-4.13 (m, 1H, H-3'), 4.45 (q, J=6.0 Hz, 1H, H-2'), 5.11 (d, J=4.8 Hz, 1H, OH-3'), 5.15 (dd, J=6.0, 5.1 Hz, 1H, OH-5'), 5.32 (d, J=6.6 Hz, 1H, OH-2'), 6.12 (d, J=6.3 Hz, 1H, H-1'), 6.24 (br. s, 2H, NH$_2$), 7.39-7.45 (m, 2H, H-5$_{Phe}$, H-6$_{Phe}$), 7.49 (d, J=7.8 Hz, 1H, H-4$_{Phe}$), 7.52 (t, J=1.8 Hz, 1H, H-2$_{Phe}$), 7.64 (s, 1H, H-6), 8.16 (s, 1H, H-2). $^{13}$C NMR (75 MHz, DMSO-$d_6$) δ: 61.63 (C-5'), 70.54 (C-3'), 73.78 (C-2'), 85.10 (C-4'), 86.97 (C-1'), 100.19 (C-4a), 114.98 (C-5), 121.89 (C-6), 126.53 (C$_{Phe}$), 126.95 (C$_{Phe}$), 127.95 (C-2$_{Phe}$), 130.67 (C-4$_{Phe}$), 133.47 (C-3$_{Phe}$), 136.58 (C-1$_{Phe}$), 151.08 (C-7a), 151.80 (C-2), 157.34 (C-4). HRMS (ESI): calculated for $C_{17}H_{18}ClN_4O_4$ ([M+H]$^+$): 377.1011, found: 377.0993.

4-amino-5-(4-fluorophenyl)-N7-(β-D-ribofuranosyl)-pyrrolo[2,3-d]pyrimidine (MS1001) MS1001 was prepared according to General Procedure A (reaction time: 1.5H). TH1003 (0.241 g, 0.7 mmol) gave rise to MS1001 as a white solid (0.075 g, 0.208 mmol). Column chromatography: 1→10% MeOH/DCM. Yield=30%. Melting point: 145-148° C. (decomposed). $^1$H NMR (300 MHz, DMSO-$d_6$) δ: 3.53 (ddd, J=12.0, 6.0, 3.9 Hz, 1H, H-5"), 3.63 (ddd, J=12.0, 5.1, 4.2 Hz, 1H, H-5'), 3.90 (q, J=3.6 Hz, 1H, H-4'), 4.11 (dd, J=3.9, 5.1 Hz, 1H, H-3'), 4.42-4.48 (m, 1H, H-2'), 5.11 (d, J=4.8 Hz, 1H, OH-3'), 5.17 (t, J=5.7 Hz, 1H, OH-5'), 5.31 (d, J=6.3 Hz, 1H, OH-2'), 6.11 (d, J=6.3 Hz, 1H, H-1'), 6.15 (br. s, 2H, NH$_2$), 7.27-7.35 (m, 2H, Ph-H), 7.46-7.51 (m, 2H, Ph-H), 7.53 (s, 1H, H-6), 8.14 (s, 1H, H-2). $^{19}$F-NMR (282 MHz, DMSO-$d_6$) δ: −116.01 (ddd, J=13.8, 9.0, 5.9 Hz, 1F). $^{13}$C NMR (75 MHz, DMSO-$d_6$) δ: 61.72 (C-5'), 70.65 (C-3'), 73.82 (C-2'), 85.15 (C-4'), 87.06 (C-1'), 100.54 (C-4a), 115.50 (d, J=26.3 Hz, 2C, C-3$_{Phe}$, C-5$_{Phe}$), 115.96 (C-5), 121.24 (C-6), 130.42 (d, J=8.0 Hz, 2C, C-2$_{Phe}$, C-6$_{Phe}$), 130.82 (d, J=3.5 Hz, 1C, C-1$_{Phe}$), 150.87 (C-7a), 151.75 (C-2), 157.37 (C-4), 161.45 (d, J=241.6 Hz, 1C, C-4$_{Phe}$). HRMS (ESI): calculated for $C_{17}H_{18}FN_4O_4$ ([M+H]$^+$): 361.1307, found: 361.1291.

4-amino-5-(3,5-dichlorophenyl)-N7-(β-D-ribofuranosyl)-pyrrolo[2,3-d]pyrimidine (FH8460) FH8460 was prepared according to General Procedure A (reaction time: 3H). TH1003 (0.241 g, 0.7 mmol) gave rise to FH8460 as a white solid (0.080 g, 0.196 mmol). Column chromatography: 1→10% MeOH/DCM. Yield=28%. Melting point: 219° C. $^1$H NMR (300 MHz, DMSO-$d_6$) δ: 3.53 (ddd, J=12.0, 6.0, 4.2 Hz, 1H, H-5"), 3.64 (ddd, J=12.0, 5.1, 4.2 Hz, 1H, H-5'), 3.90 (q, J=3.6 Hz, 1H, H-4'), 4.09-4.13 (m, 1H, H-3'), 4.44 (q, J=5.7 Hz, 1H, H-2'), 5.12-5.16 (m, 2H, OH-5', OH-3'), 5.33 (d, J=6.3 Hz, 1H, OH-2'), 6.12 (d, J=6.3 Hz, 1H, H-1'), 6.40 (br. s, 2H, NH$_2$), 7.48 (d, J=2.1 Hz, 2H, H-2$_{Phe}$, H-6$_{Phe}$), 7.54 (t, J=2.1 Hz, 1H, H-4$_{Phe}$), 7.73 (s, 1H, H-6), 8.17 (s, 1H, H-2). $^{13}$C NMR (75 MHz, DMSO-$d_6$) δ: 61.63 (C-5'), 70.49 (C-3'), 73.78 (C-2'), 85.09 (C-4'), 86.94 (C-1'), 99.94 (C-4a), 113.89 (C-5), 122.61 (C-6), 125.86 (C-4$_{Phe}$), 126.76 (2C C-2$_{Phe}$, C-6$_{Phe}$), 134.23 (2C C-3$_{Phe}$, C-5$_{Phe}$), 137.89 (C-1$_{Phe}$), 151.30 (C-7a), 151.92 (C-2), 157.40 (C-4). HRMS (ESI): calculated for $C_{17}H_{17}Cl_2N_4O_4$ ([M+H]$^+$): 411.0621, found: 411.0625.

4-amino-5-(2-naftyl)-N7-(β-D-ribofuranosyl)-pyrrolo[2,3-d]pyrimidine (FH8461) FH8461 was prepared according to General Procedure A (reaction time: 1.5H). TH1003 (0.241 g, 0.7 mmol) gave rise to FH8461 as a white solid (0.170 g, 0.43 mmol). Column chromatography: 1→10% MeOH/DCM. Yield=62%. $^1$H NMR (300 MHz, DMSO-$d_6$) δ: 3.55 (ddd, J=12.0, 6.3, 3.9 Hz, 1H, H-5"), 3.65 (ddd, J=12.0, 5.1, 3.9 Hz, 1H, H-5'), 3.93 (q, J=3.6 Hz, 1H, H-4'), 4.11-4.15 (m, 1H, H-3'), 4.49 (q, J=6.0 Hz, 1H, H-2'), 5.13 (d, J=4.8 Hz, 1H, OH-3'), 5.19 (dd, J=6.0, 5.1 Hz, 1H, OH-5'), 5.34 (d, J=6.3 Hz, 1H, OH-2'), 6.16 (d, J=6.3 Hz, 1H, H-1'), 6.21 (br. s, 2H, NH$_2$), 7.50-7.59 (m, 2H$_{Naf}$), 7.64 (dd, J=8.1, 1.8 Hz, 1H, H-3H$_{Naf}$), 7.67 (s, 1H, H-6), 7.96-7.99 (m, 3H$_{Naf}$), 8.03 (d, J=8.7 Hz, 1H, H-4$_{Naf}$), 8.18 (s, 1H, H-2). HRMS (ESI): calculated for $C_{21}H_{21}N_4O_4$ ([M+H]$^+$): 393.1557, found: 393.1557. Spectral data are in accordance to literature values.

4-amino-5-(pyrid-2-yl)-N7-(β-D-ribofuranosyl)-pyrrolo[2,3-d]pyrimidine (TH1008) TH1008 was prepared according to General Procedure D. FH8451 (0.585 g, 0.858 mmol) gave rise to TH1008 as a white solid (0.140 g, 0.408 mmol). Column chromatography: 1→10% MeOH/DCM. Yield=48%. Melting point: 238° C. $^1$H NMR (300 MHz, DMSO-$d_6$) δ: 3.57 (ddd, J=11.7, 6.6, 4.2 Hz, 1H, H-5"), 3.69 (ddd, J=12.0, 5.1, 4.2 Hz, 1H, H-5'), 3.92 (q, J=3.9 Hz, 1H, H-4'), 4.14 (dd, J=8.7, 5.1 Hz, 1H, H-3'), 4.48 (q, J=5.7 Hz, 1H, H-2'), 5.28 (d, J=6.3, 5.4 Hz, 1H, OH-5'), 5.36 (d, J=6.0 Hz, 1H, OH-2'), 6.09 (d, J=5.7 Hz, 1H, H-1'), 7.25 (ddd, J=7.2, 5.1, 0.9 Hz, 1H, H-5$_{Pyr}$), 7.29 (br. s, 1H, NH), 7.85 (ddd, J=8.1, 7.5, 1.8 Hz, 1H, H-4$_{Pyr}$), 7.98 (dt, J=8.1, 0.9 Hz, 1H, H-3$_{Pyr}$), 8.07 (s, 1H, H-2), 8.26 (s, 1H, H-6), 8.55 (ddd, J=5.1, 1.8, 0.9 Hz, 1H, H-6$_{Pyr}$), 9.88 (br. s, 1H, NH). $^{13}$C NMR (75 MHz, DMSO-$d_6$) δ: 61.59 (C-5'), 70.40 (C-3'), 73.65 (C-2'), 85.13 (C-4'), 87.30 (C-1'), 100.58 (C-4a), 116.03 (C-5), 120.35 (C-3$_{Pyr}$), 121.07 (C-5$_{Pyr}$), 123.31 (C-6), 137.69 (C-4$_{Pyr}$), 147.89 (C-6$_{Pyr}$), 151.46 (C-7a), 152.48 (C-2), 153.09 (C-2$_{Pyr}$), 158.74 (C-4). HRMS (ESI): calculated for $C_{16}H_{18}N_5O_4$: 344.1353 ([M+H]$^+$), found: 344.1370.

4-amino-5-(pyrid-3-yl)-N7-(β-D-ribofuranosyl)-pyrrolo[2,3-d]pyrimidine (FH4185) FH4185 was prepared according to General Procedure A (reaction time: 20H), with the use of 3-pyridylboronic pinacol ester. TH1003 (0.172 g, 0.5 mmol) gave rise to FH4185 as a white solid (0.060 g, 0.175 mmol). Column chromatography: 1→20% MeOH/DCM. Yield=35%. Melting point: 220° C. (decomposed). 1H NMR (300 MHz, DMSO-$d_6$) δ: 3.50-3.57 (m, 1H, H-5"), 3.60-3.67 (m, 1H, H-5'), 3.91 (dd, J=7.2, 3.9 Hz, 1H, H-4'), 4.09-4.14 (m, 1H, H-3'), 4.46 (dd, J=11.4, 6.3 Hz, 1H, H-2'), 5.13 (d, J=4.8 Hz, 1H, OH-3'), 5.17 (t, J=5.7 Hz, 1H, OH-5'), 5.33 (d, J=6.3 Hz, 1H, OH-2'), 6.13 (d, J=6.0 Hz, 1H, H-1'), 6.26 (br. s, 2H, NH$_2$), 7.48 (ddd, J=8.1, 5.1, 0.9 Hz, 1H, H-4Pyr), 7.67 (s, 1H, H-6), 7.85 (dt, J=8.1, 2.1 Hz, 1H, H-5Pyr), 8.17 (s, 1H, H-2), 8.55 (dd, J=4.8, 1.8 Hz, 1H, H-6Pyr), 8.70 (dd, J=2.4, 0.9 Hz, 1H, H-2Pyr). 13C NMR (75 MHz, DMSO-$d_6$) δ: 61.63 (C-5'), 70.56 (C-3'), 73.81 (C-2'), 85.13 (C-4'), 87.06 (C-1'), 100.40 (C-4a), 112.76 (C-5), 122.02 (C-6), 123.76 (C-5Pyr), 130.26 (C-3Pyr), 135.59 (C-4Pyr), 147.66 (C-6Pyr), 148.76 (C-2Pyr), 151.20 (C-7a), 151.83 (C-2), 157.46 (C-4). HRMS (ESI): calculated for $C_{16}H_{18}N_5O_4$: 344.1353 ([M+H]$^+$), found: 344.1353.

4-amino-5-(pyrazine-2-yl)-N7-(β-D-ribofuranosyl)-pyrrolo[2,3-d]pyrimidine (FH3179) FH3179 was prepared according to General Procedure B. The mixture was purified by column chromatography 25→100% EA/Hex. Product containing fractions were pooled and evaporated (still containing some impurities). The resulting solid was dissolved in 15 mL 7N NH$_3$/MeOH and stirred at ambient temperature overnight. Next, the mixture was evaporated till dryness. Purification by column chromatography (8→15% MeOH/

DCM). Product containing fractions were pooled and evaporated till near-dryness, after which the product precipitated out of the solution. FH3144 (0.4 g, 0.6 mmol) gave rise to FH3179 (0.075 g, 0.218 mmol) as a white solid. Yield=36%. Melting point: 257° C. $^1$H NMR (300 MHz, DMSO-$d_6$) δ: 3.54-3.62 (m, 1H, H-5"), 3.67-3.74 (m, 1H, H-5'), 3.93 (dd, J=7.5, 3.9 Hz, 1H, H-4'), 4.15 (dd, J=9.0, 5.1 Hz, 1H, H-3'), 4.47 (q, J=5.7 Hz, 1H, H-4'), 5.15 (d, J=5.1 Hz, 1H, OH-3'), 5.25 (t, J=5.7 Hz, 1H, OH-5'), 5.39 (d, J=6.0 Hz, 1H, OH-2'), 6.11 (d, J=6.0 Hz, 1H, H-1'), 7.43 (br. s, 1H, NH), 8.11 (s, 1H, H-2), 8.45 (d, J=2.7 Hz, 1H, H-6$_{Pyr}$a), 8.49 (s, 1H, H-6), 8.59 (dd, J=2.7, 1.5 Hz, 1H, H-5$_{Pyr}$a), 9.14 (br. s, 1H, NH), 9.30 (d, J=1.2 Hz, 1H, H-3$_{Pyr}$a). $^{13}$C NMR (75 MHz, DMSO-$d_6$) δ: 61.53 (C-5'), 70.31 (C-3'), 73.76 (C-2'), 85.48 (C-4'), 87.29 (C-1'), 100.52 (C-4a), 113.07 (C-5), 124.20 (C-6), 141.08 (C-6$_{Pyr}$a), 142.30 (C-5$_{Pyr}$a), 142.90 (C-3$_{Pyra}$), 148.91 (C-2$_{Pyra}$), 151.77 (C-7a), 152.85 (C-2), 158.53 (C-4). HRMS (ESI): calculated for $C_{15}H_{17}N_6O_4$ ([M+H]$^+$), found: 345.1291.

4-amino-5-(6-chloro-pyrid-2-yl)-N7-(β-D-ribofuranosyl)-pyrrolo[2,3-d]pyrimidine (MS1034) MS1034 was prepared according to General Procedure D. After evaporation, the resulting mixture was taken up in MeOH and the precipitate collected by filtration to yield pure MS1034, which did not require column chromatography. MS1029 (0.144 g, 0.201 mmol) gave rise to MS1034 (0.045 g, 0.119 mmol) as a white solid. Yield=59%. Melting point: 214° C. $^1$H NMR (300 MHz, DMSO-$d_6$) δ: 3.51-3.60 (m, 1H, H-5"), 3.62-3.72 (m, 1H, H-5'), 3.92 (q, J=3.9 Hz, 1H, H-4'), 4.14 (t, J=4.2 Hz, 1H, H-3'), 4.46 (t, J=5.4 Hz, 1H, H-2'), 5.17 (br. s, 1H, OH-3'), 5.27 (br. s, 1H, OH-5'), 5.40 (br. s, 1H, OH-2'), 6.10 (d, J=6.0 Hz, 1H, H-1'), 7.36 (dd, J=7.8, 0.9 Hz, 1H, H-5$_{Pyr}$), 7.47 (br. s, 1H, NH), 7.91 (t, J=7.8 Hz, 1H, H-4$_{Pyr}$), 7.99 (d, J=7.8 Hz, 1H, H-3$_{Pyr}$), 8.09 (s, 1H, H-2), 8.37 (s, 1H, H-6), 9.15 (br. s, 1H, NH). $^{13}$C NMR (75 MHz, DMSO-$d_6$) δ: 61.50 (C-5'), 70.34 (C-3'), 73.75 (C-2'), 85.18 (C-4'), 87.16 (C-1'), 100.16 (C-4a), 114.73 (C-5), 119.21 (C-3Pyr), 120.76 (C-5$_{Pyr}$), 124.60 (C-6), 140.98 (C-4Pyr), 148.41 (C-6$_{Pyr}$), 151.74 (C-7a), 152.64 (C-2), 154.15 (C-2Pyr), 158.61 (C-4). HRMS (ESI): calculated for $C_{16}H_{17}ClN_5O_4$ ([M+H]$^+$): 378.0964, found: 378.0964.

4-amino-5-(5-chloro-pyrid-2-yl)-N7-(β-D-ribofuranosyl)-pyrrolo[2,3-d]pyrimidine (MS1039) MS1039 was prepared according to General Procedure D. After evaporation, the resulting mixture was taken up in MeOH and the precipitate collected by filtration to yield pure MS1039, which did not require column chromatography. MS1028 (0.200 g, 0.279 mmol) gave rise to MS1039 (0.051 g, 0.135 mmol) as a white solid. Yield=49%. Melting point: 203° C. $^1$H NMR (300 MHz, DMSO-$d_6$) δ: 3.53-3.61 (m, 1H, H-5"), 3.69 (dt, J=12.3, 4.5 Hz, 1H, H-5'), 3.92 (q, J=3.6 Hz, 1H, H-4'), 4.14 (br. s, 1H, H-3'), 4.60 (br. s, 1H, H-2'), 5.14 (d, J=3.0 Hz, 1H, OH-3'), 5.25 (t, J=5.4 Hz, 1H, OH-5'), 5.38 (d, J=4.5 Hz, 1H, OH-2'), 6.10 (d, J=6.0 Hz, 1H, H-1'), 7.34 (br. s, 1H, NH), 7.98 (dd, J=8.7, 2.4 Hz, 1H, H-4$_{Pyr}$), 8.02 (dd, J=9.0, 0.9 Hz, 1H, H-3$_{Pyr}$), 8.08 (s, 1H, H-2), 8.30 (s, 1H, H-6), 8.63 (dd, J=2.4, 0.9 Hz, 1H, H-6$_{Pyr}$), 9.38 (br. s, 1H, NH). $^{13}$C NMR (75 MHz, DMSO-$d_6$) δ:61.59 (C-5'), 70.39 (C-3'), 73.65 (C-2'), 85.18 (C-4'), 87.21 (C-1'), 100.32 (C-4a), 115.07 (C-5), 121.70 (C-3Pyr), 123.97 (C-6), 127.88 (C-5$_{Pyr}$), 137.48 (C-4Pyr), 146.50 (C-6Pyr), 151.63 (C-7a), 151.84 (C-2Pyr), 152.61 (C-2), 158.61 (C-4). HRMS (ESI): calculated for $C_{16}H_{17}ClN_5O_4$ ([M+H]$^+$): 378.0964, found: 378.0961.

4-amino-5-(5-fluoro-pyrid-2-yl)-N7-(β-D-ribofuranosyl)-pyrrolo[2,3-d]pyrimidine (MS1037) MS1037 was prepared according to General Procedure D. After evaporation, the resulting mixture was taken up in MeOH and the precipitate collected by filtration to yield MS1037, which did not require column chromatography. MS1031 (0.151 g, 0.216 mmol) gave rise to MS1037 (0.046 g, 0.127 mmol) as a white solid. Yield=59%. Melting point: 220° C. $^1$H NMR (300 MHz, DMSO-$d_6$) δ: 3.50-3.60 (m, 1H, H-5"), 3.62-3.72 (m, 1H, H-5'), 3.92 (q, J=3.9 Hz, 1H, H-4'), 4.13-4.15 (m, 1H, H-3'), 4.47 (t, J=5.7 Hz, 1H, H-2'), 5.19 (br. s, 1H, OH-3'), 5.27 (br. s, 1H, OH-5'), 5.39 (br. s, 1H, OH-2'), 6.09 (d, J=6.0 Hz, 1H, H-1'), 7.28 (br. s, 1H, NH), 8.07 (dt, J=8.7, 3.0 Hz, 1H, H-4$_{Pyr}$), 8.07 (s, 1H, H-2), 8.07 (dd, J=8.7, 4.5 Hz, 1H, H-3$_{Pyr}$), 8.24 (s, 1H, H-6), 8.59 (dd, J=3.0 Hz, 1H, H-6$_{Pyr}$), 9.37 (br. s, 1H, NH). $^{19}$F-NMR (282 MHz, DMSO-$d_6$) δ: −130.98 (dd, J=8.5, 4.8 Hz). $^{13}$C NMR (75 MHz, DMSO-$d_6$) δ: 61.59 (C-5'), 70.41 (C-3'), 73.69 (C-2'), 85.14 (C-4'), 87.09 (C-1'), 100.34 (C-4a), 115.24 (C-5), 122.09 (C-3Pyr), 123.25 (C-6), 125.35 (d, J=19.43 Hz, 1C, C-4Pyr), 135.56 (d, J=24.0 Hz, 1C, C-6Pyr), 150.06 (C-2$_{Pyr}$), 151.55 (C-7a), 152.50 (C-2), 157.41 (d, J=250.7 Hz, 1C, C-5$_{Pyr}$), 158.61 (C-4). HRMS (ESI): calculated for $C_{16}H_{17}FN_5O_4$ ([M+H]$^+$): 362.1259, found: 362.1263.

4-amino-5-(2-quinolinyl)-N7-(β-D-ribofuranosyl)-pyrrolo[2,3-d]pyrimidine] (MS1017) MS1017 was prepared according to the General Procedure D. Column chromatography 0→20% MeOH/DCM. MS1006 (0.149 g, 0.204 mmol) gave rise to MS1017 (0.025 g, 0.064 mmol) as a white solid. Yield=31%. Melting point: 231-234° C. $^1$H NMR (300 MHz, DMSO-$d_6$) δ: 3.58-3.62 (m, 1H, H-5"), 3.71-3.75 (m, 1H, H-5'), 3.95 (q, J=3.6 Hz, 1H, H-4'), 4.17 (q, J=4.2 Hz, 1H, H-3'), 4.52 (q, J=5.4 Hz, 1H, H-2'), 5.16 (d, J=4.8 Hz, 1H, OH-3'), 5.30 (s, 1H, OH-5'), 5.41 (d, J=5.7 Hz, 1H, OH-2'), 6.13 (d, J=6.0 Hz, 1H, H-1'), 7.45 (br. s, 1H, NH), 7.58 (ddd, J=8.1, 6.9, 1.2 Hz, 1H, H-6$_{Quin}$), 7.79 (ddd, J=8.4, 6.9, 1.5 Hz, 1H, H-7$_{Quin}$), 7.89 (d, J=8.4 Hz, 1H, H-8$_{Quin}$), 7.97 (d, J=8.1 Hz, 1H, H-5$_{Quin}$), 8.13 (s, 1H, H-2), 8.15 (J=8.7 Hz, 1H, H-3$_{Quin}$), 8.41 (d, J=8.7 Hz, 1H, H-4$_{Quin}$), 8.52 (s, 1H, H-6), 10.64 (br.s, 1H, NH). $^{13}$C NMR (75 MHz, DMSO-$d_6$) δ:61.56 (C-5'), 70.36 (C-3'), 73.70 (C-2'), 85.21 (C-4'), 87.33 (C-1'), 100.69 (C-4a), 116.57 (C-5), 119.28 (C-3$_{Quin}$), 125.53 (C-6), 26.12 (C-6$_{Quin}$/C-4a$_{Quin}$), 126.79 (C-8$_{Quin}$), 127.95 (C-5$_{Quin}$), 130.34 (C-7$_{Quin}$), 137.17 (C-4$_{Quin}$), 146.14 (C-8a$_{Quin}$), 151.80 (C-7a), 152.64 (C-2), 153.22 (C-2$_{Quin}$), 158.70 (C-4). HRMS (ESI): calculated for $C_{20}H_{20}N_5O_4$ ([M+H]$^+$): 394.1510, found: 394.1497.

4-amino-5-(1-methyl-1H-imidazol-4-yl)-N7-(β-D-ribofuranosyl)-pyrrolo[2,3-d]pyrimidine](FH3182) FH3182 was prepared according to General Procedure B. The mixture was purified by column chromatography 0→3.5% MeOH/DCM. Product containing fractions were pooled and evaporated (still containing some impurities). The resulting solid was dissolved in 20 mL 7N NH$_3$/MeOH and stirred at ambient temperature overnight. Next, the mixture was evaporated till dryness. Purification by column chromatography (10% MeOH/DCM). FH3144 (0.4 g, 0.6 mmol) and FH3180 (0.45 g, 0.4 mL, 1.2 mmol) gave rise to FH3182 (0.025 g, 0.072 mmol) as a white solid. Yield=25%. Melting point: 162-164° C. $^1$H NMR (300 MHz, DMSO-$d_6$) δ: 3.50-3.57 (m, 1H, H-5"), 3.61-3.69 (m, 1H, H-5'), 3.70 (s, 3H, CH$_3$), 3.90 (q, J=3.6 Hz, 1H, H-4'), 4.07-4.12 (m, 1H, H-3'), 4.41 (dd, J=11.1, 6.0 Hz, 1H, H-2'). 5.10 (d, J=4.5 Hz, 1H, OH-3'). 5.25 (t, J=5.7 Hz, 1H, OH-5'). 5.30 (d, J=6.3 Hz, 1H, OH-2'), 6.03 (d, J=6.3 Hz, 1H, H-1'), 7.10 (br. s, 1H, NH), 7.47 (d, J=1.2 Hz, 1H, H-5$_{imid}$), 7.64 (s, 1H, H-6), 7.74 (d, J=0.9 Hz, 1H, H-2$_{imid}$), 8.01 (s, 1H, H-2), 9.81 (br. s, 1H, NH). $^{13}$C NMR (75 MHz, DMSO-$d_6$) δ: 33.19 (CH$_3$), 61.87 (C-5'), 70.66 (C-3'), 73.59 (C-2'), 85.01 (C-4'), 87.13 (C-1'), 100.46 (C-4a), 110.37 (C-5), 115.96 (C-5$_{imid}$), 117.70 (C-6), 135.57 (C-4$_{imid}$), 137.13 (C-2$_{imid}$), 150.38 (C-7a), 151.89 (C-2), 158.30 (C-4). HRMS (ESI): calculated for C$_{15}$H$_{19}$N$_6$O$_4$: 347.1462 ([M+H]$^+$), found: 347.1462. Purity: 92%.

4-azido-5-iodo-N7-(2',3',5'-tri-O-benzoyl-β-D-ribofuranosyl)-pyrrolo[2,3-d]pyrimidine (FH3158) FH3120 (3.56 g, 4.91 mmol) was dissolved in anhydrous DMF (50 mL, 10 mL/mmol SM). Next, NaN$_3$ (0.66 g, 10.07 mmol, 2.05 eq.) was added. The resulting mixture was heated in a pre-heated oil bath at 65° C. for 30 min. Next, the mixture was cooled to ambient temperature. Then, it was poured into half-saturated NaHCO$_3$ solution (75 mL) and EA (75 mL). The layers were separated and the water layer extracted two more times with EA. The organic layers were combined, dried over Na$_2$SO$_4$, filtered and evaporated till dryness. The residue was purified by column chromatography (35% EA/Hex) to yield FH3158 as a white foam (3.1 g, 4.24 mmol). Yield=86%. $^1$H NMR (300 MHz, DMSO-d$_6$) δ: 4.72 (dd, J=12.0, 5.1 Hz, 1H, H-5''), 4.83 (dd, J=12.0, 4.2 Hz, 1H, H-5'), 4.90-4.94 (m, 1H, H-4'), 6.12 (t, J=6.0 Hz, 1H, H-3'), 6.27 (dd, J=6.0, 5.1 Hz, 1H, H-2'), 6.83 (d, J=5.1 Hz, 1H, H-1'), 7.43-7.53 (m, 6H, OBz), 7.60-7.70 (m, 3H, OBz), 7.85-7.88 (m, 2H, OBz), 7.93-8.01 (m, 4H, OBz), 8.27 (s, 1H, H-6), 9.90 (s, 1H, H-2). $^{13}$C NMR (75 MHz, DMSO-d$_6$) δ: 55.85 (C-5), 63.55 (C-5'), 70.74 (C-3'), 74.02 (C-2'), 79.45 (C-4'), 86.73 (C-1'), 107.23 (C-4a), 128.16, 128.51, 128.77, 129.15, 129.23, 129.37, 130.62 (C-6), 133.57, 133.93, 134.02, 134.88 (C-2), 141.55 (C-7a), 145.96 (C-4), 164.43 (C=O), 164.65 (C=O), 165.41 (C=O). HRMS (ESI): calculated for C$_{32}$H$_{24}$IN$_6$O$_7$ ([M+H]$^+$): 731.0746, found: 731.0796.

4-amino-5-iodo-N7-(2',3',5'-tri-O-benzoyl-β-D-ribofuranosyl)-pyrrolo[2,3-d]pyrimidine (FH4188) FH3158 (2.10 g, 2.87 mmol, 1 eq.) was dissolved in THF (30 mL, 10 mL/mmol). Then, PMe$_3$ solution (1 M in THF; 5.75 mL, 5.74 mmol, 2 eq.) was added and the mixture stirred at ambient temperature for 30 min. Next, the solution was evaporated till dryness, and subsequently re-dissolved in MeCN (30 mL, 10 ml/mmol). To this solution was added a 1 M aq. HOAc solution (9.55 mL, 3.33 eq.), and the mixture heated in a pre-heated oil bath at 65° C. for 1H. Next, the mixture was cooled to ambient temperature and poured into sat. aq. NaHCO$_3$ solution. DCM was added, the layers were separated and the water layer extracted two more times with DCM. The organic layers were combined, dried over Na$_2$SO$_4$, filtered and evaporated till dryness. Purification by column chromatography 62.5% EA/Hex gave FH4188 as a slight yellow foam (1.89 g, 2.68 mmol). Yield=93%. $^1$H NMR (300 MHz, CDCl$_3$) δ: 4.67 (dd, J=12.3, 3.9 Hz, 1H, H-5''), 4.74-4.78 (m, 1H, H-4'), 4.87 (dd, J=12.0, 3.3 Hz, 1H, H-5'), 5.77 (br. s, 2H, NH$_2$), 6.09-6.14 (m, 2H, H-3', H-2'), 6.66 (dd, J=3.0, 1.8 Hz, 1H, H-1'), 7.20 (s, 1H, H-6), 7.33-7.40 (m, 4H, OBz), 7.47-7.64 (m, 5H, OBz), 7.92-7.99 (m, 4H, OBz), 8.14-8.15 (m, 2H, OBz), 8.26 (s, 1H, H-2). $^{13}$C NMR (75 MHz, CDCl$_3$) δ: 52.38 (C-5), 63.85 (C-5'), 71.62 (C-3'), 74.24 (C-2'), 80.43 (C-4'), 86.15 (C-1'), 104.73 (C-4a), 126.30 (C-6), 128.59, 128.63, 128.66, 128.89, 129.55, 129.87, 129.95, 130.01, 150.83 (C-7a), 152.71 (C-2), 157.13 (C-4), 165.25 (C=O), 165.53 (C=O), 166.28 (C=O). HRMS (ESI): calculated for C$_{32}$H$_{26}$IN$_4$O$_7$: 705.0841 ([M+H]$^+$), found: 705.0822.

4-azido-5-bromo-N7-(2',3'5'-tri-O-benzoyl-β-D-ribofuranosyl)-pyrrolo[2,3-d]pyrimidine (FH3142) FH3142 was prepared as has been described for FH3158. FH3133$^{32}$ (1.01 g, 1.5 mmol) gave rise to FH3142 as a white foam (0.93 g, 1.35 mmol). Yield=90%. Purification by column chromatography 30% EA/Hex. $^1$H NMR (300 MHz, DMSO-d$_6$) δ:4.72 (dd, J=12.3, 5.1 Hz, 1H, H-5''), 4.83 (dd, J=12.0, 3.9 Hz, 1H, H-5'), 4.90-4.95 (m, 1H, H-4'), 6.10-6.14 (m, 1H, H-3'), 6.26-6.30 (m, 1H, H-2'), 6.85 (d, J=5.1 Hz, 1H, H-1'), 7.41-7.53 (m, 6H, OBz), 7.61-7.70 (m, 3H, OBz), 7.86-7.89 (m, 2H, OBz), 7.93-7.97 (m, 2H, OBz), 7.98-8.01 (m, 2H, OBz), 8.30 (s, 1H, H-6), 9.94 (s, 1H, H-2). $^{13}$C NMR (75 MHz, DMSO-d$_6$) δ:63.55 (C-5'), 70.72 (C-3'), 74.00 (C-2'), 79.51 (C-4'), 88.86 (C-1'), 90.05, 103.91, 125.77 (C-6), 128.16, 128.51, 128.76, 129.16, 129.23, 129.37, 133.55, 133.92, 134.03, 135.14 (C-2), 140.63 (C-7a), 145.43 (C-4), 164.42 (C=O), 164.65 (C=O), 165.41 (C=O). HRMS (ESI): calculated for C$_{32}$H$_{24}$BrN$_6$O$_7$ ([M+H]$^+$): 683.0884, found: 683.0917.

4-amino-5-bromo-N7-(2',3',5'-tri-O-benzoyl-β-D-ribofuranosyl-pyrrolo[2,3-d]pyrimidine (FH3144) FH3144 was prepared as has been described for FH4188. FH3142 (0.515 g, 0.75 mmol) gave rise to FH3144 as a white foam (0.40 g, 0.61 mmol). Yield=81%. Purification by column chromatography (25-65% EA/Hex). $^1$H NMR (300 MHz, CDCl$_3$) δ: 4.67 (dd, J=12.3, 3.9 Hz, 1H, H-5''), 4.76 (q, J=3.6 Hz, 1H, H-4'), 4.86 (dd, J=12.3, 3.3 Hz, 1H, H-5'), 5.61 (br. s, 2H, NH$_2$), 6.07-6.13 (m, 2H, H-2', H-3'), 6.66 (d, J=5.1 Hz, 1H, H-1'), 7.11 (s, 1H, H-6), 7.33-7.41 (m, 4H, OBz), 7.47-7.64 (m, 5H, OBz), 7.92-7.99 (m, 4H, OBz), 8.11-8.14 (m, 2H, OBz), 8.26 (s, 1H, H-2). $^{13}$C NMR (75 MHz, CDCl$_3$) δ: 63.86 (C-5'), 71.60 (C-3'), 74.18 (C-2'), 80.44 (C-2'), 86.14 (C-1'), 89.31 (C-5), 102.82 (C-4a) 121.00 (C-6), 128.62, 128.66, 128.69, 128.86, 128.91, 129.58, 129.89, 129.99, 130.04, 133.59, 133.82, 150.46 (C-7a), 153.29 (C-2), 156.97 (C-4), 165.27 (C=O), 165.54 (C=O), 166.31 (C=O). HRMS (ESI): calculated for C$_{32}$H$_{26}$BrN$_4$O$_7$ ([M+H]$^+$): 657.0979, found: 657.0970.

4-azido-5-(pyrid-2-yl)-N7-(2'-3'-5'-tri-O-benzoyl-β-D-ribofuranosyl)-pyrrolo[3,2-d]pyrimidine (FH8451) FH8451 was prepared according to General Procedure C [reaction temperature=60° C.]. FH3158 (0.730 g, 1 mmol) gave rise to FH8451 as a yellowish foam (0.350 g, 0.51 mmol). Column chromatography: 0→35% EA/PET. Yield=51%. $^1$H NMR (300 MHz, DMSO-d$_6$) δ: 4.77 (dd, J=12.0, 5.10 Hz, 1H, H-5''), 4.87 (dd, J=12.3, 3.6 Hz, 1H, H-5'), 4.94-4.99 (m, 1H, H-4'), 6.14-6.18 (m, 1H, H-3'), 6.39 (t, J=6.0 Hz, 1H, H-2'), 6.98 (d, J=5.4 Hz, 1H, H-1'), 7.36 (ddd, J=7.5, 4.8, 0.9 Hz, 1H, H-5$_{Pyr}$), 7.40-7.53 (m, 6H, OBz), 7.60-7.71 (m, 3H, OBz), 7.84-7.88 (m, 2H, OBz), 7.97-8.06 (m, 5H (4+1H), OBz, H-4$_{Pyr}$), 8.62 (ddd, J=4.8, 2.1, 0.9 Hz, 1H, H-6$_{Pyr}$), 8.77 (s, 1H, H-6), 9.05 (dt, J=7.8, 0.9 Hz, 1H, H-3$_{Pyr}$), 9.98 (s, 1H, H-2). $^{13}$C NMR (75 MHz, DMSO-d$_6$) δ: 63.64 (C-5'), 70.89 (C-3'), 73.91 (C-2'), 79.62 (C-4'), 86.89 (C-1'), 100.70 (C-4a), 119.13 (C-5), 121.40 (C-3Pyr), 122.35 (C-5$_{Pyr}$), 125.84 (C-6), 128.18, 128.58, 128.71, 128.77, 128.80, 129.14, 129.26, 129.35, 129.40, 133.54, 133.93, 134.03, 134.56 (C-2), 137.38 (C-4$_{Pyr}$), 141.90 (C-7a), 146.73 (C-4), 149.58 (C-6Pyr), 150.62 (C-2$_{Pyr}$), 164.45 (C=O), 164.72 (C=O), 165.47 (C=O). HRMS (ESI): calculated for C$_{37}$H$_{38}$N$_7$O$_7$ ([M+H]$^+$): 682.2045, found: 682.2097.

4-azido-5-(2-quinolinyl)-N7-(2',3',5'-tri-O-benzoyl-β-D-ribofuranosyl)-pyrrolo[2,3-d]pyrimidine (MS1010) MS1010 was prepared according to General Procedure C [reaction temperature=60° C.]. FH3158 (0.51 g, 0.7 mmol) gave rise to MS1010 as a pink foam (0.149 g, 0.204 mmol). Column chromatography: 0→10% EA/Tol. Yield=29%. $^1$H NMR (300 MHz, DMSO-d$_6$) δ: 4.80 (dd, J=12.3, 5.4 Hz, 1H, H-5''), 4.90 (dd, J=12.3, 3.6 Hz, 1H, H-5'), 4.97-5.02 (m, 1H, H-4'), 6.20 (t, J=5.7 Hz, 1H, H-3'), 6.45 (t, J=6.0 Hz, 1H, H-2'), 7.04 (d, J=5.1 Hz, 1H, H-1'), 7.40-7.53 (m, 6H, OBz), 7.57-7.72 (m, 4H (3+1), OBz (3H), H$_{Quin}$), 7.75-7.80 (m, 1H, H$_{Quin}$), 7.86-7.89 (2H, m, OBz), 7.91 (d, J=8.4 Hz, 1H, H$_{Quin}$), 7.98-8.06 (m, 5H (4+1), OBz (4H), H$_{Quin}$), 8.59 (d, J=8.7 Hz, 1H, H-4$_{Quin}$), 8.92 (s, 1H, H-6), 9.13 (d, J=8.7 Hz, 1H, H-3$_{Quin}$), 10.00 (s, 1H, H-2). $^{13}$C NMR (75 MHz, DMSO-d$_6$) δ: 63.78 (C-5'), 70.95 (C-3'), 74.01 (C-2'), 79.70 (C-4'), 87.15 (C-1'), 101.27 (C-4a), 119.21 (C-5), 120.29 (C-3$_{Quin}$), 125.30 (C$_{Quin}$), 126.20 (C$_{Quin}$), 126.72 (C$_{Quin}$), 126.89 (C-6), 128.20 (CO$_{Quin}$), 128.58, 128.72, 128.76, 128.81, 128.89, 129.16, 129.28, 129.37, 129.42, 129.95 (C$_{Quin}$), 133.53, 133.95, 134.01, 134.64 (C-2), 137.21 (C-4$_{Quin}$), 141.92 (C-7a), 146.79 (C-4), 147.60 (C-8a$_{Quin}$), 151.05 (C-2$_{Quin}$), 164.52 (C=O), 164.74 (C=O), 165.51 (C=O). HRMS (ESI): calculated for C$_{41}$H$_{30}$N$_7$O$_7$ ([M+H]$^+$): 732.2201, found: 732.2239.

4-azido-5-(5-chloro-pyrid-2-yl)-N7-(2',3',5'-tri-O-benzoyl-β-D-ribofuranosyl)-pyrrolo[2,3-d]pyrimidine (MS1028) MS1028 was prepared according to General Procedure C [reaction temperature=60° C.]. FH3158 (0.51 g, 0.7 mmol) gave rise to MS1028 as a yellow foam (0.151 g, 0.209 mmol). Column chromatography: 0→20% EA/PET. Yield=30%. $^1$H NMR (300 MHz, DMSO-d$_6$) δ: 4.87 (dd, J=12.3, 3.9 Hz, 1H, H-5''), 4.76 (dd, J=12.3, 5.1 Hz, 1H, H-5'), 4.94-4.99 (m, 1H, H-4'), 6.16 (dd, J=6.0, 5.4 Hz, 1H, H-3'), 6.39 (dd, J=6.3, 5.4 Hz, 1H, H-2'), 6.97 (d, J=5.1 Hz, 1H, H-1'), 7.40-7.54 (m, 6H, OBz), 7.60-7.72 (m, 3H, OBz), 7.84-7.87 (m, 2H, OBz), 7.96-8.02 (m, 4H, OBz), 8.21 (dd, J=8.4, 2.7 Hz, 1H, H-4$_{Pyr}$), 8.63 (dd, J=2.7, 0.6 Hz, 1H, H-6$_{Pyr}$), 8.77 (s, 1H, H-6), 9.09 (dd, J=8.4, 0.6 Hz, 1H, H-3$_{Pyr}$), 10.00 (s, 1H, H-2). HRMS (ESI): calculated for C$_{37}$H$_{27}$ClN$_7$O$_7$ ([M+H]$^+$): 716.1655, found: 716.1642.

4-azido-5-(6-chloro-pyrid-2-yl)-N7-(2',3',5'-tri-O-benzoyl-β-D-ribofuranosyl)-pyrrolo[2,3-d]pyrimidine (MS1029) MS1029 was prepared according to General Procedure C [reaction temperature=60° C.]. FH3158 (0.51 g, 0.7 mmol) gave rise to MS1029 as a yellow foam (0.144 g, 0.201 mmol). Column chromatography: 0→20% EA/PET. Yield=29%. $^1$H NMR (300 MHz, DMSO-d$_6$) δ: 4.77 (dd, J=12.0, 5.4 Hz, 1H, H-5''), 4.88 (dd, J=12.0, 3.6 Hz, 1H, H-5'), 4.93-4.98 (m, 1H, H-4'), 6.16 (t, J=6.0 Hz, 1H, H-3'), 6.42 (t, J=6.0 Hz, 1H, H-2'), 6.98 (d, J=5.4 Hz, 1H, H-1'), 7.40-7.52 (m, 6H, OBz), 7.44 (d, J=7.8 Hz, 1H, H-5$_{Pyr}$), 7.59-7.71 (m, 3H, OBz), 7.85-7.88 (m, 2H, OBz), 7.97-8.02 (m, 4H, OBz), 8.12 (t, J=7.8 Hz, 1H, H-4$_{Pyr}$), 8.78 (s, 1H, H-6), 9.08 (dd, J=7.8, 0.6 Hz, 1H, H-3$_{Pyr}$), 9.99 (s, 1H, H-2). HRMS (ESI): calculated for C$_{37}$H$_{27}$ClN$_7$O$_7$ ([M+H]$^+$): 716.1655, found: 716.1660.

4-azido-5-(5-fluoro-pyrid-2-yl)-N7-(2',3',5'-tri-O-benzoyl-β-D-ribofuranosyl)-pyrrolo[2,3-d]pyrimidine] (MS1031) MS1031 was prepared according to General Procedure C [reaction temperature=60° C.]. FH3158 (0.51 g, 0.7 mmol) gave rise to MS1031 as a yellow foam (0.150 g, 0.214 mmol). Column chromatography: 0→20% EA/PET. Yield=31%. $^1$H NMR (300 MHz, DMSO-d$_6$) δ: 4.76 (dd, J=12.0, 5.1 Hz, 1H, H-5''), 4.87 (dd, J=12.3, 3.9 Hz, 1H, H-5'), 4.94-4.99 (m, 1H, H-4'), 6.16 (t, J=5.7 Hz, 1H, H-3'), 6.39 (t, J=5.7 Hz, 1H, H-2'), 6.97 (d, J=5.4 Hz, 1H, H-1'), 7.70-7.53 (m, 6H, OBz), 7.60-7.71 (m, 3H, OBz), 7.84-7.88 (m, 2H, OBz), 7.97-8.03 (m, 4H, OBz), 8.03 (dd, J=5.4, 3.3 Hz, 1H), 8.60 (dt, J=3.3, 0.6 Hz, 1H), 8.70 (s, 1H, H-6), 9.10 (ddd, J=9.0, 4.5, 0.6 Hz, 1H), 9.99 (s, 1H, H-2). $^{19}$F-NMR (282 MHz, DMSO-d$_6$) δ: −129.16 (dd, J=8.5, 4.8 Hz). HRMS (ESI): calculated for C$_{37}$H$_{27}$FN$_7$O$_7$ ([M+H]$^+$): 700.1951, found: 700.1985.

Alkoxy-Substituted Ribofuranose Analogues
4-methoxy-5-chloro-N7-(β-D-ribfuranosyl)-pyrrolo[2,3-d]pyrimidine (FH8446) FH3156 (0.19 g, 0.3 mmol, 1 eq.) was dissolved in 0.5 M NaOMe/MeOH solution. The mixture was heated to 50° C. for 3H. After cooling to ambient temperature, the pH was adjusted to 7 and the mixture evaporated. The residue was purified by column chromatography (1→8% MeOH/DCM) to give FH8446 (0.06 g, 0.19 mmol) as a white solid in 63% yield. $^1$H NMR (300 MHz, DMSO-d$_6$) δ: 3.54 (ddd, J=12.0, 5.7, 3.9, 1H, H-5''), 3.63 (ddd, J=12.0, 5.1, 3.9 Hz, 1H, H-5'), 3.91 (q, J=3.9 Hz, 1H, H-4'), 4.07 (s, 3H, OCH$_3$), 4.05-4.11 (m, 1H, H-3'), 4.36 (dd, J=11.4, 6.0 Hz, 1H, H-2'), 5.07 (t, J=5.4 Hz, 1H, OH-5'), 5.16 (d, J=4.8 Hz, 1H, OH-3'), 5.38 (d, J=6.3 Hz, 1H, OH-2'), 6.16 (d, J=6.0 Hz, 1H, H-1'), 7.85 (s, 1H, H-6), 8.47 (s, 1H, H-2).

4-methoxy-5-bromo-(N7-β-D-ribofuranosyl)-pyrrolo[2,3-d]pyrimidine (FH9528) FH3133 (0.25 g, 0.372 mmol, 1 eq.) was dissolved in 0.5 M NaOMe/MeOH solution. The mixture was heated to 50° C. for 3H. After cooling to ambient temperature, the pH was adjusted to 7 and the mixture evaporated. The residue was purified by column chromatography (1→8% MeOH/DCM) to give FH9528 (0.09 g, 0.25 mmol) as a white solid in 67% yield. $^1$H NMR (300 MHz, DMSO-d$_6$) δ: 3.54 (ddd, J=12.0, 5.7, 3.9 Hz, 1H, H-5''), 3.64 (ddd, J=12.0, 5.4, 4.2 Hz, 1H, H-5'), 3.91 (q, J=3.9 Hz, 1H, H-4'), 4.05 (s, 3H, OCH$_3$), 4.06-4.11 (m, 1H, H-3'), 4.34-4.39 (m, 1H, H-2'), 5.08 (t, J=5.7 Hz, 1H, OH-5'), 5.16 (d, J=4.8 Hz, 1H, OH-3'), 5.38 (d, J=6.3 Hz, 1H, OH-2'), 6.16 (d, J=6.3 Hz, 1H, H-1'), 7.88 (s, 1H, H-6), 8.46 (s, 1H, H-2).

4-ethoxy-5-chloro-N7-(β-D-ribfuranosyl)-pyrrolo[2,3-d]pyrimidine (FH9529) FH3156 (0.19 g, 0.3 mmol, 1 eq.) was dissolved in EtOH (6.9 mL) and NaOEt/EtOH (20 W/V %; 0.1 mL) was added. The resulting mixture was heated to 50° C. for 3H. After cooling to ambient temperature, the pH was adjusted to 7 and the mixture evaporated. The residue was purified by column chromatography (1→8% MeOH/DCM) to give FH9529 (0.02 g, 0.061 mmol) as a white solid in 20% yield. $^1$H NMR (300 MHz, DMSO-d$_6$) δ: 1.39 (t, J=6.9 Hz, 3H, CH$_3$), 3.54 (ddd, J=12.0, 5.7, 3.9 Hz, 1H, H-5''), 3.63 (ddd, J=12.0, 5.1, 4.2 Hz, 1H, H-5'), 3.91 (q, J=3.6 Hz, 1H, H-4'), 4.07-4.11 (m, 1H, H-3'), 4.32-4.38 (m, 1H, H-2'), 4.55 (q, J=6.9 Hz, 2H, OCH$_2$), 5.07 (t, J=5.7 Hz, 1H, OH-5'), 5.16 (d, J=4.8 Hz, 1H, OH-3'), 5.37 (d, J=6.3 Hz, 1H, OH-2'), 6.15 (d, J=6.3 Hz, 1H, H-1'), 7.83 (s, 1H, H-6), 8.44 (s, 1H, H-2). $^{13}$C NMR (75 MHz, DMSO-d$_6$) δ: 14.33 (CH$_3$), 61.38 (C-5'), 62.25 (OCH$_2$), 70.40 (C-3'), 74.14 (C-2'), 85.30 (C-4'), 86.81 (C-1'), 102.67, 102.77, 121.66 (C-6), 150.65 (C-7a), 151.63 (C-2), 161.90 (C-4). HRMS (ESI): calculated for C$_{13}$H$_{17}$ClN$_3$O$_5$ ([M+H]$^+$): 330.0851, found: 330.0774. Melting point: 140° C.

4-n-butoxy-5-chloro-N7-(β-D-ribofuranosyl)-pyrrolo[2,3-d]pyrimidine (FH9530) Na metal (0.115 g) was added to n-BuOH (10 mL) and the resulting mixture stirred at ambient temperature until a clear solution was obtained. Then, this solution (7 mL) was added to FH3156 (0.19 g, 0.3 mmol, 1 eq.), and the resulting mixture heated at 50° C. for 3 hours. After cooling to ambient temperature, the pH was adjusted to 7 and the mixture evaporated. The residue was purified by column chromatography (1→8% MeOH/DCM) to give FH9530 (0.065 g, 0.182 mmol) as a white solid in 61% yield. $^1$H NMR (300 MHz, DMSO-d$_6$) δ: 0.95 (t, J=7.5 Hz, 3H, CH$_3$), 1.42-1.54 (m, 2H, OCH$_2$H$_2$CH$_2$), 1.72-1.81 (m, 2H, OCH$_2$CH$_2$CH$_2$), 3.54 (ddd, J=12.0, 5.7, 4.2 Hz, 1H, H-5''), 3.64 (ddd, J=12.0, 5.4, 4.2 Hz, 1H, H-5'), 3.91 (q, J=3.9 Hz, 1H, H-4'), 4.09 (dd, J=8.1, 4.5 Hz, 1H, H-3'), 4.35 (dd, J=11.0, 6.0 Hz, 1H, H-2'), 4.50 (t, J=6.6 Hz, 2H, OCH$_2$), 5.08 (t, J=5.4 Hz, 1H, OH-5'), 5.16 (d, J=4.8 Hz, 1H, OH-3'), 5.37 (d, J=6.0 Hz, 1H, OH-2'), 6.15 (d, J=6.3 Hz, 1H, H-1'), 7.83 (s, 1H, H-6), 8.43 (s, 1H, H-2). $^{13}$C NMR (75 MHz, DMSO-$d_6$) δ: 13.63 ($CH_3$), 18.68 ($OCH_2CH_2CH_2$), 30.33 ($OCH_2CH_2CH_2$), 61.38 (C-5'), 65.91 ($OCH_2$), 70.42 (C-3'), 74.16 (C-2'), 85.30 (C-4'), 86.83 (C-1'), 102.74, 102.80, 121.65 (C-6), 150.62 (C-7a), 151.65 (C-2), 162.04 (C-4). HRMS (ESI): calculated for $C_{14}H_{19}ClN_3O_5$ ($[M+H]^+$): 358.1164, found: 358.1164. Melting point: 156° C.

4-isopropoxy-5-chloro-N7-(β-D-ribfuranosyl)-pyrrolo[2,3-d]pyrimidine (FH9531) Na metal (0.115 g) was added to i-PrOH (10 mL) and the resulting mixture stirred at ambient temperature until a clear solution was obtained. Then, this solution (7 mL) was added to FH3156 (0.19 g, 0.3 mmol, 1 eq.), and the resulting mixture heated at 50° C. for 3 hours. After cooling to ambient temperature, the pH was adjusted to 7 and the mixture evaporated. The residue was purified by column chromatography (1→8% MeOH/DCM) to give FH9531 (0.037 g, 0.108 mmol) as a white solid in 36% yield. $^1$H NMR (300 MHz, DMSO-$d_6$) δ:1.38 (dd, J=6.3, 2.1 Hz, 6H, 2×$CH_3$), 3.54 (ddd, J=12.0, 5.7, 3.9 Hz, 1H, H-5''), 3.63 (ddd, J=12.0, 5.1, 4.2 Hz, 1H, H-5'), 3.90 (q, J=3.9 Hz, 1H, H-4'), 4.09 (dd, J=8.1, 4.8 Hz, 1H, H-3'), 4.35 (dd, J=11.4, 6.3 Hz, 1H, H-4'), 5.08 (t, J=5.7 Hz, 1H, OH-5'), 5.16 (d, J=4.8 Hz, 1H, OH-3'), 5.36 (d, J=6.3 Hz, 1H, OH-2'), 5.52 (sept., J=6.3 Hz, 1H, CH), 6.14 (d, J=6.0 Hz, 1H, H-1'), 7.81 (s, 1H, H-6), 8.42 (s, 1H, H-2). $^{13}$C NMR (75 MHz, DMSO-$d_6$) δ: 21.77 (2C, $CH_3$), 61.40 (C-5'), 69.30 ($OCH_2$), 70.42 (C-3'), 74.17 (C-2'), 85.29 (C-4'), 86.84 (C-1'), 102.87, 102.90, 121.57 (C-6), 150.70 (C-7a), 151.65 (C-2), 161.68 (C-4). HRMS (ESI): calculated for $C_4H_{19}ClN_3O_5$ ($[M+H]^+$): 344.1008, found: 344.0901. Melting point: 127° C.

4-n-propoxy-5-chloro-N7-(β-D-ribofuranosyl)-pyrrolo[2,3-d]pyrimidine (FH9532) Na metal (0.115 g) was added to n-PrOH (10 mL) and the resulting mixture stirred at ambient temperature until a clear solution was obtained. Then, this solution (7 mL) was added to FH3156 (0.19 g, 0.3 mmol, 1 eq.), and the resulting mixture heated at 50° C. for 3 hours. After cooling to ambient temperature, the pH was adjusted to 7 and the mixture evaporated. The residue was purified by column chromatography (1→8% MeOH/DCM) to give FH9532 (0.04 g, 0.116 mmol) as a white solid in 39% yield. $^1$H NMR (300 MHz, DMSO-$d_6$) δ:1.02 (t, J=7.5 Hz, 3H, $CH_3$), 1.74-1.85 (m, 2H, $CH_2$), 3.51-3.58 (m, 1H, H-5''), 3.60-3.67 (m, 1H, H-5'), 3.91 (q, J=3.9 Hz, 1H, H-4'), 4.09 (br. s, 1H, H-3'), 4.35 (br. s, 1H, H-2'), 4.46 (t, J=6.3 Hz, 2H, $OCH_2$), 5.08 (t, J=5.4 Hz, 1H, OH-5'), 5.17 (br. s, 1H, OH-3'), 5.38 (br. s, 1H, OH-2'), 6.15 (d, J=6.3 Hz, 1H, H-1'), 7.83 (s, 1H, H-6), 8.43 (s, 1H, H-2). $^{13}$C NMR (75 MHz, DMSO-$d_6$) δ: 10.33 ($CH_3$), 21.74 ($CH_2$), 61.40 (C-5'), 67.67 ($OCH_2$), 70.42 (C-3'), 74.17 (C-2'), 85.32 (C-4'), 86.84 (C-1'), 102.75, 102.81, 121.68 (C-6), 150.64 (C-7a), 151.66 (C-2), 162.09 (C-4). HRMS (ESI): calculated for $C_{14}H_{19}ClN_3O_5$ ($[M+H]^+$): 344.1008, found: 344.0921. Melting point: 134° C.

Pyrrolo[2,3-d]Pyridine Nucleoside Analogues
1H-3,4-dichloro-pyrrolo[2,3-b]pyridine (FH5262)
1H-4-chloro-pyrrolo[2,3-b]pyridine (0.763 g, 5.0 mmol, 1 eq.) was dissolved in DMF (7.5 mL, 1.5 mL/mmol SM) and NCS (0.701 g, 5.25 mmol, 1.05 eq.) was added. The resulting mixture was stirred at ambient temperature overnight, protected from light. Then, ice-cold water (25 mL, 5 mL/mmol SM) was added and the resulting precipitate filtered. The solids were washed four additional times with ice-cold water (4×10 mL, 2 mL/mmol SM). The solid was collected and dried under high vacuum to give FH5262 (0.861 g, 4.6 mmol) as an off-white solid in 92% yield. $^1$H NMR (300 MHz, DMSO-$d_6$) δ: 7.21 (d, J=4.2 Hz, 1H, H-5), 7.77 (s, 1H, H-2), 8.20 (d, J=4.2 Hz, 1H, H-6), 12.35 (br s, 1H, N—H). $^{13}$C NMR (75 MHz, DMSO-$d_6$) δ: 101.09 (C-3), 113.67 (C-3a), 117.07 (C-5), 125.11 (C-2), 133.80 (C-4), 144.36 (C-6), 147.60 (7a). HRMS (ESI): calculated for $C_7H_4Cl_2N_2$: 185.9752, found: 186.9824 $[M+H]^+$. Melting point: 236° C. (decomposed).

1H-3-bromo-4-chloro-pyrrolo[2,3-b]pyridine (FH5295)
FH5295 was prepared as has been described for FH5262, except for the use of NBS instead of NCS. 1H-4-chloro-pyrrolo[2,3-b]pyridine (0.763 g, 5 mmol) gave rise to FH5295 (1.12 g, 4.8 mmol) as a yellow solid in 96% yield. $^1$H NMR (300 MHz, DMSO-$d_6$) δ: 7.23 (d, J=5.1 Hz, 1H, H-5), 7.81 (d, J=2.7 Hz, 1H, H-2), 8.21 (d, J=5.1 Hz, 1H, H-6), 12.44 (br. s, 1H, N—H). $^{13}$C NMR (75 MHz, DMSO-$d_6$) δ: 85.03 (C-3), 114.58 (C-3a), 117.13 (C-5), 127.71 (C-2), 134.17 (C-4), 144.18 (C-6), 147.98 (C-7a). HRMS (ESI): calculated for $C_7H_5BrClN_2$ ($[M+H]^+$): 230.9319, found: 230.9332. Melting point: 210° C. (decomposed).

1H-3-iodo-4-chloro-pyrrolo[2,3-b]pyridine (FH5296)
1H-4-chloro-pyrrolo[2,3-b]pyridine (0.763 g, 5 mmol, 1 eq.) was dissolved in DMF (7.5 mL, 1.5 mL/mmol SM) and NIS (1.18 g, 5.25 mmol, 1.05 eq.) was added. The mixture was stirred in the dark overnight. Then, ice-cold water (25 mL, 5 mL/mmol SM) was added and the resulting precipitate filtered. The solids were washed four additional times with ice-cold water (4×10 mL, 2 mL/mmol SM). The solid was collected and dried under high vacuum to give FH5296 (1.29 g, 4.6 mmol) as a yellow solid in 92% yield. $^1$H NMR (300 MHz, DMSO-$d_6$) δ: 7.19 (d, J=5.1 Hz, 1H, H-5), 7.81 (d, J=2.4 Hz, 1H, H-2), 8.18 (d, J=5.1 Hz, 1H, H-6), 12.45 (br s, 1H, N—H). 13C NMR (75 MHz, DMSO-$d_6$) δ: 49.67 (C-3), 116.32 (C-3a), 116.93 (C-5), 133.07 (C-2), 134.81 (C-5), 143.74 (C-6), 148.43 (C-7a). HRMS (ESI): calculated for $C_7H_5ClIN_2$ ($[M+H]^+$): 278.9180, found: 278.9197. Melting point: 222° C. (decomposed).

3,4-dichloro-N1-(2',3',5'-tri-O-benzoyl-β-D-ribofuranosyl)-pyrrolo[2,3-b]pyridine (FH5264) FH5264 was prepared according to General Procedure F. FH5262 (0.187 g, 1 mmol) gave rise to FH5264 (0.555 g, 0.88 mmol) as a white foam in 88% yield. $^1$H NMR (300 MHz, CDCl$_3$) δ: 4.68 (dd, J=12.0, 3.9 Hz, 1H, H-5''), 4.76-4.80 (m, 1H, H-4'), 4.86 (dd, J=12.0, 3.3 Hz, 1H, H-5'), 6.12 (dd, J=6.0, 4.8 Hz, 1H, H-3'), 6.20 (t, J=5.4 Hz, 1H, H-2'), 6.74 (d, J=5.4 Hz, 1H, H-1'), 7.12 (d, J=5.1 Hz, 1H, H-5), 7.33-7.42 (m, 5H (2×2H, 1×1H) OBz, H-2), 7.46-7.64 (m, 5H (1×2H, 3×1H), OBz), 7.92-7.95 (m, 2H, OBz), 7.97-8.00 (m, 2H, OBz), 8.10-8.13 (m, 2H, OBz), 8.18 (d, J=5.1 Hz, 1H, H-6). $^{13}$C NMR (75 MHz, CDCl$_3$) δ: 63.79 (C-5'), 71.57 (C-3'), 70.05 (C-2'), 80.24 (C-4'), 86.66 (C-1'), 106.18 (C-3), 116.50 (C-3a), 118.90 (C-5), 123.42 (C-2), 128.61, 128.65, 128.83, 128.93, 129.55, 129.86, 129.96, 130.00, 133.58, 133.80, 136.77 (C-4), 144.65 (C-6), 147.28 (C-7a), 165.24 (C=O), 165.53 (C=O), 166.31 (C=O). HRMS (ESI): calculated for $C_{33}H_{24}Cl_2N_2O_7$: 630.0961, found: 631.1021. $[M+H]^+$.

3-bromo-4-chloro-N1-(2',3',5'-tri-O-benzoyl-β-D-ribofuranosyl)-pyrrolo[2,3-b]pyridine (FH5300) FH5300 was prepared according to General Procedure F. FH5295 (0.35 g, 1.5 mmol) gave rise to FH5300 (0.777 g, 1.15 mmol) as a white foam in 77% yield. $^1$H NMR (300 MHz, CDCl$_3$) δ: 4.68 (dd, J=12, 3.9 Hz, 1H, H-5''), 4.76-4.80 (m, 1H, H-4'), 4.86 (dd, J=12, 3 Hz, 1H, H-5'), 6.13 (dd, J=5.7, 4.5 Hz, 1H, H-3'), 6.21 (dd, J=5.7, 5.4 Hz, 1H, H-2'), 6.75 (d, J=5.4 Hz, 1H, H-1'), 7.12 (d, J=5.1 Hz, 1H, H-5), 7.33-7.41 (m, 4H (2×2H), OBz), 7.45 (s, 1H, H-2), 7.46-7.64 (m, 5H (1×2H+3×1H), OBz), 7.92-8.00 (m, 4H (2×2H), OBz), 8.10-8.13

(m, 2H, OBz), 8.17 (d, J=5.1 Hz, 1H, H-6). $^{13}$C NMR (75 MHz, CDCl$_3$) δ: 63.79 (C-5'), 71.57 (C-3'), 74.11 (C-2'), 80.26 (C-4'), 86.75 (C-1'), 89.68 (C-3), 117.31 (C-3a), 118.94 (C-5), 126.10 (C-2), 128.59, 128.63, 128.72, 128.85, 128.91, 129.53, 129.85, 129.99, 133.56, 133.78, 137.07 (C-4), 144.52 (C-6), 147.58 (C-7a), 165.22 (C=O), 165.51 (C=O), 166.31 (C=O). HRMS (ESI): calculated for C$_{33}$H$_{25}$BrClN$_2$O$_7$ ([M+H]$^+$): 675.0528, found: 675.0544.

3-iodo-4-chloro-N1-(2',3',5'-tri-O-benzoyl-β-D-ribofuranosyl)-pyrrolo[2,3-b]pyridine (FH5303) FH5303 was prepared according to General Procedure F. FH5296 (0.42 g, 1.5 mmol) gave rise to FH5303 (0.854 g, 1.18 mmol) as a yellow foam in 79% yield. $^1$H NMR (300 MHz, CDCl$_3$) δ: 4.68 (dd, J=12, 3.6 Hz, H-5"), 4.77-4.80 (m, 1H, H-4'), 4.87 (dd, J=12.0, 3.3 Hz, 1H, H-5'), 6.14 (dd, J=5.7, 4.8 Hz, 1H, H-3'), 6.22 (dd, J=5.7, 5.4 Hz, 1H, H-2'), 6.73 (d, J=5.4 Hz, 1H, H-1'), 7.11 (d, J=5.1 Hz, 1H, H-5), 7.33-7.42 (m, 4H (2×2H), OBz), 7.47-7.64 (m, 6H, H-2; OBz), 7.93-8.00 (m, 4H (2×2H), OBz), 8.10-8.14 (m, 2H, OBz), 8.16 (d, J=5.1 Hz, 1H, H-6). $^{13}$C NMR (75 MHz, CDCl$_3$) δ: 52.40 (C-3), 63.79 (C-5'), 71.62 (C-3'), 74.17 (C-2'), 80.27 (C-4'), 86.81 (C-1'), 118.74 (C-3a), 118.84 (C-5), 128.57, 128.62, 128.72, 128.88, 128.91, 129.53, 129.85, 129.93, 129.98, 131.75 (C-2), 133.55, 133.77, 137.57 (C-4), 144.176 (C-6), 147.70 (C-7a), 165.21 (C=O), 165.49 (C=O), 166.30 (C=O). HRMS (ESI): calculated for C$_{33}$H$_{25}$ClIN$_2$O$_7$ ([M+H]$^+$): 723.0389, found: 723.0400.

3-chloro-4-azido-N1-(2',3',5'-tri-O-benzoyl-β-D-ribofuranosyl)-pyrrolo[2,3-b]pyridine (FH5268) FH5264 (0.095 g, 0.15 mmol, 1 eq.) was dissolved in DMF (1.5 mL, 10 mL/mmol SM) and NaN$_3$ (0.098 g, 1.5 mmol, 10 eq.) was added. Then, 15-crown-5 (0.06 mL, 0.3 mmol, 2 eq.) was added and the mixture heated at 110° C. for 8H. After cooling to ambient temperature, EA was added and the mixture partioned between EA and half saturated aq. NaHCO3. The layers were separated and the water layer extracted twice more with EA. The organic layers were combined, dried over Na2SO4, filtered and evaporated till dryness. The residue was purified by column chromatography (16% EA/hexanes) to give FH5268 (0.05 g, 0.078 mmol) as a slight yellow foam in 52% yield. $^1$H NMR (300 MHz, CDCl$_3$) δ: 4.67 (dd, J=12.0, 3.9 Hz, 1H, H-5"), 4.75-4.79 (m, 1H, H-4'), 4.85 (dd, J=12.0, 3.0 Hz, 1H, H-5'), 6.12 (dd, J=5.7, 4.8 Hz, 1H, H-3'), 5.19 (t, J=5.4 Hz, 1H, H-2'), 6.73 (d, J=5.4 Hz, 1H, H-1'), 6.89 (d, J=5.4 Hz, 1H, H-5), 7.27 (s, 1H, H-2), 7.33-7.41 (m, 4H (2×2H), OBz), 7.46-7.63 (m, 5H (3×1H, 1×2H), OBz), 7.92-7.95 (m, 2H, OBz), 7.96-7.99 (m, 2H, OBz), 8.10-8.13 (m, 2H, OBz), 8.25 (d, J=5.4 Hz, 1H, H-6). $^{13}$C NMR (75 MHz, CDCl$_3$) δ: 63.83 (C-5'), 71.57 (C-3'), 74.05 (C-2'), 80.18 (C-4'), 86.55 (C-1'), 105.57 (C-3), 106.68 (C-5), 110.68 (C-3a), 122.33 (C-2), 128.59, 128.64, 128.76, 128.83, 128.94, 129.58, 129.87, 129.98, 130.01, 133.57, 133.80, 142.42 (C-4), 145.37 (C-6), 148.01 (C-7a), 165.26 (C=O), 165.55 (C=O), 166.33 (C=O). HRMS (ESI): calculated for C$_{33}$H$_{24}$ClN$_5$O$_7$ [M+H]$^+$: 638.1437, found: 638.1448.

3-chloro-4-amino-N1-(2',3',5'-tri-O-benzoyl-β-D-ribofuranosyl)-pyrrolo[2,3-b]pyridine (FH5276) FH5276 was prepared according to General procedure D. FH5268 (0.134 g, 0.21 mmol) gave rise to FH5276 as a slight yellow foam (0.11 g, 0.18 mmol) in 86% yield. (purification: 40→75% EA/Hex). $^1$H NMR (300 MHz, CDCl$_3$) δ: 4.66 (dd, J=12.0, 3.0 Hz, 1H, H-5"), 4.72-4.76 (m, 1H, H-4'), 4.83 (dd, J=11.7, 3.0 Hz, 1H, H-5'), 4.93 (br. s, 2H, NH$_2$), 6.07-6.16 (m, 2H, H-2', H-3'), 6.25 (d, J=5.4 Hz, 1H, H-5), 6.79 (d, J=4.5 Hz, 1H, H-1'), 7.07 (s, 1H, H-2), 7.32-7.46 (m, 4H (2×2H), OBz), 7.46-7.63 (m, 5H (3×1H, 1×2H), OBz), 7.93-7.97 (m, 5H, (2×2H, 1×1H), OBz, H-6), 7.98-8.15 (m, 2H, OBz). $^{13}$C NMR (75 MHz, CDCl$_3$) δ:64.02 (C-5'), 71.62 (C-3'), 73.88 (C-2'), 80.00 (C-4'), 85.80 (C-1'), 102.6 (C-5), 105.34, 105.69, 118.41 (C-2), 128.54, 128.61, 128.80, 128.96, 129.66, 129.89, 130.01, 130.06, 133.51, 133.70, 145.69 (C-6), 148.08 (C-7a), 165.34 (C=O), 165.59 (C=O), 166.36 (C=O). HRMS (ESI): calculated for C$_{33}$H$_{26}$ClN$_3$O$_7$: 611.1459, found: 612.1545 [M+H]$^+$.

3-bromo-4-amino-N1-(2',3',5'-tri-O-benzoyl-β-D-ribofuranosyl)-pyrrolo[2,3-b]pyridine (FH5312) FH5300 (0.718 g, 1.06 mmol, 1 eq.) was dissolved in DMF (11 mL, 10 mL/mmol SM) and NaN$_3$ (0.69 g, 10.62 mmol, 10 eq.) was added followed by 15-crown-5 (0.42 mL, 2.12 mmol, 2 eq.). The resulting mixture was heated at 110° C. for approximately 10H, after which it was allowed to cool to ambient temperature. EA was added and the mixture poured into half saturated aq. NaHCO$_{03}$. The layers were separated and the water layer extracted twice more with EA. The organic layers were combined, dried over Na$_2$SO$_4$, filtered and evaporated till dryness. The residue was purified by column chromatography (0→25% EA/Hex). Product containing fractions were pooled and evaporated. The crude azidonucleoside intermediate was directly used in the next step (Staudinger reduction).

Purification 20→60% EA/Hex gave FH5312 (0.195 g, 0.297 mmol) as a white foam in 28% yield.

$^1$H NMR (300 MHz, CDCl$_3$) δ: 4.66 (dd, J=11.7, 3.6 Hz, 1H, H-5"), 4.72-4.76 (m, 1H, H-4'), 4.83 (dd, J=11.7, 3 Hz, 1H, H-5'), 4.97 (br. s, 2H, NH$_2$), 6.10 (dd, J=6, 4.5 Hz, 1H, H-3'), 6.15 (dd, J=5.7, 5.4 Hz, 1H, H-2'), 6.25 (d, J=5.7 Hz, 1H, H-5), 6.78 (d, J=5.1 Hz, 1H, H-1'), 7.13 (s, 1H, H-2), 7.33-7.39 (m, 4H (2×2H), OBz), 7.46-7.63 (m, 5H (3×1H, 1×2H), OBz), 7.93-7.98 (m, 5H (1×1H, 2×2H), H-6, OBz), 8.12-8.15 (m, 2H, OBz). $^{13}$C NMR (75 MHz, CDCl$_3$) δ: 64.02 (C-5'), 71.65 (C-3'), 73.94 (C-2'), 80.03 (C-4'), 85.88 (C-1'), 88.82 (C-3), 102.79 (C-5), 106.50 (C-3a), 120.94 (C-2), 128.54, 128.59, 128.83, 128.97, 129.67, 129.90, 130.00, 130.06, 133.49, 133.70, 145.67 (C-6), 148.10 (C-7a), 165.32 (C=O), 165.58 (C=O), 166.34 (C=O). (C-4 carbon was not observed) HRMS (ESI): calculated for C$_{33}$H$_{27}$BrN$_3$O$_7$ ([M+H]$^+$): 656.1027, found: 656.1070.

3-iodo-4-amino-N1-(2',3',5'-tri-O-benzoyl-β-D-ribofuranosyl)-pyrrolo[2,3-b]pyridine (FH5313) FH5313 was prepared as has been described for FH5312. FH5303 (0.8 g, 1.11 mmol) gave rise to FH5313 (0.164 g, 0.234 mmol) as a white foam in 21% yield. $^1$H NMR (300 MHz, CDCl$_3$) δ: 4.66 (dd, J=12, 3.9 Hz, 1H, H-5"), 4.72-4.76 (m, 1H, H-4'), 4.84 (dd, J=12, 3 Hz, 1H, H-5'), 4.98 (br. s, 2H, NH$_2$), 6.10 (dd, J=5.7, 4.2 Hz, 1H, H-4'), 6.15 (dd, J=5.7, 5.4 Hz, 1H, H-2'), 6.25 (d, J=5.4 Hz, 1H, H-5), 6.78 (d, J=5.1 Hz, 1H, H-1'), 7.22 (s, 1H, H-2), 7.32-7.39 (m, 4H (2×2H), OBz), 7.47-7.63 (m, 5H (3×1H, 1×2H), OBz), 7.93-7.98 (m, 5H (1×1H, 2×2H), H-6, OBz), 8.12-8.15 (m, 2H, OBz). $^{13}$C NMR (75 MHz, CDCl$_3$) δ: 50.98 (C-3), 64.03 (C-5'), 71.71 (C-3'), 74.03 (C-2'), 80.06 (C-4'), 85.92 (C-1'), 102.88 (C-5), 107.98 (C-4a), 126.44 (C-2), 128.54, 128.59, 128.88, 128.99, 129.67, 129.90, 129.98, 130.06, 133.49, 133.69, 145.37 (C-6), 148.07 (C-7a), 165.32 (C=O), 165.56 (C=O), 166.34 (C=O). (C-4 was not observed) HRMS (ESI): calculated for C$_{33}$H$_{27}$N$_3$O$_7$ ([M+H]$^+$): 704.0888, found: 704.0888.

3-chloro-4-amino-N1-(β-D-ribofuranosyl)-pyrrolo[2,3-b]pyridine (FH5278) FH5276 (0.1 g, 0.163 mmol) was dissolved in 7N NH$_3$/MeOH and stirred at ambient temperature overnight. The resulting mixture was evaporated till dryness and the residue purified by column chromatography (6% MeOH/DCM) to give FH5278 (0.04 g, 0.135 mmol) as a white solid in 83% yield. $^1$H NMR (300 MHz, DMSO-d$_6$) δ:

3.48-3.55 (m, 1H, H-5"), 3.58-3.65 (m, 1H, H-5'), 3.87 (dd, J=6.6, 3.6 Hz, 1H, H-4'), 4.04-4.08 (m, 1H, H-3'), 4.40 (dd, J=11.4, 6.3 Hz, 1H, H-2'), 5.06 (d, J=4.8 Hz, 1H, OH-3'), 5.24 (d, J=6.3 Hz, 1H, OH-2'), 5.40 (dd, J=6.6, 4.8 Hz, 1H, OH-5'), 6.04 (d, J=6.3 Hz, 1H, H-1'), 6.17 (br s, 2H, $NH_2$), 6.28 (d, J=5.4 Hz, 1H, H-5), 7.51 (s, 1H, H-2), 7.76 (d, J=5.4 Hz, 1H, H-6). $^{13}$C NMR (75 MHz, DMSO-$d_6$) δ: 61.75 (C-5'), 70.63 (C-3'), 73.43 (C-2'), 85.03 (C-4'), 87.45 (C-1'), 101.44 (C-5), 101.90 (C-3), 104.19 (C-3a), 119.63 (C-2), 144.72 (C-6), 147.25 (7a), 148.53 (C-4). Melting point: 208° C.

3-bromo-4-amino-N1-(β-D-ribofuranosyl)-pyrrolo[2,3-b]pyridine (FH5314) FH5311 (0.184 g, 0.28 mmol) was dissolved in 7N NH3/MeOH (5 mL). The resulting mixture was stirred at ambient temperature overnight, and evaporated till dryness. The residue was purified by column chromatography (6% MeOH/DCM) to give FH5314 (0.095 g, 0.275 mmol) as a white solid in 95% yield. $^1$H NMR (300 MHz, DMSO-$d_6$) δ: 3.48-3.55 (m, 1H, H-5"), 3.58-3.65 (m, 1H, H-5'), 3.87 (dd, J=6.3, 3.6 Hz, 1H, H-4'), 4.04-4.08 (m, 1H, H-3'), 4.37-4.43 (m, 1H, H-2'), 5.05 (d, J=4.5 Hz, 1H, OH-3'), 5.24 (d, J=6.3 Hz, 1H, OH-2'), 5.40 (dd, J=6.6, 4.5 Hz, 1H, OH-5'), 6.04 (d, J=6.3 Hz, 1H, H-1'), 6.15 (br. s, 2H, $NH_2$), 6.30 (d, J=5.4 Hz, 1H, H-5), 7.56 (s, 1H, H-2), 7.77 (d, J=5.4 Hz, 1H, H-6). $^{13}$C NMR (75 MHz, DMSO-$d_6$) δ: 61.73 (C-5'), 70.62 (C-3'), 73.43 (C-2'), 85.04 (C-4'), 85.74 (C-1'), 87.47 (C-3), 101.51 (C-5), 105.03 (C-3a), 122.20 (C-2), 144.53 (C-6), 147.57 (C-7a), 148.61 (C-4). Melting point: 240° C.

3-iodo-4-amino-N1-(β-D-ribofuranosyl)-pyrrolo[2,3-b]pyridine (FH5319) FH5313 (0.15 g, 0.213 mmol) was dissolved in 7N NH3/MeOH. The mixture was stirred at ambient temperature overnight and evaporated. The residue was purified by column chromatography (5→7.5% MeOH/DCM) to give FH5319 (0.065 g, 0.166 mmol) as a white solid in 78% yield. $^1$H NMR (300 MHz, DMSO-$d_6$) δ: 3.51 (dd, J=12 Hz, 3.3 Hz, 1H, H-5"), 3.61 (dd, J=12, 3.3 Hz, 1H, H-5'), 3.88 (dd, J=6.6, 3.3 Hz, 1H, H-4'), 4.04-4.08 (m, 1H, H-3'), 4.41 (dd, J=11.4 Hz, 6 Hz, 1H, H-2'), 5.05 (d, J=4.5 Hz, 1H, OH-5'), 5.23 (d, J=6.6 Hz, 1H, OH-3'), 5.49 (br s, 1H, OH-2'), 6.02 (d, J=6.3 Hz, 1H, H-1'), 6.10 (br s, 2H, $NH_2$), 6.30 (d, J=5.4 Hz, 1H, H-5), 7.59 (s, 1H, H-2), 7.77 (d, J=5.4 Hz, 1H, H-6). $^{13}$C NMR (75 MHz, DMSO-$d_6$) δ: 49.76 (C-3), 61.75 (C-5'), 70.65 (C-3'), 73.38 (C-2'), 85.09 (C-4'), 87.55 (C-1'), 101.50 (C-5), 106.70 (C-3a), 127.69 (C-2), 143.95 (C-6), 147.89 (C-4), 148.78 (C-7a). HRMS (ESI): calculated for $C_{12}H_{15}BrN_3O_4$ ([M+H]$^+$): 344.0240, found: 344.0234. Melting point: 218-220° C.

3-iodo-4-azido-N1-(2',3',5'-tri-O-benzoyl-β-D-ribofuranosyl)-pyrrolo[2,3-b]pyridine (FH9615) FH9615 was prepared according to General Procedure E. FH7381 (1.425 g, 5 mmol) gave rise to FH9615 (2.65 g, 3.6 mmol) as a yellow foam 76% yield. Purification 15% EA/PET. $^1$H NMR (300 MHz, CDCl$_3$) δ: 4.67 (dd, J=12.0, 3.9 Hz, 1H, H-5"), 4.75-4.79 (m 1H, H-4'), 4.85 (dd, J=12.0, 3.0 Hz, 1H, H-5'), 6.13 (dd, J=5.7, 4.8 Hz, 1H, H-3'), 6.20 (t, J=5.7 Hz, 1H, H-2'), 6.72 (d, J=5.4 Hz, 1H, H-1'), 6.89 (d, J=5.4 Hz, 1H, H-5), 7.33-7.40 (m, 4H, OBz), 7.41 (s, 1H, H-2), 7.47-7.64 (m, 5H, OBz), 7.92-7.99 (m, 4H, OBz), 8.10-8.14 (m, 2H, OBz), 8.25 (d, J=5.4 Hz, 1H, H-6). HRMS (ESI): calculated for $C_{33}H_{25}IN_5O_7$ ([M+H]$^+$): 730.0793, found: 730.0807.

B.4. Biological Evaluation

Strains and Cultures of *Trypanosoma brucei Brucei* and *T. brucei* Rhodesiense

The following clonal strains of *T. b. brucei* were cultured at the University of Glasgow, all as long-slender bloodstream trypomastigotes only: Lister 427 (wild-type); TbAT1-KO, derived from 427WT by genetic deletion of the TbAT1 gene; B48, derived from TbAT1-KO by in vitro exposure to increasing concentrations of pentamidine; and ISMR1, derived from 427WT by increasing exposure to isometamidium in vitro. At the University of Antwerp, *T. brucei* Squib 427 (suramin-sensitive) and *T. b. rhodesiense* STIB-900 were used for the in vitro susceptibility tests. All trypanosome strains were cultured in the standard HMI-9 medium supplemented with 10% fetal bovine serum (FBS) at 37° C. in a 5% $CO_2$ atmosphere, exactly as described before (Fueyo Gonzalez et al., 2017).

Drug Susceptibility Tests

*Trypanosoma brucei*

Drug susceptibility tests with Lister 427WT, TbAT1-KO, B48 and ISMR1 were performed exactly as described by Omar et al. (2016) using an assay based on the viability indicator dye resazurin (Alamar blue) in 96-well plates, each well containing $2 \times 10^4$ cells. The plates were incubated for 48 h with a doubling dilution series of the test compounds in HMI-9/FBS at 37° C./5% $CO_2$ (23 dilutions starting at 100 μM, except for the pentamidine control (50 μM)), after which resazurin was added to each well and the plates incubated for another 24 h. Fluorescence was determined using a FLUOstar Optima (BMG Labtech, Durham, N.C.) and the results fitted to a sigmoid curve with variable slope using Prism 5.0 (GraphPad, San Diego, Ca).

Susceptibility assays with *T. brucei* Squib 427 (suramin-sensitive) or *T. b. rhodesiense* STIB-900 were performed under similar conditions as above but using 10 concentrations of a 4-fold compound dilution series starting at 64 μM. *T. brucei* Squib 427 was seeded at $1.5 \times 10^4$ parasites/well and *T. b. rhodesiense* at $4 \times 10^3$ parasites/well, followed by addition of resazurin after 24 hours (*T. brucei*) or 6 hours (*T. b. rhodesiense*).

*Trypanosoma cruzi*

Drug activity against *T. cruzi* was tested with the nifurtimox-sensitive Tulahuen CL2 β galactosidase strain (Buckner et al., 1996). This strain was maintained on MRC-5$_{SV2}$ (human lung fibroblast) cells in MEM medium, supplemented with 200 mM L-glutamine, 16.5 mM NaHCO$_3$ and 5% inactivated fetal calf serum. All cultures and assays were conducted at 37° C./5% $CO_2$. Assays were with 4.103 MRC-5 cells/well and 4.104 parasites/well. Impact of test compound dilution series (10 concentrations of a 4-fold compound dilution series starting at 64 μM) on parasite growth was analyzed after 7 days incubation by adding the substrate CPRG (chlorophenolred β-D-galactopyranoside). The change in color was measured spectrophotometrically at 540 nm after 4 hours incubation at 37° C. The results were expressed as % reduction in parasite burdens compared to control wells from which an EC$_{50}$ was calculated.

*Trichomonas vaginalis*

*T. vaginalis* trophozoites (metronidazole susceptible G3 strain) were grown in vitro in modified Diamond's media (MDM) with 10% heat inactivated horse serum (HIHS) acquired from Gibco Life Technologies. After medium preparation, the pH was adjusted to 6.3-6.4 employing 1.0 M aq. HCl. Parasites cultures were passaged every day by taking 1 mL of cell culture into a 25 mL bottle of fresh media to ensure the cells were kept at the appropriate concentration of ~$2 \times 10^6$ cells/mL. The culture flasks were filled completely and tightly capped to provide the cells with an anaerobic environment. The parasites were maintained in incubation at 37° C. When culturing in multiwell plates, the plates were sealed with Nescofilm® and inserted in BD GasPak EZ pouches (BD Diagnostics, UK) in order to create anaerobic conditions. Assays were performed with $5\times10^4$ trophozoites/well (100 µL) to which compound dilutions were added (100 µL). Outside wells of columns and rows were filled with 200 µL of sterile water. Plates were sealed with Nescofilm® and incubated under anaerobic conditions as described above. After 24 h, 30 µL of assay dye solution (resorufin) was added, and incubated for 1-2 h before being read using Fluostar Optima (BMG Labtech, UK) at an excitation wavelength of 544 nm and an emission wavelength of 620 nm.

Transport Assays

Transport via P1 was measured using B48 cells, which lack the P2 transport system, whereas the transport via P2 was assessed in B48 cells transfected with TbAT1/P2 gene (B48+TbAT1) for a constant, high level of expression, in presence of 100 µM of inosine to block P1 transporter. The transport of [$^3$H]-Adenosine (40 Ci/mmol; American Radiolabeled Chemicals, St Louis, Mo.) was measured using a previously described uptake protocol (Wallace et al., 2002). $1\times10^7$ cells were incubated with 100 nM [$^3$H]-Adenosine for 60 seconds and rapid termination by addition of ice-cold 2 mM adenosine followed by immediate centrifugation through an oil layer for one minute at maximum speed. The incubation times used were well within the linear phase of uptake. Inhibition constants were calculated from 50% inhibition values ($IC_{50}$) calculated from non-linear regression (sigmoid curve with variable slope; GraphPad 5.0) and the Cheng-Prusoff equation, as described (Wallace et al., 2002).

In Vivo Antiparasitic Activity Analysis in Mice

Female Swiss mice (BW 20-24 g; Janvier France) were allocated randomly to groups of 3 animals and infected intraperitoneally (IP) with 104 *T. b. brucei* Squib 427 derived from a heavily infected donor mouse. Drinking water and food were available ad libitum throughout the experiment. The test compound of the invention was formulated in 10% (V/V) PEG400 in water at 2 mg/mL and was freshly prepared at every administration. The test compound was administered orally (PO) b.i.d. for 5 days at 25 mg/kg. The reference drug suramin was formulated in PBS at 2.5 mg/mL and administered s.i.d. IP for 5 days at 10 mg/kg. Treatment was initiated ½ hour prior to the IP infection. Animals were observed for the occurrence/presence of clinical or adverse effects during the course of the experiment and were weighed daily. Parasitemia analysis was performed by microscopic evaluation of tail vein blood samples at 4, 7, 10, 14 and 21 dpi (pre-set endpoint). As a test of cure, blood samples (250 µL) were collected from treated mice at 21 dpi and were sub-inoculated IP in naive Swiss mice followed by parasitemia follow-up.

Results

In Vitro Evaluation

All synthesized nucleosides were tested in vitro against *T. b. brucei* Squib 427, *T. b. rhodesiense* STIB-900 and *T. cruzi* parasites. Cytotoxicity was assayed against MRC-5 fibroblasts. Results are depicted in Tables 4 and 5.

TABLE 4

In vitro anti-trypanosomal activity of prepared nucleosides analogues. $EC_{50}$ values are given in µM and are the average of 2-6 independent determinations. Suramin was used as a reference drug and gave $EC_{50}$ values of 0.05 µM and 0.04 µM for *T. b. brucei* and *T. b. rhodesiense*, respectively. N.D.: Not determined.

| Compound | T.b. brucei (µM) | T.b. rhod. (µM) | MRC-5 (µM) |
| --- | --- | --- | --- |
| FH5284 | 0.48 | N.D. | 2.23 |
| TH1004 | 32.34 | 4.10 | 56.2 |
| TH1011 | 29.1 | N.D. | 26.2 |
| TH1013 | 41.6 | N.D. | 28.0 |
| FH8459 | 9.90 | 6.88 | 32.8 |
| TH1012 | 7.58 | N.D. | 27.0 |
| FH3147 | 3.07 | 0.32 | 14.7 |
| FH8460 | 8.17 | 3.66 | >64.0 |
| FH7435 | 33.3 | 26.3 | 61.0 |
| MS1001 | 8.81 | 14.7 | >64.0 |
| TH1008 | 0.36 | 0.031 | 15.1 |
| FH4185 | >64.0 | N.D. | >64.00 |
| FH4187 | >64.0 | N.D. | 55.8 |
| FH3179 | 1.95 | N.D. | 0.55 |
| FH5278 | 0.12 | 11.43 | >64.0 |
| FH5314 | 0.49 | 36.59 | >64.0 |
| FH8446 | 0.16 | 0.04 | 48.0 |
| FH9529 | 0.12 | 0.06 | 48.49 |
| FH9531 | 0.09 | 0.10 | >64.0 |
| FH3169 | 1.33 | 0.12 | 33.40 |
| FH3155 | 2.26 | N.D. | 14.3 |
| FH4184 | 52.4 | N.D. | >64.0 |
| FH3176 | 33.3 | N.D. | >64.00 |
| FH3182 | 4.76 | N.D. | 23.4 |
| MS1016 | 38.2 | 25.1 | >64.00 |
| MS1019 | 25.5 | 8.15 | 7.59 |
| MS1034 | 1.75 | 0.62 | >64.0 |
| MS1039 | 8.97 | 4.60 | >64.0 |
| MS1013 | 8.92 | 6.88 | 27.3 |
| MS1037 | 4.77 | 1.69 | >64.0 |
| FH8461 | 7.83 | 6.79 | 7.53 |
| MS1017 | 6.45 | 3.72 | >64.0 |
| MS1026 | 14.7 | 6.16 | >64.0 |
| MS1021 | >64.0 | 55.6 | >64.0 |
| FH5319 | 0.40 | >64.0 | >64.0 |
| FH9530 | 0.07 | 0.04 | 1.32 |
| FH9528 | 0.19 | 0.04 | >64.0 |

TABLE 4-continued

In vitro anti-trypanosomal activity of prepared nucleosides analogues. $EC_{50}$ values are given in μM and are the average of 2-6 independent determinations. Suramin was used as a reference drug and gave $EC_{50}$ values of 0.05 μM and 0.04 μM for *T. b. brucei* and *T. b. rhodesiense*, respectively. N.D.: Not determined.

| Compound | T.b. brucei (μM) | T.b. rhod. (μM) | MRC-5 (μM) |
|---|---|---|---|
| FH9532 | 0.08 | 0.08 | 2.81 |
| TH1003 | 1.24 | 0.12 | 33.26 |

TABLE 5

In vitro activity of selected analogues against *Trypanosoma cruzi*. $EC_{50}$ values are given in μM as average of 2-4 independent replicates. Benznidazole was included as a reference compound and gave an $EC_{50}$ of 2.40 μM.

| Compound | T. cruzi (μM) | MRC-5 (μM) | Compound | T. cruzi (μM) | MRC-5 (μM) |
|---|---|---|---|---|---|
| FH5284 | 0.34 | 2.23 | FH3155 | 6.94 | 14.25 |
| TH1004 | 3.44 | 56.23 | FH4184 | 18.09 | >64 |
| TH1011 | 1.5 | 26.2 | FH3176 | 23.91 | >64 |
| TH1013 | 9.66 | 27.97 | FH3182 | 8.34 | 23.35 |
| FH8459 | 1.42 | 32.84 | MS1016 | >64 | >64 |
| TH1012 | 0.47 | 26.97 | MS1019 | 8.56 | 7.59 |
| FH3147 | 0.19 | 14.7 | MS1034 | >64 | >64 |
| FH8460 | 1.72 | >64 | MS1039 | 2.39 | >64 |
| FH7435 | 1.64 | 60.98 | MS1013 | 41.13 | 27.32 |
| MS1001 | 0.49 | >64 | MS1037 | 31.88 | >64 |
| TH1008 | 5.02 | 15.1 | FH8461 | 2.48 | 7.53 |
| FH4185 | 15.4 | >64 | MS1017 | 34.09 | >64 |
| FH4187 | 18.75 | 55.78 | MS1026 | 48.49 | >64 |
| FH3179 | 0.86 | 0.55 | MS1021 | 49.94 | >64 |
| FH5278 | 0.19 | >64 | FH5319 | 0.04 | >64 |
| FH5314 | 0.22 | >64 | FH9530 | 0.45 | 1.32 |
| FH8446 | 12.71 | 48.0 | FH9528 | 24.13 | >64 |
| FH9529 | 6.29 | 48.49 | FH9532 | 1.04 | 2.81 |
| FH9531 | 22.66 | >64 | TH1003 | 0.39 | 33.26 |
| FH3169 | 0.52 | 33.4 | | | |

TABLE 6

Activity of prepared analogues against *T. vaginalis*. $EC_{50}$ values are given in μM as average of 2-5 independent replicates.

| Compound code | T. vaginalis $EC_{50}$ (μM) |
|---|---|
| TH1004 | 0.43 |
| TH1011 | 0.06 |
| TH1013 | 0.21 |
| TH1012 | 0.03 |
| FH3147 | 0.02 |
| FH7435 | 0.21 |
| MS1001 | 0.11 |
| FH8459 | 0.24 |
| FH8461 | 0.58 |
| MS1039 | 0.86 |
| Metronidazole | 0.53 |

Our initial subset, comprising of tubercidin (FH5284; REF) and four C-7 phenyl-substituted derivatives (TH1004, TH1011, TH1013 and TH1012), delivered weakly active analogues, with TH1012 being the most active one (low μM $EC_{50}$). Further derivatisation focused on electron-poor and/or lipophilic phenyl analogues (FH3147, FH8459, FH8460, FH8461 and MS1001), which all displayed $EC_{50}$ values <10 μM against *T. brucei*; the 3,4-dichloro analogue FH3147 exerted the most potent anti-trypanosomal activity ($EC_{50}$=3.0 μM). However, these modifications resulted only in moderately active analogues for which cytotoxicity was often equally increased (FH3147 has SI~5), therefore a bio-isosteric replacement for the phenyl group was considered. Taking the observed preference for an electron-poor substituent into account, a pyridine moiety was envisioned. Of the three possible isomers, the 2-substituted pyridine TH1008 showed nanomolar antitrypanosomal activity, with reasonable selectivity indices, i.e. 50 for *T. b. brucei* and ~500 for *T. b. rhodesiense*, whereas the 3- and 4-pyridines FH4185 and FH4187 displayed no discernible trypanocidal effects. Continued investigation into electron deficient 6-membered heteroaromatics, led to the preparation of pyrimidine (FH3155, FH4184) and pyrazine (FH3179) derivatives, which did not result in improved activity. Remarkably, FH3179 showed submicromolar cytotoxicity. A switch to N—methyl imidazole analogues (FH3176 & FH3182), found that only N—methyl-4-imidazolyl derivative FH3182 had low μM activity. To mimic the position of the pyridine-N electron density, ortho-F phenyl analogue FH7435 was synthesized, again with poor biological activity. Upon examination of the present set of hetero-aromatic C-7 substituted tubercidin analogues, it was noticed that only derivatives which feature an ortho-N atom, are active against the *T. brucei* parasite (compare pairs TH1008, FH4185 & FH4187; FH3155 & FH4184; FH3176 & FH3182). Examination of the $^1$H-NMR spectrum of TH1008 clearly showed the splitting of the C-6 NH$_2$ signal into two broad signals (one at δ=7.29 and one at δ=9.88 ppm). Both this splitting pattern, as well as the significant downfield shift of the NH-proton, are indicative for the formation of an intramolecular H-bond.[62] Crystallization from water and subsequent X-ray analysis confirmed the presence of this H-bond (data not shown).

Subsequently, TH1008 was further evaluated in three drug resistant *T. b. brucei* cell lines (Table 7). Drug resistance in trypanosomes has mostly been attributed to altered transport phenomena. This is of particular importance for nucleoside analogues, firstly, because their polar nature excludes passive diffusion across the cell membrane; secondly, because some of them have been shown to rely completely on uptake by the TbAT1/P2 transporter. This transporter is encoded by a single gene, which is non-essential, and is therefore likely to yield drug-resistant mutants, and indeed resistance of *T. brucei* spp. to the veterinary trypanocide diminazene has been clearly linked to loss of TbAT1/P2. From the data presented in Table 7, it is clear that TH1008 is much less dependent on the P2 transporter than is tubercidin (FH5284), with the deletion of the P2 (TbAT1-KO strain) resulting in only a 2.4-fold loss of sensitivity to TH1008 but a >17-fold resistance to FH5284. The advantage of a nucleoside analogue recognized by more than one transporter is even more evident when comparing sensitivities between the wild-type (Lister 427) strain and the multi-drug resistant strain B48, which displayed resistance factors (RF) of 28.7 and 1.6 for FH5284 and TH1008, respectively. The trend further held for the isometamidium-resistant cell line ISMR1 (Table 7).

TABLE 7

In vitro anti-trypanosomal evaluation against three drug-resistant *T. b. brucei* cell lines. $EC_{50}$ values are given in μM. RF = Resistance factor: ratio of $EC_{50}$ between resistant and reference (Lister-427) cell line. TbAT1-KO: *T. brucei* cell line lacking the TbAT1/P2 transporter gene. B48: pentamidine, diminazene and melaminophenyl arsenical resistant cell line. ISMR1: isometamidium resistant cell line.

| Compound | Lister-427 (μM) | TbAT1-KO (μM) | RF | B48 (μM) | RF | ISMR1 (μM) | RF |
|---|---|---|---|---|---|---|---|
| FH5284 | 0.15 ± 0.03 | 2.6 ± 0.7 | 17.2 | 4.3 ± 1.3 | 28.7 | 1.7 ± 0.5 | 11.1 |
| TH1008 | 0.17 ± 0.04 | 0.40 ± 0.09 | 2.4 | 0.27 ± 0.04 | 1.6 | 0.43 ± 0.07 | 2.5 |
| Pentamidine | 0.011 ± 0.001 | 0.018 ± 0.002 | 1.8 | 0.99 ± 0.16 | 94.6 | 0.14 ± 0.04 | 13.8 |
| Diminazene | 0.42 ± 0.064 | 4.5 ± 0.9 | 10.6 | 7.2 ± 1.6 | 16.9 | 2.9 ± 0.42 | 6.9 |
| Isometamidium | 0.65 ± 0.085 | 0.75 ± 0.14 | 1.2 | 0.56 ± 0.13 | 0.85 | 3.1 ± 0.50 | 4.81 |

In Vivo Evaluation

Figure 2:
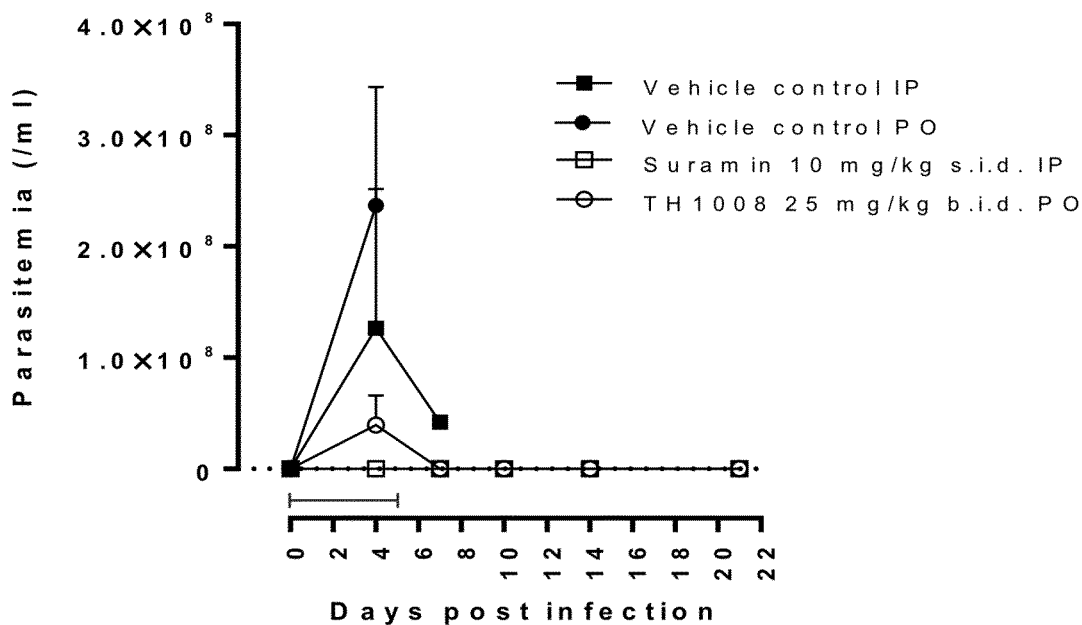
FIG. 2: Parasitemia (A) and survival analysis (B) of *T. brucei* Squib 427 infected mice orally treated for 5 days with TH1008, suramin and vehicle. Presented data are obtained from 3 mice per group.
Figure 2:
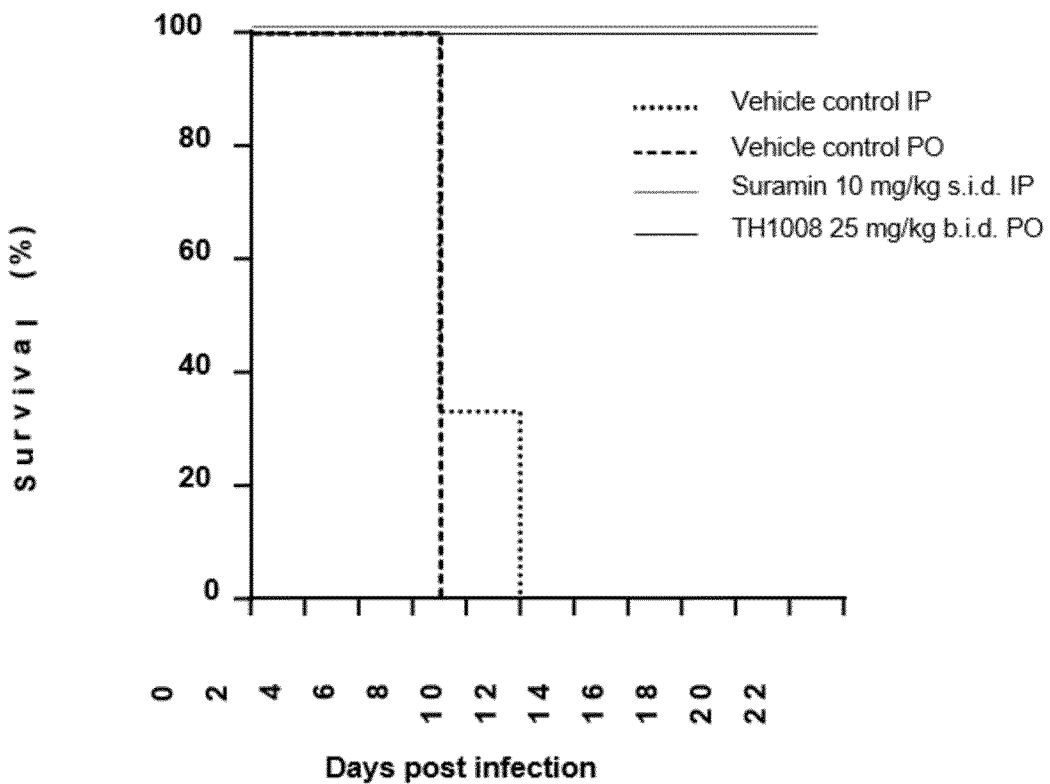

To extend the in vitro observations into an in vivo setting, the anti-trypanosomal activity of TH1008 was evaluated in a *T. brucei* infection model in mice (FIG. 2). All mice in the vehicle control groups developed severe clinical trypanosomiasis and died by day 7, except for one mouse in the IP vehicle control group that succumbed by day 10 of infection. In the suramin-treated reference group (10 mg/kg for 5 consecutive days), no symptoms nor parasitemia developed and all mice survived until day 21. TH1008 administration at 25 mg/kg POb.i.d. for 5 consecutive days resulted in very good activity given that no clinical symptoms of trypanosomiasis were observed. At 4 dpi, parasites were detected in the peripheral blood (mean $Log_{10}$ of 7.5), but were undetectable from 8 dpi onwards. All TH1008 treated mice survived until day 21. Sub-inoculations in naive mice were carried and ascertained total parasitological cure in the animals surviving until day 21 post infection without detectable parasitemia levels following treatment. These results are indicative of sterile cure in the surviving animals by the oral treatment with TH1008. No signs of adverse drug effects were observed.

Figure 6:
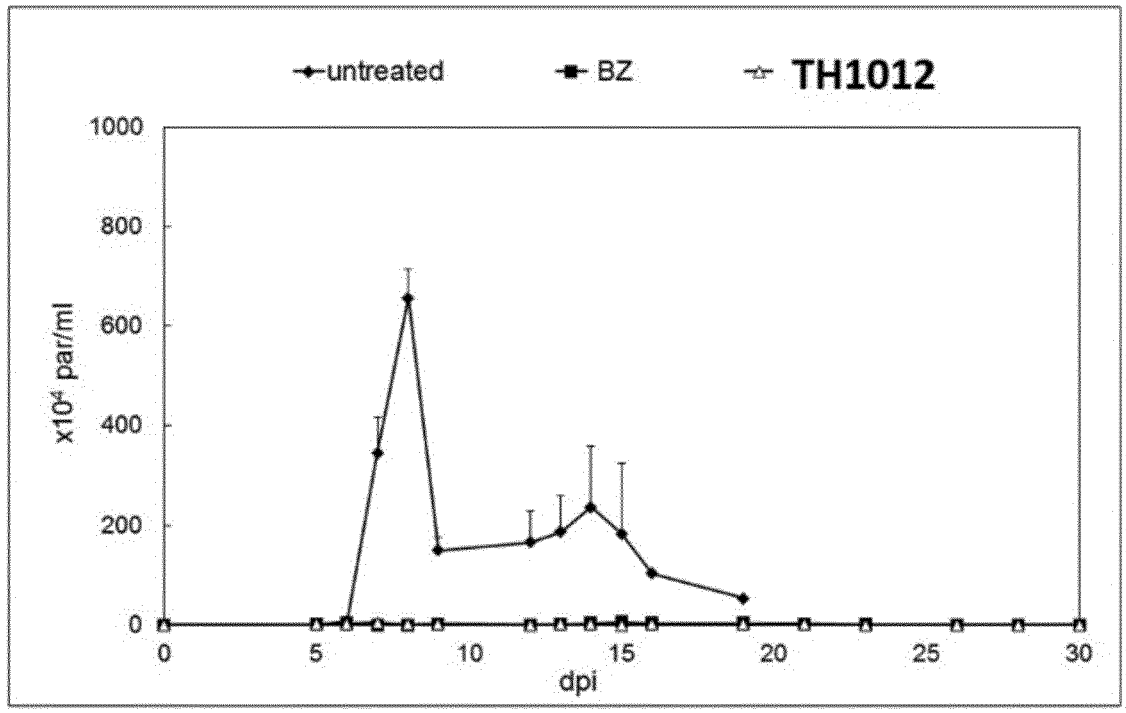
FIG. 6: Parasitemia (A) and survival analysis (B) of *T. cruzi* (Y-strain) infected mice orally treated with TH1012, benznidazole (BZ) and vehicle for 5 days.
Figure 6:
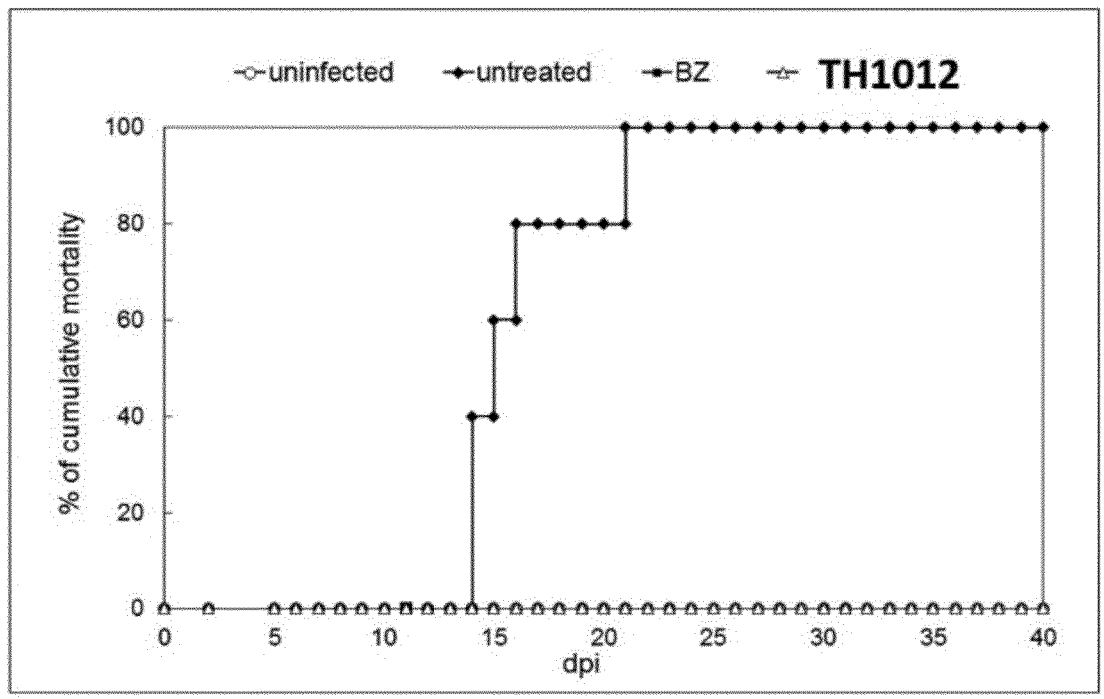

Analog TH012 was evaluated in an in vivo model of Y-strain *T. cruzi* infection. It elicited full suppression of parasitemia when dosed PO(oral gavage) at 25 mg/kg b.i.d. for five consecutive days starting at 5 dpi (FIG. 6). Additionally, it protected animals from mortality caused by the infection.

TABLE 8

| structure | name |
|---|---|
| (7-deaza-adenosine structure with NH₂) | FH5284-REF |
| (7-Cl, 4-OMe pyrrolopyrimidine nucleoside) | FH8446 |
| (7-Br, 4-OMe pyrrolopyrimidine nucleoside) | FH9528 |
| (7-Cl, 4-OEt pyrrolopyrimidine nucleoside) | FH9529 |

TABLE 8-continued

| structure | name |
|---|---|
| 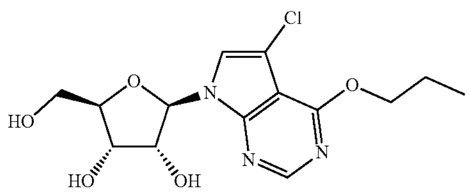 [SMILES: CCCOc1ncnc2c1c(Cl)cn2[C@@H]1O[C@H](CO)[C@@H](O)[C@H]1O] | FH9532 |
| 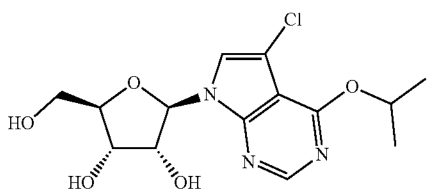 [SMILES: CC(C)Oc1ncnc2c1c(Cl)cn2[C@@H]1O[C@H](CO)[C@@H](O)[C@H]1O] | FH9531 |
| 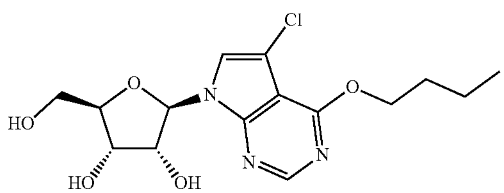 [SMILES: CCCCOc1ncnc2c1c(Cl)cn2[C@@H]1O[C@H](CO)[C@@H](O)[C@H]1O] | FH9530 |
| 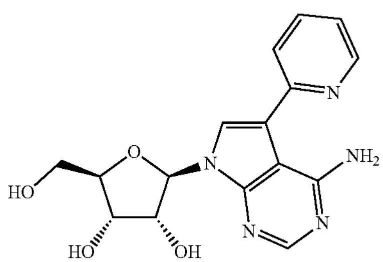 [SMILES: Nc1ncnc2c1c(-c1ccccn1)cn2[C@@H]1O[C@H](CO)[C@@H](O)[C@H]1O] | TH1008 |
| 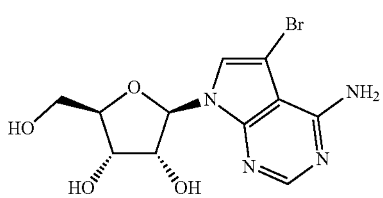 [SMILES: Nc1ncnc2c1c(Br)cn2[C@@H]1O[C@H](CO)[C@@H](O)[C@H]1O] | FH5314 |
| 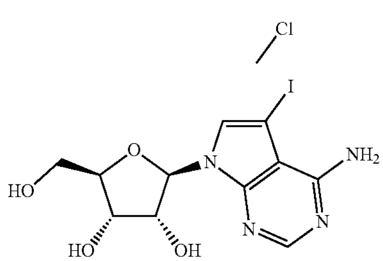 | FH5278 |
| | FH5319 |
| | FH7429_down/ FH7429_D |

TABLE 8-continued

| structure | name |
|---|---|
| (5-bromo-7-deaza-2'-deoxyadenosine structure) | FH7429_UP/ FH7429_U |
| (5-chloro-7-deaza-2'-deoxyadenosine structure) | FH8470 |
| (5-iodo-7-deaza-2'-deoxyadenosine structure) | FH8496 |
| (5-fluoro-7-deaza-2'-deoxyadenosine structure) | FH8517 |
| (5-phenylethynyl-7-deaza-2'-deoxyadenosine structure) | FH8504 |
| (5-ethynyl-7-deaza-2'-deoxyadenosine structure) | FH8505 |

TABLE 8-continued

| structure | name |
|---|---|
| 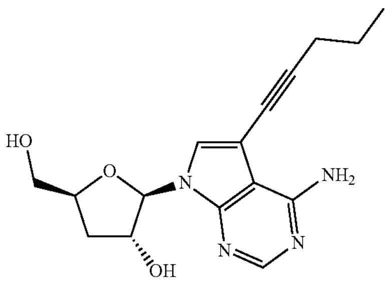 [SMILES: CCCC#Cc1cn([C@@H]2O[C@H](CO)C[C@H]2O)c2ncnc(N)c12] | FH9610 |
| 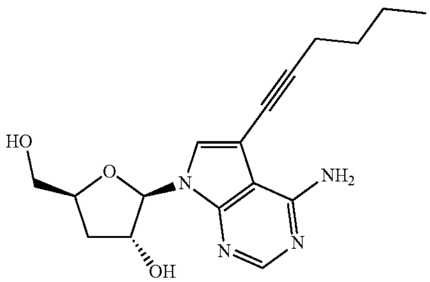 [SMILES: CCCCC#Cc1cn([C@@H]2O[C@H](CO)C[C@H]2O)c2ncnc(N)c12] | FH9611 |
| 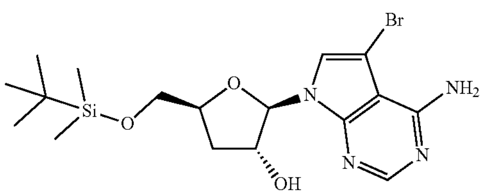 [SMILES: CC(C)(C)[Si](C)(C)OC[C@@H]1C[C@@H](O)[C@H](n2cc(Br)c3c(N)ncnc32)O1] | FH8471 |
| 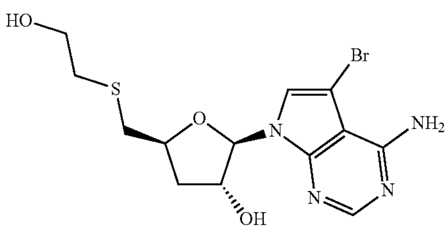 [SMILES: Nc1ncnc2c1c(Br)cn2[C@@H]1O[C@H](CSCCO)C[C@H]1O] | FH9591 |
| 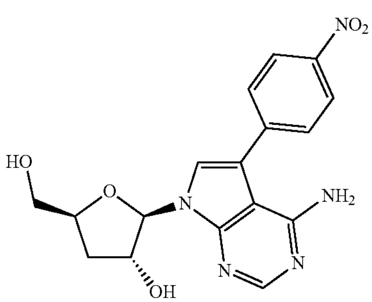 [SMILES: Nc1ncnc2c1c(-c1ccc([N+](=O)[O-])cc1)cn2[C@@H]1O[C@H](CO)C[C@H]1O] | FH9582 |
| 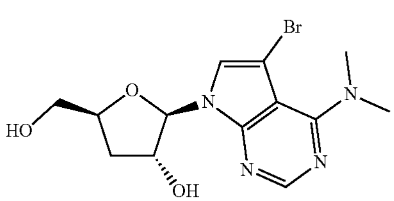 [SMILES: CN(C)c1ncnc2c1c(Br)cn2[C@@H]1O[C@H](CO)C[C@H]1O] | FH8522 |

TABLE 8-continued

| structure | name |
| --- | --- |
| (structure) | FH9539 |
| (structure) | FH9552 |
| (structure) | FH9613 |
| (structure) | FH9526 |
| (structure) | FH8512 |
| (structure) | FH8513 |

TABLE 8-continued
| structure | name |
|---|---|
| 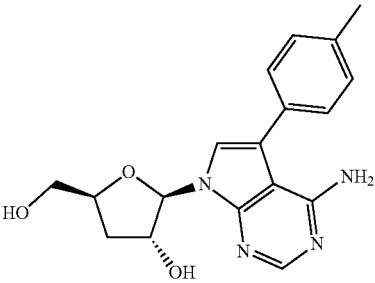 [SMILES: Cc1ccc(-c2cn([C@@H]3O[C@H](CO)C[C@H]3O)c3ncnc(N)c23)cc1] | FH8481 |
| 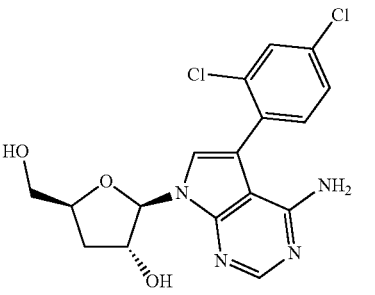 [SMILES: Nc1ncnc2c1c(-c1ccc(Cl)cc1Cl)cn2[C@@H]1O[C@H](CO)C[C@H]1O] | FH9581 |
| 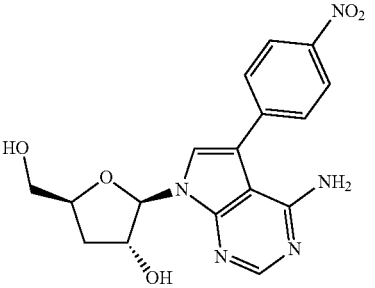 [SMILES: Nc1ncnc2c1c(-c1ccc([N+](=O)[O-])cc1)cn2[C@@H]1O[C@H](CO)C[C@H]1O] | FH9582 |
| 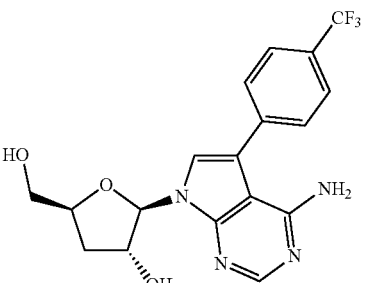 | FH9576 |
| 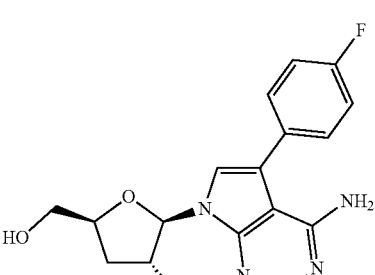 | FH10680 |

TABLE 8-continued

| structure | name |
| --- | --- |
| 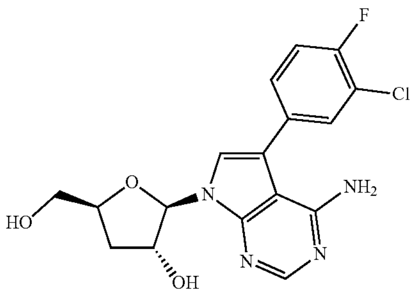 [SMILES: Nc1ncnc2c1c(-c1ccc(F)c(Cl)c1)cn2[C@@H]1O[C@H](CO)C[C@H]1O] | FH10681 |
| 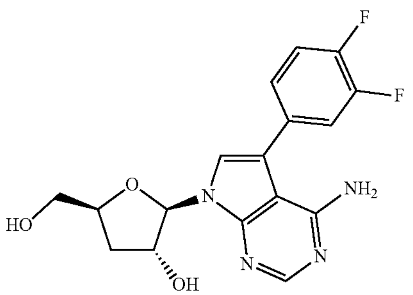 | FH10682 |
| 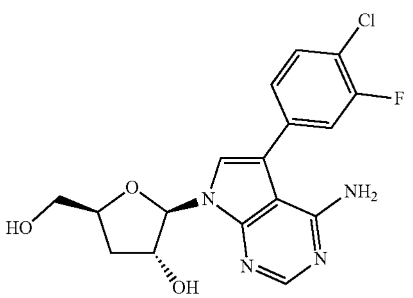 [SMILES: Nc1ncnc2c1c(-c1ccc(F)c(F)c1)cn2[C@@H]1O[C@H](CO)C[C@H]1O] | FH10683 |
| 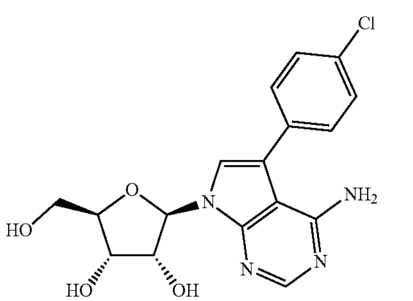 [SMILES: Nc1ncnc2c1c(-c1ccc(Cl)cc1)cn2[C@@H]1O[C@H](CO)[C@@H](O)[C@H]1O] | TH1012 |
| 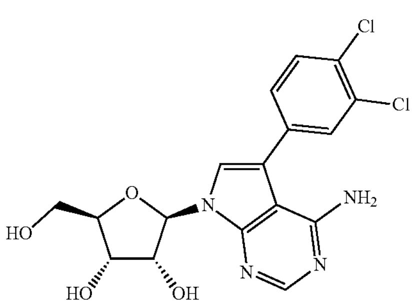 [SMILES: Nc1ncnc2c1c(-c1ccc(Cl)c(Cl)c1)cn2[C@@H]1O[C@H](CO)[C@@H](O)[C@H]1O] | FH3147 |

TABLE 8-continued
| structure | name |
|---|---|
| 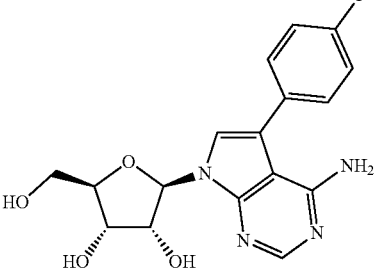 | MS1001 |
| 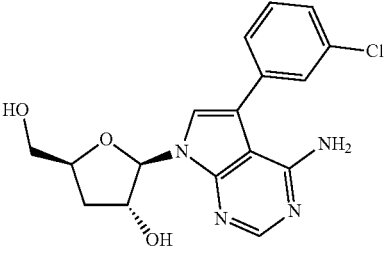 [SMILES: Nc1ncnc2c1c(-c1cccc(Cl)c1)cn2[C@@H]1O[C@H](CO)C[C@H]1O] | FH10641 |
| 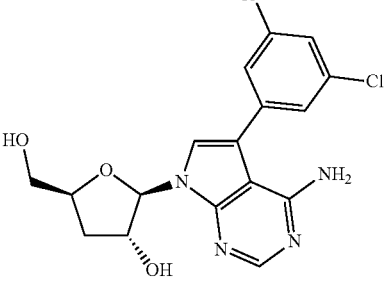 | FH10642 |
| 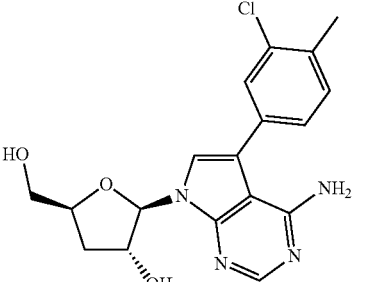 | FH10644 |
| 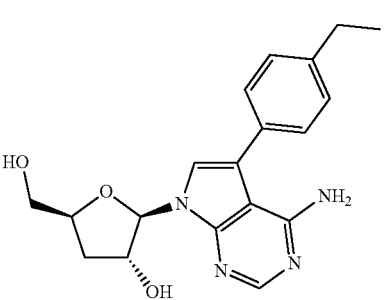 [SMILES: CCc1ccc(-c2cn([C@@H]3O[C@H](CO)C[C@H]3O)c3ncnc(N)c23)cc1] | FH10647 |

TABLE 8-continued
| structure | name |
|---|---|
| 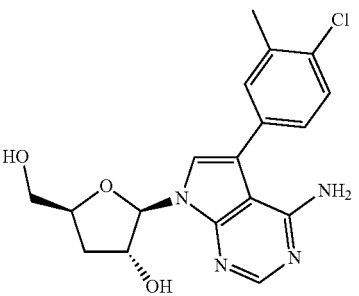 [SMILES: Cc1cc(-c2cn([C@@H]3O[C@H](CO)C[C@H]3O)c3ncnc(N)c23)ccc1Cl] | FH10648 |
| 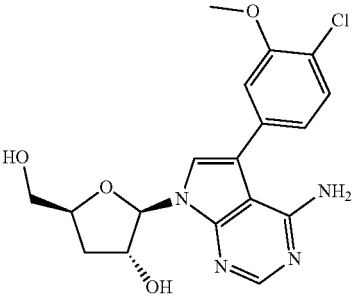 [SMILES: COc1cc(-c2cn([C@@H]3O[C@H](CO)C[C@H]3O)c3ncnc(N)c23)ccc1Cl] | FH10649 |
| 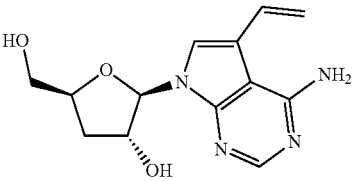 [SMILES: C=Cc1cn([C@@H]2O[C@H](CO)C[C@H]2O)c2ncnc(N)c12] | FH10659 |
| 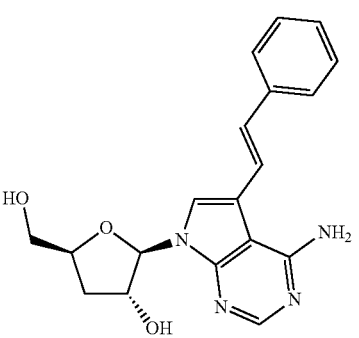 [SMILES: Nc1ncnc2c1c(/C=C/c1ccccc1)cn2[C@@H]1O[C@H](CO)C[C@H]1O] | FH10660 |
| 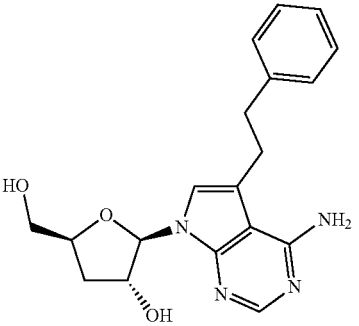 [SMILES: Nc1ncnc2c1c(CCc1ccccc1)cn2[C@@H]1O[C@H](CO)C[C@H]1O] | FH10661 |

TABLE 8-continued

| structure | name |
| --- | --- |
| [structure image] | FH10650 |
| [structure image] | FH10628 |

REFERENCES

Jordheim, L. P.; Durantel, D.; Zoulim, F.; Dumontet, C., Advances in the development of nucleoside and nucleotide analogues for cancer and viral diseases. *Nat Rev Drug Discov* 2013, 12 (6), 447-464.

Shelton, J.; Lu, X.; Hollenbaugh, J. A.; Cho, J. H.; Amblard, F.; Schinazi, R. F., Metabolism, Biochemical Actions, and Chemical Synthesis of Anticancer Nucleosides, Nucleotides, and Base Analogs. *Chemical Reviews* 2016.

Berg, M.; Van der Veken, P.; Goeminne, A.; Haemers, A.; Augustyns, K., Inhibitors of the Purine Salvage Pathway: A Valuable Approach for Antiprotozoal Chemotherapy? *Current Medicinal Chemistry* 2010, 17 (23), 2456-2481.

Snášel, J.; Nauš, P.; Dostál, J.; Hnízda, A.; Fanfrlík, J.; Brynda, J.; Bourderioux, A.; Dušek, M.; Dvořáková, H.; Stolaříková, J.; Zábranská, H.; Pohl, R.; Konečný, P.; Džubák, P.; Votruba, I.; Hajdúch, M.; Řezáčová, P.; Veverka, V.; Hocek, M.; Pichová, I., Structural Basis for Inhibition of Mycobacterial and Human Adenosine Kinase by 7-Substituted 7-(Het)aryl-7-deazaadenine Ribonucleosides. *Journal of Medicinal Chemistry* 2014, 57 (20), 8268-8279.

Bourderioux, A.; Nauš, P.; Perlíková, P.; Pohl, R.; Pichová, I.; Votruba, I.; Džubák, P.; Konečný, P.; Hajdúch, M.; Stray, K. M.; Wang, T.; Ray, A. S.; Feng, J. Y.; Birkus, G.; Cihlar, T.; Hocek, M., Synthesis and Significant Cytostatic Activity of 7-Hetaryl-7-deazaadenosines. *Journal of Medicinal Chemistry* 2011, 54 (15), 5498-5507.

Robins, M. J.; Hansske, F.; Low, N. H.; Park, J. I., A mild conversion of vicinal diols to alkenes. Efficient transformation of ribonucleosides into 2'-ene and 2t',3'-dideoxynucleosides. *Tetrahedron Letters* 1984, 25 (4), 367-370.

Jain, T. C.; Russell, A. F.; Moffatt, J. G., Reactions of 2-acyloxyisobutyryl halides with nucleosides. III. Reactions of tubercidin and formycin. *The Journal of Organic Chemistry* 1973, 38 (18), 3179-3186. Robins, M. J.; McCarthy Jr, J. R.; Jones, R. A.; Mengel, R., Nucleic Acid Related Compounds. 5. The Transformation of Formycin and Tubercidin into 2'- and 3'-Deoxynucleosides. *Canadian Journal of Chemistry* 1973, 51 (9), 1313-1321.

Hansske, F.; J. Robins, M., Regiospecific and stereoselective conversion of ribonucleosides to 3'-deoxynucleosides. A high yield three-stage synthesis of cordycepin from adenosine. *Tetrahedron Letters* 1985, 26 (36), 4295-4298.

Honeker, R.; Ernst, J. B.; Glorius, F., Transition-metal-free trifluoromethylthiolation of N—heteroarenes. *Chemistry* 2015, 21 (22), 8047-51.

Seela, F.; Ming, X., 7-Functionalized 7-deazapurine β-d and β-l-ribonucleosides related to tubercidin and 7-deazainosine: glycosylation of pyrrolo[2,3-d]pyrimidines with 1-O-acetyl-2,3,5-tri-O-benzoyl-β-d or β-l-ribofuranose. *Tetrahedron* 2007, 63 (39), 9850-9861.

Gonda, Z.; Kovács, S.; Wéber, C.; Gáti, T.; Mészáros, A.; Kotschy, A.; Novák, Z., Efficient Copper-Catalyzed Trifluoromethylation of Aromatic and Heteroaromatic Iodides: The Beneficial Anchoring Effect of Borates. *Organic Letters* 2014, 16 (16), 4268-4271.

Miles, R. W.; Samano, V.; Robins, M. J., Nucleic Acid Related Compounds. 86. Nucleophilic Functionalization of Adenine, Adenosine, Tubercidin, and Formycin Derivatives via Elaboration of the Heterocyclic Amino Group into a Readily Displaced 1,2,4-Triazol-4-yl Substituent. *Journal of the American Chemical Society* 1995, 117 (22), 5951-5957.

Kawana, M.; Nishikawa, M.; Yamasaki, N.; Kuzuhara, H., Facile transformation of [small beta]-D-ribofuranosyl purines and pyrimidines into their respective 3[prime or minute]-deoxy-threo-pentofuranosyl nucleosides. *Journal of the Chemical Society, Perkin Transactions 1* 1989, (9), 1593-1596.

Garcia, Y.; Naik, A.; Marchand-Brynaert, J., A Simplified Approach to N—and N,N'-Linked 1,2,4-Triazoles by Transamination. *Synthesis* 2008, 2008 (1), 149-154.

Kudo, N.; Perseghini, M.; Fu, G. C., A Versatile Method for Suzuki Cross-Coupling Reactions of Nitrogen Heterocycles. *Angewandte Chemie International Edition* 2006, 45 (8), 1282-1284.

Milne, J. E.; Buchwald, S. L., An Extremely Active Catalyst for the Negishi Cross-Coupling Reaction. *Journal of the American Chemical Society* 2004, 126 (40), 13028-13032.

Omar, R. M. K.; Igoli, J.; Gray, A. I.; Ebiloma, G. U.; Clements, C.; Fearnley, J.; Edrada Ebel, R. A.; Zhang, T.; De Koning, H. P.; Watson, D. G., Chemical characterisation of Nigerian red propolis and its biological activity against *Trypanosoma Brucei*. *Phytochemical Analysis* 2016, 27 (2), 107-115. Buckner, F. S.; Verlinde, C. L.; La Flamme, A. C.; Van Voorhis, W. C., Efficient technique for screening drugs for activity against *Trypanosoma cruzi* using parasites expressing beta-galactosidase. *Antimicrobial agents and chemotherapy* 1996, 40 (11), 2592-2597.

Wallace, L. J. M.; Candlish, D.; De Koning, H. P., Different Substrate Recognition Motifs of Human and Trypanosome Nucleobase Transporters: SELECTIVE UPTAKE OF PURINE ANTIMETABOLITES. *Journal of Biological Chemistry* 2002, 277 (29), 26149-26156.

The invention claimed is:

1. A compound according to formula I or a stereoisomer, tautomer, racemic mixture, prodrug, salt, hydrate, N—oxide form or solvate thereof,

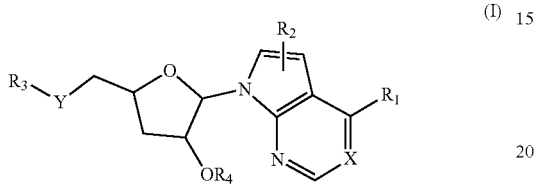

(I)

wherein

X is selected from C and N;
Y is selected from O and S;
$R_1$ is selected from —H, —$NR_5R_6$, —OH, —S—$C_{1-6}$alkyl and —O—$C_{1-6}$alkyl;
$R_2$ is selected from —$C_{1-6}$alkyl, —$C_{3-7}$cycloalkyl, —$C_{2-10}$alkenyl, —$CF_3$, —S—$CF_3$, —$Cy_1$ and —$Ar_1$; wherein the —$C_{1-6}$alkyl, —$C_{2-10}$alkynyl, or —$C_{2-10}$alkenyl is optionally further substituted with one or more —$Cy_2$, or —$Ar_2$;
$R_3$ is selected from —H, —$C_{1-6}$alkyl, —$SO_2$—$NH_2$, and optionally substituted silyl; wherein the —$C_{1-6}$alkyl is optionally further substituted with one or more —OH;
$R_4$ is selected from —H, —$C_{1-6}$alkyl, and tert-butyldimethylsilyl;
$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N and S;
$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$; and
$Ar_1$ and $Ar_2$ are each independently selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$.

2. The compound as defined in claim 1 and in accordance with formula (Ia),

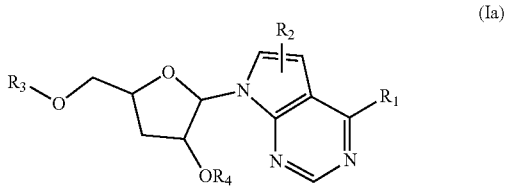

(Ia)

wherein $R_1$ is selected from —H, —$NR_5R_6$, —OH, —S—$C_{1-6}$alkyl and —O—$C_{1-6}$alkyl;
$R_2$ is selected from —$C_{1-6}$alkyl, —$C_{3-7}$cycloalkyl, —$C_{2-10}$ alkynyl, —$CF_3$, —S—$CF_3$, —$Cy_1$ and —$Ar_1$; wherein the —$C_{1-6}$alkyl, —$C_{2-10}$alkynyl, or —$C_{2-10}$alkenyl is optionally further substituted with one or more —$Cy_2$, or —$Ar_2$;
$R_3$ is selected from —H, —$C_{1-6}$alkyl, —$SO_2$—$NH_2$, and optionally substituted silyl; wherein the —$C_{1-6}$alkyl is optionally further substituted with one or more —OH;
$R_4$ is selected from —H, —$C_{1-6}$alkyl, and tert-butyldimethylsilyl;
$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N and S;
$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$; and
$Ar_1$ and $Ar_2$ are each independently selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$.

3. The compound as defined in claim 1, and in accordance with formula (Ib)

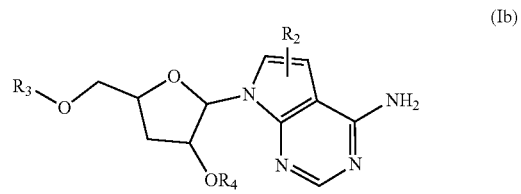

(Ib)

wherein $R_2$ is selected from —$C_{1-6}$alkyl, —$C_{3-7}$cycloalkyl, —$C_{2-10}$alkenyl, —$C_{2-10}$alkynyl, —$CF_3$, —S—$CF_3$, —$Cy_1$ and —$Ar_1$; wherein the —$C_{1-6}$alkyl, —$C_{2-10}$alkynyl, or —$C_{2-10}$alkenyl is optionally further substituted with one or more —$Cy_2$, or —$Ar_2$;
$R_3$ is selected from —H, —$C_{1-6}$alkyl, —$SO_2$—$NH_2$, and optionally substituted silyl; wherein the —$C_{1-6}$alkyl is optionally further substituted with one or more OH;
$R_4$ is selected from —H, —$C_{1-6}$alkyl, and tert-butyldimethylsilyl;
$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$; and
$Ar_1$ and $Ar_2$ are each independently selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$.

4. The compound as defined in claim 1, and in accordance with formula (Ic)

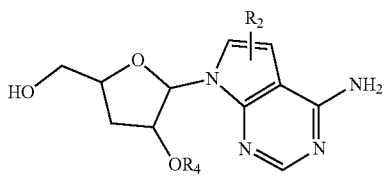

(Ic)

Wherein
- R₂ is selected from —C₁₋₆alkyl, —C₃₋₇cycloalkyl, —C₂₋₁₀ alkenyl, —C₂₋₁₀alkynyl, —CF₃, —S—CF₃, —Cy₁ and —Ar₁; wherein the —C₁₋₆alkyl, —C₂₋₁₀alkynyl, or —C₂₋₁₀alkenyl is optionally further substituted with one or more —Cy₂, or —Ar₂;
- R₄ is selected from —H, —C₁₋₆alkyl, and tert-butyldimethylsilyl;
- Cy₁ and Cy₂ are each independently selected from a mono- or bicyclic non-aromatic cycle optionally containing one or more heteroatoms, and optionally being further substituted with one or more halo, —C₁₋₆alkyl, —CF₃, —NO₂, —O—C₁₋₆alkyl, or —OCF₃; and
- Ar₁ and Ar₂ are each independently selected from a mono- or bicyclic aromatic cycle optionally containing one or more heteroatoms, and optionally being further substituted with one or more halo, —C₁₋₆alkyl, —CF₃, —NO₂, —O—C₁₋₆alkyl, or —OCF₃.

5. The compound as defined in claim 1, and in accordance with formula (Ic)

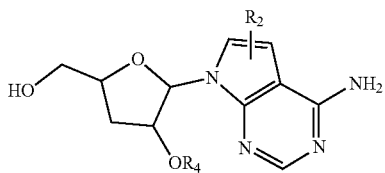

(Ic)

wherein
- R₂ is —C₁₋₆alkynyl, optionally further substituted with one or more —Ar₂, or —C₁₋₆alkyl; R₄ is selected from —H, —C₁₋₆alkyl, and tert-butyldimethylsilyl; and
- Ar₂ is selected from a mono- or bicyclic aromatic cycle optionally containing one or more heteroatoms, and optionally being further substituted with one or more halo, —C₁₋₆alkyl, —CF₃, —NO₂, —O—C₁₋₆alkyl, or —OCF₃.

6. The compound as defined in claim 1, and in accordance with formula (Ic)

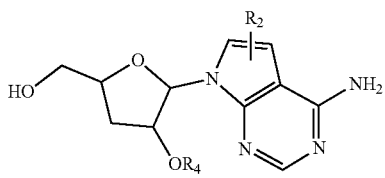

(Ic)

wherein
- R₂ is —Ar₁;
- R₄ is selected from —H, —C₁₋₆alkyl, and tert-butyldimethylsilyl; and Ar₁ is selected from a mono- or bicyclic aromatic cycle optionally containing one or more heteroatoms, and optionally being further substituted with one or more halo, —C₁₋₆alkyl, —CF₃, —NO₂, —O—C₁₋₆alkyl, or —OCF₃.

7. The compound as defined in claim 1, wherein the ribose moiety has the D-stereochemistry as defined in formula (Id)

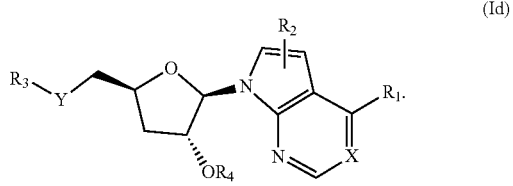

(Id)

8. The compound according to claim 1 selected from the group consisting of:

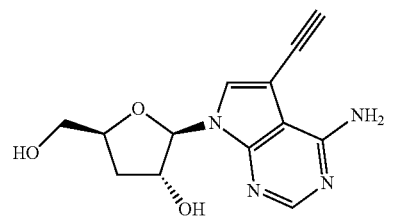

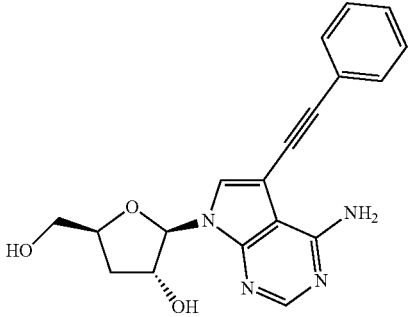

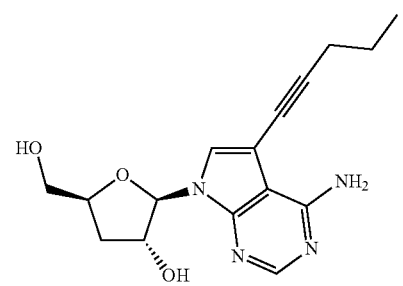

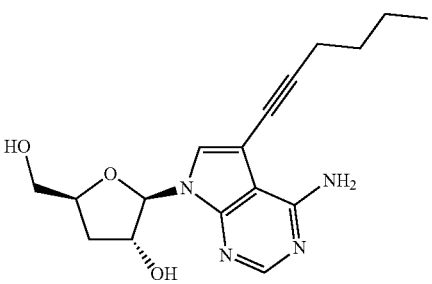

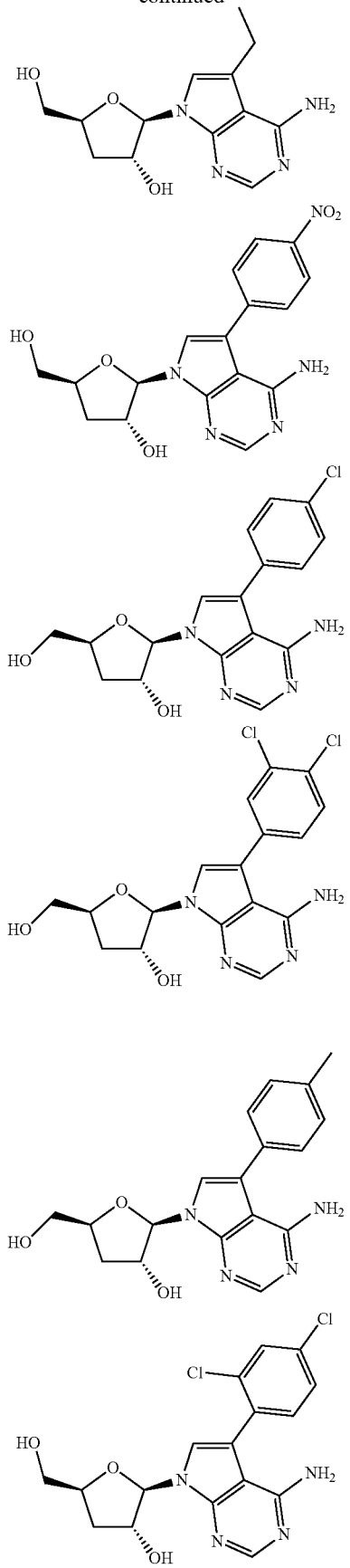
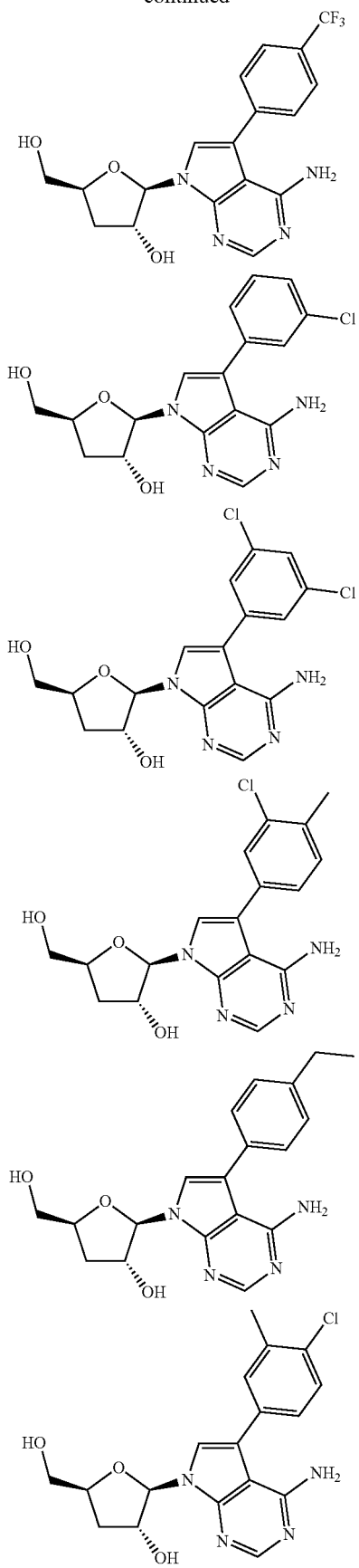

-continued

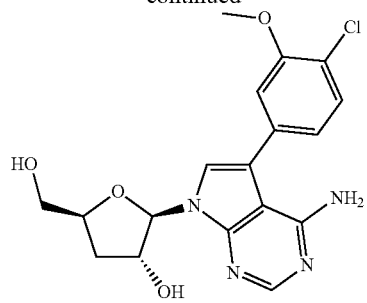

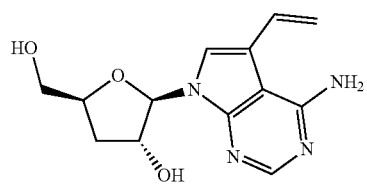

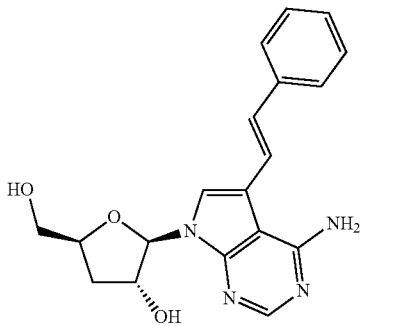

and

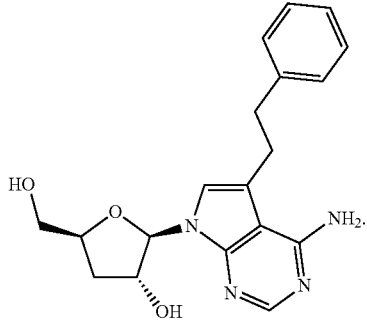

9. A pharmaceutical composition comprising a compound as defined in claim 1; and at least one pharmaceutically acceptable excipient, diluent and/or carrier.

10. A method of preventing or treating a *Trypanosoma* infection in a subject in need thereof, the method comprising administering to the subject a compound as defined in claim 1.

11. A method of treating or reducing the risk of a *Trypanosoma* infection in a subject in need thereof, the method comprising administering to the subject a compound according to formula II or a stereoisomer, tautomer, racemic mixture, prodrug, salt, hydrate, N—oxide form or solvate thereof,

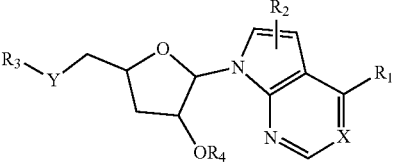

(II)

wherein

X is selected from C and N;

Y is selected from O and S;

$R_1$ is selected from —H, —$NR_5R_6$, —OH, —S—$C_{1-6}$alkyl and —O—$C_{1-6}$alkyl;

$R_2$ is selected from —H, halo, —$C_{1-6}$alkyl, —$C_{3-7}$cycloalkyl, —$C_{2-10}$alkynyl, —$CF_3$, —S—$CF_3$, —$Cy_1$ and —$Ar_1$; wherein the —$C_{1-6}$alkyl, —$C_{2-10}$alkynyl, or —$C_{2-10}$alkenyl is optionally further substituted with one or more —$Cy_2$, or —$Ar_2$, $R_3$ is selected from —H, —$C_{1-6}$alkyl, —$SO_2$—$NH_2$, and optionally substituted silyl; wherein the —$C_{1-6}$alkyl is optionally further substituted with one or more —OH;

$R_4$ is selected from —H, —$C_{1-6}$alkyl, and tert-butyldimethylsilyl;

$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N and S;

$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$; and $Ar_1$ and $Ar_2$ are each independently selected from a mono- or bicyclic aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$.

12. The method according to claim 11, wherein the compound comprises formula (IIa),

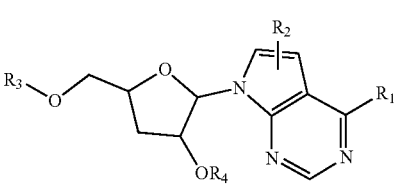

(IIa)

wherein $R_1$ is selected from —H, —$NR_5R_6$, —OH, —S—$C_{1-6}$alkyl and —O—$C_{1-6}$alkyl;

$R_2$ is selected from —H, halo, —$C_{1-6}$alkyl, —$C_{3-7}$cycloalkyl, —$C_{2-10}$alkenyl, —$C_{2-10}$alkynyl, —$CF_3$, —S—$CF_3$, —$Cy_1$ and —$Ar_1$; wherein the —$C_{1-6}$alkyl, —$C_{2-10}$alkynyl, or —$C_{2-10}$alkenyl is optionally further substituted with one or more —$Cy_2$, or —$Ar_2$;

$R_3$ is selected from —H, —$C_{1-6}$alkyl, —$SO_2$—$NH_2$, and optionally substituted silyl; wherein the —$C_{1-6}$alkyl is optionally further substituted with one or more —OH;

$R_4$ is selected from —H, —$C_{1-6}$alkyl, and tert-butyldimethylsilyl;

R$_5$, R$_6$ are each independently selected from —H, —C$_{3-7}$ cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

13. The method according to claim 11, wherein the compound comprises formula (IIb)

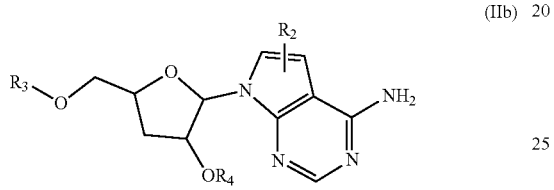
(IIb)

wherein

R$_2$ is selected from —H, halo, —C$_{1-6}$alkyl, —C$_{3-7}$cycloalkyl, —C$_{2-10}$alkynyl, —CF$_3$, —S—CF$_3$, —Cy$_1$ and —Ar$_1$; wherein the —C$_{1-6}$alkyl, —C$_{2-10}$alkynyl, or —C$_{2-10}$alkenyl is optionally further substituted with one or more —Cy$_2$, or —Ar$_2$;

R$_3$ is selected from —H, —C$_{1-6}$alkyl, —SO$_2$—NH$_2$, and optionally substituted silyl; wherein the —C$_{1-6}$alkyl is optionally further substituted with one or more —OH;

R$_4$ is selected from —H, —C$_{1-6}$alkyl, and tert-butyldimethylsilyl;

R$_5$, R$_6$ are each independently selected from —H, —C$_{3-7}$ cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

14. The method according to claim 11, wherein the compound comprises formula (IIc)

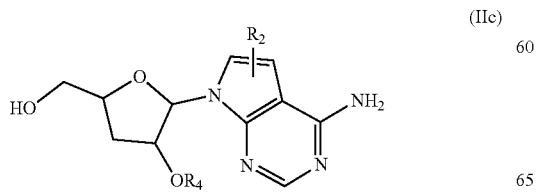
(IIc)

wherein

R$_2$ is selected from —H, halo, —C$_{1-6}$alkyl, —C$_{3-7}$cycloalkyl, —C$_{2-10}$alkynyl, —CF$_3$, —S—CF$_3$, —Cy$_1$ and —Ar$_1$; wherein the —C$_{1-6}$alkyl, —C$_{2-10}$alkynyl, or —C$_{2-10}$alkenyl is optionally further substituted with one or more —Cy$_2$, or —Ar$_2$;

R$_4$ is selected from —H, —C$_{1-6}$alkyl, and tert-butyldimethylsilyl;

R$_5$, R$_6$ are each independently selected from —H, —C$_{3-7}$ cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N and S;

Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$; and Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

15. The method according to claim 11, wherein the compound comprises formula (IIc)

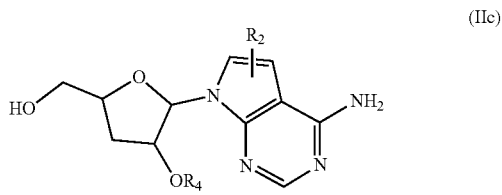
(IIc)

wherein

R$_2$ is —C$_{2-10}$alkynyl, optionally further substituted with one or more —Cy$_2$, or —Ar$_2$; R$_4$ is selected from —H, —C$_{1-6}$alkyl, and tert-butyldimethylsilyl;

Cy$_2$ is selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$; and Ar$_2$ is selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

16. The method according to claim 11, wherein the compound comprises formula (IIc)

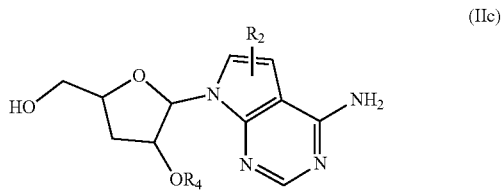
(IIc)

wherein
R$_2$ is —Ar$_1$;
R$_4$ is selected from —H, —C$_{1-6}$alkyl, and tert-butyldimethylsilyl; and
Ar$_1$ is selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

17. The method according to claim 11, wherein the ribose moiety of the compound has the D-stereochemistry as defined in formula (IId)

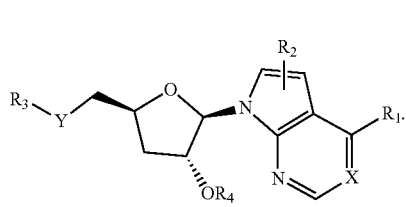

(IId)

18. A compound according to formula III or a stereoisomer, tautomer, racemic mixture, prodrug, salt, hydrate, N—oxide form or solvate thereof

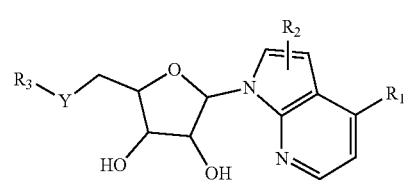

(III)

wherein
Y is selected from O and S;
R$_1$ is selected from —H, —NR$_5$R$_6$, halo, —OH, S—C$_{1-6}$alkyl and —O—C$_{1-6}$alkyl;
R$_2$ is selected from —C$_{1-6}$alkyl, —C$_{3-7}$cycloalkyl, —C$_{2-10}$alkenyl, —C$_{2-10}$alkynyl, halo, —CF$_3$, —S—CF$_3$, —Cy$_1$ and —Ar$_1$; wherein the —C$_{1-6}$alkyl, —C$_{2-10}$alkynyl, or —C$_{2-10}$alkenyl is optionally further substituted with one or more —Cy$_2$, or —Ar$_2$;
R$_3$ is selected from —H, —C$_{1-6}$alkyl, —SO$_2$—NH$_2$, and optionally substituted silyl; wherein the —C$_{1-6}$alkyl is optionally further substituted with one or more —OH;
R$_5$, R$_6$ are each independently selected from —H, —C$_{3-7}$cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N or S;
Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$; and
Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

19. A method of treating or reducing the risk of a Trypanosoma infection in a subject in need thereof, the method comprising administering to the subject a compound according to formula III or a stereoisomer, tautomer, racemic mixture, prodrug, salt, hydrate, N—oxide form or solvate thereof

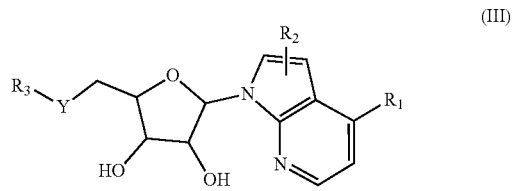

(III)

wherein
Y is selected from O and S;
R$_1$ is selected from —H, —NR$_5$R$_6$, halo, —OH, S—C$_{1-6}$alkyl and —O—C$_{1-6}$alkyl;
R$_2$ is selected from —C$_{1-6}$alkyl, —C$_{3-7}$cycloalkyl, —C$_{2-10}$alkenyl, —C$_{2-10}$alkynyl, halo, —CF$_3$, —S—CF$_3$, —Cy$_1$ and —Ar$_1$; wherein the —C$_{1-6}$alkyl, —C$_{2-10}$alkynyl, or —C$_{2-10}$alkenyl is optionally further substituted with one or more —Cy$_2$, or —Ar$_2$;
R$_3$ is selected from —H, —C$_{1-6}$alkyl, —SO$_2$—NH$_2$, and optionally substituted silyl; wherein the —C$_{1-6}$alkyl is optionally further substituted with one or more —OH;
R$_5$, R$_6$ are each independently selected from —H, —C$_{3-7}$cycloalkyl and —C$_{1-6}$alkyl; or R$_5$ and R$_6$ taken together with the N atom to which they are attached form a 5- to 6-membered heterocycle, further optionally comprising one or more heteroatoms selected from O, N or S;
Cy$_1$ and Cy$_2$ are each independently selected from a mono- or bicyclic non-aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$; and
Ar$_1$ and Ar$_2$ are each independently selected from a mono- or bicyclic aromatic cycle optionally containing one or more heteroatoms, and optionally being further substituted with one or more halo, —C$_{1-6}$alkyl, —CF$_3$, —NO$_2$, —O—C$_{1-6}$alkyl, or —OCF$_3$.

20. A method of treating or reducing the risk of a Trypanosoma infection in a subject in need thereof, the method comprising administering to the subject a compound according to formula IV or a stereoisomer, tautomer, racemic mixture, prodrug, salt, hydrate, N—oxide form or solvate thereof

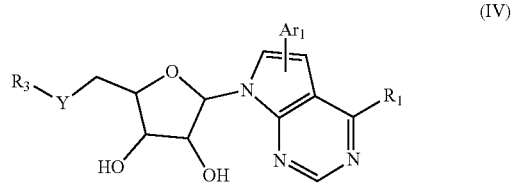

(IV)

wherein
Y is selected from O;
R$_1$ is selected from —H, —NR$_5$R$_6$, halo, —OH, S—C$_{1-6}$alkyl and —O—C$_{1-6}$alkyl;
R$_3$ is selected from —H, —C$_{1-6}$alkyl, —SO$_2$—NH$_2$, and optionally substituted silyl; wherein the —C$_{1-6}$alkyl is optionally further substituted with one or more —OH;

$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N or S; and $Ar_1$ is selected from a mono- or bicyclic aromatic cycle optionally containing one or heteroatoms, and optionally being further substituted with one or more halo, —$C_{1-6}$alkyl, —$CF_3$, —$NO_2$, —O—$C_{1-6}$alkyl, or —$OCF_3$.

21. A method of treating or reducing the risk of a *Trypanosoma* infection in a subject in need thereof, the method comprising administering to the subject a compound according to formula V or a stereoisomer, tautomer, racemic mixture, prodrug, salt, hydrate, N—oxide form or solvate thereof

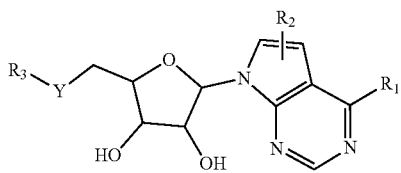

(V)

wherein
Y is selected from O;
$R_1$ is —O—$C_{1-6}$alkyl;
$R_2$ is selected from —$C_{1-6}$alkyl, —$C_{3-7}$cycloalkyl, —$C_{2-10}$alkenyl, —$C_{2-10}$alkynyl, halo, —$CF_3$, —S—$CF_3$, —$Cy_1$ and —$Ar_1$; wherein the —$C_{1-6}$alkyl, —$C_{2-10}$alkynyl, or —$C_{2-10}$alkenyl is optionally further substituted with one or more —$Cy_2$, or —$Ar_2$;
$R_3$ is selected from —H, —$C_{1-6}$alkyl, —$SO_2$—$NH_2$, and optionally substituted silyl; wherein the —$C_{1-6}$alkyl is optionally further substituted with one or more —OH;
$R_5$, $R_6$ are each independently selected from —H, —$C_{3-7}$cycloalkyl and —$C_{1-6}$alkyl; or $R_5$ and $R_6$ taken together with the N atom to which they are attached form a 5- to 6-membered heterocycle, further optionally comprising one or more heteroatoms selected from O, N or S;
$Ar_1$ and $Ar_2$ are each independently selected from a mono- or bicyclic aromatic cycle optionally containing one or heteroatoms, and optionally being further substituted with one or more halo, —$C_{1-6}$alkyl, —$CF_3$, —$NO_2$, —O—$C_{1-6}$alkyl, or —$OCF_3$; and
$Cy_1$ and $Cy_2$ are each independently selected from a mono- or bicyclic non-aromatic cycle optionally containing one or more heteroatoms, and optionally being further substituted with one or more halo, —$C_{1-6}$alkyl, —$CF_3$, —$NO_2$, —O—$C_{1-6}$alkyl, or —$OCF_3$.

* * * * *